(12) United States Patent
Zhou et al.

(10) Patent No.: US 11,427,593 B2
(45) Date of Patent: Aug. 30, 2022

(54) BROMODOMAIN INHIBITOR COMPOUND AND USE THEREOF

(71) Applicants: SHANGHAI INSTITUTE OF MATERIA MEDICA, CHINESE ACADEMY OF SCIENCES, Shanghai (CN); SUZHOU SUPLEAD LIFE SCIENCES CO., LTD., Jiangsu (CN)

(72) Inventors: Bing Zhou, Shanghai (CN); Cheng Luo, Shanghai (CN); Zizhou Li, Shanghai (CN); Yaxi Yang, Shanghai (CN); Shijie Chen, Shanghai (CN); Hong Ding, Shanghai (CN); Hualiang Jiang, Shanghai (CN); Gang Qiao, Jiangsu (CN); Xinjun Wang, Jiangsu (CN); Senhao Xiao, Shanghai (CN)

(73) Assignees: Shanghai Institute of Materia Medica, Chinese Academy of Sciences, Shanghai (CN); Suzhou Suplead Life Sciences Co., Ltd., Suzhou (CN)

( * ) Notice: Subject to any disclaimer, the term of this patent is extended or adjusted under 35 U.S.C. 154(b) by 11 days.

(21) Appl. No.: 16/962,347

(22) PCT Filed: Jan. 11, 2019

(86) PCT No.: PCT/CN2019/071258
§ 371 (c)(1),
(2) Date: Jul. 15, 2020

(87) PCT Pub. No.: WO2019/141131
PCT Pub. Date: Jul. 25, 2019

(65) Prior Publication Data
US 2020/0354371 A1 Nov. 12, 2020

(30) Foreign Application Priority Data
Jan. 16, 2018 (CN) .......................... 201810040756.7
Sep. 17, 2018 (CN) .......................... 201811081153.8

(51) Int. Cl.
C07D 487/04 (2006.01)
A61P 35/00 (2006.01)
A61P 35/02 (2006.01)

(52) U.S. Cl.
CPC ............ C07D 487/04 (2013.01); A61P 35/00 (2018.01); A61P 35/02 (2018.01)

(58) Field of Classification Search
CPC ......... C07D 487/04; A61P 35/00; A61P 35/02
See application file for complete search history.

(56) References Cited

FOREIGN PATENT DOCUMENTS

| WO | 2013142269 | | 9/2013 | |
| WO | WO 2013/142269 | * | 9/2013 | ........... C07D 487/00 |

OTHER PUBLICATIONS

International Search Report and Written Opinion of the International Searching Authority of International Application No. PCT/CN2019/071258 dated Apr. 17, 2019.

* cited by examiner

*Primary Examiner* — Erich A Leeser
(74) *Attorney, Agent, or Firm* — Ping Wang; Rimon Law

(57) ABSTRACT

The present invention relates to a bromodomain inhibitor. Provided are a compound represented by general formula I or a pharmaceutically acceptable salt, enantiomer, diastereomer, atropisomer, racemate, polymorph, solvate, or isotopically labeled compound (including deuterium substitution) thereof, a preparation method of the same, a pharmaceutical composition comprising the same, and a pharmaceutical use thereof.

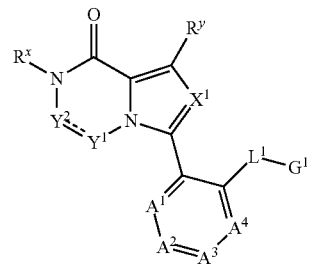

I

13 Claims, No Drawings

BROMODOMAIN INHIBITOR COMPOUND AND USE THEREOF

TECHNICAL FIELD

The present invention relates to a bromodomain inhibitor compound, a preparation method thereof, a pharmaceutical composition containing the same and use thereof. Specifically, the present invention relates to a bromodomain inhibitor compound, its pharmaceutically acceptable salts, enantiomers, diastereomers, atropisomers, racemates, polymorphs, solvates, or isotopically labeled compounds (including deuterium substituted compounds), a preparation method thereof, a pharmaceutical composition containing the same, and pharmaceutical use thereof.

BACKGROUND ART

The bromodomain refers to a conserved protein fold connected with N-acetylated lysine residues, which is found in certain proteins. There are currently 46 human bromodomain-containing proteins, which are divided into eight families based on their sequence and structural similarities. Among others, the BET family includes BRD2, BRD3, BRD4, and BRDT. These proteins have two highly conserved bromodomains (BDT and BD2) that can recognize and bind acetylated histones at the N-terminus, and a highly conserved bromodomain that is involved in protein interactions regulated by non-BRD proteins at the C-terminus. The BET family proteins other than BRDT are widely expressed in the human body and have multiple cell functions. One of the most important functions of BET family proteins is to bind with acetylated histones, thereby recruiting regulatory proteins to chromosomal regions, such as the catalytic subunit of NuRD recombinant complex, histone demethylase JMJD6 and SWI/SNF nucleosome remodeling complex or methyltransferase NSD3 (Rahman, et al. Molecular and cellular biology 2011, 31 (13), 2641-52), etc., to combine acetylation of histones and function of chromatin to play the role of identifying genes. BET family proteins can also interact with acetylated transcription factors such as NF-KB, etc. to promote the binding of nuclear chromatin to other proteins (Shi, et al. Molecular cell 2014, 54 (5), 728-36).

Genomic data analysis shows that there is overlap part between the binding sites of chromatin and BRD4, BRD3 and BRD2, but there are significant differences in functions due to their own difference (Anders et al. Nat. Biotech. 2014; 32:92-6). For example, the deletion of BRD4 will kill the embryos of mice, indicating that BRD4 protein plays a vital role in the important physiological process of mouse growth and development (Houzelstein et al. Molecular and Cellular Biology 2002; 22:3794-802); physiological functional defects of BRD3 protein deletions are currently not reported but it plays an important role in the maturation of red blood cells (Lamonica, et al. Proceedings of the National Academy of Sciences of the United States of America 2011; 108:E159-E68); the mice with BRD2 deletion can survive, but have obvious obesity (Wang et al. Vitamins and hormones 2013; 91:49-75); the deletion of the first Broman region of BRDT can lead to incorrect reorganization of chromatin and abnormal transcriptional regulation, causing sperm defects (Berkovits et al. Current topics in developmental biology 2013; 102:293-326).

Therefore, there is currently a medical need to develop compounds that can inhibit the binding of the bromodomains of the BET family with their homologous acetylated lysine proteins for the treatment of cancer, inflammatory diseases, kidney diseases, diseases involving metabolism or fat accumulation, and some viral infections, and for providing methods for male contraception. At the same time, a large number of experiments have shown that although the BET family has similar structure, their physiological functions are quite different. Therefore, it is necessary to develop selective small molecule inhibitors for specific proteins in the BET family to avoid physiological dysfunction caused by the inhibition of other BET family proteins and reduce the adverse reactions of small molecule compounds. In summary, the development of inhibitors involving bromodomains is currently very hot in the industry and is conducive to the related new drug development.

SUMMARY OF THE INVENTION

In one aspect, the present invention provides a compound of formula I, a pharmaceutically acceptable salt, enantiomer, diastereomer, atropisomer, racemate, polymorph, solvate, or isotopically labeled compound (including deuterium substituted compound) thereof,

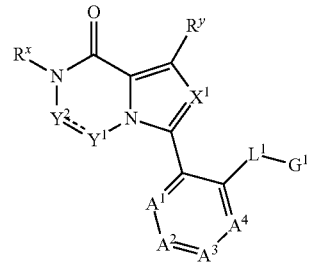

I

------ is a single bond or a double bond;

$R^x$ is hydrogen, $C_1$-$C_3$ alkyl, or $C_1$-$C_3$ haloalkyl;

$R^y$ is hydrogen, $C_1$-$C_3$ alkyl, or $C_1$-$C_3$ haloalkyl;

$X^1$ is N or $CR^{x1}$, wherein $R^{x1}$ is hydrogen, $C_1$-$C_6$ alkyl, $C_1$-$C_6$ haloalkyl, halogen or CN;

$Y^1$ is N, $CR^{y1}$ or $CR^{y1}R^{y2}$, wherein $R^{y1}$ and $R^{y2}$ are each independently hydrogen, $C_1$-$C_6$ alkyl, $C_1$-$C_6$ haloalkyl, halogen, CN;

$Y^2$ is N, $CR^3$ or $CR^{y3}R^{y4}$, wherein $R^{y3}$ and $R^{y4}$ are each independently hydrogen, CN, $C_1$-$C_6$ alkyl, $C_1$-$C_6$ haloalkyl, —($C_1$-$C_6$ alkylene)-$OR^{2a}$, —C(O)—$R^{ax1}$, —($C_1$-$C_6$ alkylene)—C(O)—$R^{ax1}$, —C(O)$OR^{ax1}$, —($C_1$-$C_6$ alkylene)—C(O)$NHR^{ax1}$, —($C_1$-$C_6$ alkylene)—N($R^{ax1}$)$R^{ax2}$, —C(O)N($R^{ax1}$)$R^{ax2}$, $G^a$, or —($C_1$-$C_6$ alkylene)-$G^a$;

$R^{ax1}$ and $R^{ax2}$ at each occurrence are each independently hydrogen, $C_1$-$C_6$ alkyl, $C_1$-$C_6$ haloalkyl, $G^a$, or —($C_1$-$C_6$ alkylene)-$G^a$;

particularly, $Y^1$ and $Y^2$ are not N simultaneously; and when $Y^1$ or $Y^2$ is N, ------ is a double bond;

$A^1$ is N or $CR^1$, $A^2$ is N or $CR^2$, $A^3$ is N or $CR^3$, $A^4$ is N or $CR^4$, with the proviso that none, one, two or three of $A^1$, $A^2$, $A^3$ and $A^4$ is/are N;

$R^1$ is hydrogen, $C_1$-$C_6$ alkyl, $C_2$-$C_6$ alkenyl, $C_2$-$C_6$ alkynyl, halogen, $C_1$-$C_6$ haloalkyl, CN, or $NO_2$;

$R^2$, $R^3$ and $R^4$ are each independently hydrogen, $C_1$-$C_6$ alkyl, $C_2$-$C_6$ alkenyl, $C_2$-$C_6$ alkynyl, halogen, $C_1$-$C_6$ haloalkyl, CN, $NO_2$, $G^{2a}$,

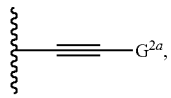

—OR$^{2a}$, —OC(O)R$^{2d}$, —OC(O)NR$^{2b}$R$^{2c}$, —SR$^{2a}$, —S(O)$_2$R$^{2d}$, —S(O)$_2$NR$^{2b}$R$^{2c}$, —C(O)R$^{2d}$, —C(O)OR$^{2a}$, —C(O)NR$^{2b}$R$^{2c}$, —NR$^{2b}$R$^{2c}$, —N(R$^{2e}$)C(O)R$^{2d}$, —N(R$^{2e}$)S(O)$_2$R$^{2d}$, —N(R$^{2e}$)C(O)OR$^{2d}$, —N(R$^{2e}$)C(O)NR$^{2b}$R$^{2c}$, —N(R$^{2e}$)S(O)$_2$NR$^{2b}$R$^{2c}$, —(C$_1$-C$_6$ alkylene)-G$^{2a}$, —(C$_1$-C$_6$ alkylene)—OR$^{2a}$, —(C$_1$-C$_6$ alkylene)—OC(O)R$^{2d}$, —(C$_1$-C$_6$ alkylene)—OC(O)NR$^{2b}$R$^{2c}$, —(C$_1$-C$_6$ alkylene)—S(O)$_2$R$^{2d}$, —(C$_1$-C$_6$ alkylene)—S(O)$_2$NR$^{2b}$R$^{2c}$, —(C$_1$-C$_6$ alkylene)—C(O)R$^{2d}$, —(C$_1$-C$_6$ alkylene)—C(O)OR$^{2a}$, —(C$_1$-C$_6$ alkylene)—C(O)NR$^{2b}$R$^{2c}$, —(C$_1$-C$_6$ alkylene)—NR$^{2b}$R$^{2c}$, —(C$_1$-C$_6$ alkylene)—N(R$^{2e}$)C(O)R$^{2d}$, —(C$_1$-C$_6$ alkylene)—N(R$^{2e}$)S(O)$_2$R$^{2d}$, —(C$_1$-C$_6$ alkylene)—N(R$^{2e}$)C(O)OR$^{2a}$, —(C$_1$-C$_6$ alkylene)—N(R$^{2e}$)C(O)NR$^{2b}$R$^{2c}$, —(C$_1$-C$_6$alkylene)—N(R$^{2e}$)S(O)$_2$NR$^{2b}$R$^{2c}$, —(C$_1$-C$_6$alkylene)—CN, —S(=O)(=NH)R$^{2d}$, —(C$_1$-C$_6$ alkylene)—S(=O)(=NH)R$^{2d}$; wherein C$_1$-C$_6$ alkylene is unsubstituted or substituted with 1 to 6 substituents selected from CN, OH and C$_1$-C$_3$ alkyl; R$^{2a}$, R$^{2b}$, R$^{2c}$ and R$^{2e}$ at each occurrence are each independently hydrogen, C$_2$-C$_6$ alkenyl, C$_2$-C$_6$ alkynyl, C$_1$-C$_6$ haloalkyl, G$^{2b}$, C$_1$-C$_6$ alkyl, or C$_1$-C$_6$ alkyl substituted by one selected from —OR$^{z1}$, —NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$ and G$^{2b}$;

R$^{2d}$ at each occurrence is independently C$_2$-C$_6$ alkenyl, C$_2$-C$_6$ alkynyl, C$_1$-C$_6$ haloalkyl, G$^{2b}$, C$_1$-C$_6$ alkyl, or C$_1$-C$_6$ alkyl substituted by one selected from —OR$^{z1}$, —NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$ and G$^{2b}$; R$^{z1}$ and R$^{z2}$ at each occurrence are each independently hydrogen, C$_1$-C$_6$ alkyl, or C$_1$-C$_6$ haloalkyl;

G$^a$, G$^{2a}$ and G$^{2b}$ at each occurrence are each independently aryl, heteroaryl, heterocyclyl, cycloalkyl, or cycloalkenyl, which are each independently unsubstituted or substituted by 1, 2, 3, 4, or 5 R$^v$'s;

L$^1$ is absent, or is —CH$_2$—, —C(O)—, —C(H)(OH)—, —(CH$_2$)$_m$O—, —(CH$_2$)$_m$S(O)$_n$—, —NHC(O)—, —C(O)NH—, —NHC(O)NH—, —NHS(O)$_2$—, —S(O)$_2$NH— or —(CH$_2$)$_m$N(R$^z$)—, wherein n is 0, 1, or 2; m is 0 or 1; R$^z$ is hydrogen, C$_1$-C$_3$ alkyl, C$_1$-C$_3$ haloalkyl; (C$_2$-C$_3$ alkylene)—OH, or unsubstituted cyclopropyl;

G$^1$ is C$_1$-C$_6$ alkyl, alkoxyalkyl, G$^{1a}$ or —(C$_1$-C$_6$ alkylene)-G$^{1a}$; wherein each G$^{1a}$ is independently aryl, heteroaryl, heterocyclyl, cycloalkyl, or cycloalkenyl, and each G$^{1a}$ is independently unsubstituted or substituted with 1, 2, 3, 4, or 5 R$^v$'s;

R$^v$ and R$^w$ at each occurrence are each independently C$_1$-C$_6$ alkyl, C$_2$-C$_6$ alkenyl, C$_2$-C$_6$ alkynyl, halogen, C$_1$-C$_6$ haloalkyl, —CN, oxo (=O), —OR$^h$, —OC(O)R$^i$, —OC(O)NR$^j$R$^k$, —SR$^h$, —S(O)$_2$R$^h$, —S(O)$_2$NR$^j$R$^k$, —C(O)R$^h$, —C(O)-monocyclic heterocyclyl, —C(O)-monocyclic heteroaryl, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)OR$^i$, —N(R$^h$)C(O)NR$^j$R$^k$, —(C$_1$-C$_6$ alkylene)—OR$^h$, —(C$_1$-C$_6$ alkylene)—OC(O)R$^i$, —(C$_1$-C$_6$ alkylene)—OC(O)NR$^j$R$^k$, —(C$_1$-C$_6$ alkylene)—S(O)$_2$R$^h$, —(C$_1$-C$_6$ alkylene)—S(O)$_2$NR$^j$R$^k$, —(C$_1$-C$_6$ alkylene)—C(O)R$^h$, —(C$_1$-C$_6$ alkylene)—C(O)OR$^h$, —(C$_1$-C$_6$ alkylene)—C(O)NR$^j$R$^k$, —(C$_1$-C$_6$ alkylene)—NR$^j$R$^k$, —(C$_1$-C$_6$ alkylene)—N(R$^h$)C(O)R$^i$, —(C$_1$-C$_6$ alkylene)—N(R$^h$)S(O)$_2$R$^i$, —(C$_1$-C$_6$ alkylene)—N(R$^h$)C(O)OR$^i$, —(C$_1$-C$_6$ alkylene)—N(R$^h$)C(O)NR$^j$R$^k$, or —(C$_1$-C$_6$ alkylene)—CN;

R$^h$, R$^j$, R$^k$ at each occurrence are each independently hydrogen, C$_1$-C$_6$ alkyl, or C$_1$-C$_6$ haloalkyl; and R$^i$ at each occurrence is independently C$_1$-C$_6$ alkyl, or C$_1$-C$_6$ haloalkyl.

Preferably, the compound of formula I is a compound represented by formula Ia, Ib, Ic, or Ie:

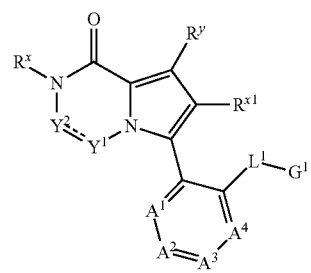

Ia

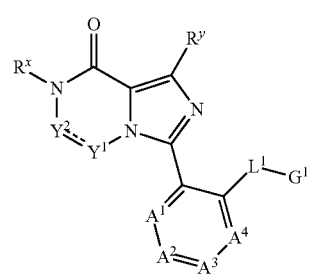

Ib

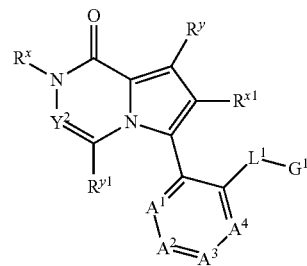

Ic

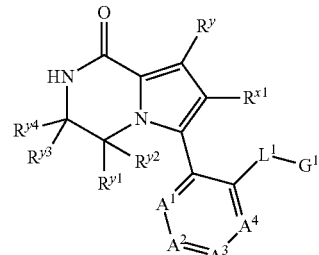

Ie

╌╌╌╌ is a single bond or a double bond;

R$^x$, R$^y$, R$^{x1}$, R$^{y1}$, R$^{y2}$, R$^{y3}$, R$^{y4}$, Y$^1$, Y$^2$, A, A$^2$, A$^3$, A$^4$, L$^1$ and G$^1$ at occurrence have the same definition as those in the formula I described above.

Preferably, the compound of formula I is a compound represented by formula Id or If:

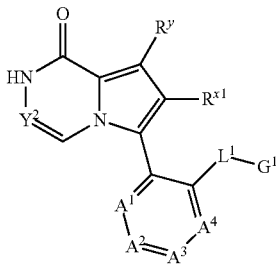

Id

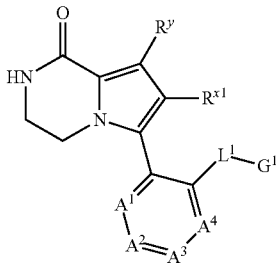

If wherein, $A^1, A^2, A^3, A^4, L^1$ and $G^1$ at occurrence have the same definition as those in the formula I described above;

$Y^2$ is N or CH;

$R^y$ is $C_1$-$C_3$ alkyl;

$R^{x1}$ is H, $CH_3$ or halogen.

Preferably, the compound of formula I is a compound represented by formula Ig or Ih:

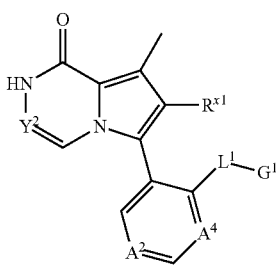

Ig

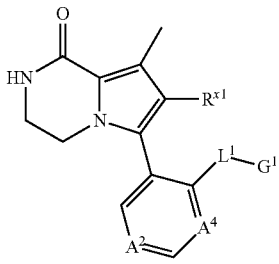

Ih wherein, $A^2$ has the same definition as that in the formula I described above;

$L^1$ is O or NH;

$Y^2$ is CH or N;

$R^{x1}$ is H, $CH_3$ or halogen;

$A^4$ is CH or N;

$G^1$ is $G^{1a}$ or —($CH_2$)-$G^{1a}$; wherein each $G^{1a}$ is independently aryl, heteroaryl, heterocyclyl, cycloalkyl, or cycloalkenyl, and each $G^{1a}$ is independently unsubstituted or substituted with 1 or 2 $R^w$s;

$R^w$ has the same definition as that in the formula I described above.

Preferably, the compound of formula I is a compound represented by formula Ii or Ij:

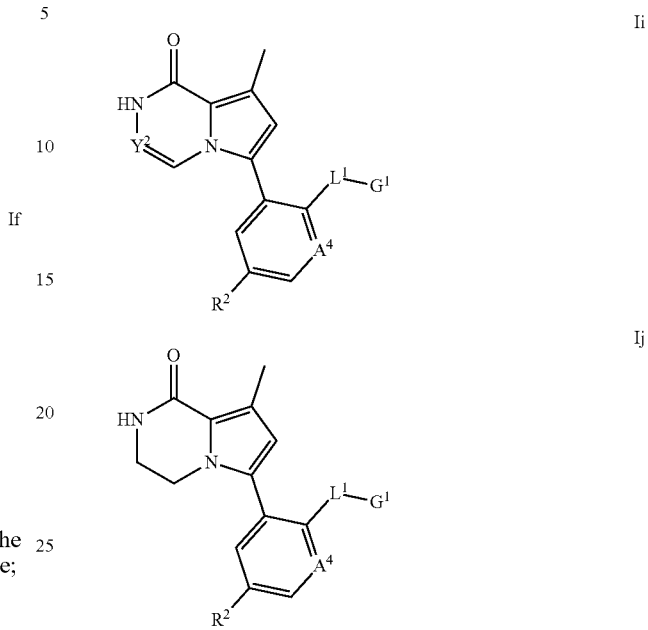

Ii

Ij wherein, $Y^2$ is N or CH;

$L^1$ is O or NH;

$A^4$ is CH or N;

$G^1$ is pyridyl,

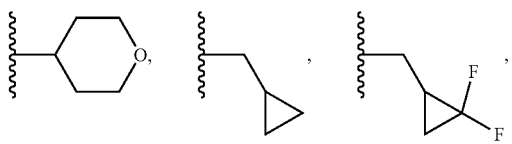

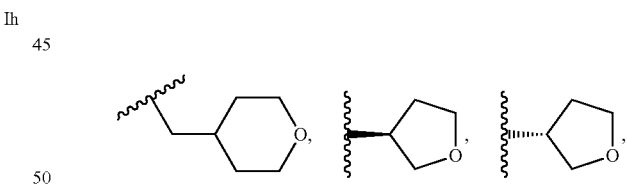

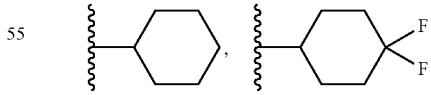

or phenyl substituted with 1 or 2 halogens;

$R^2$ is —$S(O)_2R^{2d}$, —$NHS(O)_2R^{2d}$, —$S(O)_2NR^{2b}R^{2c}$ or —($CH_2$)—$S(O)_2R^{2d}$; wherein $R^{2d}$ is an unsubstituted $C_1$-$C_3$ alkyl, and $R^{2b}$ and $R^{2c}$ are each independently hydrogen or an unsubstituted $C_1$-$C_3$ alkyl.

Preferably, the compound of formula I is selected from the group consisting of the following compounds:

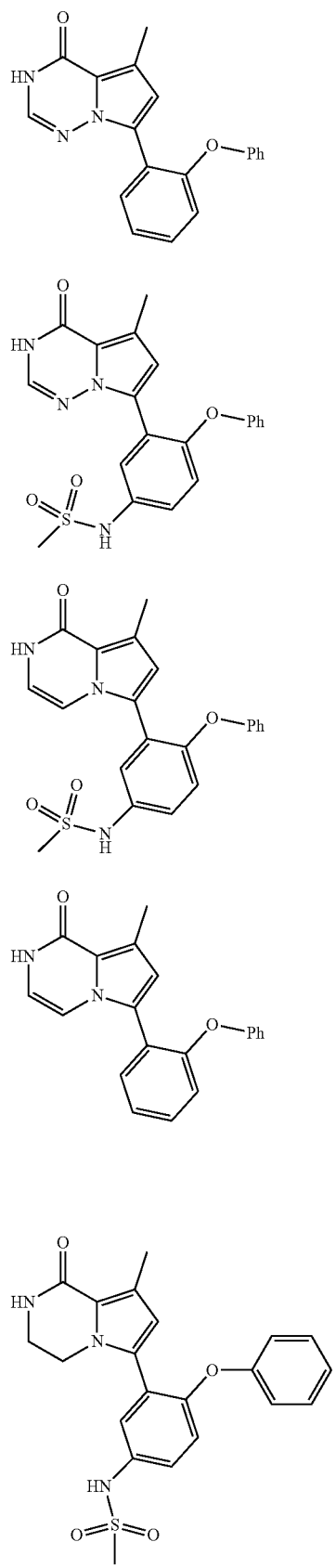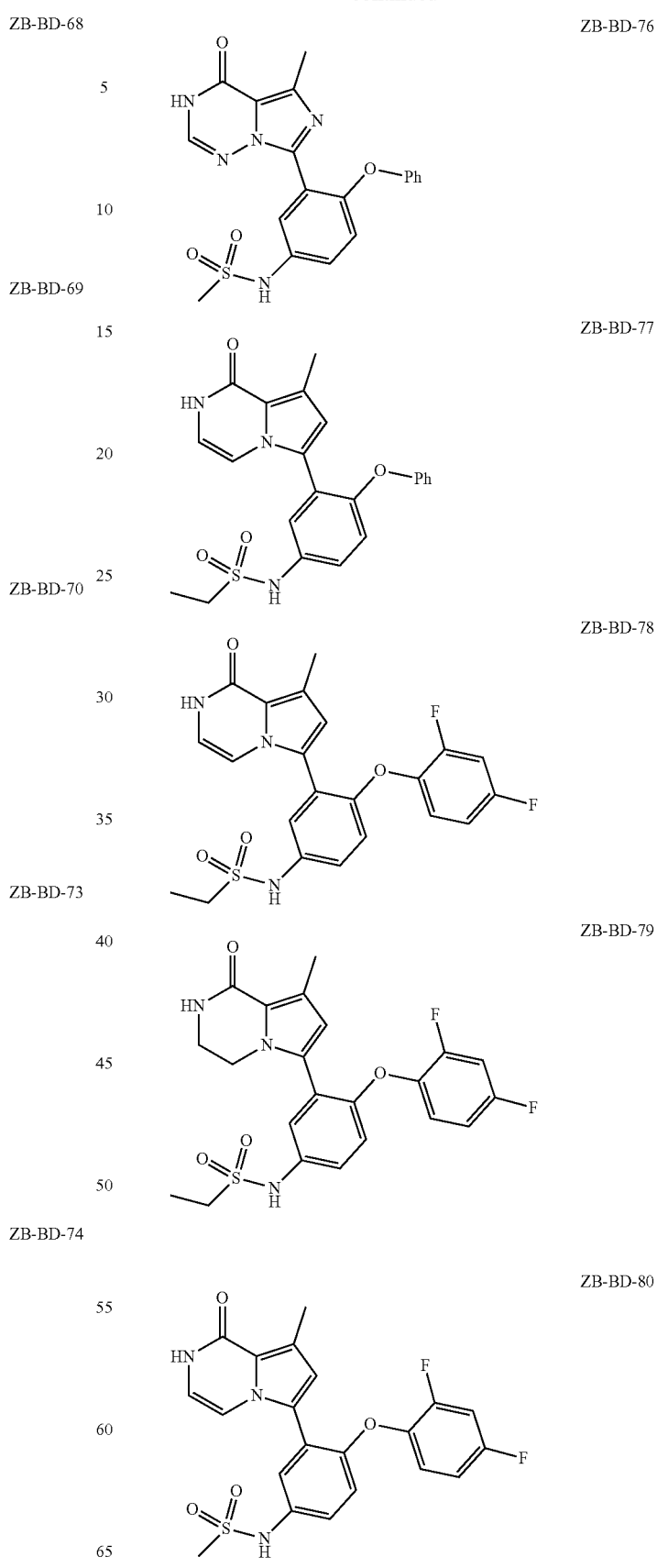

ZB-BD-81
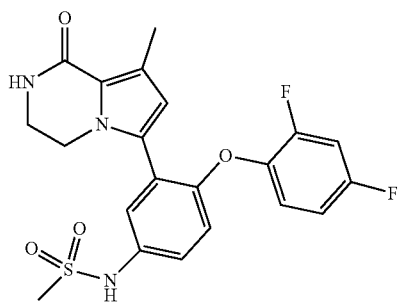
ZB-BD-82
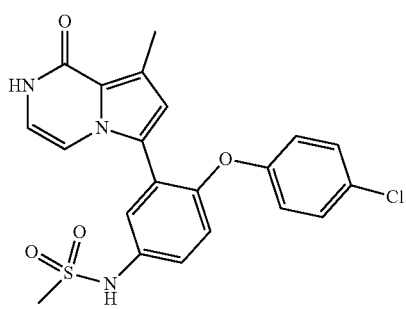
ZB-BD-83
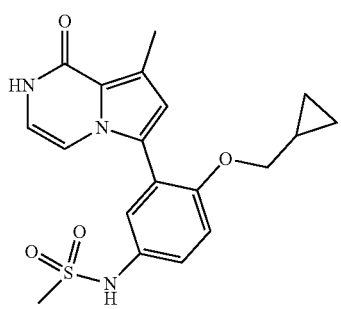
ZB-BD-86
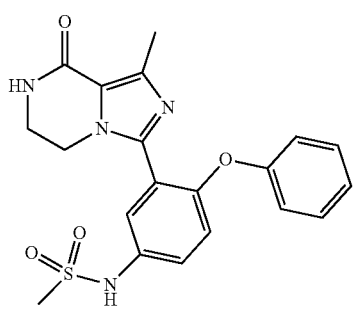
ZB-BD-87
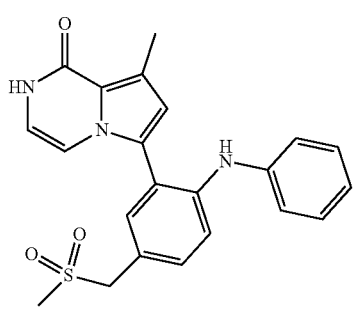
ZB-BD-90
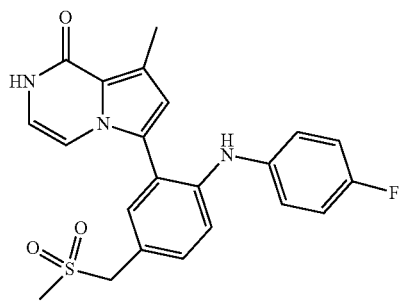
ZB-BD-91
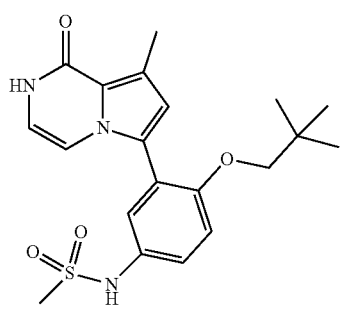
ZB-BD-92
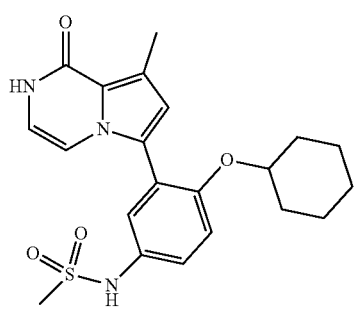
ZB-BD-93
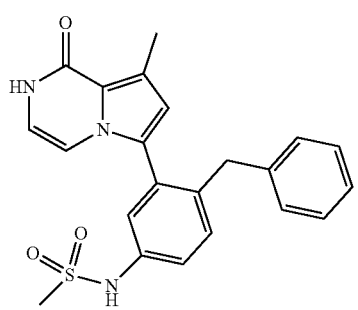
ZB-BD-94
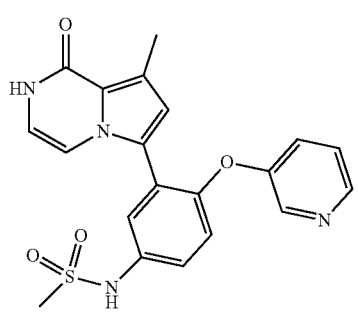

ZB-BD-95
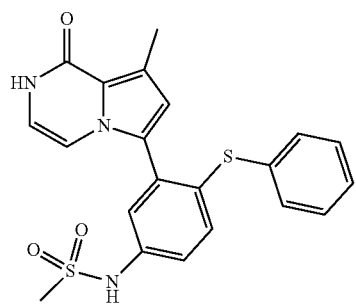
ZB-BD-96
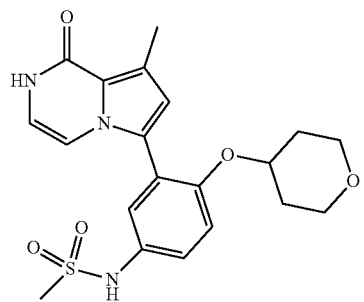
ZB-BD-97
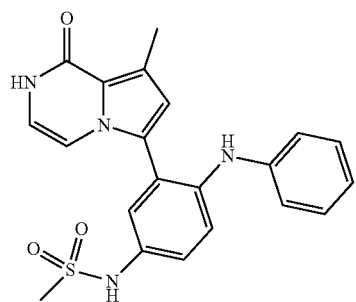
ZB-BD-98
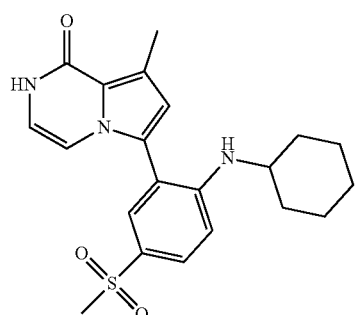
ZB-BD-99
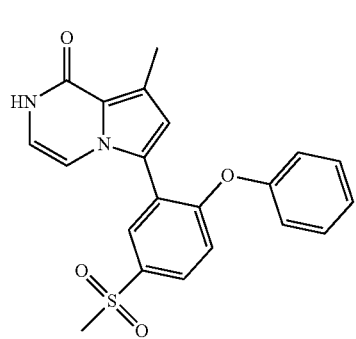
ZB-BD-100
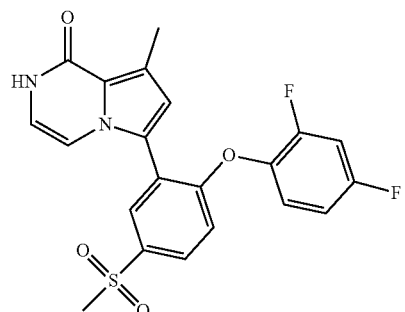
ZB-BD-102
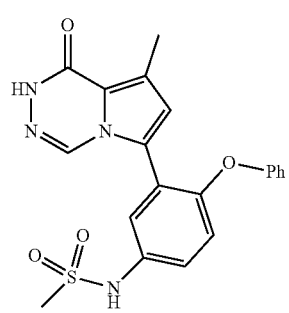
ZB-BD-103
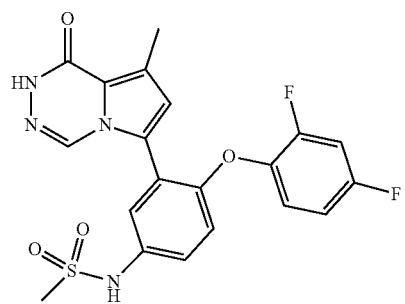
ZB-BD-105
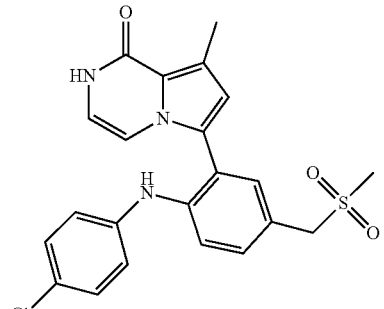
ZB-BD-110
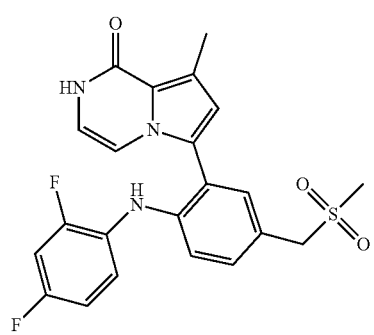

ZB-BD-112
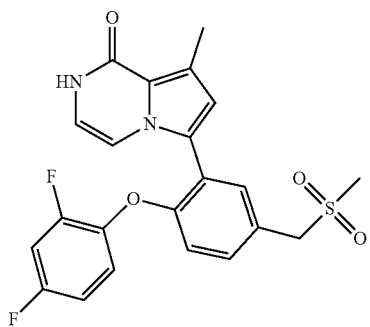
ZB-BD-113
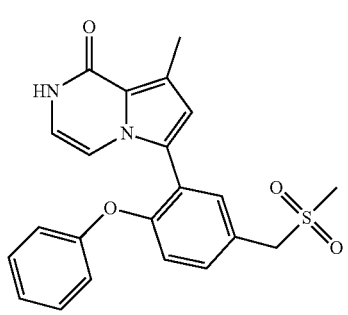
ZB-BD-114
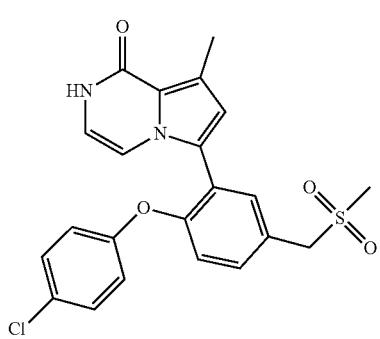
ZB-BD-115
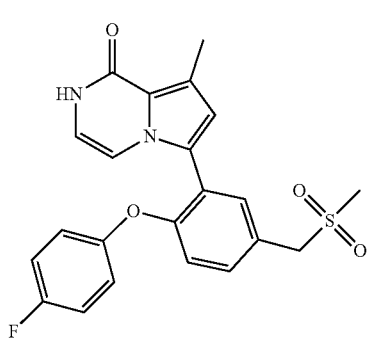
ZB-BD-116
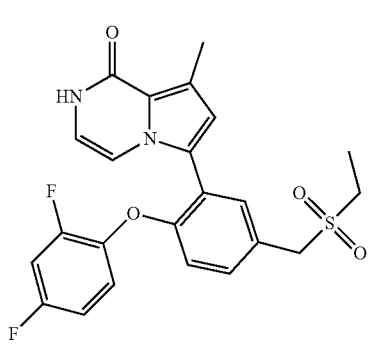
ZB-BD-117
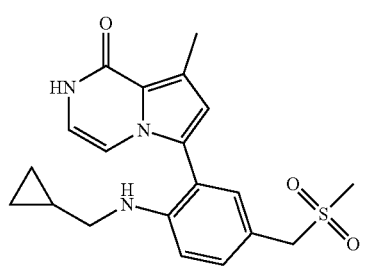
ZB-BD-118
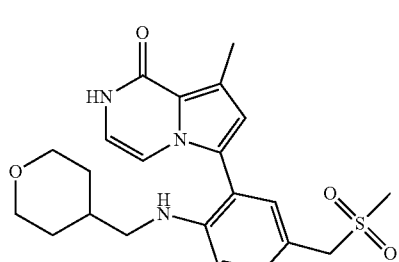
ZB-BD-119
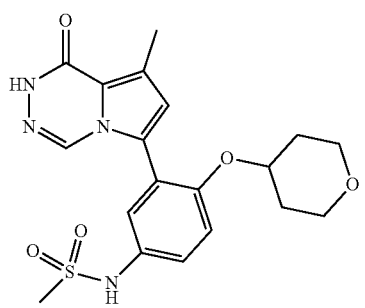
ZB-BD-120
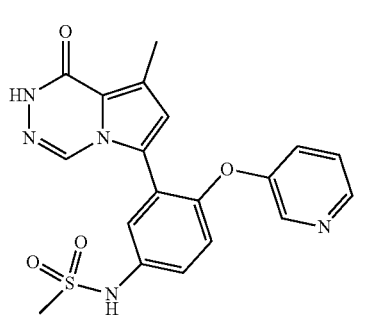
ZB-BD-121
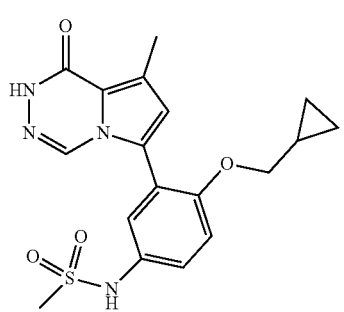

ZB-BD-122
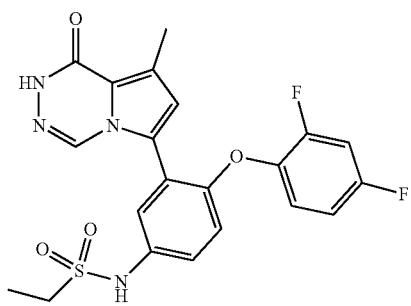
ZB-BD-123
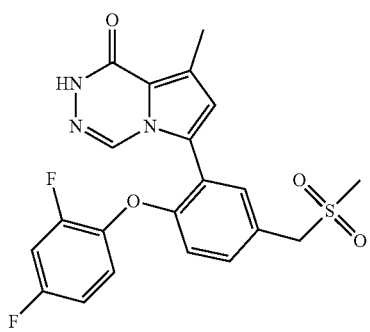
ZB-BD-124
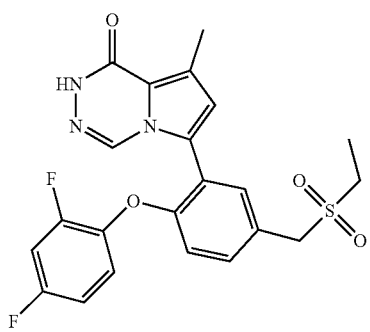
ZB-BD-125
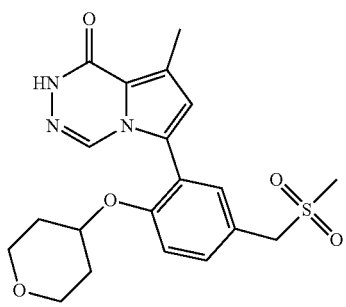
ZB-BD-126
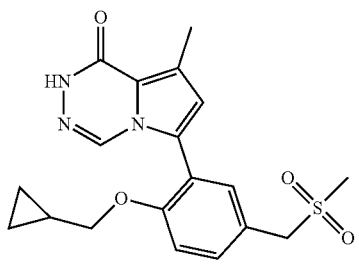
ZB-BD-127
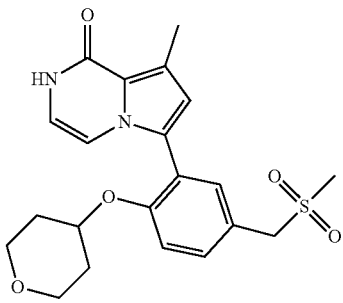
ZB-BD-128
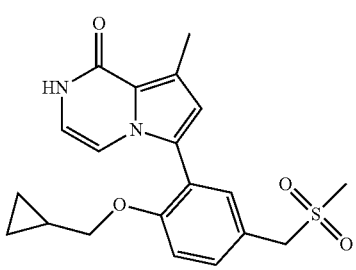
ZB-BD-129
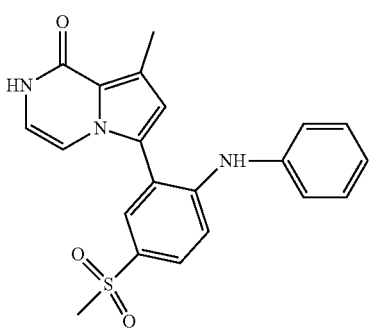
ZB-BD-130
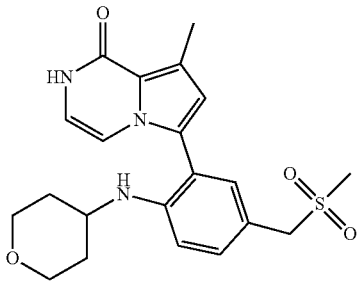
ZB-BD-131

ZB-BD-132
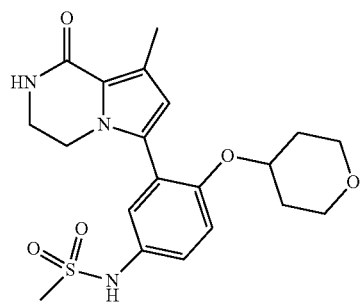
ZB-BD-133
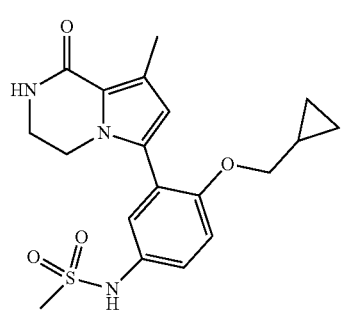
ZB-BD-134
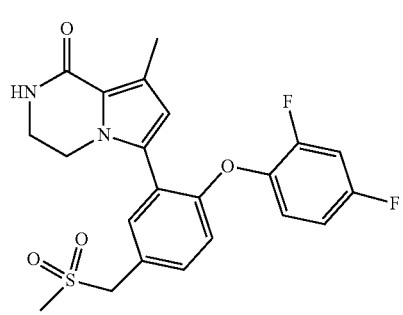
ZB-BD-135
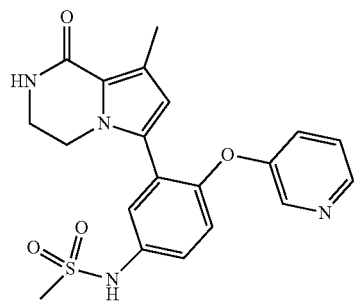
ZB-BD-136
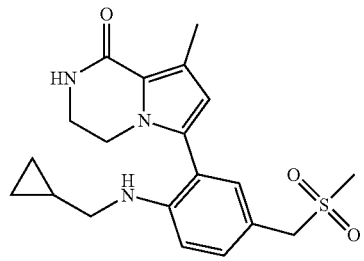
ZB-BD-137
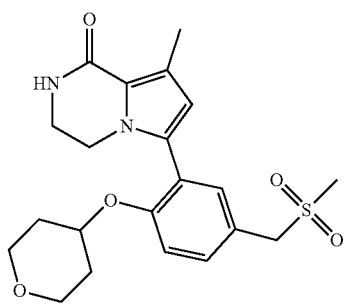
ZB-BD-140
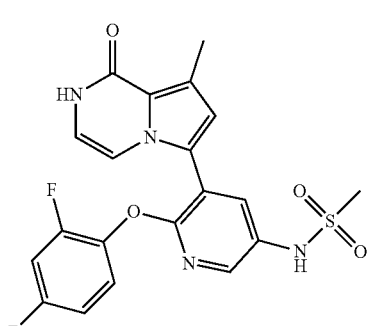
ZB-BD-141
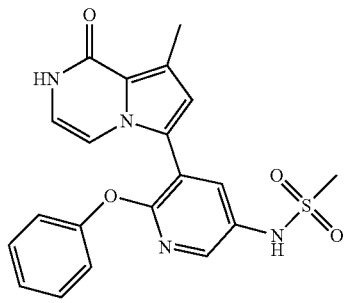
ZB-BD-142
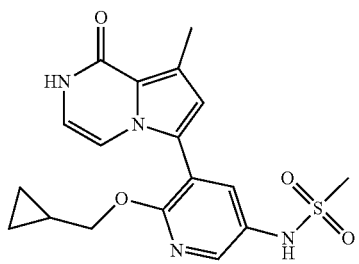
ZB-BD-143
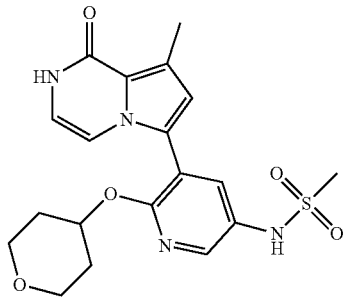

ZB-BD-144
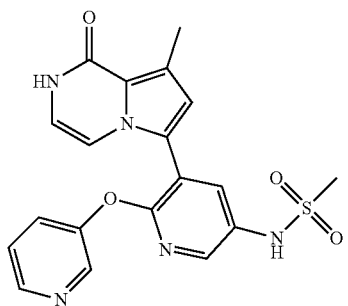
ZB-BD-145
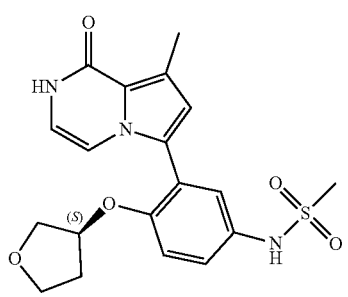
ZB-BD-146
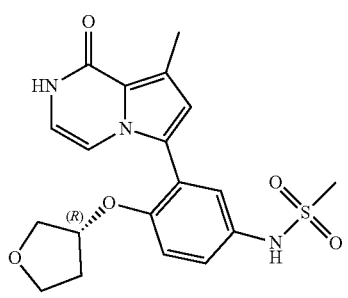
ZB-BD-147
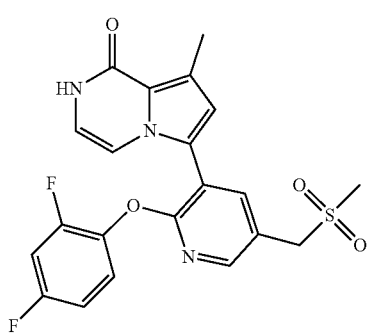
ZB-BD-148
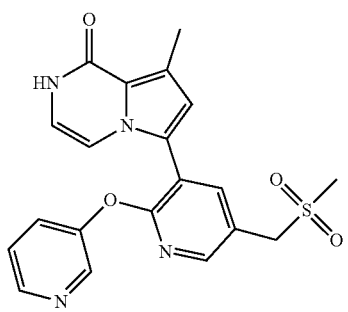
ZB-BD-149
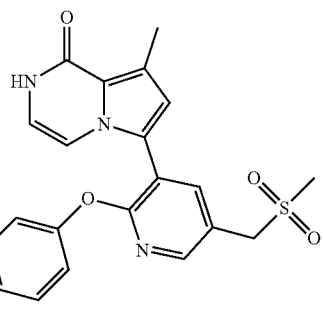
ZB-BD-150
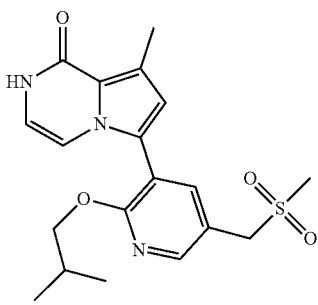
ZB-BD-151
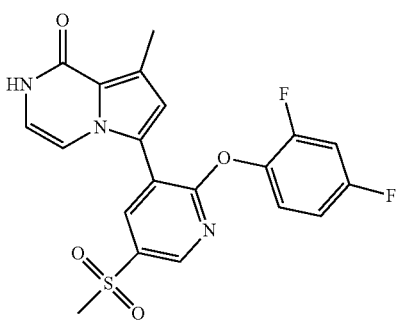
ZB-BD-152
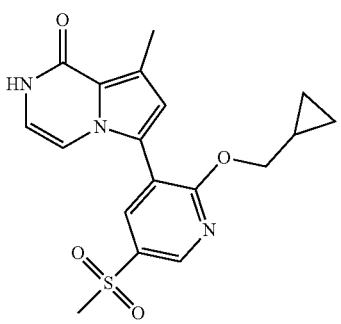
ZB-BD-153
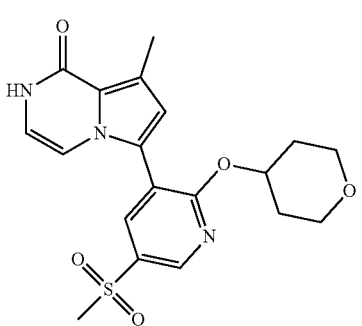

ZB-BD-154
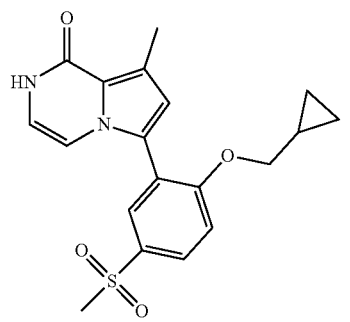
ZB-BD-155
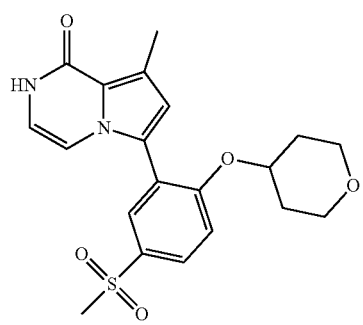
ZB-BD-156
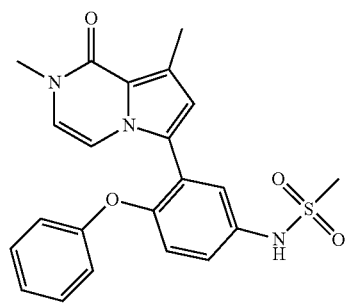
ZB-BD-162
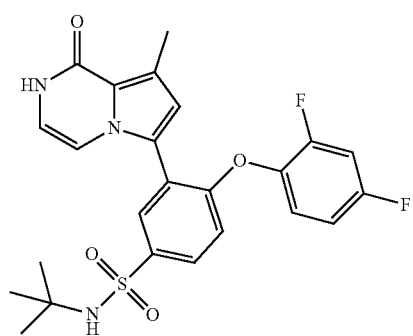
ZB-BD-163
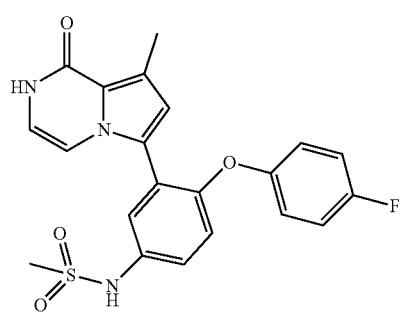
ZB-BD-164
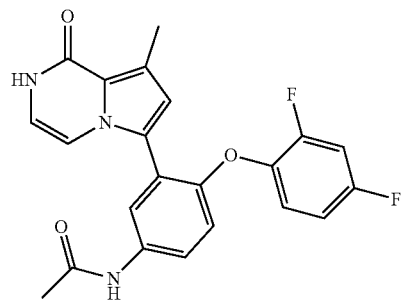
ZB-BD-166
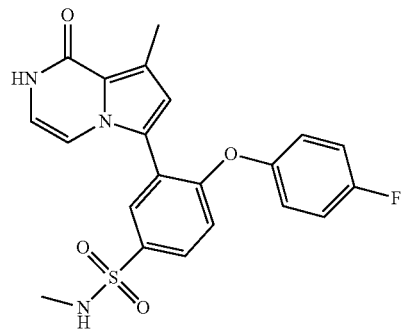
ZB-BD-167
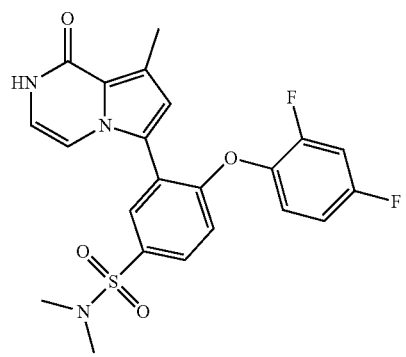
ZB-BD-172
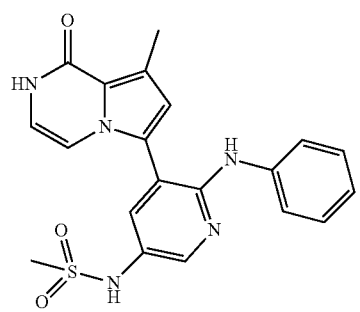
ZB-BD-173
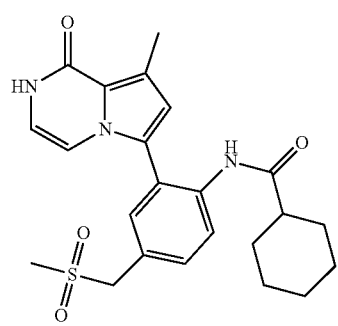

ZB-BD-174
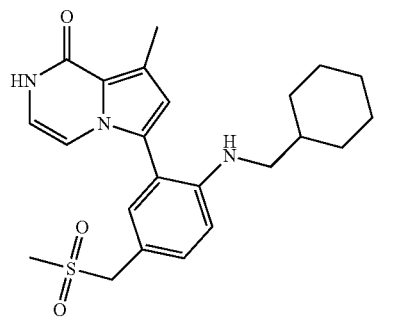
ZB-BD-175
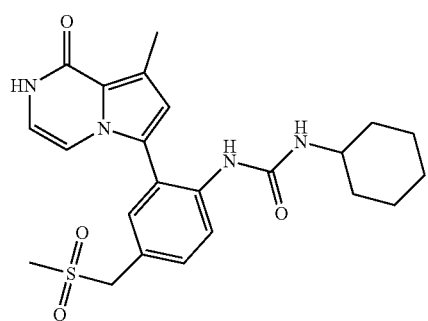
ZB-BD-179
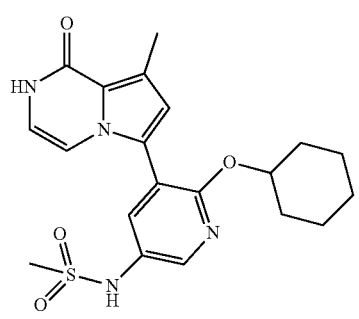
ZB-BD-183
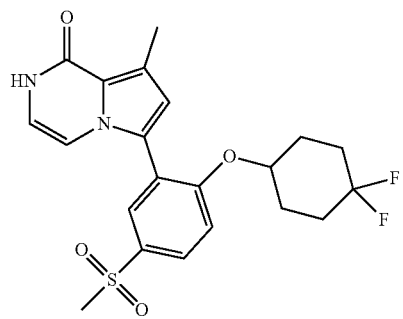
ZB-BD-184
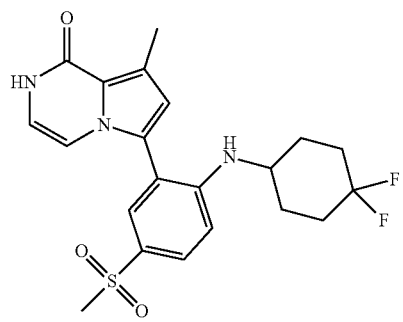
ZB-BD-185
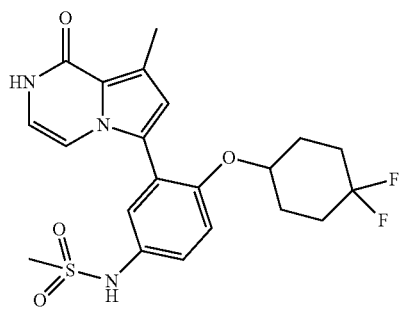
ZB-BD-187
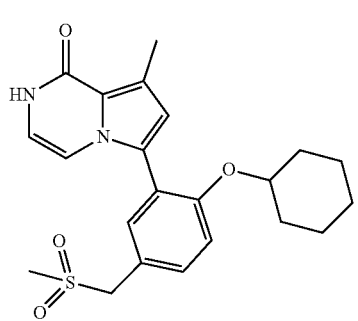
ZB-BD-188
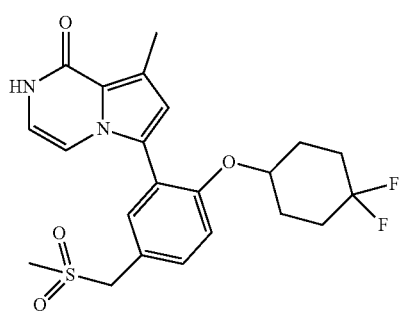
ZB-BD-189
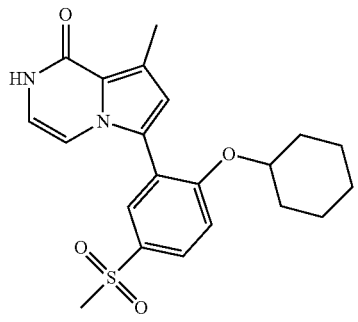
ZB-BD-190
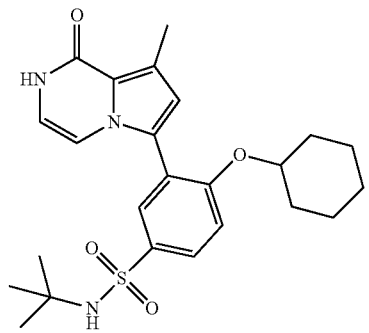

ZB-BD-191
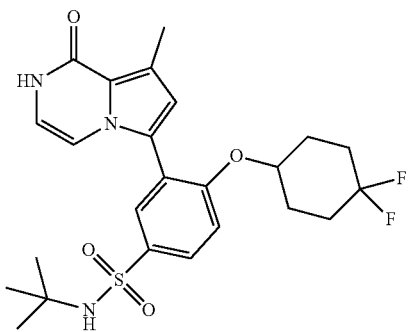
ZB-BD-194
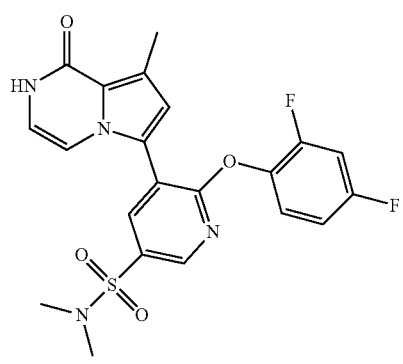
ZB-BD-195
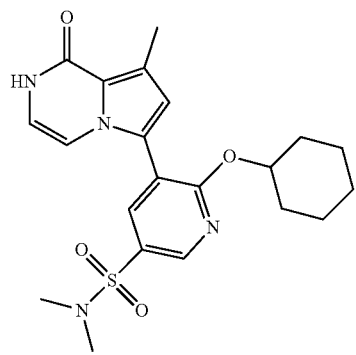
ZB-BD-196
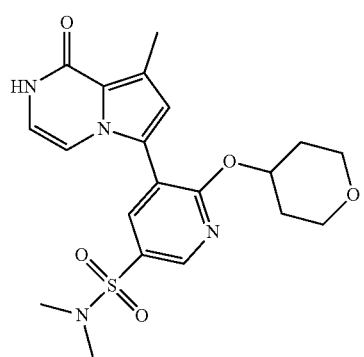
ZB-BD-197
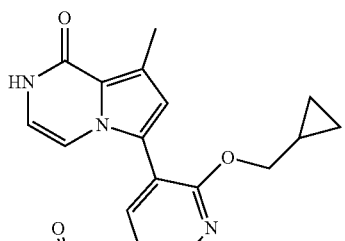
ZB-BD-198
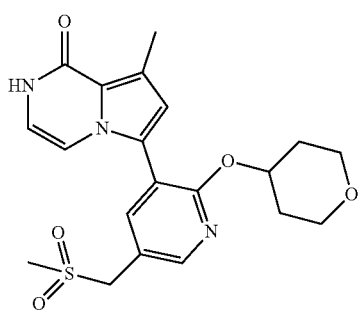
ZB-BD-202
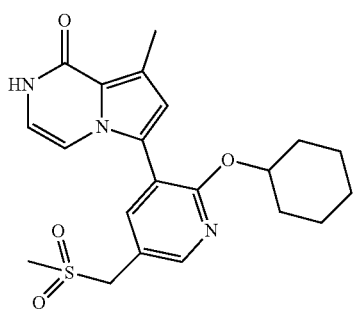
ZB-BD-216
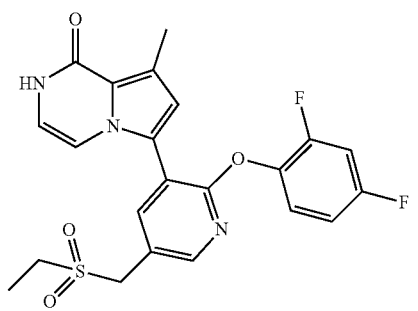
ZB-BD-217
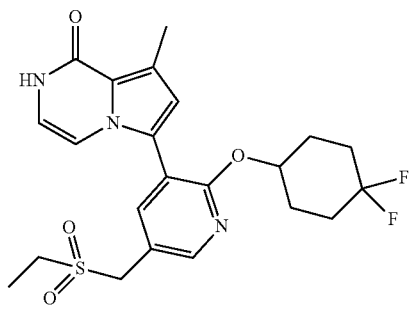

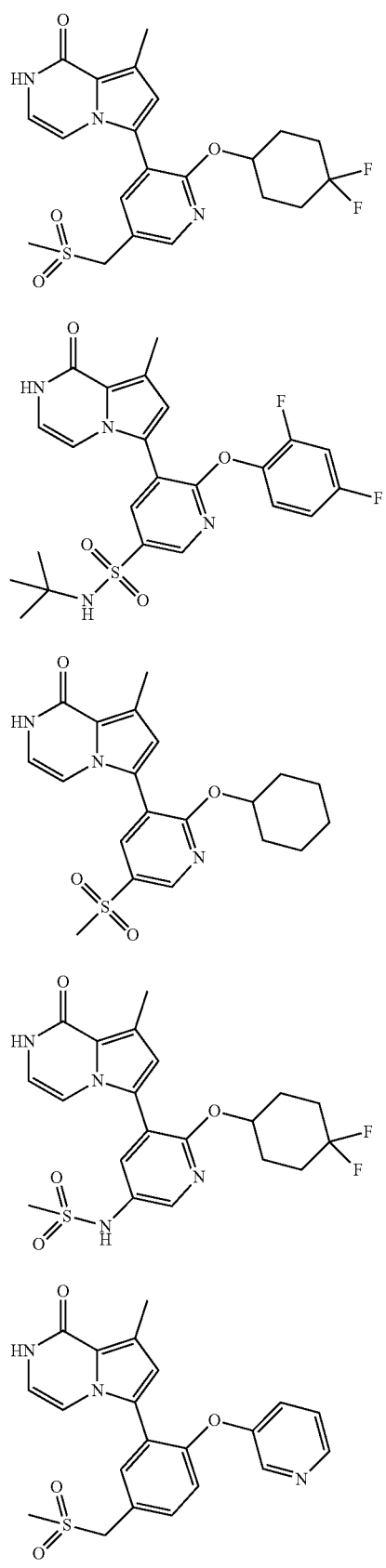
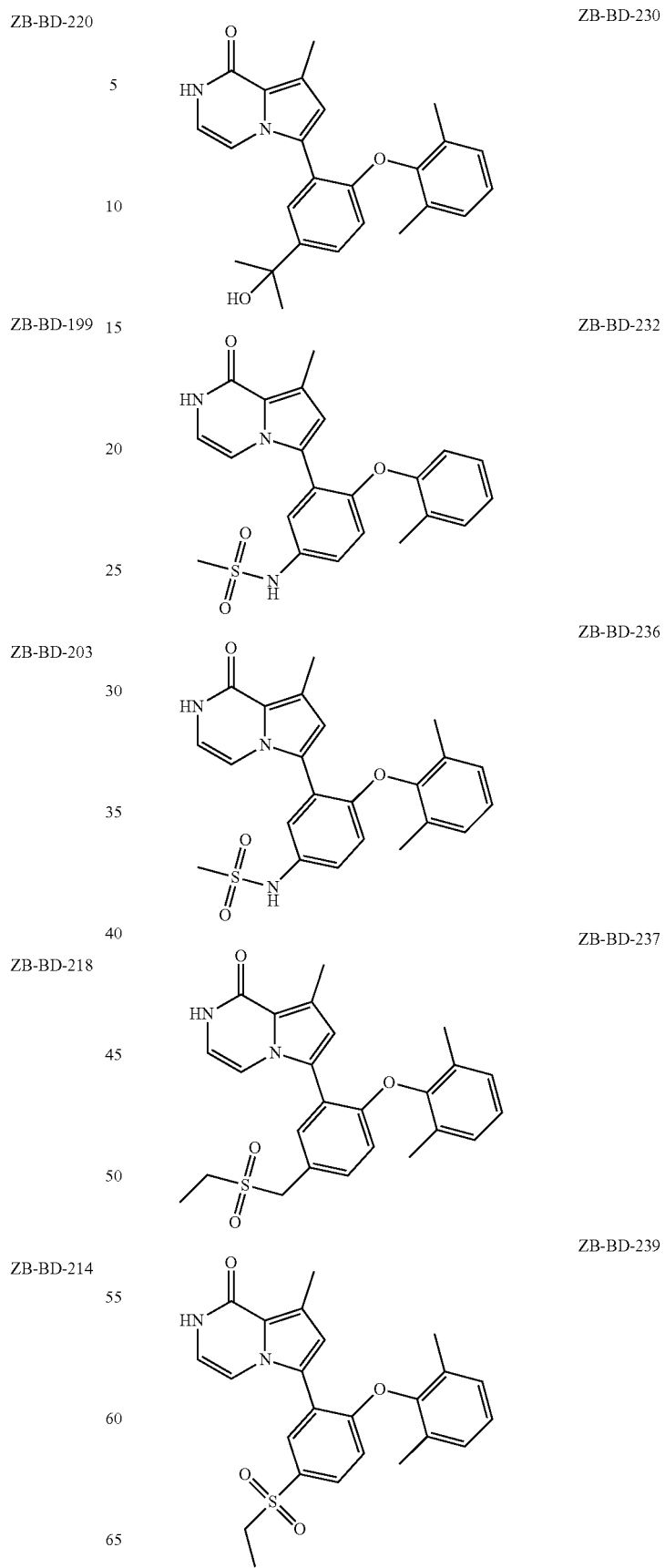

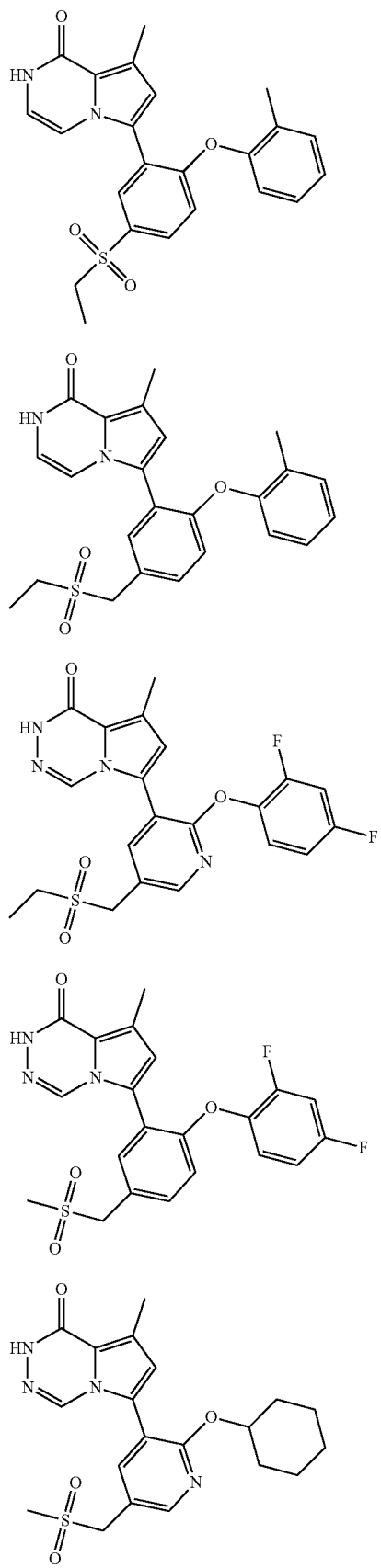
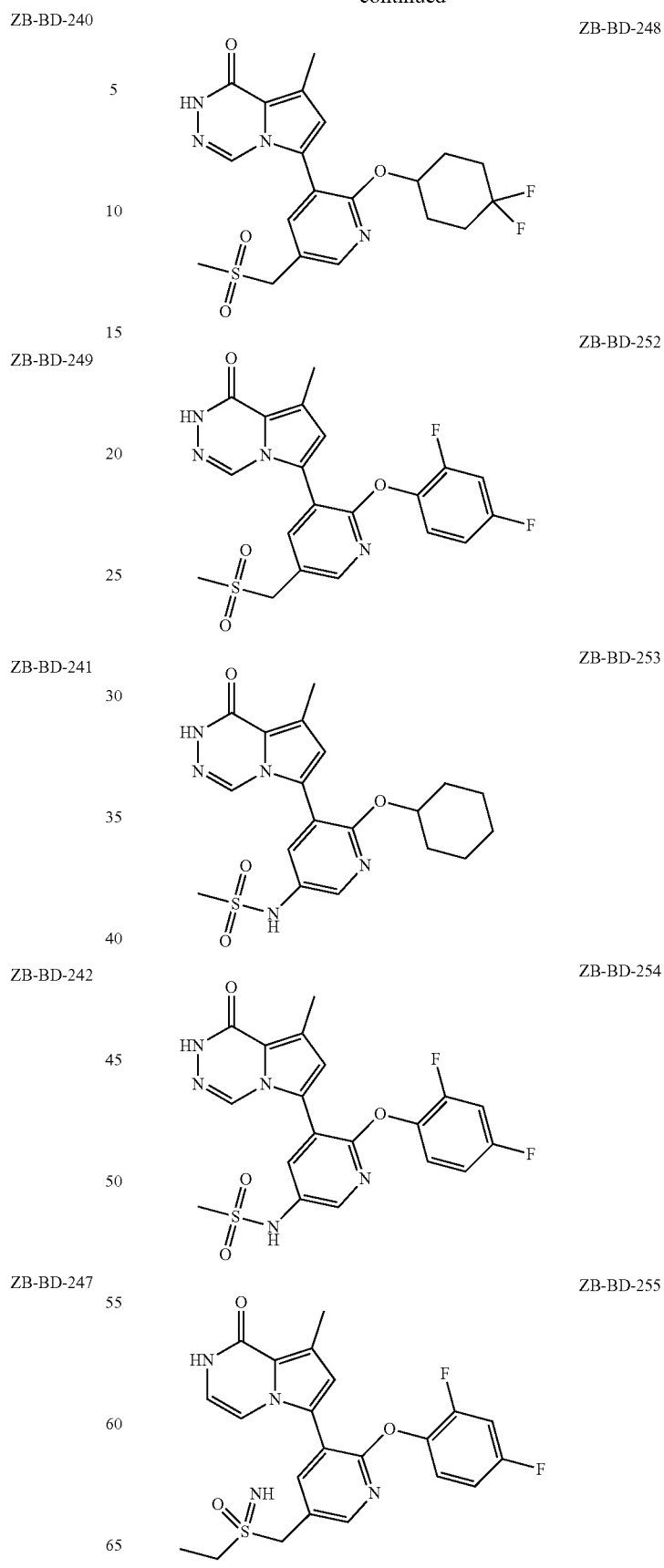

-continued

ZB-BD-256

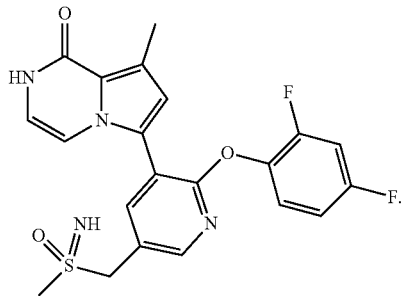

Preferably, the isotopically labeled compound is, for example, a deuterium-substituted compound. The isotopically labeled compounds may be used in applications such as metabolic detection.

In another aspect, the present invention provides a pharmaceutical composition comprising a therapeutically effective amount of a compound of formula I, or a pharmaceutically acceptable salt, enantiomer, diastereomer, atropisomer, racemate, polymorph, solvate, or isotopically labeled compound thereof as described above, and a pharmaceutically acceptable carrier.

In another aspect, the present invention provides a method of treating or preventing a disease or disorder or condition that is improved by inhibiting BET. The method includes administering to a subject a therapeutically effective amount of the compound of formula I, or a pharmaceutically acceptable salt, enantiomer, diastereomer, atropisomer, racemate, polymorph, solvate, or isotopically labeled compound thereof, alone or in combination with a pharmaceutically acceptable carrier.

In another aspect, the present invention provides use of the compound of formula I, or a pharmaceutically acceptable salt, enantiomer, diastereomer, atropisomer, racemate, polymorph, solvate, or isotopically labeled compound thereof or the pharmaceutical composition in preparation of a medicament for treating a disease or disorder or condition in a subject.

Some methods or uses involve the treatment or prevention of an inflammatory disease or a cancer or acquired immunodeficiency syndrome (AIDS).

In another aspect, the method or use relates to a cancer selected from the group consisting of acoustic neuroma, acute leukemia, acute lymphocytic leukemia, acute myeloid leukemia (monocytic, myeloblastic, adenocarcinoma, angiosarcoma, astrocytoma, myelomonocytic and promyelocytic), acute t-cell leukemia, basal cell carcinoma, cholangiocarcinoma, bladder cancer, brain cancer, breast cancer, bronchial cancer, cervical cancer, chondrosarcoma, chordoma, choriocarcinoma, chronic leukemia, chronic lymphocytic leukemia, chronic myeloid (granulocytic) leukemia, chronic myelogenous leukemia, colon cancer, colorectal cancer, craniopharyngioma, cystadenocarcinoma, diffuse large B-cell lymphoma, adverse proliferative changes (dysplasia and metaplasia), embryonic cancer, endometrial cancer, endothelial sarcoma, ependymoma, epithelial cancer, erythroleukemia, esophageal cancer, estrogen receptor positive breast cancer, primary thrombocythemia, Ewing's sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, leukemia, liposarcoma, lung cancer, lymphatic endothelial sarcoma, lymphangiosarcoma, lymphoblastic leukemia, (Hodgkin's and Non-Hodgkin's) lymphoma, malignant tumors and hyperproliferative disorders of bladder, breast, colon, lung, ovary, pancreas, prostate, skin and uterus, T-cell or B-cell derived lymphoma, leukemia, lymphoma, medullary carcinoma, medulloblastoma, melanoma, meningioma, mesothelioma, multiple myeloma, myeloid leukemia, myeloma, myxosarcoma, neuroblastoma, NUT midline carcinoma (NMC), non-small cell lung cancer, oligodendroglioma, oral cancer, osteogenicsarcoma, ovarian cancer, pancreatic cancer, papillary adenocarcinoma, papillary carcinoma, pinealoma, polycythemia vera, prostate cancer, rectal cancer, renal cell carcinoma, retinoblastoma, rhabdomyosarcoma, sarcoma, sebaceous carcinoma, seminoma, skin cancer, small cell lung cancer, solid tumors (carcinoma and sarcoma), small cell lung cancer, gastric cancer, squamous cell carcinoma, synovial tumor, sweat adenoma, thyroid cancer, primary macroglobulinemia, testicular tumor, uterine cancer, and nephroblastoma. In certain embodiments, the method or use further comprises administering or adding a therapeutically effective amount of at least one additional therapeutic agent. In certain embodiments, the additional therapeutic agent is an anticancer agent. In a particular embodiment, the additional therapeutic agent is selected from cytarabine, bortezomib and 5-azacytidine.

In another aspect, the disease or disorder or condition is selected from the group consisting of Addison's disease, acute gout, ankylosing spondylitis, asthma, atherosclerosis, Behcet's disease, bullous skin disease, chronic obstructive pulmonary disease, Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, organs transplant rejection, osteoarthritis, pancreatitis, pericarditis, polyarteritis nodosa, localized pneumonia, primary biliary cirrhosis, psoriasis, psoriatic arthritis, rheumatoid arthritis, scleritis, sclerosing cholangitis, sepsis, systemic lupus erythematosus, Gauer's arteritis, toxic shock, thyroiditis, type I diabetes, ulcerative colitis, uveitis, vitiligo, vasculitis, and Wegener's Granuloma. In certain embodiments, the method or use further comprises administering or adding a therapeutically effective amount of at least one additional therapeutic agent.

In another aspect, the disease or disorder or condition is selected from the group consisting of diabetic nephropathy, hypertensive nephropathy, HIV-related nephropathy, glomerulonephritis, lupus nephritis, IgA nephropathy, focal stage glomerulosclerosis, membranous glomerulonephritis, minimal change disease, polycystic kidney disease, and tubulointerstitial nephritis. In certain embodiments, the method or use further comprises administering or adding a therapeutically effective amount of at least one additional therapeutic agent.

In another aspect, the disease or disorder or condition is acute kidney injury or a related condition, wherein the acute kidney injury or the related condition is selected from the group consisting of acute kidney injury or related conditions induced by ischemia-reperfusion, cardiotonics and major surgical procedures, percutaneous coronary intervention, radiocontrast agents, sepsis, pneumonia, or drug poisoning. In certain embodiments, the method further comprises administering or adding a therapeutically effective amount of at least one additional therapeutic agent.

In another aspect, the disease or disorder or condition is AIDS. In certain embodiments, the method or use further comprises administering or adding a therapeutically effective amount of at least one additional therapeutic agent.

In another aspect, the disease or disorder or condition is obesity, dyslipidemia, hypercholesterolemia, Alzheimer's disease, metabolic syndrome, fatty liver, type II diabetes, insulin resistance, diabetic retinopathy or diabetic neuropathy. In certain embodiments, the method or use further comprises administering or adding a therapeutically effective amount of at least one additional therapeutic agent.

In another aspect, the invention provides a method of preventing pregnancy comprising administering to a subject in need thereof a therapeutically effective amount of the compound of formula I, or a pharmaceutically acceptable salt, enantiomer, diastereomer, racemate, or isotopically labeled compound thereof. The present invention provides use of the compound of formula I, or a pharmaceutically acceptable salt, enantiomer, diastereomer, atropisomer, racemate, polymorph, solvate, or isotopically labeled compound thereof in preparation of a medicament for preventing pregnancy. In certain embodiments, the method or use further comprises administering or adding a therapeutically effective amount of at least one additional therapeutic agent. The compound of formula I, or a pharmaceutically acceptable salt, enantiomer, diastereomer, atropisomer, racemate, polymorph, solvate, or isotopically labeled compound thereof according to the present invention achieves the object of preventing pregnancy by inhibiting sperm production in an individual.

According to another aspect of the invention, provided is a method for preparing the compound of the invention, wherein the method is as shown in Scheme 1 below.

(eg, a borate) thereof under Suzuki coupling conditions. As shown in scheme I, the compound of formula (A), wherein $R^{101}$ is Br, Cl, I, methanesulfonate or trifluoromethanesulfonate, is coupled with the compound of formula (B), wherein $R^{102}$ is a boronic acid or a derivative (eg, borate) thereof, or the compound of formula (A), wherein $R^{101}$ is a boronic acid or a derivative (eg, borate) thereof, is coupled with the compound of formula (B), wherein $R^{102}$ is Br, Cl, I, methanesulfonate or trifluoromethanesulfonate, to provide the compound of formula I. Generally, the coupling reaction is performed in the presence of a palladium catalyst, a base, and optionally a ligand, in a suitable solvent at an elevated temperature (for example, about 80 to 150° C.). The reaction can be promoted by microwave radiation. Examples of the palladium catalyst include, but are not limited to, tetrakis(triphenylphosphine)palladium(0), tris(dibenzylideneacetone)dipalladium(0), allylpalladium(II) chloride dimer, [1,1'-bis(diphenylphosphino)ferrocene]palladium dichloride ((dppf)PdCl$_2$), palladium(II) acetate. Examples of the suitable base that may be used include, but are not limited to, a carbonate or phosphate of sodium, potassium and cesium, and cesium fluoride. Examples of the suitable ligand include, but are not limited to 2-dicyclohexylphosphino-2,4,6-tri-i-propyl-biphenyl (X-Phos), 1,3,5,7-tetramethyl-6-phenyl-2,4,8-trioxa-6-phosphoryl-adamantane, sodium 2'-dicyclohexylphosphino-2,6-dimethoxy-1,1'-biphenyl-3-sulfonate hydrate and 1,1'-bis(diphenylphosphino)ferrocene. Non-limiting examples of the suitable solvent include methanol, acetonitrile, dimethoxyethane, N,N-dimethylformamide, dimethyl sulfoxide, dioxane, tetrahydrofuran, ethylene glycol dimethyl ether, toluene and water, or the mixture thereof.

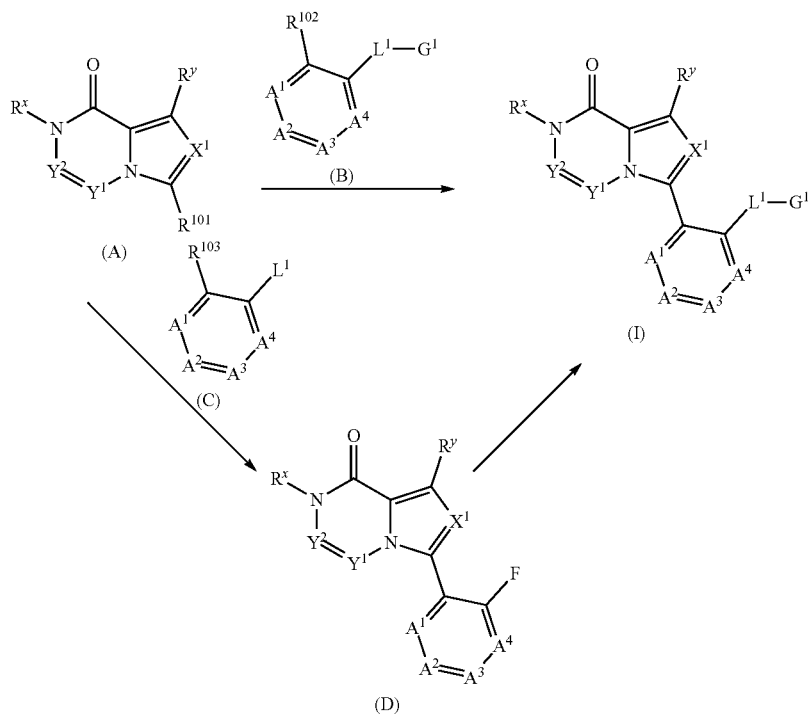

Scheme 1

The compound of formula I may be prepared by the general procedure described in Scheme 1, that is, an aryl halide, aryl methanesulfonate or aryl trifluoromethanesulfonate is treated with an arylboronic acid or a derivative Alternatively, the compound of formula (C), wherein $R^{103}$ is boronic acid or a derivative (eg, borate) thereof, is coupled with the compound of formula (A), wherein $R^{101}$ is Br, Cl, I, methanesulfonate or trifluoromethanesulfonate, to prepare a compound of formula D, then the fluorine atom in formula (D) is replaced with a suitable alcohol, amine or thiol of formula $G^1$-$L^1$-H, wherein L is O, NH or S, to provide a compound of formula I. The replacement of fluorine with an alcohol, amine or thiol can be performed in a solvent in the presence of a base at a temperature of about 30 to 140° C., the solvent is, for example, but not limited to, dimethyl sulfoxide, dimethyl formamide, dioxane or tetrahydrofuran. The base is, for example, but not limited to, cesium carbonate, potassium carbonate, or sodium hydride.

The compound of formula (A), wherein ===== is a double bond, $R^x$ is hydrogen, $Y^1$ is $CR^{y1}$, and $Y^2$ is CH, may be prepared by a general synthetic method shown in Scheme 2.

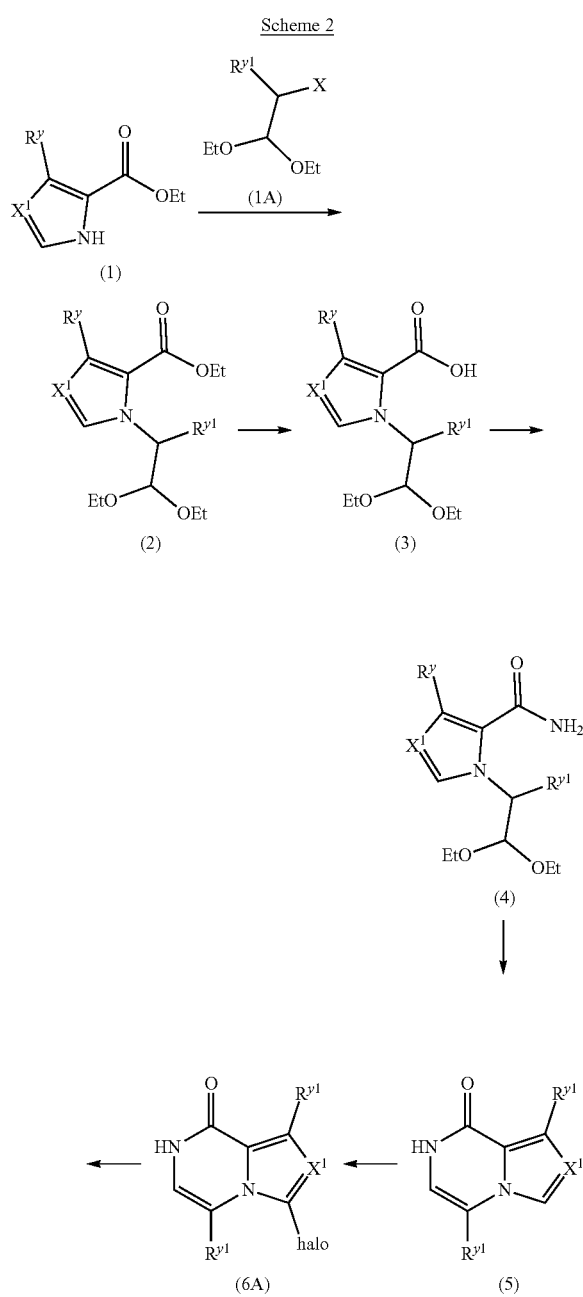

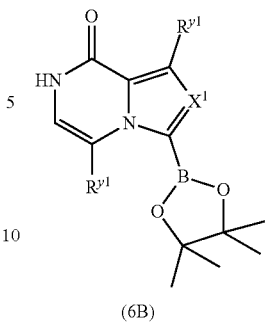

The compound of formula (1) is treated by the compound of formula (1A), wherein X is halogen or OMs, to give a N-substituted compound of formula (2), the solvent is, for example, but not limited to, N-methylpyrrolidone, DMF or acetonitrile, the reaction temperature is about 60 to 150° C., the base used is, for example, but not limited to, sodium hydride, sodium hydroxide or potassium t-butoxide. The ester group is then hydrolyzed under a basic condition to give a carboxylic acid of formula (3), wherein the used base is, for example, but not limited to, lithium hydroxide, potassium hydroxide or sodium hydroxide. A condensation reaction is performed with $NH_3$ or ammonium chloride in the presence of a condensing agent to give an amide (4), wherein the condensing agent is selected from the group consisting of, for example, but not limited to, carbonyldiimidazole, dicyclohexylcarbodiimide, diisopropylcarbodiimide, 1-(-3-dimethylaminopropyl)-3-ethylcarbodiimide, 1-hydroxybenzotriazole, 2-(7-azobenzotriazole)-N,N,N',N'-tetramethyluronium hexafluorophosphate, benzotriazole-N, N,N',N'-tetramethyluronium hexafluorophosphate, 6-chlorobenzotriazole-1,1,3,3-tetramethyluronium hexafluorophosphate, o-benzotriazole-N,N,N',N'-tetramethyluronium tetrafluoroborate, 6-chlorobenzotriazole-1,1,3,3-tetramethyluronium tetrafluoroborate, 2-succinimidyl-1,1,3,3-tetramethyluronium tetrafluoroborate and 2-(5-norbornene-2,3-dicarboximido)-1,1,3,3-tetramethyluronium tetrafluoroborate, the condensation reaction may be performed in an organic solvent in the presence of a base, the base is, for example, but not limited to, triethylamine, diisopropylethylamine or 1,5-diazabicyclo[5.4.0]undec-5-ene, the organic solvent is, for example, but not limited to, dichloromethane, chloroform, N,N-dimethylformamide or tetrahydrofuran. Then, a cyclization reaction is performed through acid treatment at a reaction temperature of about 100 to 130° C., to give the compound of formula (5), wherein the used acid is, for example, but not limited to, glacial acetic acid and hydrochloric acid. Finally, a halogenation is performed through treatment with a halogenating agent to give a halide (6A), wherein the used halogenating agent is, for example, but not limited to, N-bromosuccinimide (NBS), N-iodosuccinimide (NIS), bromine or iodine. Alternatively, the halide (6A) may be further coupled with bis(pinacolato)diboron under palladium catalysts to give a borate (6B).

The compound of formula (A), wherein ===== is a single bond, $R^x$ is hydrogen, $Y^1$ is $CR^{y1}R^{y2}$, and $Y^2$ is $CR^{y3}R^{y4}$ may be prepared by the general synthetic method shown in Scheme 3.

Scheme 3

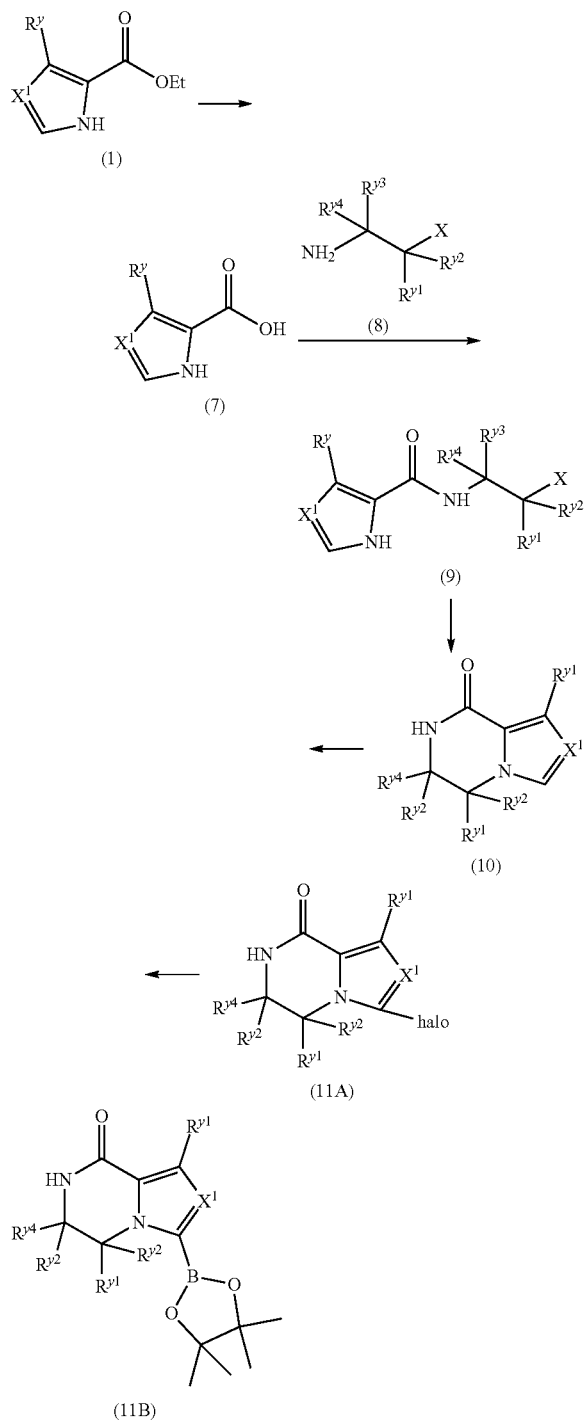

The ester group of formula (1) is hydrolyzed under a basic condition to give the carboxylic acid of formula (7), wherein the used base is, for example, but not limited to, lithium hydroxide, potassium hydroxide or sodium hydroxide. The carboxylic acid is condensated with an amine of formula (8) (in the formula (8), X is halogen or OMs) in the present of a condensing agent to give an amide (9), the condensing agent is selected from the group consisting of, for example, but not limited to, carbonyldiimidazole, dicyclohexylcarbodiimide, diisopropylcarbodiimide, 1-(-3-dimethylaminopropyl)-3-ethylcarbodiimide, 1-hydroxybenzotriazole, 2-(7-azobenzotriazole)-N,N,N',N'-tetramethyluronium hexafluorophosphate, benzotriazole-N,N,N',N'-tetramethyluronium hexafluorophosphate, 6-chlorobenzotriazole-1,1,3,3-tetramethyluronium hexafluorophosphate, o-benzotriazole-N,N,N',N'-tetramethyluronium tetrafluoroborate, 6-chlorobenzotriazole-1,1,3,3-tetramethyluronium tetrafluoroborate, 2-succinimidyl-1,1,3,3-tetramethyluronium tetrafluoroborate and 2-(5-norbornene-2,3-dicarboximido)-1,1,3,3-tetramethyluronium tetrafluoroborate, the condensation may be performed in an organic solvent in the presence of a base, the base includes, for example, but not limited to, triethylamine, diisopropylethylamine and 1,5-diazabicyclo [5.4.0]undec-5-ene, the organic solvent is, for example, but not limited to, dichloromethane, chloroform, N,N-dimethylformamide or tetrahydrofuran. Then, cyclization is performed under a basic condition to give a compound of formula (10), wherein the used base is, for example, but not limited to, triethylamine or diisopropylethylamine. Finally, halogenation is performed by treating with a halogenating agent to give a compound of formula (11A), wherein the used halogenating agent is, for example, but not limited to, N-bromosuccinimide (NBS), N-iodosuccinimide (NIS), bromine or iodine. Alternatively, the halide (11A) may be further coupled with bis(pinacolato)diboron under palladium catalysis to give a borate (11B).

The compound of formula (A), wherein ------ is a double bond, $R^x$ is hydrogen, $Y^2$ is CH, and $Y^1$ is N, may be prepared by a general synthetic method shown in Scheme 4.

Scheme 4

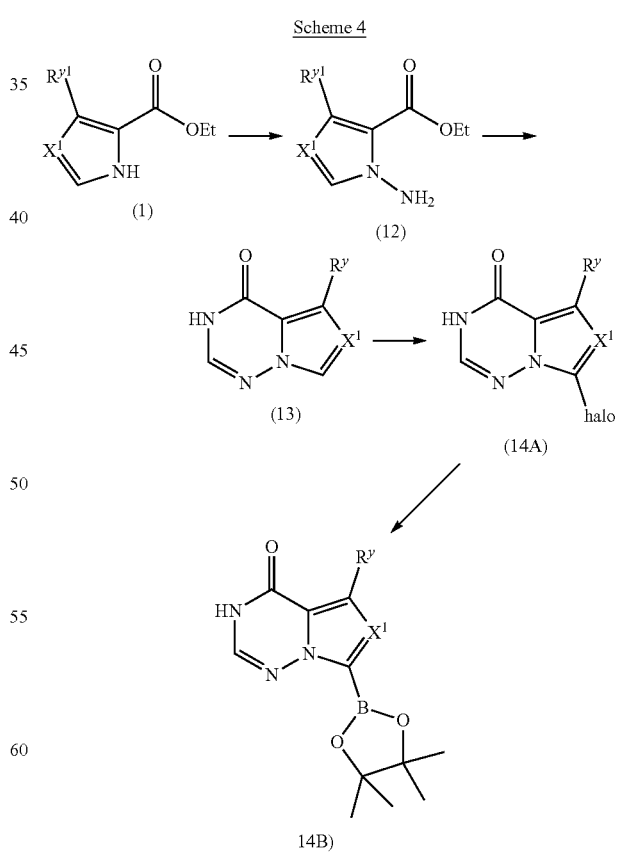

The compound of formula (1) is treated with a base, and reacted with diphenylphosphorylhydroxylamine (CAS:

72804-96-7) to give the compound of formula (12), wherein the used base is, for example, but not limited to, lithium bis(trimethylsilyl)amide (LHMDS), sodium bis(trimethylsilyl)amide (NaHMDS) or lithium diisopropylamide (LDA), the reaction temperature is about −78 to 10° C. The compound of formula (12) is then reacted with formamide at a high temperature of about 100 to 200° C. to give a cyclized product (13). Finally, halogenation is performed by treating with a halogenating reagent to give the compound (14A), wherein the used halogenating reagent is, for example, but not limited to, N-bromosuccinimide (NBS), N-iodosuccinimide (NIS), bromine or iodine. Alternatively, the halide (14A) may be further coupled with bis(pinacolato)diboron under palladium catalysis to give a borate (14B).

The compound of formula (A), wherein ===== is a double bond, $R^x$ is hydrogen, $Y^2$ is N, and $Y^1$ is $CR^{y1}$, may be prepared by a general synthetic method shown in Scheme 5.

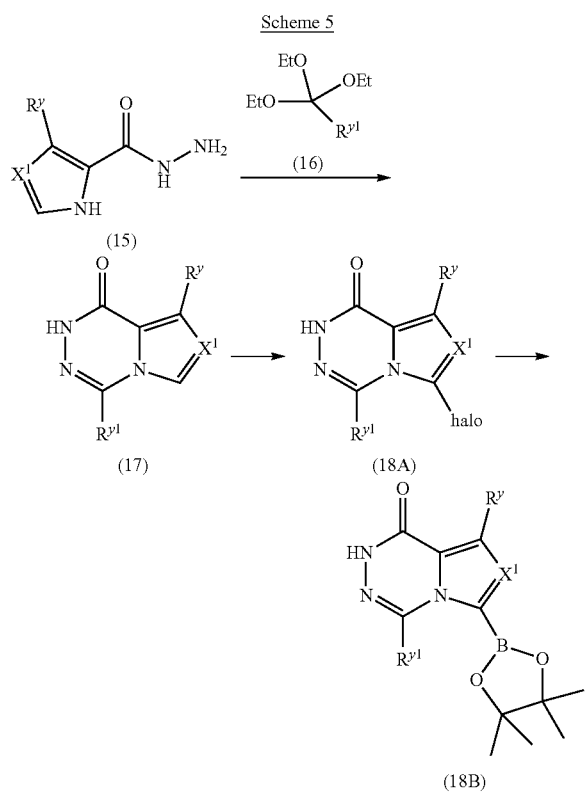

The hydrazide of Formula (15), which may be prepared by reacting the compound of formula (1) with hydrazine hydrate, is directly cyclized with the compound of formula (16) at an elevated temperature to give the product (17), or (15) is first reacted with (16) to give a precursor for cyclization, which is then cyclized under a basic condition to give the cyclized product (17), wherein the reaction temperature is about 50 to 150° C. Then, halogenation is performed by treating with a halogenating agent to give the compound of formula (18A), wherein the used halogenating agent is, for example, but not limited to, N-bromosuccinimide (NBS), N-iodosuccinimide (NIS), bromine or iodine. Alternatively, the halide (18A) may be further coupled with bis(pinacolato)diboron under palladium catalysis to give a borate (18B).

The compound of formula (A), wherein $R^x$ is $C_1$-$C_3$ alkyl or $C_1$-$C_3$ haloalkyl, may be prepared by the general synthetic method shown in Scheme 6.

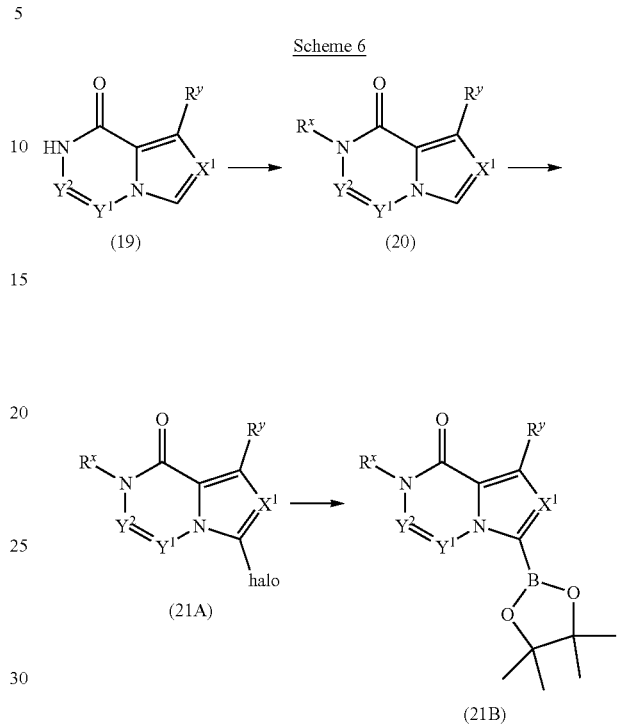

The compound of formula (19) is alkylated with a halide or methanesulfonate in the present of a base to give the product of formula (20), wherein the base is, for example, but not limited to, sodium hydride, cesium carbonate or potassium carbonate, the alkylation reaction may be conducted in an organic solvent, wherein the solvent is, for example, but not limited to, dimethylformamide or dimethylsulfoxide. The compound (20) is then treated with a halogenating reagent to conduct a halogenation reaction to give the compound (21A), wherein the used halogenating agent is, for example, but not limited to, N-bromosuccinimide (NBS), N-iodosuccinimide (NIS), bromine or iodine. Alternatively, the halide (21A) may be further coupled with bis(pinacolato)diboron under palladium catalysis to give a borate (21B).

When $R^{102}$ in the compound of formula (B) is a borate, the synthesis may be performed by the general synthetic method shown in Scheme 7.

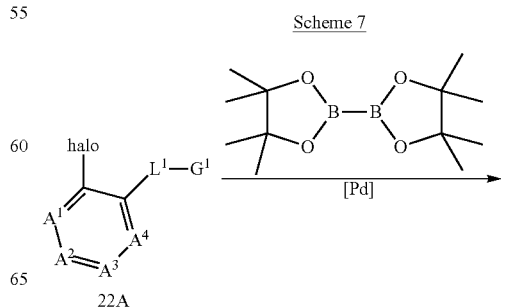

-continued

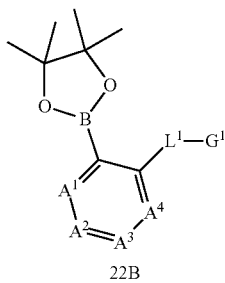

22B

The halide (22A) may be coupled with bis(pinacolato) diboron under palladium catalysis to give a borate (22B). Among others, the halide (22A) are commercially available or prepared according to a conventional method known in the art (for example, reference is made to *J Med. Chem.*, 2017, 60, 8369; WO 2015058160; US 2014275026). The coupling reaction is performed in the presence of a palladium catalyst, a base, and optionally, a ligand, in a suitable solvent at an elevated temperature (for example, about 80 to 150° C.). Examples of the palladium catalysts include, but are not limited to, tetrakis(triphenylphosphine)palladium (0), tris(dibenzylideneacetone)dipalladium (0), allylpalladium (II) chloride dimer, [1,1'-bis(diphenylphosphino)ferrocene]palladium dichloride ((dppf)PdCl$_2$), palladium (II) acetate. Examples of the suitable base that may be used include, but are not limited to, carbonate, phosphate or acetate of sodium, potassium and cesium, and cesium fluoride. Examples of the suitable ligand include, but are not limited to, 2-dicyclohexylphosphino-2,4,6-tri-i-propyl-biphenyl (X-Phos), 1,3,5,7-tetramethyl-6-phenyl-2,4,8-trioxa-6-phosphoryl-adamantane, sodium 2'-dicyclohexylphosphino-2,6-dimethoxy-1,1'-biphenyl-3-sulfonate hydrate and 1,1'-bis(diphenylphosphino)ferrocene. Non-limiting examples of the suitable solvent include methanol, acetonitrile, dimethoxyethane, N,N-dimethylformamide, dimethyl sulfoxide, dioxane, tetrahydrofuran, ethylene glycol dimethyl ether, toluene and water, or the mixture thereof.

The optimal reaction conditions and reaction time for each individual step can vary according to the specific reactants used and the substituents present in all reactants. Unless otherwise specified, the solvent, the temperature and other reaction conditions can be easily selected by those skilled in the art. Specific steps are provided in Synthetic Examples. The reaction can be further processed in a conventional manner, for example by removing the solvent from the residue, and further purified by a method generally known in the art, for example, but not limited to, crystallization, distillation, extraction, grinding and chromatography. Unless otherwise stated, the starting materials and reactants are commercially available or may be prepared by those skilled in the art from commercially available materials using a method described in chemical literatures.

Routine tests, including appropriate adjustment of the reaction conditions, the reagents and sequence of the synthetic route, the protection of any chemical functional groups (which may not be compatible with the reaction conditions) and deprotection at an appropriate point in the reaction sequence of the method, are included within the scope of the present invention. Suitable protecting groups and methods for protecting and deprotecting different substituents using such suitable protecting groups are well known to those skilled in the art, and examples thereof may be found in T. Greene and P. Wuts, Protecting Groups in Chemical Synthesis (Third Edition), John Wiley & Sons, NY (1999), which is incorporated herein by reference in its entirety. The synthesis of the compounds of the invention can be achieved by methods similar to those described in the synthetic schemes described above and in the specific examples.

If a starting material is not commercially available, it may be prepared by steps selected from the group consisting of standard organic chemical techniques, techniques similar to the synthesis of known structural analogs, or techniques similar to the above schemes or steps described in Synthetic Examples. When an optically active form of the compound of the present invention is required, it may be obtained by performing one of the steps described herein using an optically active starting material (e.g., prepared by asymmetric induction of an appropriate reaction step), or by resolving a stereoisomer mixture of a compound or intermediate by using a standard procedure (e.g., chromatographic separation, recrystallization or enzymatic resolution).

Similarly, when a pure geometric isomer of the compound of the present invention is required, it may be obtained by performing one of the steps described herein using a pure geometric isomer as a starting material, or by resolving a geometric isomer mixture of a compound or intermediate by using a standard procedure, such as chromatographic separation.

DETAILED DESCRIPTION OF EXEMPLARY EMBODIMENTS

For exemplary purposes, the following examples may be used. The following examples are only used to explain the technical solutions of the present invention, and are not intended to limit the invention.

Example 1: Preparation of Intermediate I-6

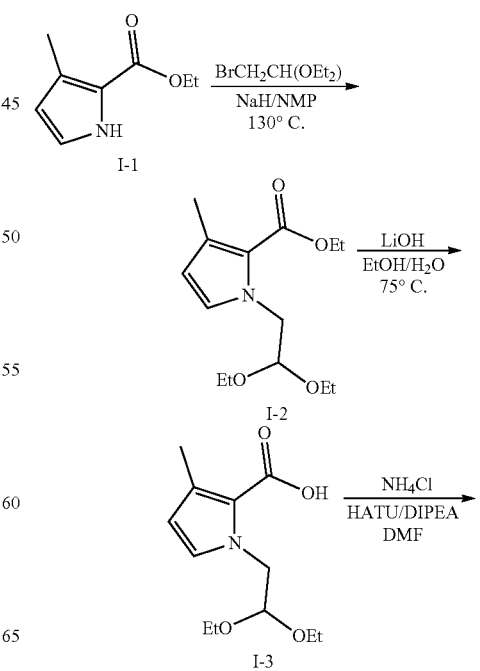

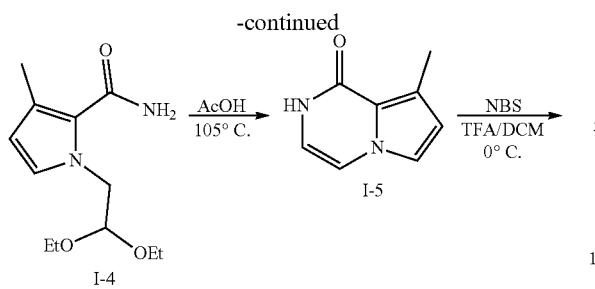

Synthesis of Compound I-2

Ethyl 3-methyl-1H-pyrrole-2-carboxylate (I-1) (2.298 g, 15 mmol) was dissolved in a mixture of 8 mL of N-methylpyrrolidone and 2-bromo-1,1-diethoxyethane (3.843 g, 19.5 mmol), followed by batch addition of 60% sodium hydride (720 mg, 18 mmol) at room temperature. The resulting solution was heated to 130° C. for 5 h under argon, and then cooled to room temperature. The solution was diluted with water, extracted, dried, concentrated, and purified by silica gel chromatography to give compound I-2 (2.7 g) as a white solid. HPLC-MS: [M+H]$^+$=270.1.

Synthesis of Compound I-3

Compound I-2 (2.7 g, 10 mmol) was dissolved in 60 mL of a mixture of ethanol and water at 1:1, added with lithium hydroxide monohydrate (2.402 g, 57 mmol), and heated to 75° C. to react overnight, before cooled to room temperature. The ethanol was rotary evaporated under vacuum. The residue was diluted with water, added with 2M hydrochloric acid solution, and extracted with ethyl acetate. The combined organic layer was dried over anhydrous sodium sulfate, rotary evaporated under vacuum to remove ethyl acetate to give compound I-3 (2.156 g) as a white solid. HPLC-MS: [M−H]$^+$=240.2.

Synthesis of Compound I-4

Compound I-3 (1.674 g, 6.94 mmol), ammonium chloride (928 mg, 17.36 mmol) and 2-(7-azabenzotriazol-1-yl)-N,N,N',N'-tetramethyluronium hexafluorophosphate (HATU) (3.950 g, 10.41 mmol) were mixed and dissolved in 20 mL of anhydrous dimethylformamide (DMF), added with N,N-diisopropylethylamine (DIPEA) (4.6 mL, 27.77 mmol) and stirred overnight. The resultant was diluted with water and extracted with ethyl acetate. The organic layer was washed three times with water, dried over anhydrous sodium sulfate, and purified by silica gel chromatography to give compound I-4 (1.467 g) as a white solid. HPLC-MS: [M+H]$^+$=241.1.

Synthesis of Compound I-5

Compound I-4 (1.678 g, 6.98 mmol) was dissolved in 30 mL of glacial acetic acid, heated to 105° C. for 4 h, rotary evaporated under vacuum to remove most of the glacial acetic acid, diluted with 30 mL of n-hexane, rotary evaporated under vacuum to remove the solvent to give compound I-5 (1.023 g) as a brownish solid. HPLC-MS: [M+H]$^+$=149.1.

Synthesis of Compound I-6

Compound I-5 (1.226 g, 8.27 mmol) and N-bromosuccinimide (NBS) (1.325 g, 7.45 mmol) were dissolved in 24 mL of dichloromethane (DCM), added with 15 mL of trifluoroacetic acid (TFA) at 0° C., stirred for 1 h, rotary evaporated under vacuum to remove dichloromethane and most of trifluoroacetic acid, added with a saturated sodium bicarbonate solution under stirring at 0° C., stirred for 20 minutes to precipitate a solid, which was filtered to give compound I-6 (1.01 g) as a grayish solid. HPLC-MS: [M+H]$^+$=227.1/229.1. $^1$H NMR (400 MHz, DMSO-d$_6$) δ 10.43 (s, 1H), 7.01 (d, J=5.9 Hz, 1H), 6.60 (d, J=5.9 Hz, 1H), 6.52 (s, 1H), 2.43 (s, 3H).

Example 2: Preparation of Intermediate II-5

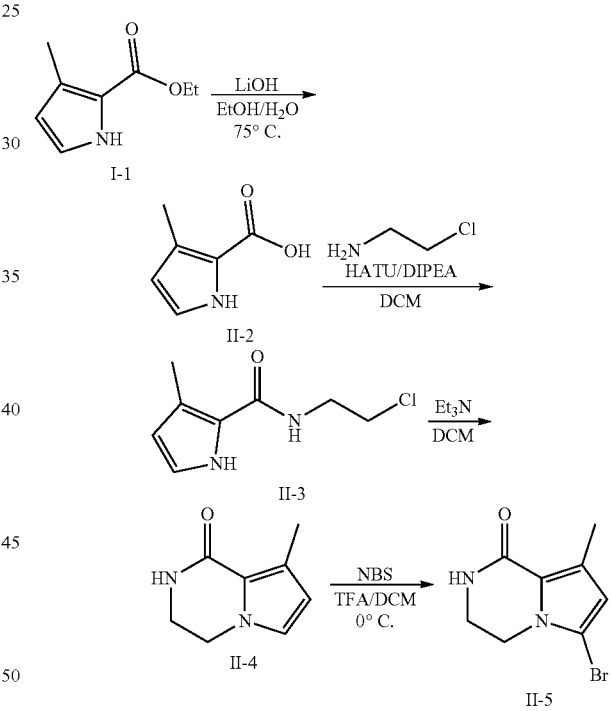

Synthesis of Compound II-2

Compound I-1 (1.6 g, 10 mmol) was dissolved in 60 mL of a mixture of ethanol and water at 1:1, added with lithium hydroxide monohydrate (2.402 g, 57 mmol), heated to 75° C. overnight, before cooled to room temperature. The ethanol was rotary evaporated under vacuum. The residue was diluted with water, added with 2M hydrochloric acid solution, and extracted with ethyl acetate. The combined organic layer was dried over anhydrous sodium sulfate, rotary evaporated under vacuum to remove ethyl acetate to give compound II-2 (1.562 g) as a colorless oil. HPLC-MS: [M−H]$^+$=124.1.

Synthesis of Compound II-3

Compound II-2 (1.562 g, 12.5 mmol), 2-chloroethylamine hydrochloride (1.882 g, 16.2 mmol) and HATU (6.170 g, 16.2 mmol) were dissolved in 50 mL of dichloromethane, added with 5.2 mL of DIPEA, reacted at room temperature for 2 h, added with 100 mL of saturated aqueous sodium bicarbonate solution, extracted with dichloromethane, and purified by silica gel column chromatography to give compound II-3 (1.852 g) as a yellowish oil. HPLC-MS: [M+H]$^+$=187.2.

Synthesis of Compound II-4

Compound II-3 (1.852 g, 9.9 mmol) was dissolved in 30 mL of dichloromethane, added with 4.2 mL of triethylamine, stirred overnight, rotary evaporated under vacuum to remove the solvent, and purified by silica gel column chromatography to give compound II-4 (758 mg) as a white solid. HPLC-MS: [M+H]$^+$=151.1.

Synthesis of Compound II-5

Compound II-4 (1.24 g, 8.27 mmol) and NBS (1.325 g, 7.45 mmol) were dissolved in 24 mL of dichloromethane, added with 15 mL of trifluoroacetic acid at 0° C., stirred for 1 h, rotary evaporated under vacuum to remove dichloromethane and most trifluoroacetic acid, added with a saturated sodium bicarbonate solution under stirring at 0° C., stirred for 20 minutes to precipitate a solid, which was filtered to give compound II-5 (0.22 g). HPLC-MS: [M+H]$^+$=229.1/231.1.

Example 3: Preparation of Intermediate III-4

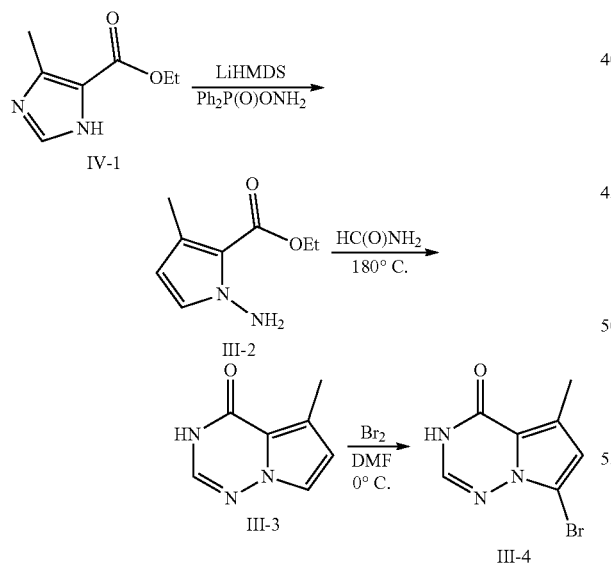

Synthesis of Compound III-2

LiHMDS (2.5 mL, 1M in THF) was slowly dropped into a solution of compound I-1 (309 mg, 2 mmol) in anhydrous DMF (30 mL) at −10° C. After stirred for 10 minutes, the solution was transferred to be under 0° C., added with o-diphenylphosphinylhydroxylamine (0.56 g, 2.4 mmol), and stirred for 5 h. After completion of the reaction, water was added to quench until a clear solution was formed. The solvent was rotary evaporated under vacuum.

The residue was purified by silica gel column chromatography to give compound III-2 (220 mg) as a white solid. HPLC-MS: [M+H]$^+$=169.2.

Synthesis of Compound III-3

Compound III-2 (295 mg, 1.7 mmol) was dissolved in 3 mL of formamide, placed in a sealed tube and heated to 180° C. to react overnight. An off-white solid was precipitated. After cooled to room temperature, the reaction mixture was filtered. The filtered cake was washed with ethyl acetate to give compound III-3 (120 mg) as an off-white solid. HPLC-MS: [M+H]$^+$=150.1.

Synthesis of Compound III-4

Compound III-3 (150 mg, 1 mmol) was dissolved in 6 mL of anhydrous DMF, and added with Br$_2$ (60 μL, 1.2 mmol) at 0° C. The reaction was monitored by TLC. After completion of the reaction, a saturated sodium bicarbonate aqueous solution was added to quench the reaction. The solvent was rotary evaporated under vacuum. The residue was purified by silica gel column chromatography to give compound III-4 (68 mg) as an off-white solid. HPLC-MS: [M+H]$^+$=228.1/230.1. $^1$H NMR (400 MHz, DMSO-d$_6$) δ 11.61 (s, 1H), 7.83 (s, 1H), 6.54 (s, 1H), 2.40 (s, 3H).

Example 4: Preparation of Intermediate IV-4

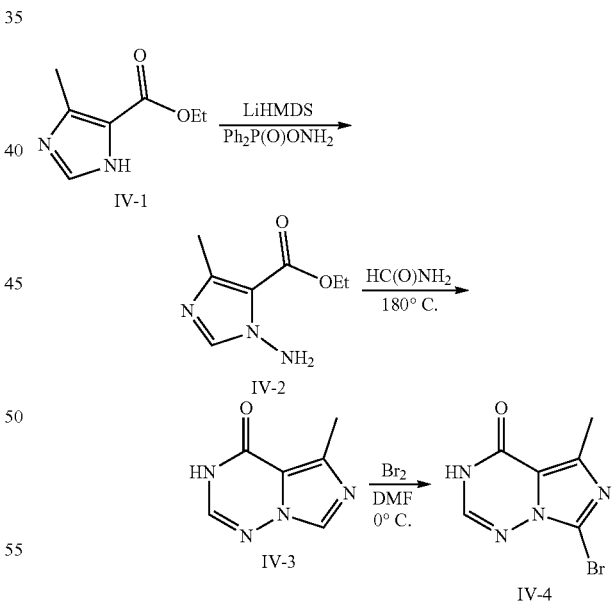

Synthesis of Compound IV-2

LiHMDS (5.5 mL, 1M in THF) was slowly dropped into a solution of compound IV-1 (771 mg, 5 mmol) in anhydrous DMF (50 mL) at −10° C. After stirred for 10 minutes, the solution was transferred to be under 0° C., added with o-(diphenylphosphinyl)hydroxylamine (1.411 g, 6 mmol), and stirred for 5 h. After completion of the reaction, water was added to quench the reaction until a clear solution was formed. The solvent was rotary evaporated under vacuum. The residue was purified by silica gel column chromatography to give compound IV-2 (595 mg) as a white solid. HPLC-MS: [M+H]$^+$=170.2.

Synthesis of Compound IV-3

Compound IV-2 (595 mg, 3.52 mmol) was dissolved in 5 mL of formamide, placed in a sealed tube and heated to 180° C. to react overnight. An off-white solid was precipitated. After cooled to room temperature, the reaction mixture was filtered. The filtered cake was washed with ethyl acetate to give compound IV-3 (331 mg) as an off-white solid. HPLC-MS: [M+H]$^+$=151.1. $^1$H NMR (400 MHz, DMSO-d$_6$) δ 11.85 (s, 1H), 7.91 (s, 1H), 2.46 (s, 3H).

Synthesis of Compound IV-4

Compound IV-3 (75 mg, 0.5 mmol) was dissolved in 6 mL of anhydrous DMF, and added with Br$_2$ (50 μL, 1 mmol) at 0° C. The reaction was monitored by TLC. After completion of the reaction, a saturated sodium bicarbonate aqueous solution was added to quench the reaction. The solvent was rotary evaporated under vacuum. The residue was purified by silica gel column chromatography to give compound IV-4 (44 mg) as an off-white solid. $^1$H NMR (400 MHz, DMSO-d$_6$) δ 11.85 (s, 1H), 7.91 (s, 1H), 2.46 (s, 3H). HPLC-MS: [M+H]$^+$=229.1/231.1.

Example 5: Preparation of Intermediate V-5

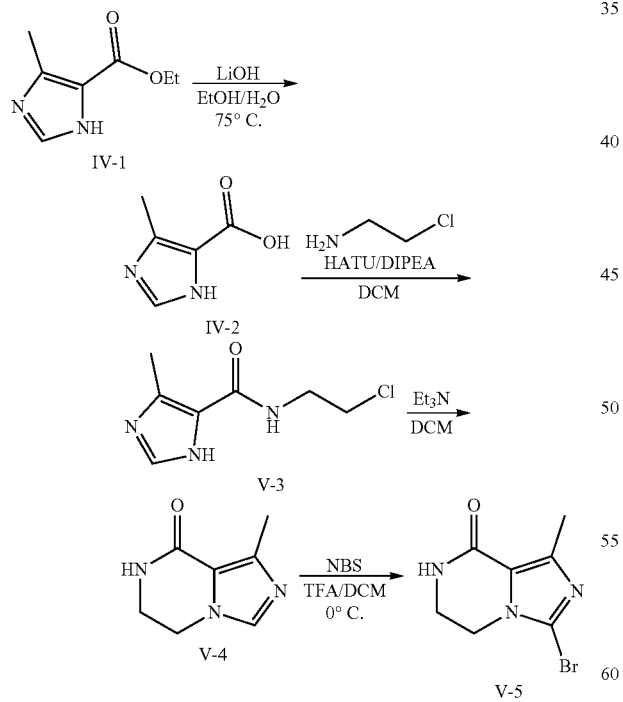

Synthesis of Compound V-2

Compound IV-1 (6.167 g, 40 mmol) was dissolved in 120 mL of a mixture of ethanol and water at 1:1, added with lithium hydroxide monohydrate (3.2 g, 80 mmol), and heated to 75° C. to react overnight, and then cooled to room temperature. The ethanol was rotary evaporated under vacuum. The residue was diluted with water, added with 2M hydrochloric acid solution, extracted with ethyl acetate. The combined organic layer was dried over anhydrous sodium sulfate, rotary evaporated under vacuum to remove ethyl acetate to give compound V-2 (3.86 g) as colorless oil. HPLC-MS: [M−H]$^+$=125.1.

Synthesis of Compound V-3

Compound V-2 (1.262 g, 10 mmol), 2-chloroethylamine hydrochloride (1.74 g, 15 mmol) and HATU (5.70 g, 15 mmol) were dissolved in 75 mL of dichloromethane, added with 8.2 mL of DIPEA, reacted at room temperature for 2 h, added with 100 mL of saturated aqueous sodium bicarbonate solution, extracted with dichloromethane, and purified by silica gel column chromatography to give compound V-3 (0.752 g) as a yellowish oil. HPLC-MS: [M+H]$^+$=188.1.

Synthesis of Compound V-4

Compound V-3 (0.65 g) was dissolved in 20 mL of dichloromethane, added with triethylamine (2.3 g), reacted at room temperature overnight, and purified by silica gel column chromatography to give compound V-4 (380 mg) as a white solid. HPLC-MS: [M+H]$^+$=152.1.

Synthesis of Compound V-5

Compound V-4 (380 mg) and NBS (710 mg) were dissolved in 24 mL of dichloromethane, added with 5 mL of trifluoroacetic acid (TFA) at 0° C., stirred for 1 h, rotary evaporated under vacuum to remove dichloromethane, and purified by silica gel column chromatography to give compound V-5 (180 mg). HPLC-MS: [M+H]$^+$=230.1/232.1.

Example 6: Synthesis of Intermediate VI-5

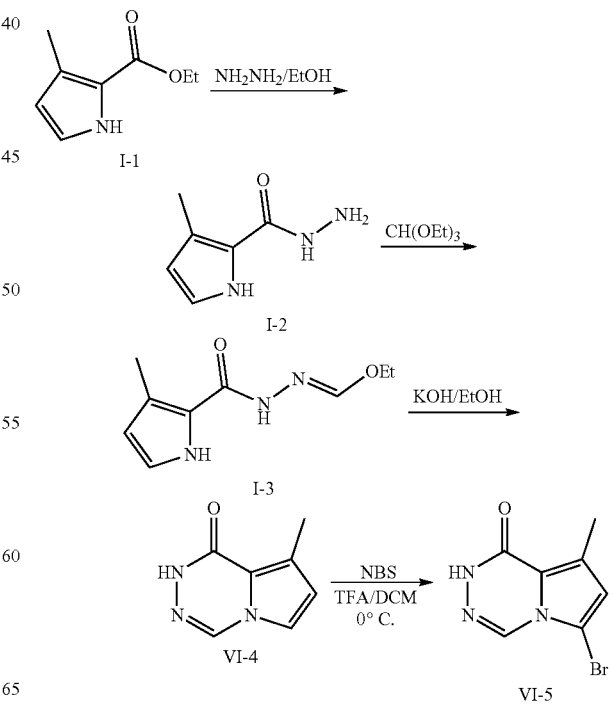

Synthesis of Compound VI-2

Compound I-1 (1.532 g, 10 mmol) was dissolved in 5 mL of ethanol, added with 20 mL of 98% hydrazine hydrate, heated to reflux and stirred for 2 h, cooled to room temperature to precipitate a solid, and filtered to give compound VI-2 (1.204 g). HPLC-MS: [M+H]$^+$=140.1.

Synthesis of Compound VI-3

Compound VI-2 (1.204 g, 8.65 mmol) was dissolved in 10 mL of triethyl orthoformate, heated to reflux and stirred for 1 h, cooled to room temperature to precipitate a solid, and filtered to give compound VI-3 (1.213 g). HPLC-MS: [M+H]$^+$=196.1.

Synthesis of Compound VI-4

Compound VI-3 (1.613 g, 6.21 mmol) was dissolved in 20 mL of absolute ethanol, added with potassium hydroxide (1.390 g, 24.38 mmol), heated to reflux and stirred for 1 h, and purified by silica gel column chromatography to give compound VI-4 (530 mg). HPLC-MS: [M+H]$^+$=150.1.

Synthesis of Compound VI-5

Compound VI-4 (987 mg, 6.62 mmol) and NBS (1.060 g, 5.86 mmol) were dissolved in 24 mL of dichloromethane, added with 15 mL of trifluoroacetic acid at 0° C., stirred for 1 h, rotary evaporated under vacuum to remove dichloromethane and most of trifluoroacetic acid, and purified by silica gel column chromatography to give compound VI-5 (247 mg). $^1$H NMR (400 MHz, DMSO-d$_6$) δ 11.70 (s, 1H), 8.28 (s, 1H), 6.74 (s, 1H), 2.42 (s, 3H). HPLC-MS: [M+H]$^+$= 228.1/230.1.

Example 7: Synthesis of Borate B-1

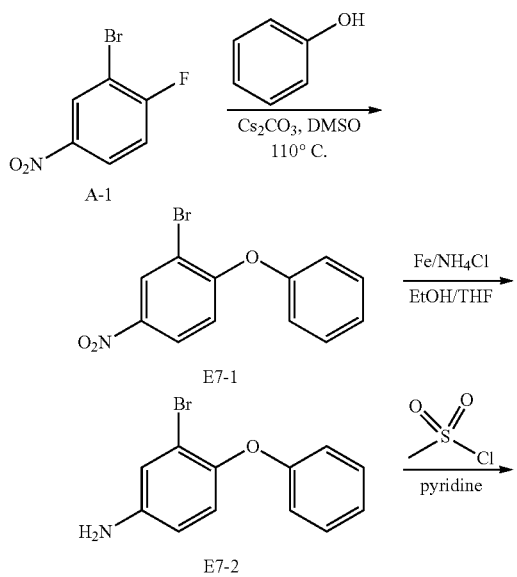

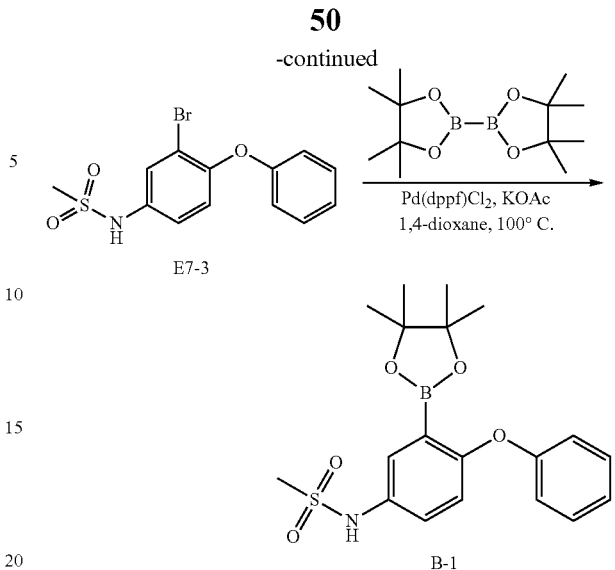

Step 1

3-bromo-4-fluoronitrobenzene (22.0 g, 0.1 mol, CAS: 701-45-1), phenol (11.3 g, 0.12 mol), cesium carbonate (39.1 g, 0.12 mol) were suspended in 100 mL of dimethyl sulfoxide, heated to 110° C. to react for 1 h, cooled to room temperature, filtered to remove the solid, and added with water and ethyl acetate for layering. The organic phase was washed with saturated saline, dried over anhydrous sodium sulfate, and rotary evaporated under vacuum to give intermediate E7-1 (26.4 g).

Step 2

E7-1 (26.4 g) was dissolved in 200 mL of ethanol and 200 mL of tetrahydrofuran, added with 100 mL of water, followed by batch addition of iron powder (27 g) and ammonium chloride (15 g) at room temperature. After completion of the addition, the temperature was slowly raised to 95° C. and the reaction was carried out under stirring for 2 h. The reaction solution was filtered through celite. The filtrate was poured into water, and extracted twice with ethyl acetate. The combined organic phase was washed with saturated saline, dried over anhydrous sodium sulfate, and concentrated to give intermediate E7-2 (22.0 g).

Step 3

E7-2 (13.2 g, 50.0 mmol) was dissolved in 50 mL of pyridine, cooled to 0° C., followed by slow dropwise addition of methylsulfonyl chloride (5.7 g, 50 mmol). After completion of the dropwise addition, the mixture was warmed to room temperature to react for 2 h, added with ice water and ethyl acetate for layering. The organic phase was washed with 2M dilute hydrochloric acid and saturated saline successively, dried over anhydrous sodium sulfate, rotary evaporated under vacuum to remove ethyl acetate, and slurried in petroleum ether to give intermediate E7-3 (12.8 g).

Step 4

E7-3 (12.8 g, 36.0 mmol), potassium acetate (7.1 g, 72.0 mmol), bis(pinacolato)diboron (18.3 g, 72 mmol, CAS: 73183-34-3) were dissolved in 150 mL of dioxane, added with [1,1'-bis(diphenylphosphino)ferrocene]palladium dichloride (1.3 g, 1.8 mmol, CAS: 72287-26-4), heated to 100° C. to react for 14 h, cooled to room temperature and the filtrate was added through celite. The filtrate was added with water and ethyl acetate for layering. The organic layer was washed with saturated saline, dried over anhydrous sodium sulfate, rotary evaporated under vacuum to remove solvent, purified by silica gel column chromatography, and slurried in diethyl ether to give borate B-1 (5.6 g). $^1$H NMR (400 MHz, DMSO-$d_6$) δ 9.63 (s, 1H), 7.51 (d, J=2.8 Hz, 1H), 7.39 (dd, J=8.7, 2.8 Hz, 1H), 7.33-7.24 (m, 2H), 7.00 (dd, J=8.0, 6.2 Hz, 2H), 6.84-6.72 (m, 2H), 2.97 (s, 3H), 1.09 (s, 12H). HPLC-MS: [M−H]$^+$=388.1.

Example 8: Synthesis of Borate B-2

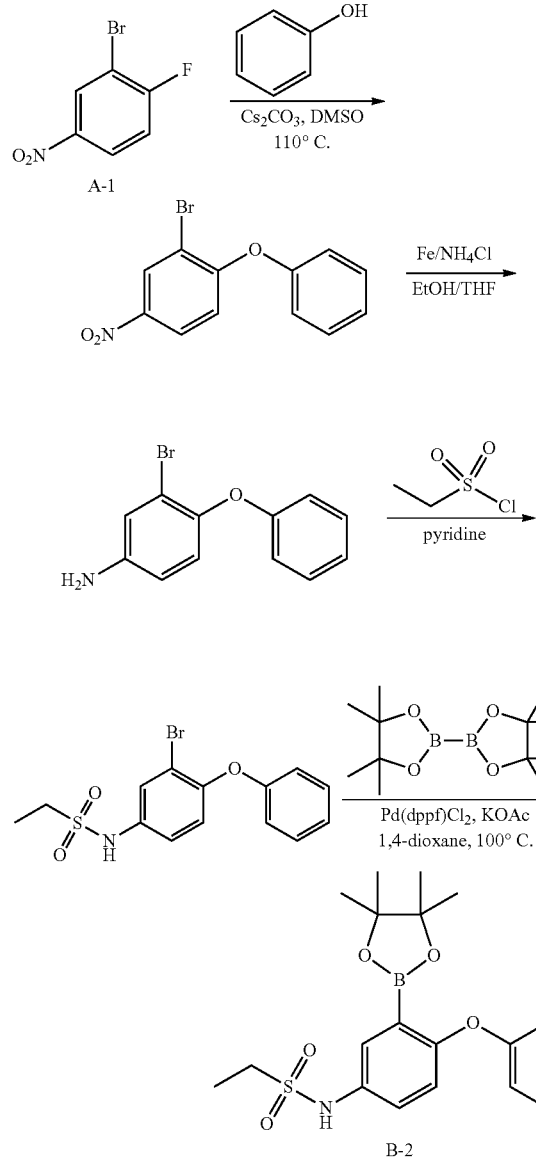

Example 9: Synthesis of Borate B-3

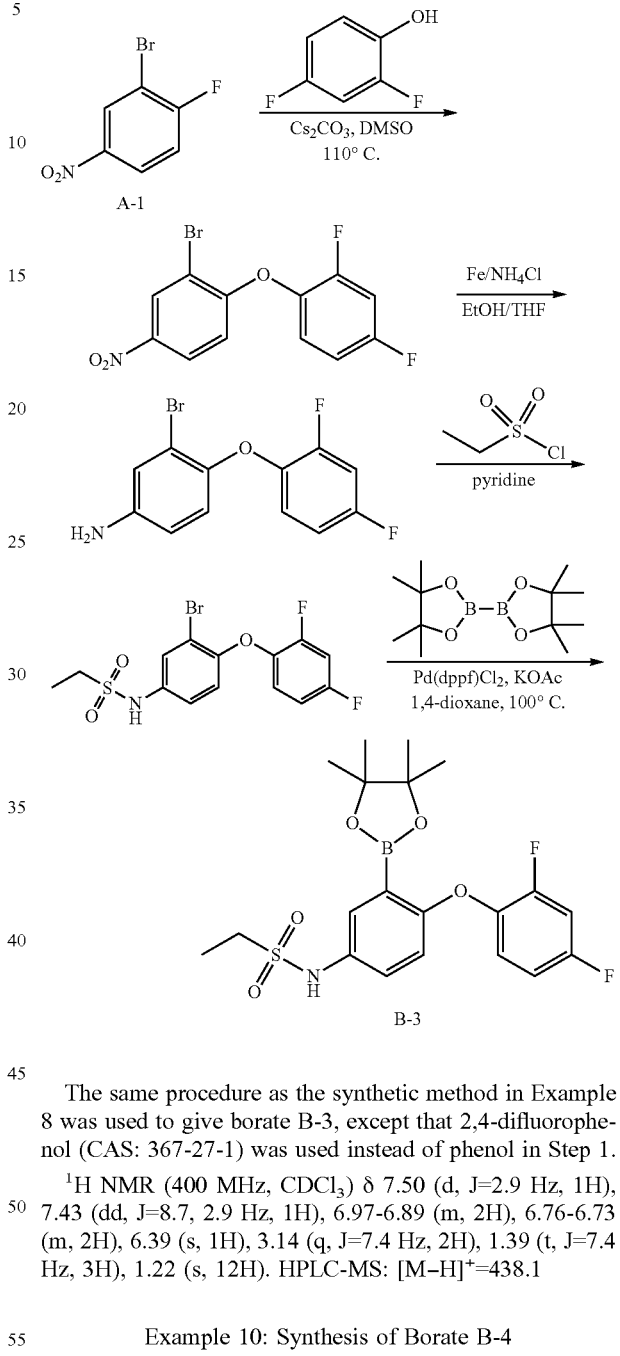

The same procedure as the synthetic method in Example 8 was used to give borate B-3, except that 2,4-difluorophenol (CAS: 367-27-1) was used instead of phenol in Step 1.

$^1$H NMR (400 MHz, CDCl$_3$) δ 7.50 (d, J=2.9 Hz, 1H), 7.43 (dd, J=8.7, 2.9 Hz, 1H), 6.97-6.89 (m, 2H), 6.76-6.73 (m, 2H), 6.39 (s, 1H), 3.14 (q, J=7.4 Hz, 2H), 1.39 (t, J=7.4 Hz, 3H), 1.22 (s, 12H). HPLC-MS: [M−H]$^+$=438.1

Example 10: Synthesis of Borate B-4

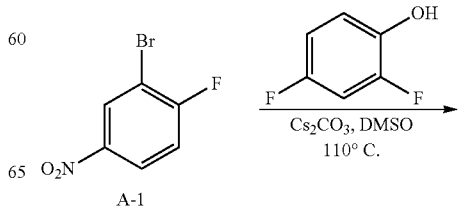

The same procedure as the synthetic method in Example 7 was used to give borate B-2, except that ethylsulfonyl chloride (CAS: 594-44-5) was used instead of methylsulfonyl chloride in Step 3.

$^1$H NMR (400 MHz, CDCl$_3$) δ 7.48 (d, J=2.9 Hz, 1H), 7.41 (dd, J=8.7, 2.9 Hz, 1H), 7.28-7.24 (m, 2H), 7.02-6.97 (m, 2H), 6.87-6.85 (m, 2H), 6.74 (brs, 1H), 3.14 (q, J=7.4 Hz, 2H), 1.40 (t, J=7.4 Hz, 3H), 1.16 (s, 12H). HPLC-MS: [M−H]$^+$=402.2

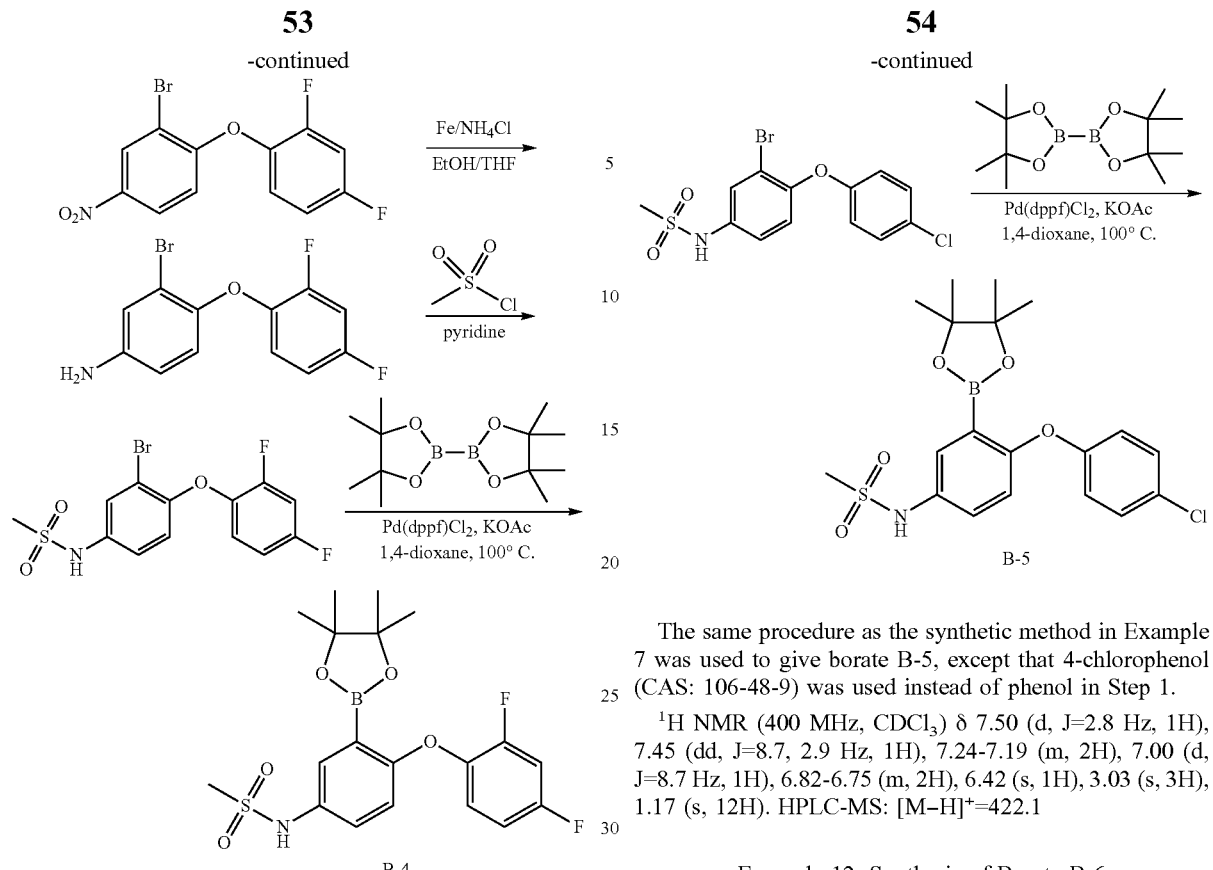

The same procedure as the synthetic method in Example 7 was used to give borate B-4, except that 2,4-difluorophenol (CAS: 367-27-1) was used instead of phenol in Step 1.

$^1$H NMR (400 MHz, CDCl$_3$) δ 7.52 (d, J=2.9 Hz, 1H), 7.41 (dd, J=8.7, 2.9 Hz, 1H), 6.95-6.87 (m, 2H), 6.80-6.71 (m, 2H), 6.53 (s, 1H), 3.00 (s, 3H), 1.23 (s, 12H). HPLC-MS: [M−H]$^+$=424.1

Example 11: Synthesis of Borate B-5

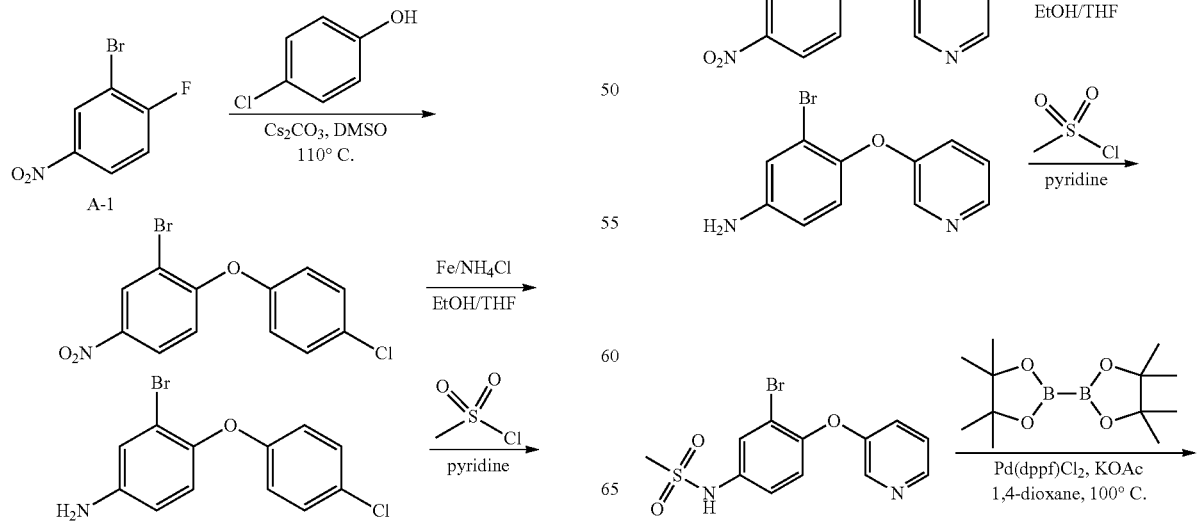

The same procedure as the synthetic method in Example 7 was used to give borate B-5, except that 4-chlorophenol (CAS: 106-48-9) was used instead of phenol in Step 1.

$^1$H NMR (400 MHz, CDCl$_3$) δ 7.50 (d, J=2.8 Hz, 1H), 7.45 (dd, J=8.7, 2.9 Hz, 1H), 7.24-7.19 (m, 2H), 7.00 (d, J=8.7 Hz, 1H), 6.82-6.75 (m, 2H), 6.42 (s, 1H), 3.03 (s, 3H), 1.17 (s, 12H). HPLC-MS: [M−H]$^+$=422.1

Example 12: Synthesis of Borate B-6

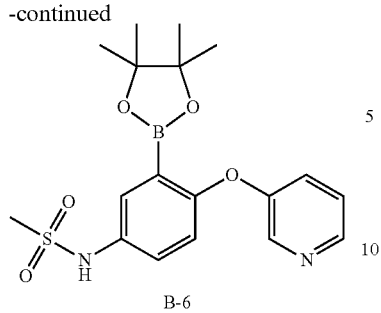

B-6

The same procedure as the synthetic method in Example 7 was used to give borate B-6, except that 3-hydroxypyridine (CAS: 109-00-2) was used instead of phenol in Step 1.

$^1$H NMR (400 MHz, CDCl$_3$) δ 8.30 (d, J=2.6 Hz, 1H), 8.27 (d, J=4.3 Hz, 1H), 7.55 (d, J=2.7 Hz, 1H), 7.49 (dd, J=8.7, 2.9 Hz, 1H), 7.19 (dd, J=8.4, 4.7 Hz, 1H), 7.12-7.07 (m, 1H), 7.06 (d, J=8.7 Hz, 1H), 6.69 (s, 1H), 3.03 (s, 3H), 1.15 (s, 12H). HPLC-MS: [M+H]$^+$=391.2

Example 13: Synthesis of Borate B-7

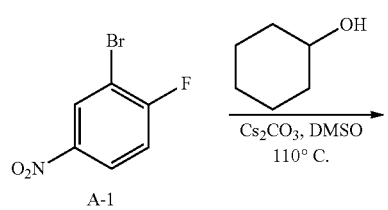

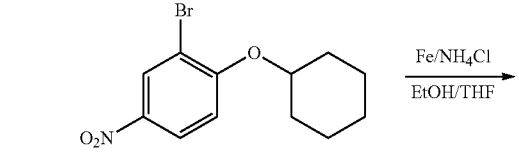

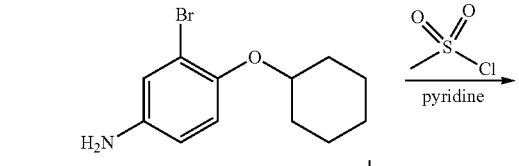

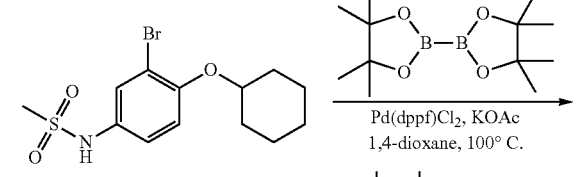

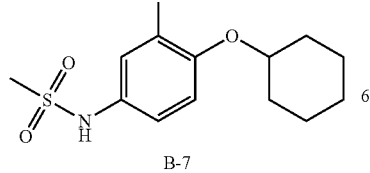

B-7

The same procedure as the synthetic method in Example 7 was used to give borate B-7, except that cyclohexanol (CAS: 108-93-0) was used instead of phenol in Step 1.

$^1$H NMR (400 MHz, CDCl$_3$) δ 7.39-7.35 (m, 2H), 6.90 (d, J=8.6 Hz, 1H), 6.33 (s, 1H), 4.28 (t, J=7.6 Hz, 1H), 2.95 (s, 3H), 1.86 (m, 4H), 1.68 (m, 2H), 1.48 (m, 2H), 1.38 (m, 2H), 1.36 (s, 12H). HPLC-MS: [M−H]$^+$=394.1

Example 14: Synthesis of Borate B-8

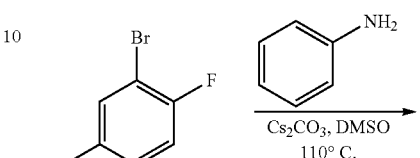

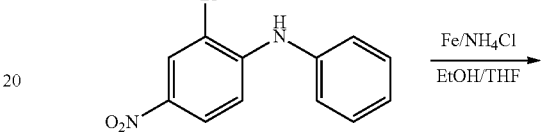

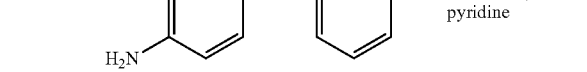

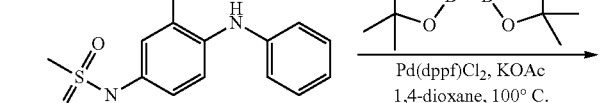

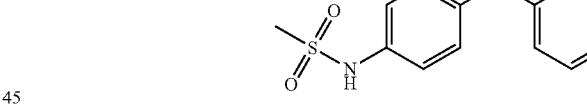

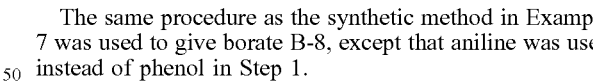

B-8

The same procedure as the synthetic method in Example 7 was used to give borate B-8, except that aniline was used instead of phenol in Step 1.

$^1$H NMR (400 MHz, CDCl$_3$) δ 7.49 (d, J=2.5 Hz, 1H), 7.33 (t, J=7.9 Hz, 2H), 7.28 (dd, J=9.5, 3.2 Hz, 1H), 7.20 (dd, J=9.6, 8.5 Hz, 3H), 7.04 (t, J=7.4 Hz, 1H), 6.08 (s, 1H), 2.97 (s, 3H), 1.36 (s, 12H). HPLC-MS: [M+H]$^+$=389.2

Example 15: Synthesis of Borate B-9

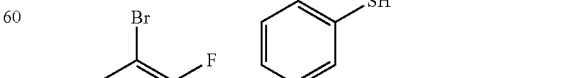

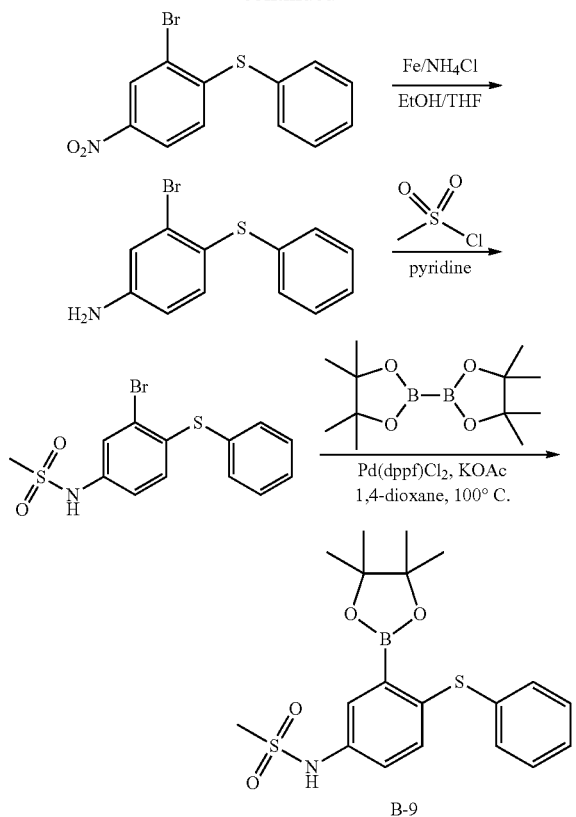

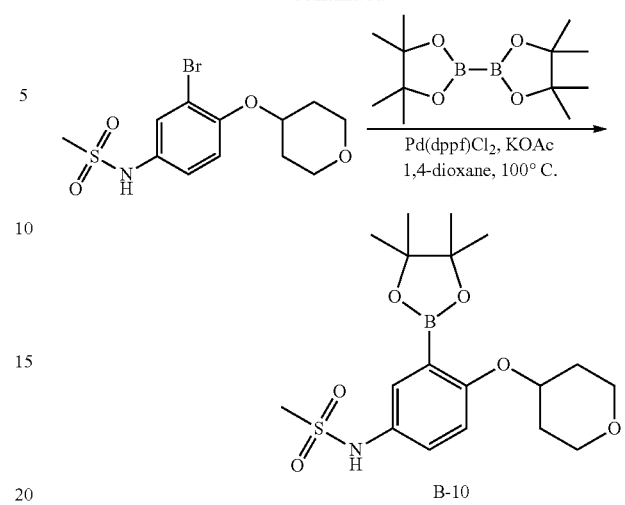

B-10

The same procedure as the synthetic method in Example 7 was used to give borate B-10, except that tetrahydro-2H-pyran-4-ol (CAS: 2081-44-9) was used instead of phenol in Step 1.

$^1$H NMR (400 MHz, CDCl$_3$) δ 7.44 (d, J=2.8 Hz, 1H), 7.40 (dd, J=8.7, 2.9 Hz, 1H), 6.90 (d, J=8.7 Hz, 1H), 6.33 (s, 1H), 4.59-4.52 (m, 1H), 4.10-4.02 (m, 2H), 3.66-3.58 (m, 2H), 2.97 (s, 3H), 2.04-1.95 (m, 2H), 1.89-1.79 (m, 2H), 1.37 (s, 12H). HPLC-MS: [M−H]$^+$=396.2

Example 17: Synthesis of Borate B-11

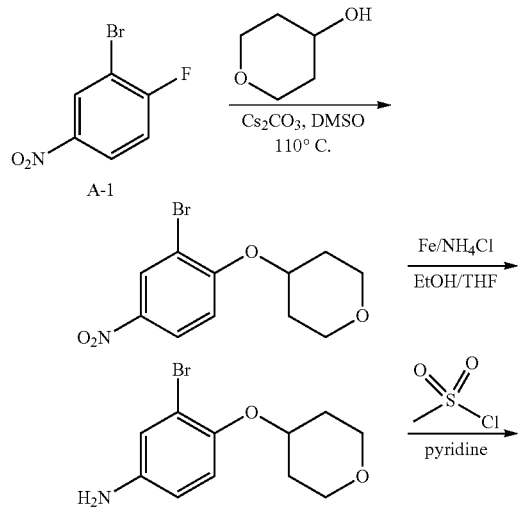

B-9

The same procedure as the synthetic method in Example 7 was used to give borate B-9, except that thiophenol was used instead of phenol in Step 1.

$^1$H NMR (400 MHz, CDCl$_3$) δ 7.41 (d, J=2.6 Hz, 1H), 7.38-7.34 (m, 2H), 7.34-7.29 (m, 2H), 7.28 (m, 1H), 7.24 (m, 1H), 7.07 (d, J=8.5 Hz, 1H), 6.40 (s, 1H), 2.99 (s, 3H), 1.31 (s, 12H). HPLC-MS: [M−H]$^+$=404.2

Example 16: Synthesis of Borate B-10

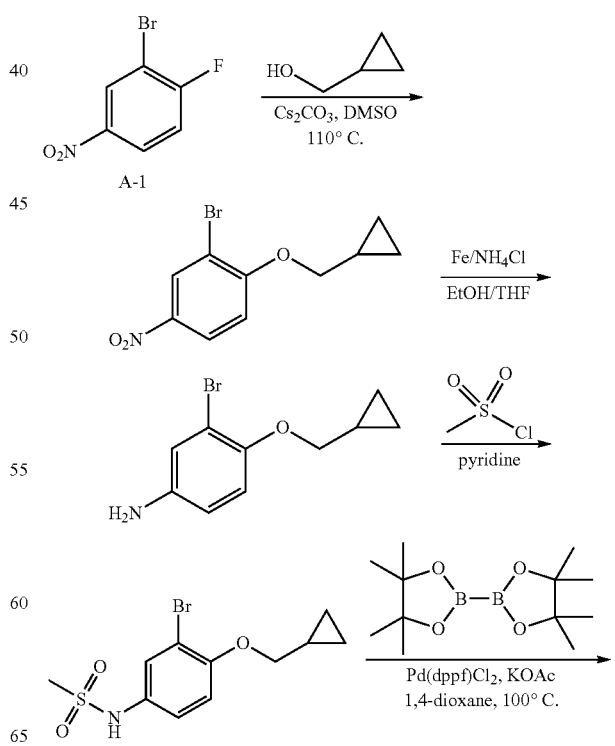

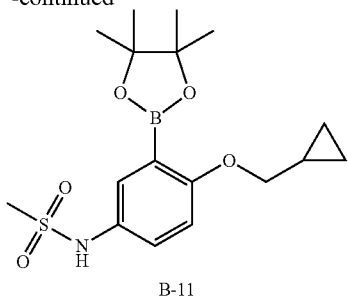

B-11

The same procedure as the synthetic method in Example 7 was used to give borate B-11, except that cyclopropylmethanol (CAS: 2516-33-8) was used instead of phenol in Step 1.

$^1$H NMR (400 MHz, CDCl$_3$) δ 7.41-7.36 (m, 2H), 6.85 (d, J=8.6 Hz, 1H), 6.14 (s, 1H), 3.89 (d, J=6.1 Hz, 2H), 2.95 (s, 3H), 1.38 (s, 12H), 1.30-1.22 (m, 1H), 0.62-0.55 (m, 2H), 0.49-0.42 (m, 2H). HPLC-MS: [M–H]$^+$=366.2

Example 18: Synthesis of Borate B-12

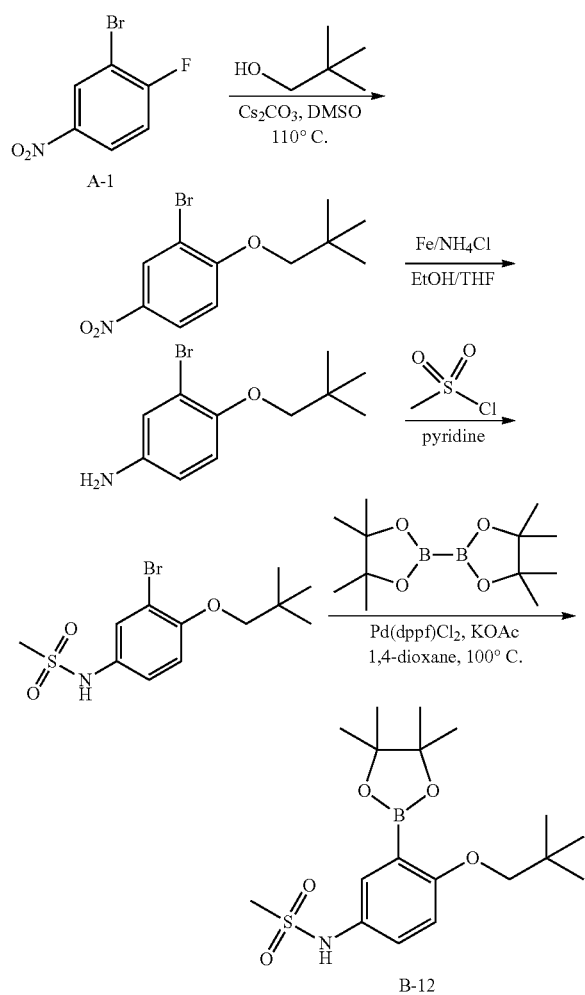

B-12

The same procedure as the synthetic method in Example 7 was used to give borate B-12, except that neopentanol (CAS: 75-84-3) was used instead of phenol in Step 1.

$^1$H NMR (400 MHz, CDCl$_3$) δ 7.40-7.36 (m, 2H), 6.79 (d, J=8.8 Hz, 1H), 6.18 (s, 1H), 3.59 (s, 2H), 2.92 (s, 3H), 1.34 (s, 12H), 1.07 (s, 9H).

Example 19: Synthesis of Borate B-13

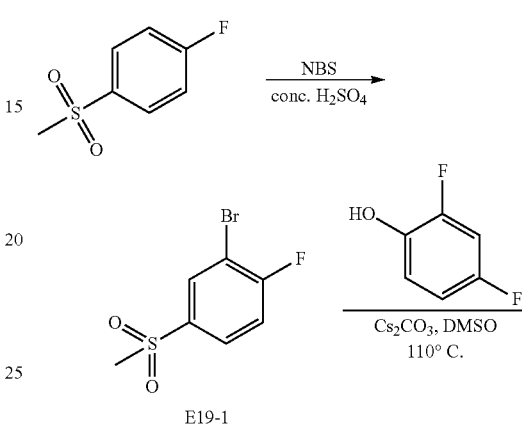

E19-1

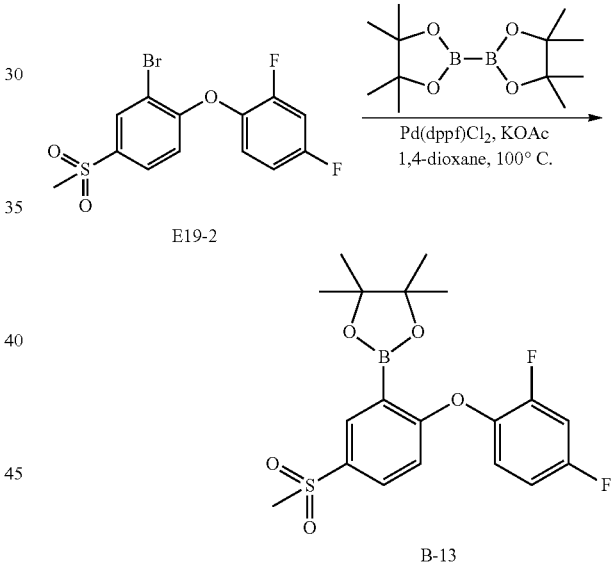

B-13

Step 1

4-Fluorophenylmethylsulfone (1.0 g, 5.74 mmol, CAS: 455-15-2) was dissolved in 6 mL of concentrated sulfuric acid (conc. H$_2$SO$_4$), followed by batch addition of NBS (1.13 g, 6.35 mmol) under ice water bath. After completion of the addition, the temperature was raised to room temperature to react for 16 h. The reaction solution was slowly poured into 50 mL of ice water, stirred for 5 min and filtered. The filtered cake was slurried in 20 mL of petroleum ether, filtered with suction and dried to give compound E19-1 (1.25 g).

Step 2

E19-1 (3.0 g, 11.85 mmol), 2,4-difluorophenol (1.85 g, 14.22 mmol) and cesium carbonate (5.0 g, 15.34 mmol) were added to 50 mL of dimethyl sulfoxide in sequence, and heated to 110° C. to react for 2 h under argon. The reaction solution was added with 500 mL of water and extracted with ethyl acetate (150 mL×3). The combined organic phase was washed three times with saturated saline, dried over anhydrous sodium sulfate, rotary evaporated under vacuum to remove solvent, and purified by silica gel column chromatography to give compound E19-2 (4.0 g).

Step 3

E19-2 (3.73 g, 10.27 mmol), potassium acetate (2.05 g, 20.89 mmol), bis(pinacolato)diboron (5.2 g, 20.52 mmol) were dissolved in 150 mL of dioxane, added with [1,1'-bis(diphenylphosphino)ferrocene]palladium dichloride (447 mg, 0.61 mmol) under argon, heated to 100° C. to react for 14 h, and cooled to room temperature. The reaction solution was filtered through celite. The filtrate was added with water and ethyl acetate for layering. The organic layer was washed with saturated saline, dried over anhydrous sodium sulfate, rotary evaporated under vacuum to remove solvent, purified by silica gel chromatography, and slurried in diethyl ether to give borate B-13 (1.18 g).

$^1$H NMR (400 MHz, CDCl$_3$) δ 8.36 (d, J=2.5 Hz, 1H), 7.93 (dd, J=8.7, 2.5 Hz, 1H), 7.10-7.03 (m, 1H), 7.02-6.95 (m, 1H), 6.92-6.87 (m, 1H), 6.85 (d, J=8.7 Hz, 1H), 3.08 (s, 3H), 1.33 (s, 12H).

Example 20: Synthesis of Borate B-14

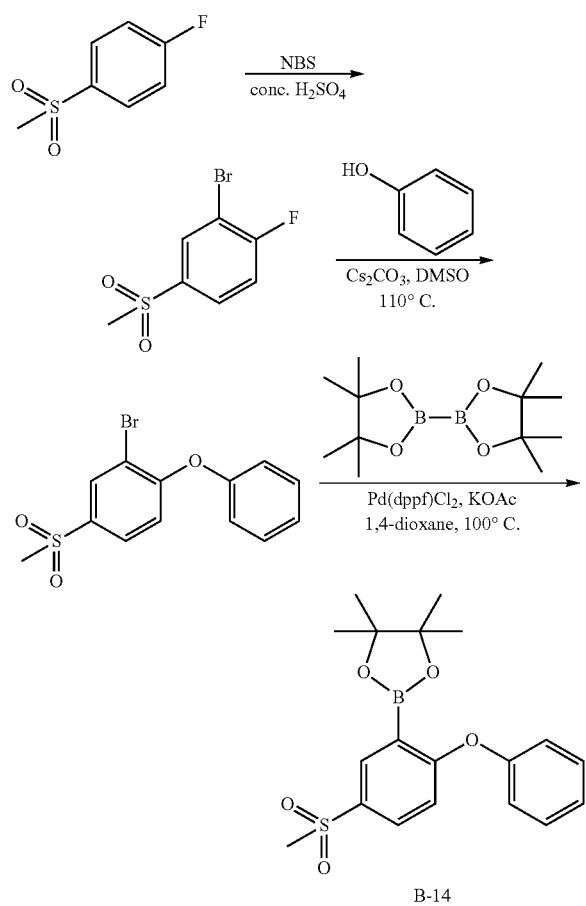

B-14

The same procedure as the synthetic method in Example 19 was used to give borate B-14, except that phenol was used instead of 2,4-difluorophenol in Step 2.

$^1$H NMR (400 MHz, CDCl$_3$) δ 8.34 (d, J=2.5 Hz, 1H), 7.93 (dd, J=8.7, 2.5 Hz, 1H), 7.38 (t, J=8.0 Hz, 2H), 7.16 (t, J=7.4 Hz, 1H), 7.04-6.96 (m, 3H), 3.08 (s, 3H), 1.28 (s, 12H).

Example 21: Synthesis of Borate B-15

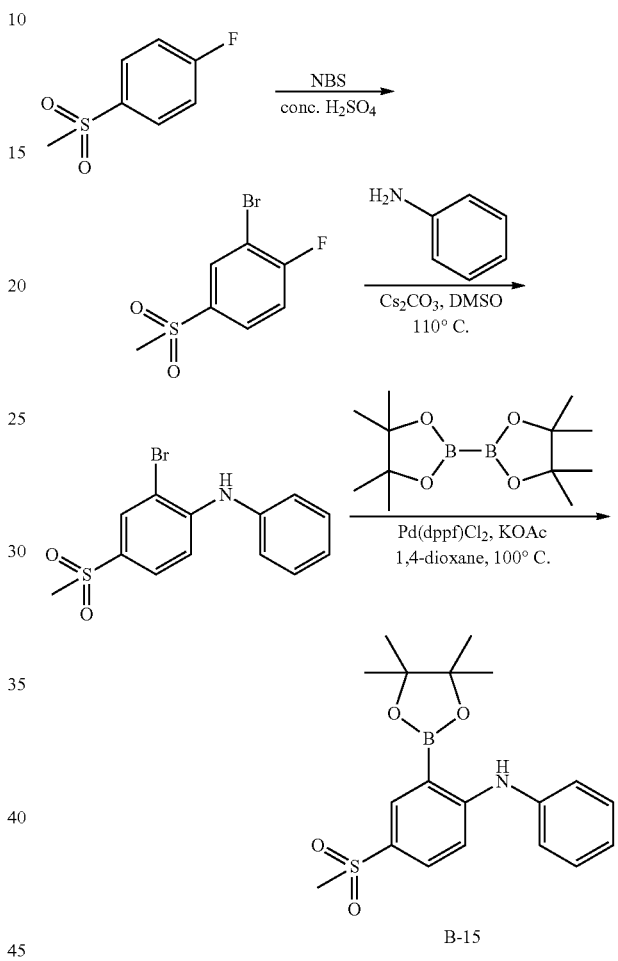

B-15

The same procedure as the synthetic method in Example 19 was used to give borate B-15, except that aniline was used instead of 2,4-difluorophenol in Step 2.

$^1$H NMR (400 MHz, CDCl$_3$) δ 8.28 (d, J=2.4 Hz, 1H), 8.18 (s, 1H), 7.75 (dd, J=8.9, 2.4 Hz, 1H), 7.41 (t, J=7.9 Hz, 2H), 7.26 (d, J=7.4 Hz, 2H), 7.20 (d, J=8.1 Hz, 1H), 7.15 (d, J=8.9 Hz, 1H), 3.04 (s, 3H), 1.39 (s, 12H). HPLC-MS: [M−H]$^+$=374.2

Example 22: Synthesis of Borate B-16

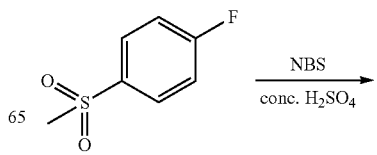

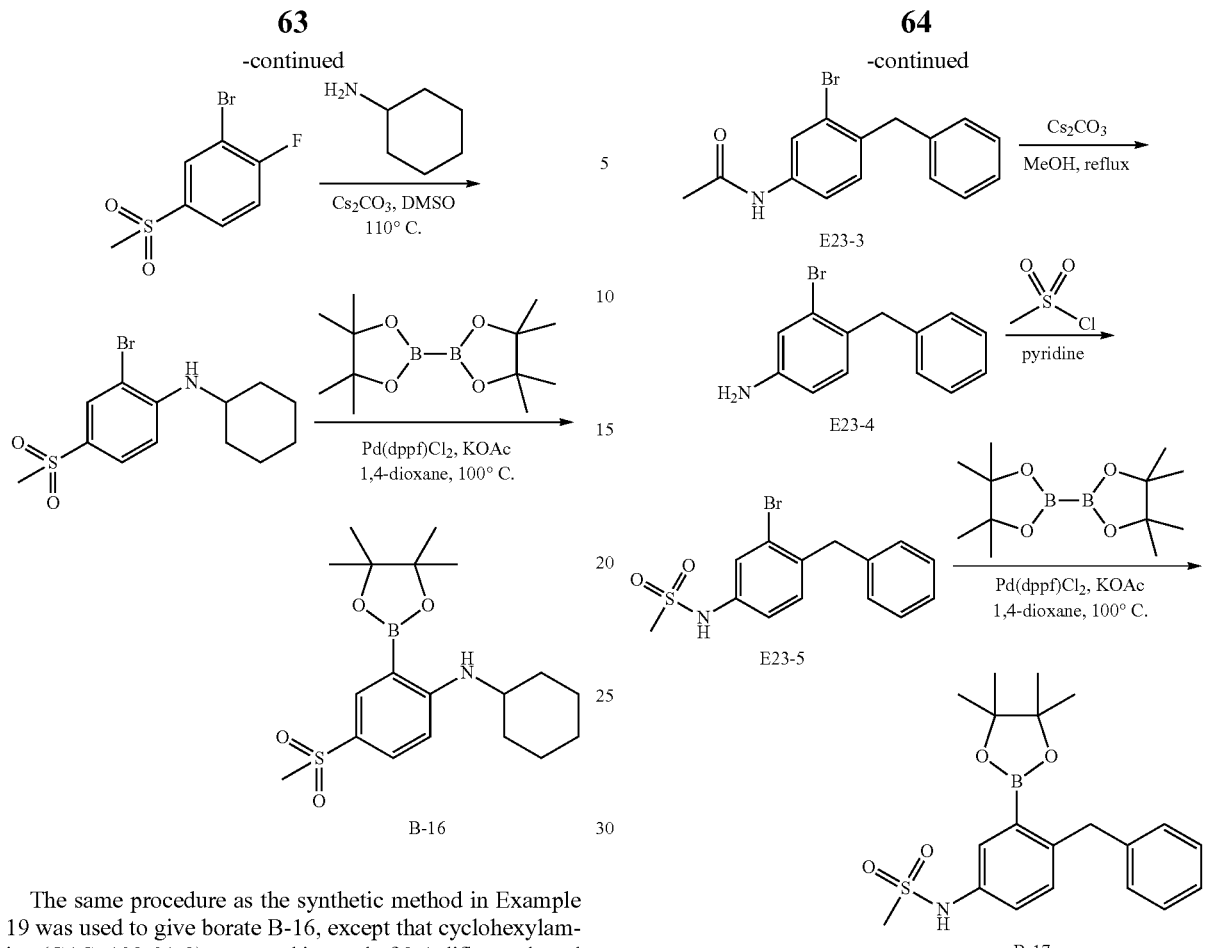

The same procedure as the synthetic method in Example 19 was used to give borate B-16, except that cyclohexylamine (CAS: 108-91-8) was used instead of 2,4-difluorophenol in Step 2.

$^1$H NMR (400 MHz, CDCl$_3$) δ 8.15 (d, J=2.4 Hz, 1H), 7.75 (dd, J=8.9, 2.5 Hz, 1H), 6.59 (d, J=9.0 Hz, 2H), 3.41 (m, 1H), 3.01 (s, 3H), 1.96 (m, 2H), 1.74 (m, 2H), 1.60 (m, 2H), 1.46 (m, 2H), 1.36 (s, 12H), 1.29 (m, 2H).

Example 23: Synthesis of Borate B-17

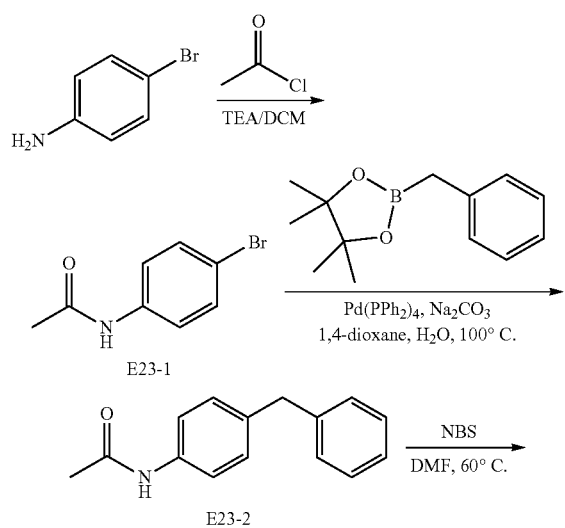

Step 1

4-Bromoaniline (5.0 g, 29.1 mmol, CAS: 106-40-1) was dissolved in 80 mL of dichloromethane, added with 8.1 mL of triethylamine, and cooled in an ice water bath, followed by slow dropwise addition of acetyl chloride (2.74 g, 34.9 mmol) under argon. After completion of the addition, the temperature was raised to room temperature, and the resultant was stirred overnight, added with 80 mL of water, and extracted three times with DCM. The combined organic phase was washed three times with saturated saline, dried over anhydrous sodium sulfate, rotary evaporated under vacuum to remove the solvent, and purified by silica gel column chromatography to give intermediate E23-1 (5.8 g).

Step 2

Intermediate E23-1 (2.2 g, 10.3 mmol) and benzyl borate (3.7 g, 17.0 mmol) were dissolved in 8 mL of 1,4-dioxane and 2 mL of water, added with sodium carbonate (2.2 g, 20.6 mmol), followed by addition of tetrakis(triphenylphosphine)palladium (0.58 g, 0.5 mmol) under argon. The mixture was heated to 110° C. to react for 24 h, cooled to room temperature, added with 60 mL of water, and filtered through celite. The filtered cake was washed twice with ethyl acetate. The filtrate was extracted twice with ethyl acetate, and the combined organic phase was washed with saturated saline three times, dried over anhydrous sodium sulfate, rotary evaporated under vacuum to remove the solvent, and purified by silica gel column chromatography to give intermediate E23-2 (1.0 g).

Step 3

Intermediate E23-2 (1.0 g, 4.44 mmol) and NBS (1.2 g, 6.66 mmol) were dissolved in 30 mL DMF, heated to 60° C.

and stirred overnight, cooled to room temperature, and added with water and ethyl acetate for layering. The organic phase was washed three times with saturated saline, dried over anhydrous sodium sulfate, rotary evaporated under vacuum to remove the solvent, and purified by silica gel column chromatography to give intermediate E23-3 (840 mg).

Step 4

Intermediate E23-3 (40 mg, 0.13 mmol) and cesium carbonate (211 mg, 0.65 mmol) were dissolved in 5 mL of methanol, added with 5 drops of water, heated to reflux to react overnight, cooled to room temperature, added with 10 mL of water, and extracted three times with ethyl acetate. The combined organic phase was washed three times with saturated saline, dried over anhydrous sodium sulfate, rotary evaporated under vacuum to remove the solvent to give intermediate E23-4 (18 mg).

Step 5

Intermediate E23-4 (400 mg, 1.53 mmol) was dissolved in 8 mL of pyridine, cooled in an ice water bath under argon, followed by slow dropwise addition of methanesulfonyl chloride (526 mg, 4.59 mmol). After completion of the addition, the mixture was warmed to room temperature and stirred for 2 h, cooled in an ice water bath again, and added with 2 mL of water to quench the reaction, followed by addition of 50 mL of ethyl acetate. The organic phase was washed three times with 1.5M hydrochloric acid and then three times with saturated saline, dried over anhydrous sodium sulfate, rotary evaporated under vacuum to remove the solvent, and purified by silica gel column chromatography to give E23-5 (245 mg).

Step 6

E23-5 (440 mg, 1.29 mmol), potassium acetate (380 mg, 3.87 mmol) and bis(pinacolato)diboron (665 mg, 258 mmol) were dissolved in 15 mL of dioxane, added with [1,1'-bis(diphenylphosphino)ferrocene]palladium dichloride (47 mg, 0.065 mmol) under argon, heated to 100° C. to react for 14 h, cooled to room temperature, and filtered through celite. The filtrate was added with water and ethyl acetate for layering. The organic layer was washed with saturated saline, dried over anhydrous sodium sulfate, rotary evaporated under vacuum to remove the solvent, and purified by silica gel column chromatography to give borate B-17 (139 mg).

$^1$H NMR (400 MHz, CDCl$_3$) δ 8.36 (s, 1H), 7.68 (s, 1H), 7.53 (d, J=8.4 Hz, 1H), 7.34-7.27 (m, 3H), 7.21 (dd, J=11.8, 7.3 Hz, 3H), 3.96 (s, 2H), 2.95 (s, 3H), 1.39 (s, 12H).

Example 24: Synthesis of Compound ZB-BD-70

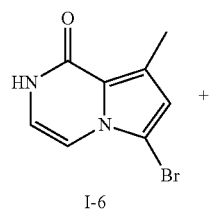

I-6

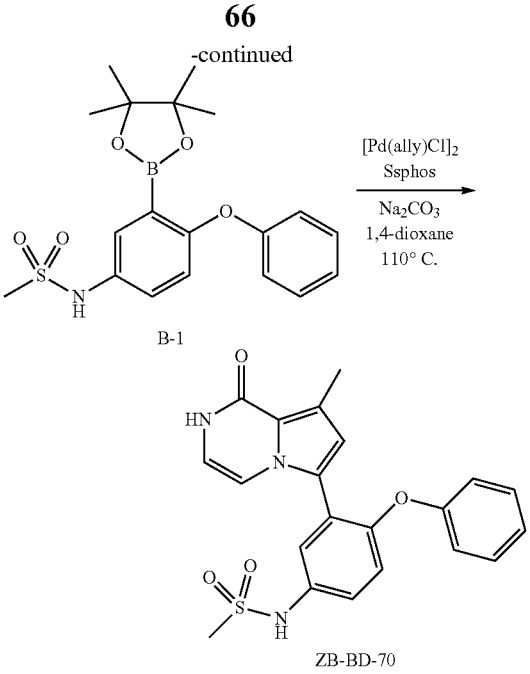

Compound I-6 (46 mg, 0.2 mmol) and borate B-1 (156 mg, 0.4 mmol) were dissolved in 6 mL of 1,4-dioxane, added with 2 mL of 2M sodium carbonate solution, followed by addition of allyl palladium (II) chloride dimer ([Pd(allyl)Cl]$_2$, CAS number: 12012-95-2) (7 mg, 0.02 mmol) and sodium 2'-(dicyclohexylphosphanyl)-2,6-dimethoxy-[1,1'-biphenyl]-3-sulfonate hydrate (Ssphos, CAS number: 1049726-96-6) (21 mg, 0.04 mmol) under Ar. The mixture was stirred at 110° C. for 2 h, diluted with water, extracted with ethyl acetate, and purified by silica gel column chromatography to give compound ZB-BD-70 (9 mg).

$^1$H NMR (400 MHz, CDCl$_3$) δ 9.37 (d, J=5.0 Hz, 1H), 8.62 (s, 1H), 7.40 (d, J=2.7 Hz, 1H), 7.36 (dd, J=8.8, 2.7 Hz, 1H), 7.29-7.23 (m, 2H), 7.06 (d, J=7.4 Hz, 1H), 7.02 (d, J=8.7 Hz, 1H), 6.93 (d, J=5.8 Hz, 1H), 6.90-6.82 (m, 2H), 6.42 (s, 1H), 6.37 (t, J=5.7 Hz, 1H), 3.08 (s, 3H), 2.55 (s, 3H). HPLC-MS: [M+H]$^+$=410.3.

Example 25: Synthesis of Compound ZB-BD-77

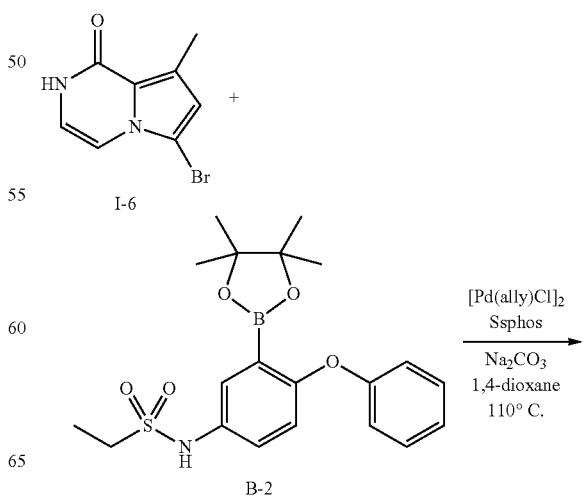

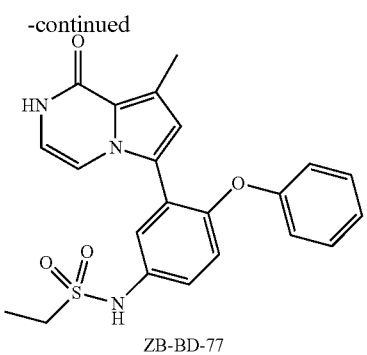

ZB-BD-77

The same method as that in Example 24 was used to give compound ZB-BD-77, except that compound B-2 was used instead of compound B-1.

$^1$H NMR (400 MHz, CDCl$_3$) δ 9.55 (d, J=4.4 Hz, 1H), 8.98 (s, 1H), 7.40 (d, J=2.6 Hz, 1H), 7.35 (dd, J=8.8, 2.7 Hz, 1H), 7.23 (t, J=8.0 Hz, 2H), 7.04-6.96 (m, 2H), 6.91 (d, J=5.8 Hz, 1H), 6.84 (d, J=7.7 Hz, 2H), 6.40 (s, 1H), 6.36 (t, J=5.6 Hz, 1H), 3.18 (q, J=7.4 Hz, 2H), 2.53 (s, 3H), 1.40 (t, J=7.4 Hz, 3H). HPLC-MS: [M+H]$^+$=424.3.

Example 26: Synthesis of Compound ZB-BD-78

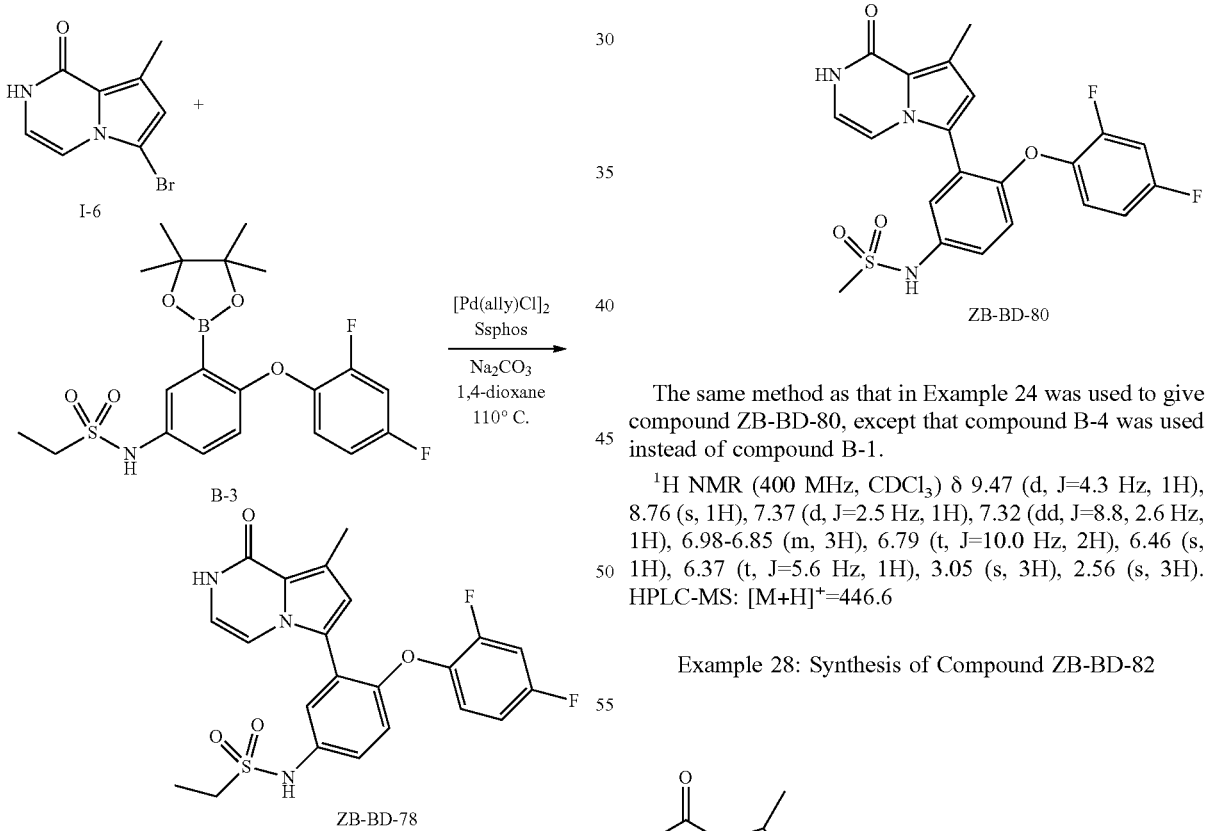

ZB-BD-78

The same method as that in Example 24 was used to give compound ZB-BD-78, except that compound B-3 was used instead of compound B-1.

$^1$H NMR (400 MHz, CDCl$_3$) δ 9.12 (s, 1H), 8.28 (s, 1H), 7.35 (d, J=2.7 Hz, 1H), 7.29 (dd, J=8.8, 2.7 Hz, 1H), 6.97-6.87 (m, 3H), 6.83-6.79 (m, 1H), 6.77 (d, J=8.6 Hz, 1H), 6.47 (s, 1H), 6.36 (t, J=5.7 Hz, 1H), 3.15 (q, J=7.6 Hz, 2H), 2.59 (s, 3H), 1.40 (t, J=7.4 Hz, 3H). HPLC-MS: [M+H]$^+$=460.3.

Example 27: Synthesis of Compound ZB-BD-80

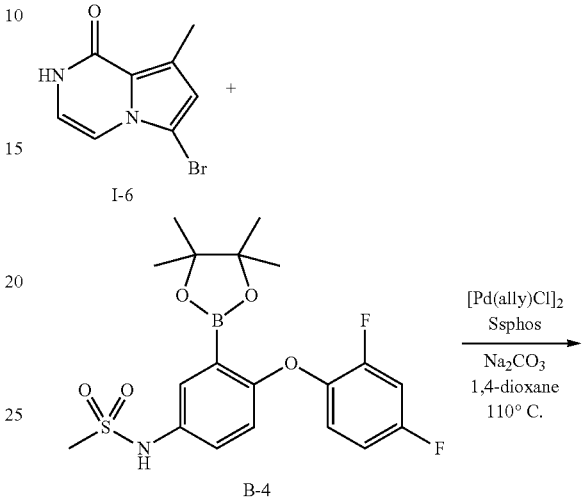

ZB-BD-80

The same method as that in Example 24 was used to give compound ZB-BD-80, except that compound B-4 was used instead of compound B-1.

$^1$H NMR (400 MHz, CDCl$_3$) δ 9.47 (d, J=4.3 Hz, 1H), 8.76 (s, 1H), 7.37 (d, J=2.5 Hz, 1H), 7.32 (dd, J=8.8, 2.6 Hz, 1H), 6.98-6.85 (m, 3H), 6.79 (t, J=10.0 Hz, 2H), 6.46 (s, 1H), 6.37 (t, J=5.6 Hz, 1H), 3.05 (s, 3H), 2.56 (s, 3H). HPLC-MS: [M+H]$^+$=446.6

Example 28: Synthesis of Compound ZB-BD-82

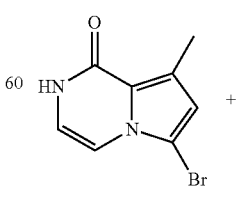

I-6

-continued

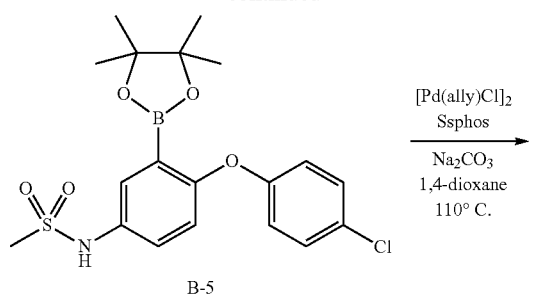

B-5

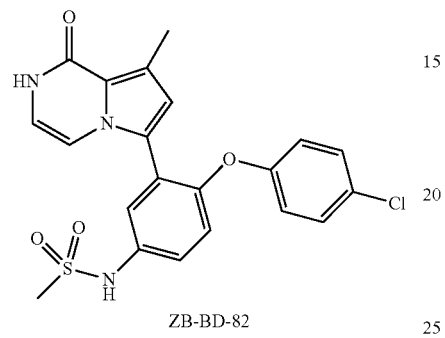

ZB-BD-82

The same method as that in Example 24 was used to give compound ZB-BD-82, except that compound B-5 was used instead of compound B-1.

$^1$H NMR (400 MHz, CDCl$_3$) δ 9.31 (d, J=4.8 Hz, 1H), 8.60 (s, 1H), 7.41-7.33 (m, 2H), 7.21-7.13 (m, 2H), 7.02 (d, J=9.0 Hz, 1H), 6.87 (d, J=5.9 Hz, 1H), 6.78-6.72 (m, 2H), 6.41-6.32 (m, 2H), 3.08 (s, 3H), 2.53 (s, 3H). HPLC-MS: [M+H]$^+$=444.2.

Example 29: Synthesis of Compound ZB-BD-83

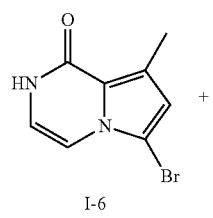

I-6

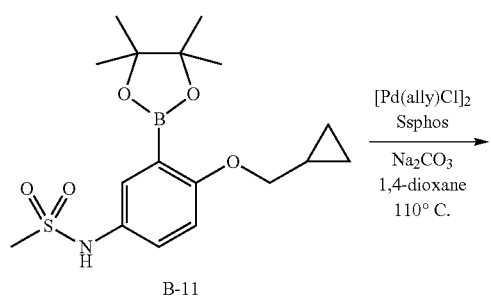

B-11

-continued

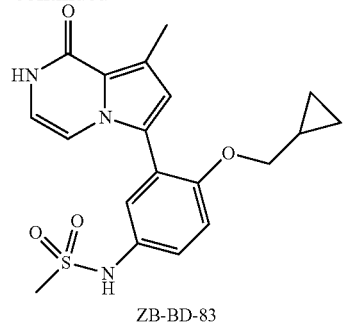

ZB-BD-83

The same method as that in Example 24 was used to give compound ZB-BD-83, except that compound B-11 was used instead of compound B-1.

$^1$H NMR (400 MHz, CDCl$_3$) δ 9.67 (s, 1H), 8.40 (s, 1H), 7.36 (d, J=8.7 Hz, 1H), 7.29 (s, 1H), 6.95 (d, J=8.8 Hz, 1H), 6.75 (d, J=5.7 Hz, 1H), 6.41 (s, 1H), 6.34 (t, J=5.3 Hz, 1H), 3.78 (d, J=6.7 Hz, 2H), 3.01 (s, 3H), 2.61 (s, 3H), 1.11 (m, 1H), 0.51 (d, J=7.5 Hz, 2H), 0.21 (d, J=4.6 Hz, 2H). HPLC-MS: [M+H]$^+$=388.2.

Example 30: Synthesis of Compound ZB-BD-91

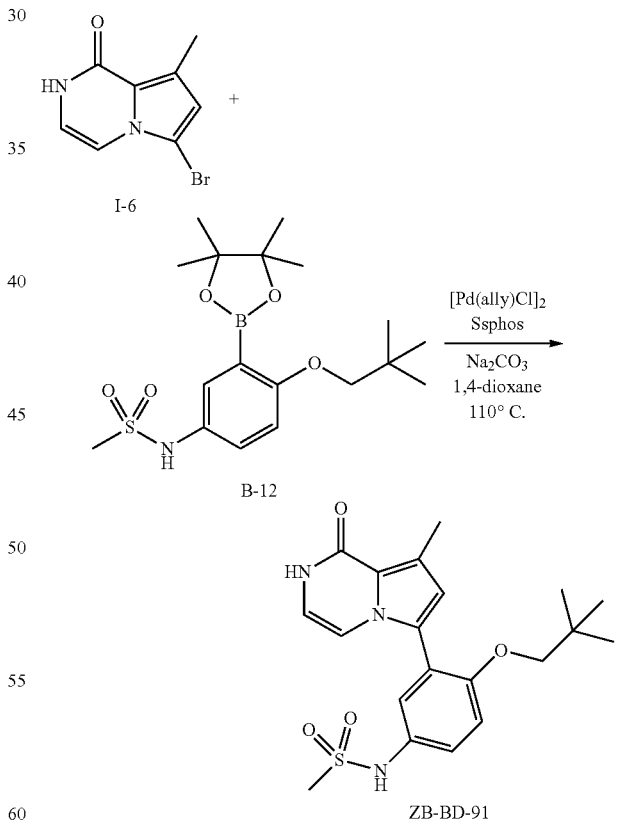

The same method as that in Example 24 was used to give compound ZB-BD-91, except that compound B-12 was used instead of compound B-1.

$^1$H NMR (400 MHz, MeOD) δ 7.36 (dd, J=8.8, 2.8 Hz, 1H), 7.25 (d, J=2.7 Hz, 1H), 7.10 (d, J=8.9 Hz, 1H), 6.78 (d,

J=5.9 Hz, 1H), 6.44 (s, 1H), 6.41 (d, J=5.9 Hz, 1H), 3.62 (s, 2H), 2.96 (s, 3H), 2.60 (s, 3H), 0.82 (s, 9H). HPLC-MS: [M+H]⁺=404.3.

Example 31: Synthesis of Compound ZB-BD-92

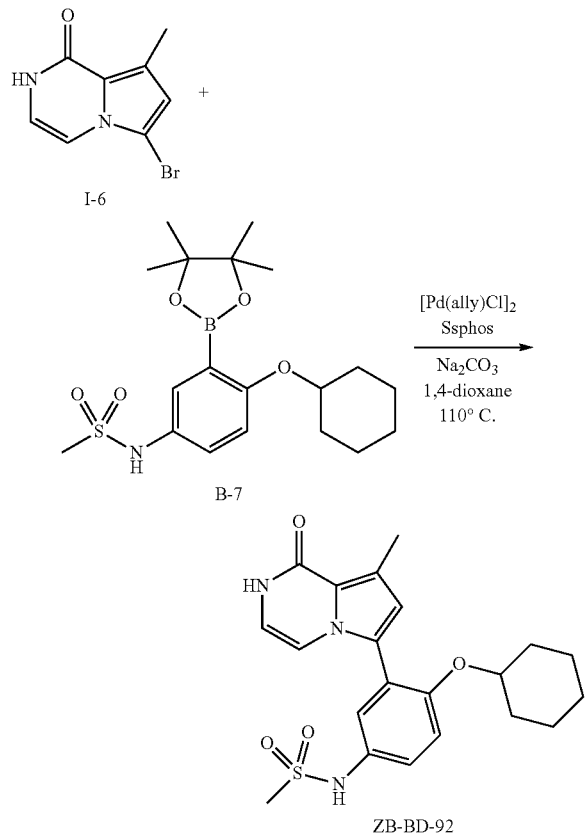

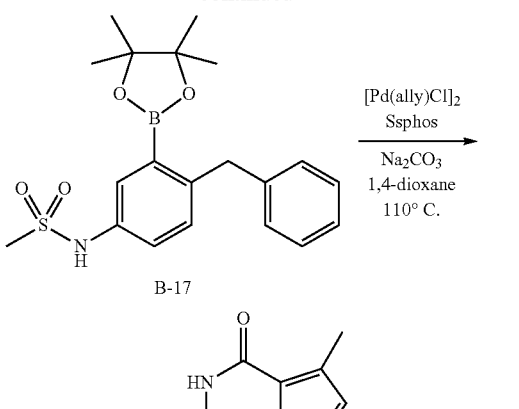

The same method as that in Example 24 was used to give compound ZB-BD-92, except that compound B-7 was used instead of compound B-1.

¹H NMR (400 MHz, MeOD) δ 7.34-7.29 (m, 1H), 7.23 (d, J=2.7 Hz, 1H), 7.10 (d, J=8.9 Hz, 1H), 6.80 (d, J=5.9 Hz, 1H), 6.41 (d, J=5.8 Hz, 2H), 4.31-4.22 (m, 1H), 2.94 (s, 3H), 2.57 (s, 3H), 1.80-1.72 (m, 2H), 1.54-1.23 (m, 8H). HPLC-MS: [M+H]⁺=416.3.

Example 32: Synthesis of Compound ZB-BD-93

The same method as that in Example 24 was used to give compound ZB-BD-93, except that compound B-17 was used instead of compound B-1.

¹H NMR (400 MHz, CDCl₃) δ 9.29 (s, 1H), 8.42 (s, 1H), 7.51 (d, J=8.4 Hz, 1H), 7.32-7.25 (m, 3H), 7.24-7.17 (m, 3H), 7.15 (d, J=1.6 Hz, 1H), 6.66 (d, J=5.9 Hz, 1H), 6.42 (s, 1H), 6.29 (d, J=5.8 Hz, 1H), 3.97 (s, 2H), 3.10 (s, 3H), 2.45 (s, 3H). HPLC-MS: [M+H]⁺=408.3.

Example 33: Synthesis of Compound ZB-BD-94

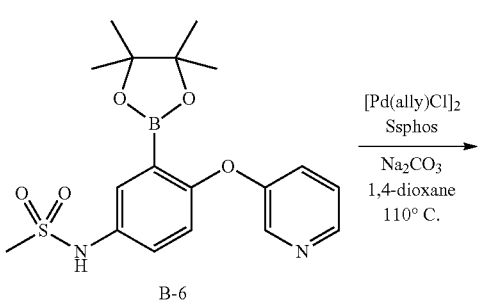

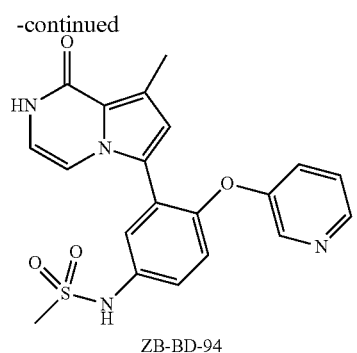

ZB-BD-94

The same method as that in Example 24 was used to give compound ZB-BD-94, except that compound B-6 was used instead of compound B-1. $^1$H NMR (400 MHz, MeOD) δ 8.14 (d, J=4.0 Hz, 1H), 8.05 (m, 1H), 7.46 (dd, J=8.8, 2.7 Hz, 1H), 7.40 (d, J=2.7 Hz, 1H), 7.30-7.21 (m, 2H), 7.21 (m, 1H), 6.98 (d, J=5.9 Hz, 1H), 6.51 (d, J=5.9 Hz, 1H), 6.39 (s, 1H), 3.06 (s, 3H), 2.46 (s, 3H). HPLC-MS: [M+H]$^+$=411.3.

Example 34: Synthesis of Compound ZB-BD-95

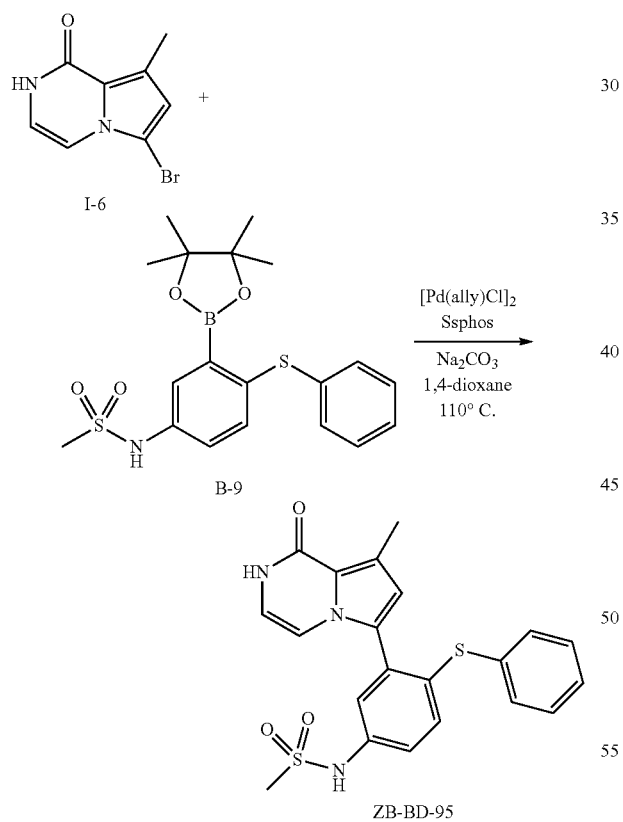

ZB-BD-95

The same method as that in Example 24 was used to give compound ZB-BD-95, except that compound B-9 was used instead of compound B-1.

$^1$H NMR (400 MHz, MeOD) δ 7.35 (d, J=8.6 Hz, 1H), 7.29 (dd, J=8.6, 2.5 Hz, 1H), 7.23-7.17 (m, 4H), 7.12-7.07 (m, 2H), 6.67 (d, J=5.9 Hz, 1H), 6.38 (d, J=5.9 Hz, 1H), 6.29 (s, 1H), 3.02 (s, 3H), 2.50 (s, 3H). HPLC-MS: [M+H]$^+$= 426.4.

Example 35: Synthesis of Compound ZB-BD-96

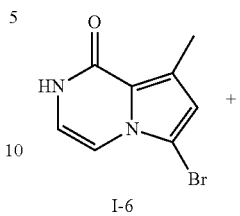

I-6

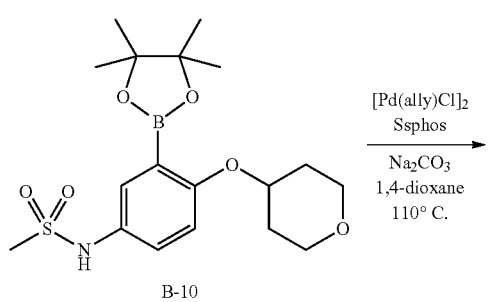

B-10

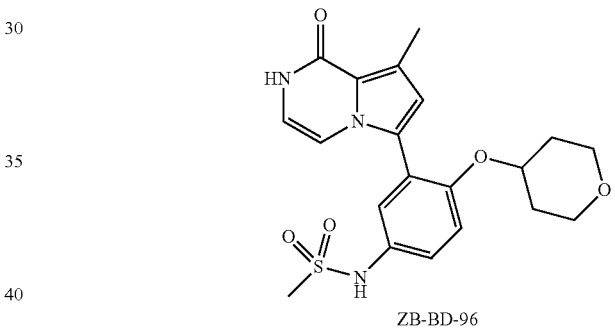

ZB-BD-96

The same method as that in Example 24 was used to give compound ZB-BD-96, except that compound B-10 was used instead of compound B-1.

$^1$H NMR (400 MHz, MeOD) δ 7.32 (dd, J=8.8, 2.8 Hz, 1H), 7.25 (d, J=2.7 Hz, 1H), 7.13 (d, J=8.9 Hz, 1H), 6.80 (d, J=5.9 Hz, 1H), 6.42 (s, 1H), 6.39 (d, J=5.9 Hz, 1H), 4.51-4.44 (m, 1H), 3.61-3.53 (m, 2H), 3.50-3.40 (m, 2H), 2.95 (s, 3H), 2.58 (s, 3H), 1.90-1.82 (m, 2H), 1.62-1.52 (m, 2H). HPLC-MS: [M+H]$^+$=418.4.

Example 36: Synthesis of Compound ZB-BD-97

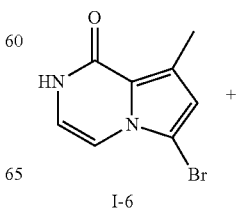

I-6

-continued

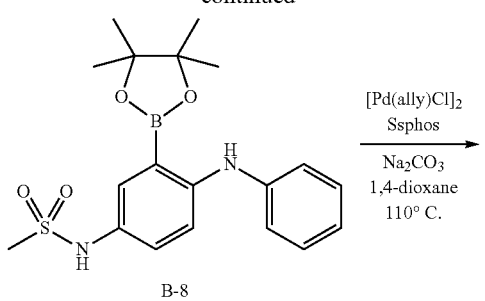

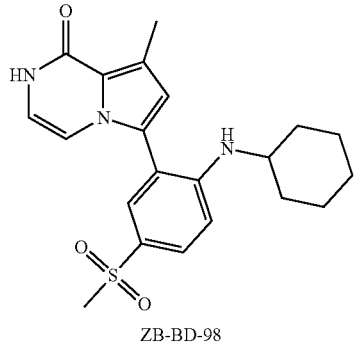

ZB-BD-98

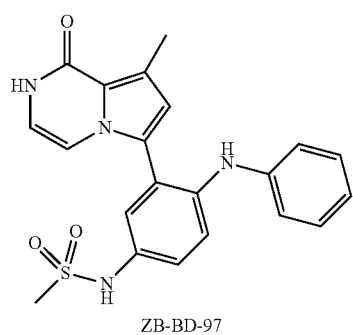

ZB-BD-97

The same method as that in Example 24 was used to give compound ZB-BD-97, except that compound B-8 was used instead of compound B-1. HPLC-MS: [M+H]$^+$=409.2

Example 37: Synthesis of Compound ZB-BD-98

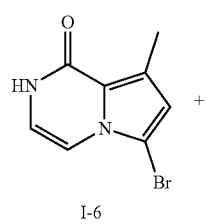

I-6

Compound I-6 (46 mg, 0.2 mmol) and borate B-16 (156 mg, 0.4 mmol) were dissolved in 3 mL of ethylene glycol dimethyl ether, added with 1 mL of 2M sodium carbonate solution, followed by addition of [1,1'-bis(diphenylphosphino)ferrocene] palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-98 (12 mg).

$^1$H NMR (400 MHz, CDCl$_3$) δ 10.24 (s, 1H), 7.79 (dd, J=8.8, 2.2 Hz, 1H), 7.66 (d, J=2.3 Hz, 1H), 6.76 (d, J=8.9 Hz, 1H), 6.61 (d, J=5.8 Hz, 1H), 6.46-6.39 (m, 2H), 4.28 (d, J=7.7 Hz, 1H), 3.40-3.29 (m, 1H), 3.03 (s, 3H), 2.64 (s, 3H), 1.96 (d, J=10.2 Hz, 2H), 1.75-1.60 (m, 2H), 1.43-1.05 (m, 6H). HPLC-MS: [M+H]$^+$=400.3

Example 38: Synthesis of Compound ZB-BD-99

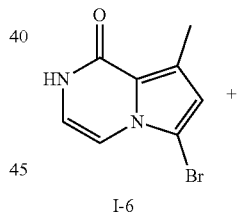

I-6

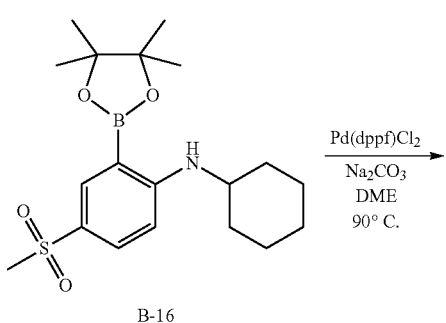

B-16

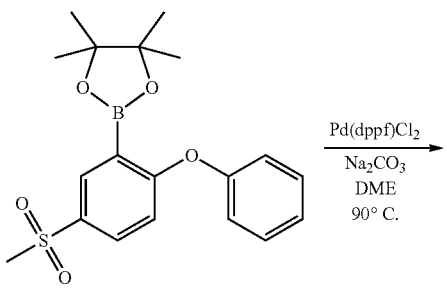

B-14

-continued

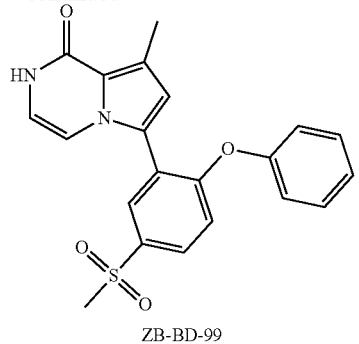

ZB-BD-99

The same method as that in Example 37 was used to give compound ZB-BD-99, except that compound B-14 was used instead of compound B-16. HPLC-MS: [M+H]⁺=395.2.

Example 39: Synthesis of Compound ZB-BD-100

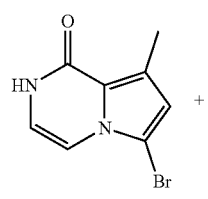

I-6

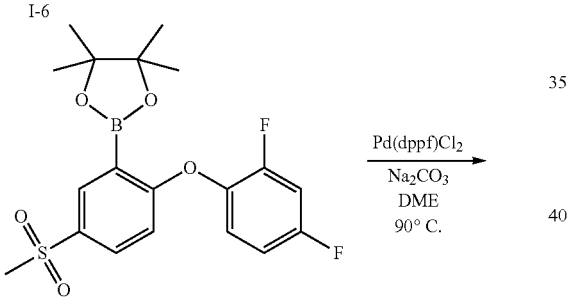

ZB-BD-100

The same method as that in Example 37 was used to give compound ZB-BD-100, except that compound B-13 was used instead of compound B-16.

$^1$H NMR (400 MHz, MeOD) δ 8.04 (d, J=2.3 Hz, 1H), 8.00 (dd, J=8.7, 2.4 Hz, 1H), 7.28 (td, J=9.0, 5.4 Hz, 1H), 7.20 (m, 1H), 7.07-7.01 (m, 2H), 6.99 (d, J=5.9 Hz, 1H), 6.61 (s, 1H), 6.51 (d, J=5.9 Hz, 1H), 3.19 (s, 3H), 2.60 (s, 3H). HPLC-MS: [M+H]⁺=431.3.

Example 40: Synthesis of Compound ZB-BD-74

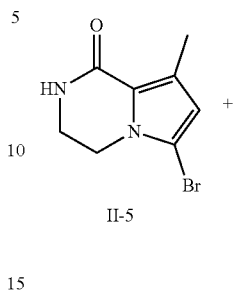

II-5

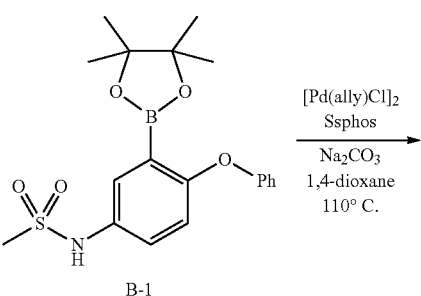

B-1

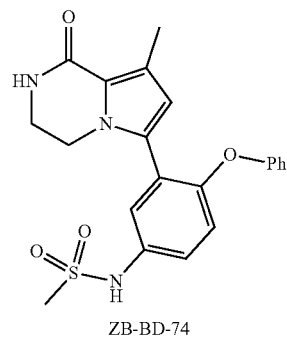

ZB-BD-74

The same method as that in Example 24 was used to give compound ZB-BD-74, except that compound II-5 was used instead of compound I-6.

$^1$H NMR (400 MHz, CDCl₃) δ 8.81 (s, 1H), 7.37-7.22 (m, 4H), 7.06 (t, J=7.4 Hz, 1H), 6.97-6.93 (m, 1H), 6.89-6.85 (m, 2H), 6.34 (s, 1H), 6.10 (s, 1H), 4.07-3.99 (m, 2H), 3.60-3.52 (m, 2H), 3.05 (s, 3H), 2.39 (s, 3H). HPLC-MS: [M+H]⁺=412.2.

Example 41: Synthesis of Compound ZB-BD-79

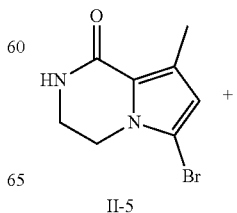

II-5

-continued

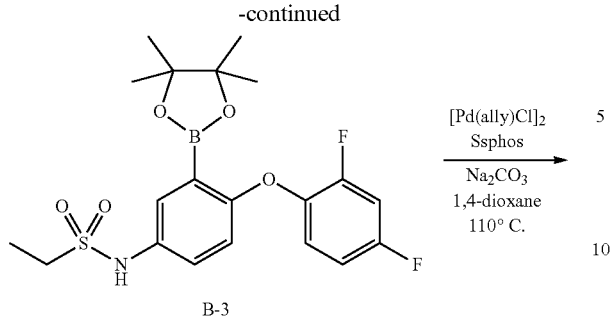

B-3

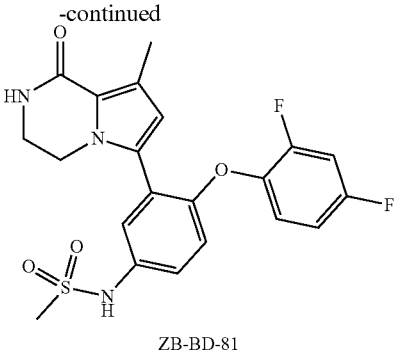

ZB-BD-81

The same method as that in Example 24 was used to give compound ZB-BD-81, except that compound II-5 was used instead of compound I-6 and compound B-4 was used instead of compound B-1. HPLC-MS: [M+H]$^+$=448.2.

Example 43: Synthesis of Compound ZB-BD-69

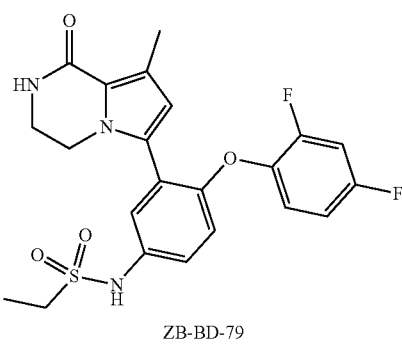

ZB-BD-79

The same method as that in Example 24 was used to give compound ZB-BD-79, except that compound II-5 was used instead of compound I-6 and compound B-3 was used instead of compound B-1. HPLC-MS: [M+H]$^+$=462.3.

Example 42: Synthesis of Compound ZB-BD-81

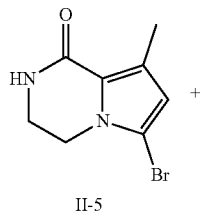

II-5

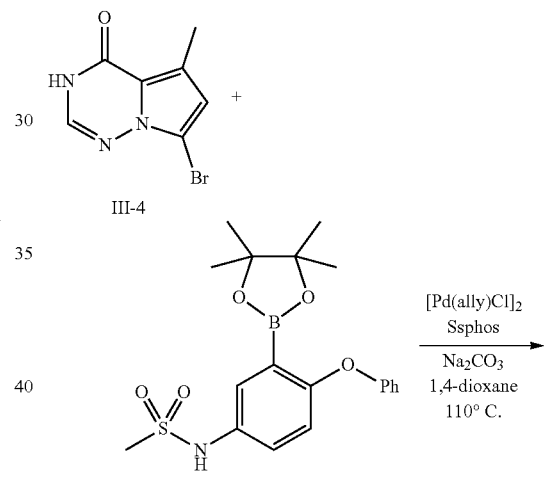

III-4

B-1

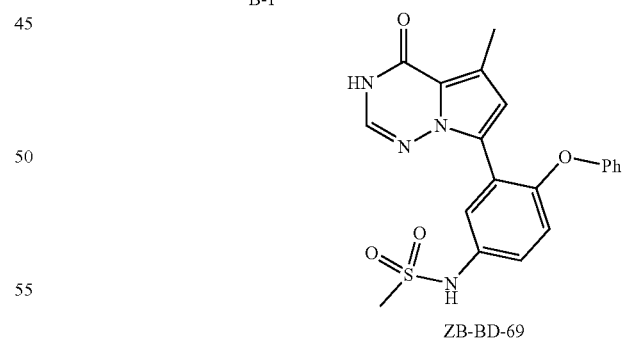

ZB-BD-69

The same method as that in Example 24 was used to give compound ZB-BD-69, except that compound III-4 was used instead of compound I-6.

$^1$H NMR (400 MHz, CDCl$_3$) δ 10.40 (s, 1H), 7.61 (d, J=2.7 Hz, 1H), 7.52 (s, 1H), 7.35 (s, 1H), 7.29-7.24 (m, 2H), 7.20 (dd, J=8.8, 2.7 Hz, 1H), 7.04 (t, J=7.4 Hz, 1H), 6.97-6.88 (m, 3H), 6.54 (s, 1H), 3.02 (s, 3H), 2.46 (s, 3H). HPLC-MS: [M+H]$^+$=411.2.

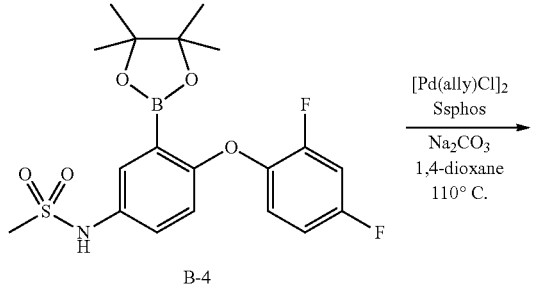

B-4

Example 44: Synthesis of Compound ZB-BD-76

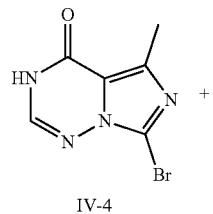

IV-4

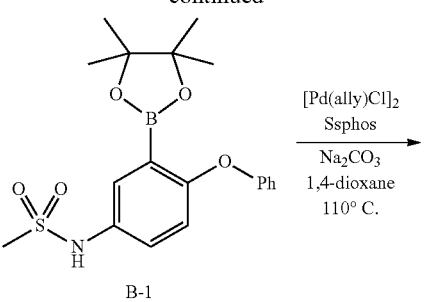

B-1

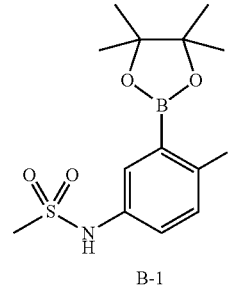

B-1

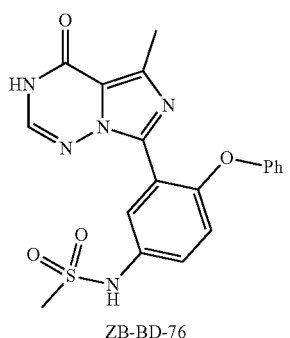

ZB-BD-76

The same method as that in Example 24 was used to give compound ZB-BD-76, except that compound IV-4 was used instead of compound I-6.

$^1$H NMR (400 MHz, CDCl$_3$) δ 10.42 (s, 1H), 7.83 (s, 1H), 7.51 (d, J=2.7 Hz, 1H), 7.39-7.32 (m, 2H), 7.30-7.22 (m, 2H), 7.06 (t, J=7.4 Hz, 1H), 6.99 (s, 1H), 6.97 (s, 1H), 6.90 (d, J=8.9 Hz, 1H), 2.99 (s, 3H), 2.63 (s, 3H). HPLC-MS: [M+H]$^+$=412.5

Example 45: Synthesis of Compound ZB-BD-86

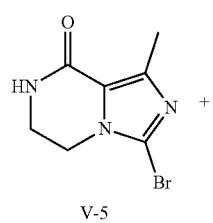

V-5

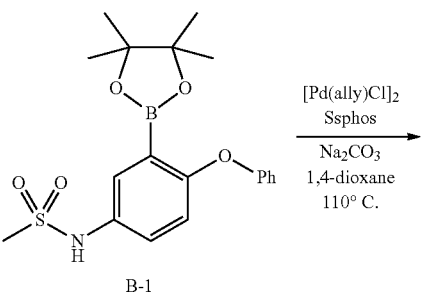

B-1

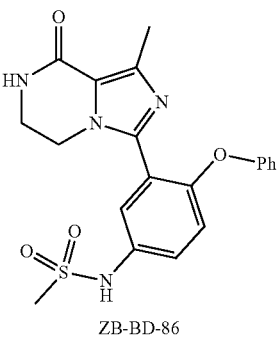

ZB-BD-86

The same method as that in Example 24 was used to give compound ZB-BD-86, except that compound V-5 was used instead of compound I-6.

$^1$H NMR (400 MHz, MeOD) δ 7.87 (s, 1H), 7.40-7.33 (m, 2H), 7.29 (dd, J=8.9, 2.7 Hz, 1H), 7.14 (t, J=7.4 Hz, 1H), 7.04 (d, J=7.9 Hz, 2H), 6.90 (d, J=8.9 Hz, 1H), 4.48 (t, J=9.4 Hz, 2H), 3.99 (t, J=9.5 Hz, 2H), 3.01 (s, 3H), 2.48 (s, 3H). HPLC-MS: [M+H]$^+$=413.6

Example 46: Synthesis of Compound ZB-BD-102

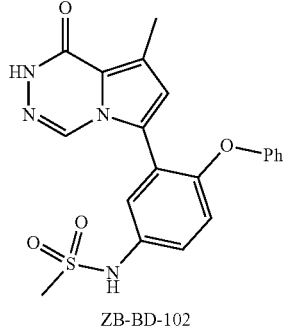

ZB-BD-102

The same method as that in Example 24 was used to give compound ZB-BD-102, except that compound VI-5 was used instead of compound I-6.

$^1$H NMR (400 MHz, DMSO-d$_6$) δ 11.57 (s, 1H), 9.84 (s, 1H), 8.12 (s, 1H), 7.35-7.28 (m, 4H), 7.11-7.01 (m, 2H), 6.93 (m, 2H), 6.60 (s, 1H), 3.05 (s, 3H), 2.42 (s, 3H). HPLC-MS: [M+H]$^+$=411.2.

Example 47: Synthesis of Compound ZB-BD-103

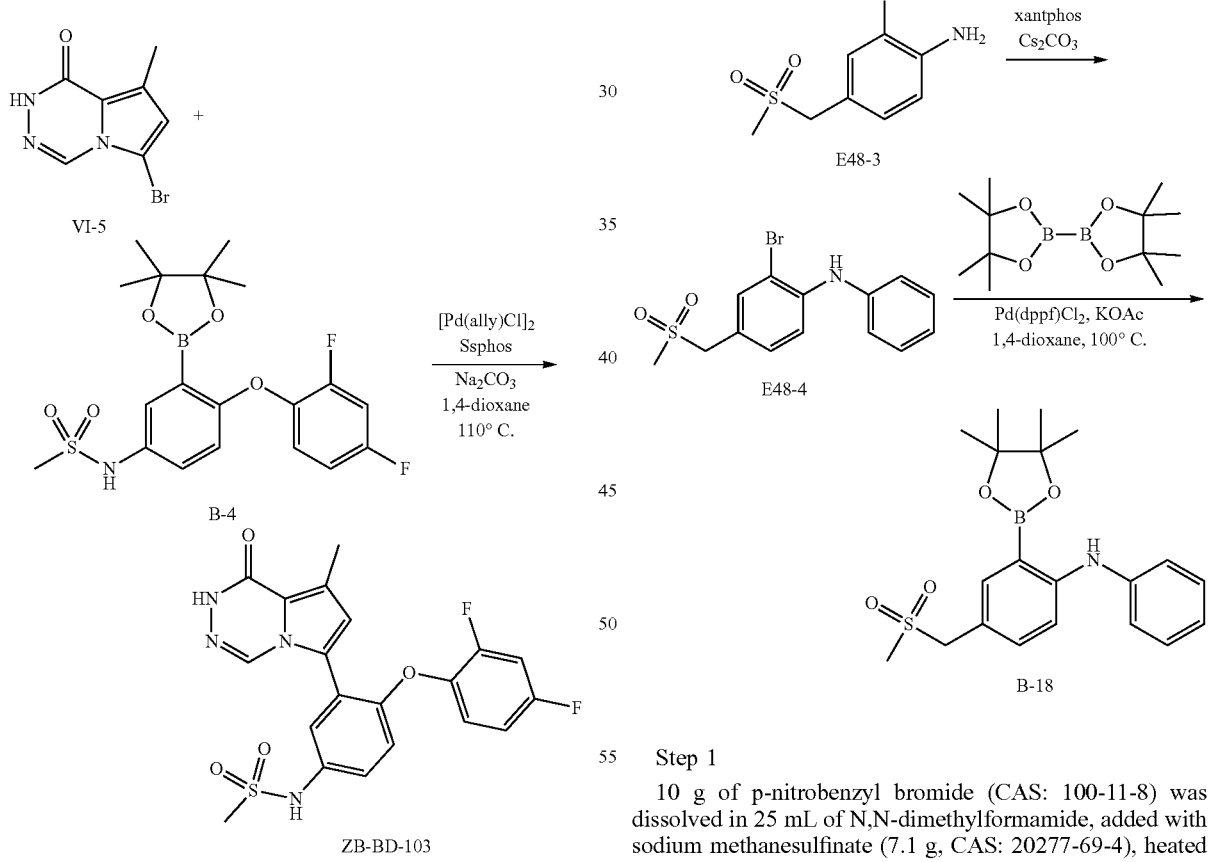

ZB-BD-103

The same method as that in Example 24 was used to give compound ZB-BD-103, except that compound VI-5 was used instead of compound I-6 and compound B-4 was used instead of compound B-1.

$^1$H NMR (400 MHz, DMSO-d$_6$) δ 11.60 (s, 1H), 9.82 (s, 1H), 8.10 (s, 1H), 7.44 (ddd, J=11.4, 8.7, 2.9 Hz, 1H), 7.33 (d, J=2.7 Hz, 1H), 7.31-7.22 (m, 2H), 7.11-7.05 (m, 1H), 6.92 (d, J=8.9 Hz, 1H), 6.66 (s, 1H), 3.03 (s, 3H), 2.46 (s, 3H). HPLC-MS: [M+H]$^+$=447.2

Example 48: Synthesis of Borate B-18

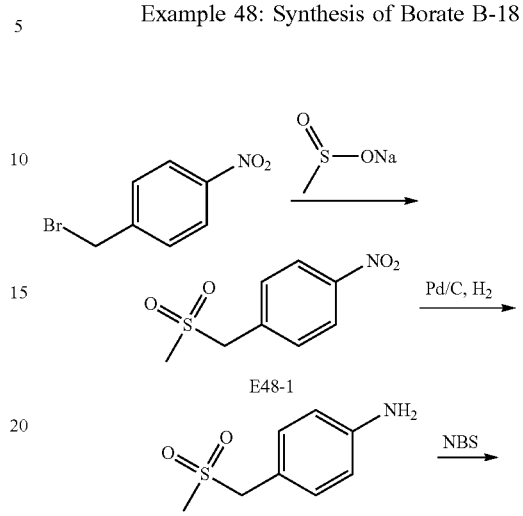

Step 1

10 g of p-nitrobenzyl bromide (CAS: 100-11-8) was dissolved in 25 mL of N,N-dimethylformamide, added with sodium methanesulfinate (7.1 g, CAS: 20277-69-4), heated to 70° C. to react for 2 h. The mixture was cooled, diluted with water, and stirred for 10 minutes to precipitate a solid, which was filtered to give 9.3 g of E48-1 as a white solid. HPLC-MS: [M+H]$^+$=216.2.

Step 2

The nitrocompound E48-1 (9 g) was dissolved in 500 mL of ethyl acetate, added with 1 g of 10% Pd/C, kept at 40° C. and purged continually with hydrogen gas to react overnight.

85

The catalyst was removed by filtration. The resultant was concentrated to give an amino product E48-2 (7.5 g). HPLC-MS: [M+H]⁺=186.2.

Step 3

The amino compound E48-2 (2 g) was dissolved in 60 mL of N,N-dimethylformamide, added with 1.9 g of N-bromosuccinimide, kept at 15° C. to react for 1 h, followed by addition of 10% aqueous sodium thiosulfate solution to quench the reaction. The mixture was extracted with ethyl acetate. The organic layer was washed with saturated saline, and concentrated to give a crude. The crude was added with 200 mL of water, stirred for 30 minutes to precipitate a solid, which was filtered and dried in vacuo to give a brominated product E48-3 (1.8 g). HPLC-MS: [M+H]⁺=264.2/266.2.

Step 4

1 g of the brominated product E48-3, palladium acetate (42.5 mg, CAS: 3375-31-3), 9,9-Dimethyl-4,5-bis(diphenylphosphino)xanthene (xantphos, 175 mg, CAS: 161265-03-8), cesium carbonate (2.45 g), iodobenzene (1.8 g, CAS: 591-50-4) were dissolved in 50 mL of anhydrous dioxane and heated to 110° C. to react for 18 h. After completion of the reaction, the mixture was filtered through celite, dried and concentrated, and purified by column chromatography to give the product E48-4 (750 mg). ¹H NMR (400 MHz, CDCl₃) δ 7.56 (d, J=1.7 Hz, 1H), 7.35 (t, J=7.9 Hz, 2H), 7.22-7.12 (m, 4H), 7.10 (t, J=7.4 Hz, 1H), 6.22 (s, 1H), 4.13 (s, 2H), 2.80 (s, 3H). HPLC-MS: [M+H]⁺=340.2/342.2.

Step 5

E48-4 (440 mg, 1.29 mmol), potassium acetate (380 mg, 3.87 mmol), bis(pinacolato)diboron (665 mg, 258 mmol) were dissolved in 15 mL of dioxane, added with [1,1′-bis(diphenylphosphino)ferrocene]palladium dichloride (47 mg, 0.065 mmol) under argon, heated to 100° C. to react for 2 h, cooled to room temperature, and filtered through celite. The filtrate was added with water and ethyl acetate for layering. The organic layer was washed with saturated saline, dried over anhydrous sodium sulfate, rotary evaporated under vacuum to remove the solvent, and purified by silica gel column chromatography to give borate B-18 (120 mg). ¹H NMR (400 MHz, CDCl₃) δ 7.86 (s, 1H), 7.66 (d, J=1.9 Hz, 1H), 7.33 (t, J=7.8 Hz, 3H), 7.22 (t, J=7.3 Hz, 3H), 7.05 (t, J=7.4 Hz, 1H), 4.15 (s, 2H), 2.76 (s, 3H), 1.36 (s, 12H). HPLC-MS: [M+H]⁺=388.2.

Example 49: Synthesis of Borate B-19

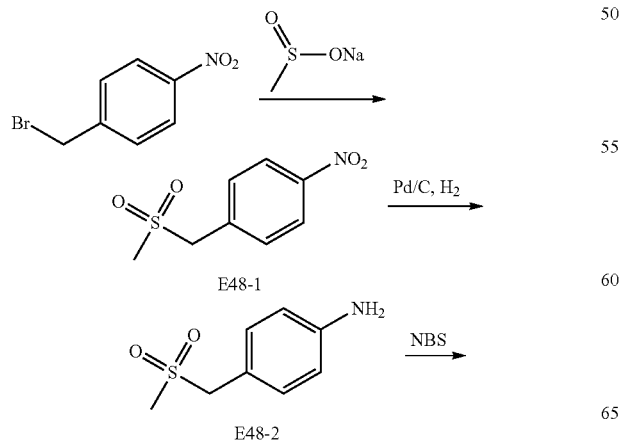

86

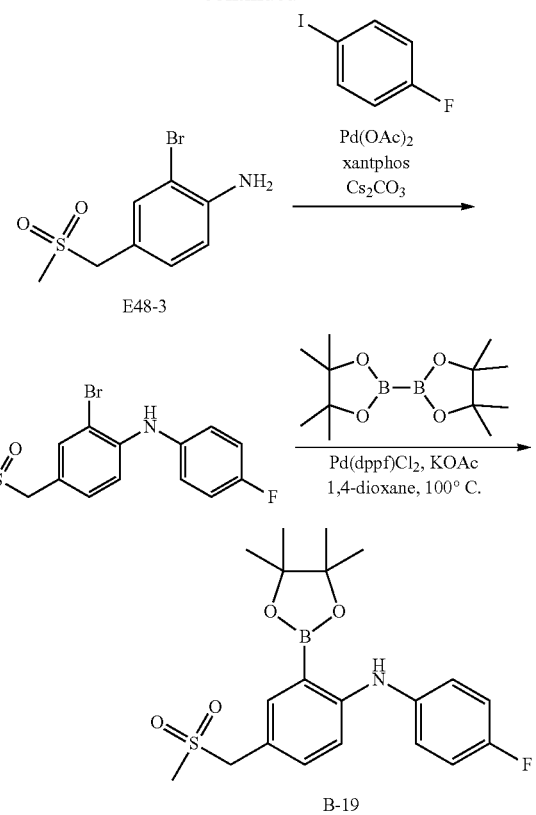

The same method as that in Example 48 was used to give borate B-19, except that p-fluoroiodobenzene (CAS: 352-34-1) was used instead of iodobenzene in step 4. HPLC-MS: [M+H]⁺=406.2.

Example 50: Synthesis of Borate B-20

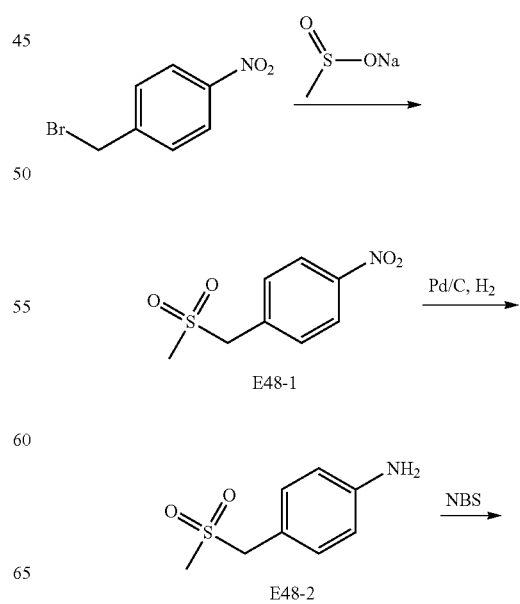

-continued

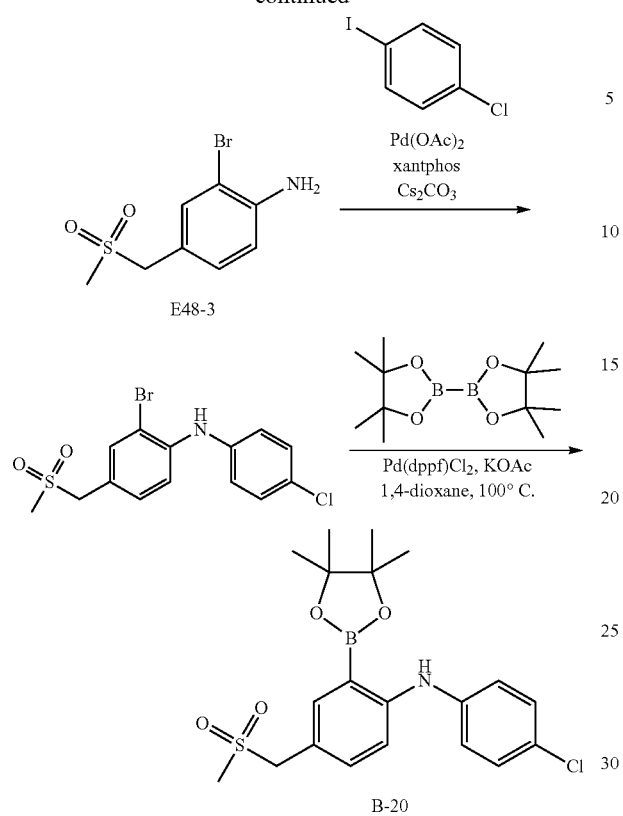

The same method as that in Example 48 was used to give borate B-20, except that p-chloroiodobenzene (CAS: 637-87-6) was used instead of iodobenzene in step 4. HPLC-MS: [M+H]$^+$=422.1.

Example 51: Synthesis of Borate B-21

-continued

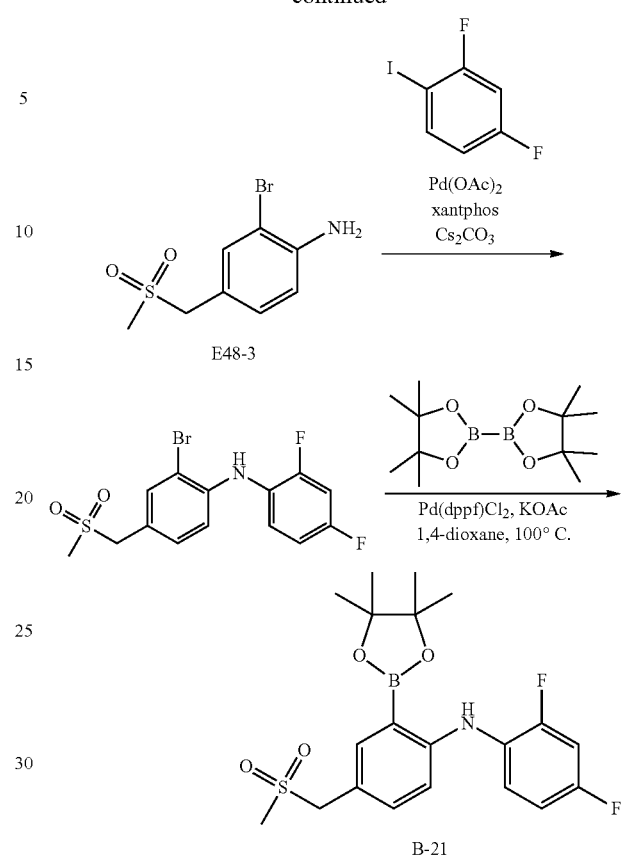

The same method as that in Example 48 was used to give borate B-21, except that 2,4-difluoroiodobenzene (CAS: 2265-93-2) was used instead of iodobenzene in step 4. HPLC-MS: [M+H]$^+$=424.1.

Example 52: Synthesis of Compound ZB-BD-87

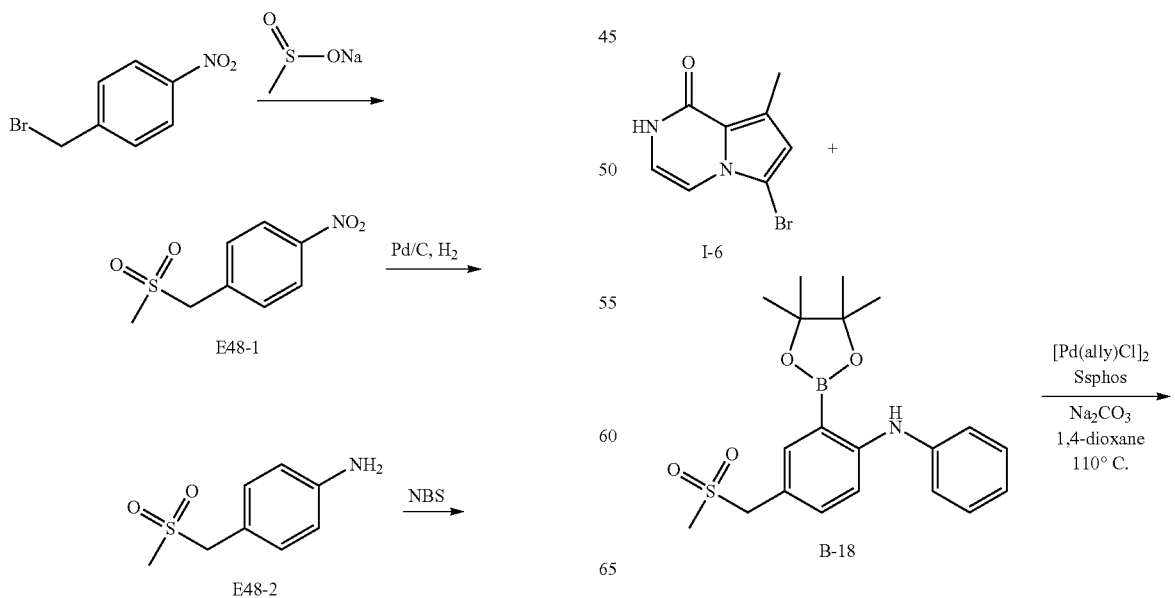

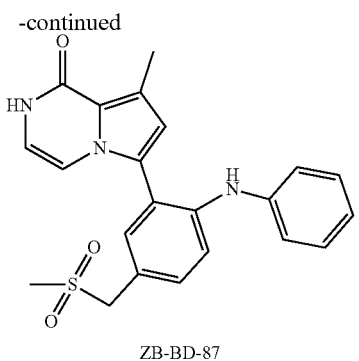

ZB-BD-87

Compound I-6 (46 mg, 0.2 mmol) and borate B-18 (155 mg, 0.4 mmol) were dissolved in 9 mL of 1,4-dioxane, added with 3 mL of 2M sodium carbonate aqueous solution, followed by addition of allylpalladium (II) chloride dimer (7.3 mg, 0.02 mmol) and sodium 2'-dicyclohexylphosphino-2,6-dimethoxy-1,1'-biphenyl-3-sulfonate hydrate (21 mg, 0.04 mmol) under argon. The mixture was stirred at 110° C. for 2 h, diluted with 20 mL of water, extracted with ethyl acetate (20 mL×3), and purified by silica gel column chromatography to give compound ZB-BD-87 (15 mg). $^1$H NMR (400 MHz, DMSO-d$_6$) δ 10.19 (d, J=5.3 Hz, 1H), 7.44 (s, 1H), 7.32 (d, J=7.0 Hz, 3H), 7.19 (t, J=7.8 Hz, 2H), 7.05 (d, J=7.8 Hz, 2H), 6.84 (t, J=7.3 Hz, 1H), 6.67 (d, J=5.7 Hz, 1H), 6.43 (s, 1H), 6.37 (t, J=5.7 Hz, 1H), 4.43 (s, 2H), 2.92 (s, 3H), 2.49 (s, 3H). HPLC-MS: [M+H]$^+$=408.1.

Example 53: Synthesis of Compound ZB-BD-90

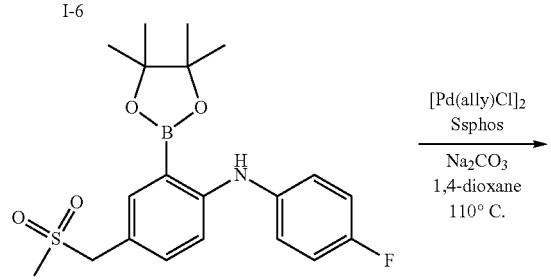

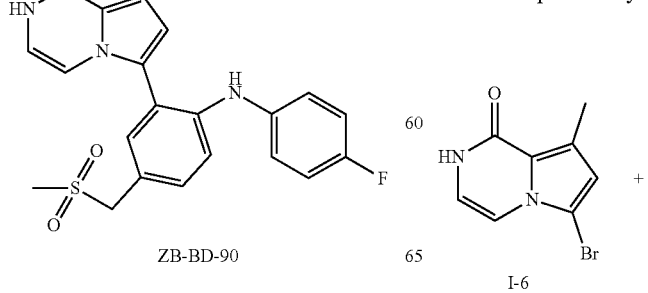

ZB-BD-90

The same method as that in Example 52 was used to give compound ZB-BD-90, except that compound B-19 was used instead of compound B-18. $^1$H NMR (400 MHz, MeOD) 7.37 (d, J=7.5 Hz, 2H), 7.21 (d, J=9.0 Hz, 1H), 7.04 (dd, J=9.0, 4.8 Hz, 2H), 6.94 (t, J=8.7 Hz, 2H), 6.87 (d, J=5.9 Hz, 1H), 6.51 (s, 1H), 6.41 (d, J=5.9 Hz, 1H), 4.39 (s, 2H), 2.93 (s, 3H), 2.58 (s, 3H). HPLC-MS: [M+H]$^+$=426.1.

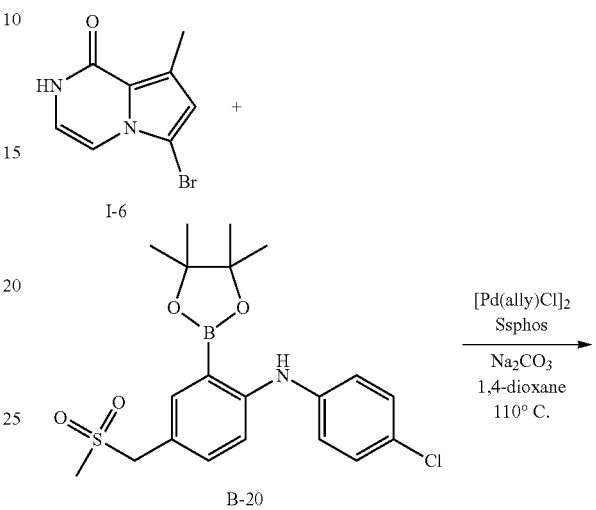

ZB-BD-105

Example 54: Synthesis of Compound ZB-BD-105

The same method as that in Example 52 was used to give compound ZB-BD-105, except that compound B-20 was used instead of compound B-18. $^1$H NMR (400 MHz, MeOD) 10.19 (d, J=5.1 Hz, 1H), 7.62 (s, 1H), 7.41-7.28 (m, 3H), 7.19 (d, J=8.8 Hz, 2H), 7.01 (d, J=8.8 Hz, 2H), 6.63 (d, J=5.9 Hz, 1H), 6.40 (s, 1H), 6.35 (t, J=5.7 Hz, 1H), 4.44 (s, 2H), 2.91 (s, 3H), 2.48 (s, 3H). HPLC-MS: [M+H]$^+$=442.1.

Example 55: Synthesis of Compound ZB-BD-110

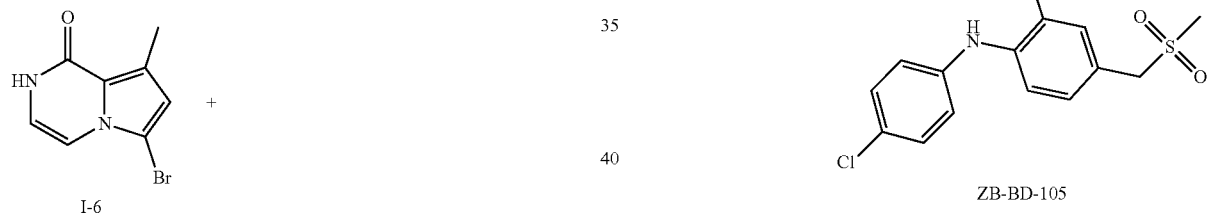

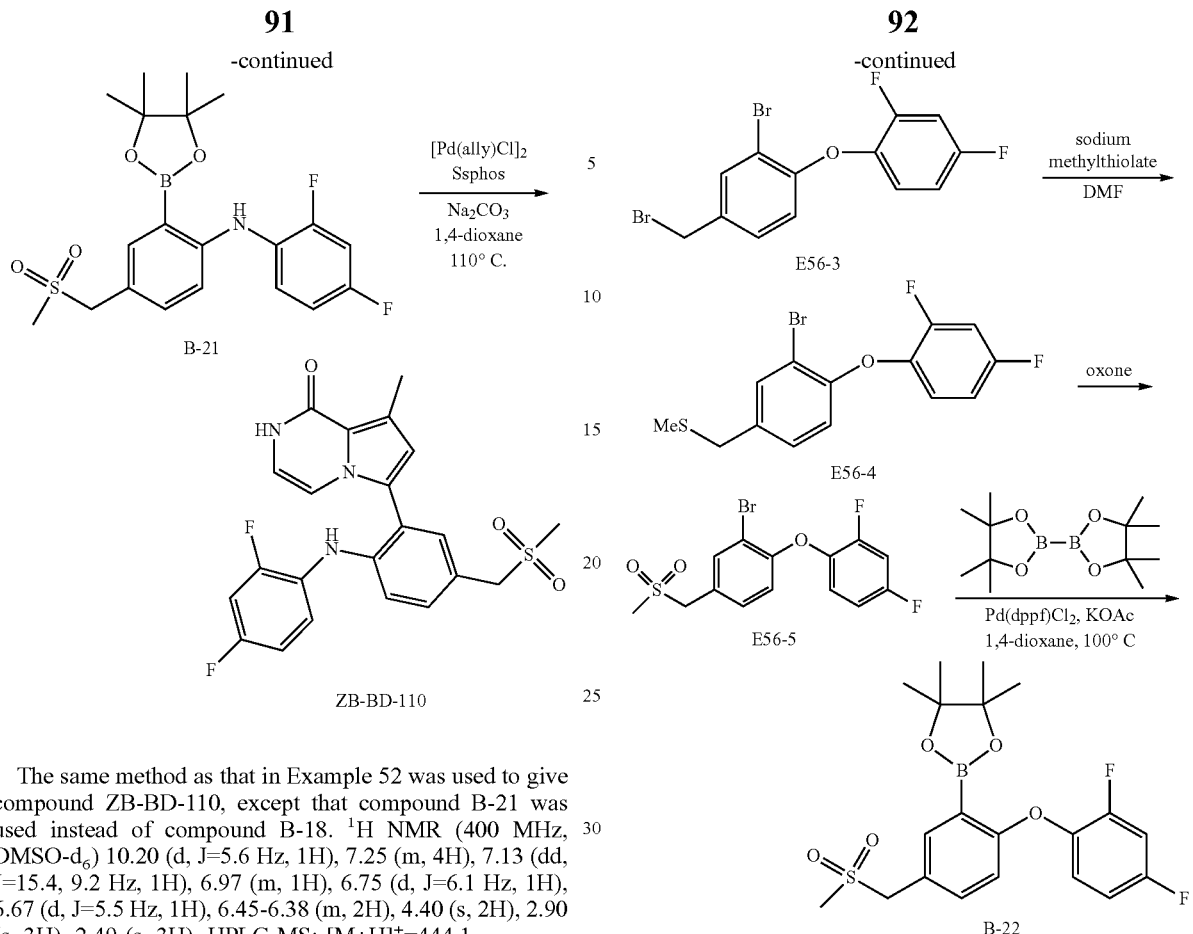

The same method as that in Example 52 was used to give compound ZB-BD-110, except that compound B-21 was used instead of compound B-18. ¹H NMR (400 MHz, DMSO-$d_6$) 10.20 (d, J=5.6 Hz, 1H), 7.25 (m, 4H), 7.13 (dd, J=15.4, 9.2 Hz, 1H), 6.97 (m, 1H), 6.75 (d, J=6.1 Hz, 1H), 6.67 (d, J=5.5 Hz, 1H), 6.45-6.38 (m, 2H), 4.40 (s, 2H), 2.90 (s, 3H), 2.49 (s, 3H). HPLC-MS: [M+H]⁺=444.1.

Example 56: Synthesis of Borate B-22

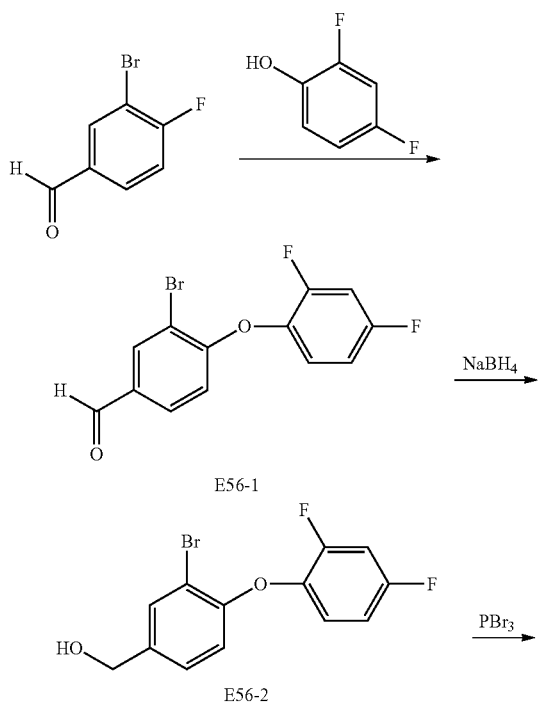

The synthetic method of Example 56 can refer to the literatures J Med. Chem., 2017, 60, 8369; WO 2015058160; US 2014275026.

Step 1

3-bromo-4-fluorobenzaldehyde (2.1 g, 10 mmol, CAS: 77771-02-9), 2,4-difluorophenol (1.43 g, 11 mmol) and cesium carbonate (3.6 g, 11 mmol) were added to 50 mL of dimethyl sulfoxide in sequence, and heated to 100° C. under argon to react for 2 h. The reaction solution was added with 500 mL of water and extracted with ethyl acetate (150 mL×3). The combined organic phase was washed three times with saturated saline, dried over anhydrous sodium sulfate, rotary evaporated under vacuum to remove the solvent, and purified by silica gel column chromatography to give compound E56-1 (2.9 g).

Step 2

Compound E56-1 (1.9 g, 6 mmol) was dissolved in 5 mL of ethanol and 5 mL of tetrahydrofuran, added with sodium borohydride (0.07 g, 1.8 mmol), and reacted at room temperature for 1 h. After part of the solvent was removed, the residue was dissolved with ethyl acetate, added with water and extracted. The combined organic phase was washed three times with saturated saline, dried over anhydrous sodium sulfate, rotary evaporated under vacuum to remove the solvent to give compound E56-2 (1.8 g).

Step 3

Compound E56-2 (1.8 g, 5.6 mmol) was dissolved in 10 mL of dichloromethane, added dropwisely with phosphorus tribromide (0.55 mL, 5.6 mmol) to react at room temperature for 3 h, and poured with ice water. The mixture was adjusted the pH to be basic with aqueous sodium bicarbonate solution, and extracted with dichloromethane. The combined organic phase was washed three times with saturated saline, dried over anhydrous sodium sulfate, and rotary evaporated under vacuum to remove the solvent to give compound E56-3 (1.9 g).

Step 4

Compound E56-3 (1.5 g, 4 mmol) was dissolved in 8 mL of N,N-dimethylformamide (DMF), added with sodium methylthiolate (0.28 g, 4 mmol) to react at room temperature for 6 h. The mixture was dissolved in ethyl acetate, added with water and extraced. The combined organic phase was washed three times with saturated saline, dried over anhydrous sodium sulfate, and rotary evaporated under vacuum to remove the solvent to give compound E56-4 (1.2 g).

Step 5

Compound E56-4 (0.7 g, 2 mmol) was dissolved in 8 mL of methanol, added with Potassiumhydrogenperoxymonosulfate (oxone, CAS: 70693-62-8) (2.6 g, 4.2 mmol, dissolved in 8 mL of water) 0° C., returned to room temperature to react for 1 h. The mixture was dissolved with ethyl acetate, added with water and extracted. The combined organic phase was washed three times with saturated saline, dried over anhydrous sodium sulfate, rotary evaporated under vacuum to remove the solvent, and separated through column chromatography to give compound E56-5 (0.6 g). HPLC-MS: [M+H]$^+$=377.1/379.1.

Step 6

E56-5 (488 mg, 1.29 mmol), potassium acetate (380 mg, 3.87 mmol), bis(pinacolato)diboron (665 mg, 258 mmol) were dissolved in 15 mL of dioxane, added with [1,1'-bis(diphenylphosphino)ferrocene]palladium dichloride (47 mg, 0.065 mmol) under argon, heated to 100° C. to react for 2 h, cooled to room temperature, and filtered through celite. The filtrate was added with water and ethyl acetate for layering. The organic layer was washed with saturated saline, dried over anhydrous sodium sulfate, rotary evaporated under vacuum to remove the solvent, and passed through silica gel column chromatography to give borate B-22 (150 mg).

Example 57: Synthesis of Borate B-23

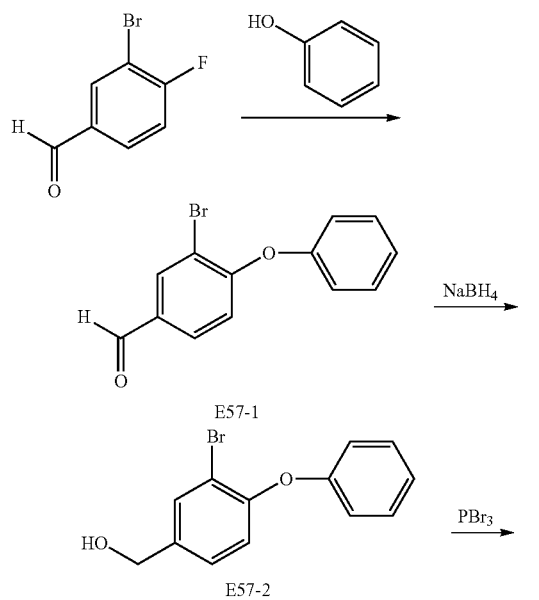

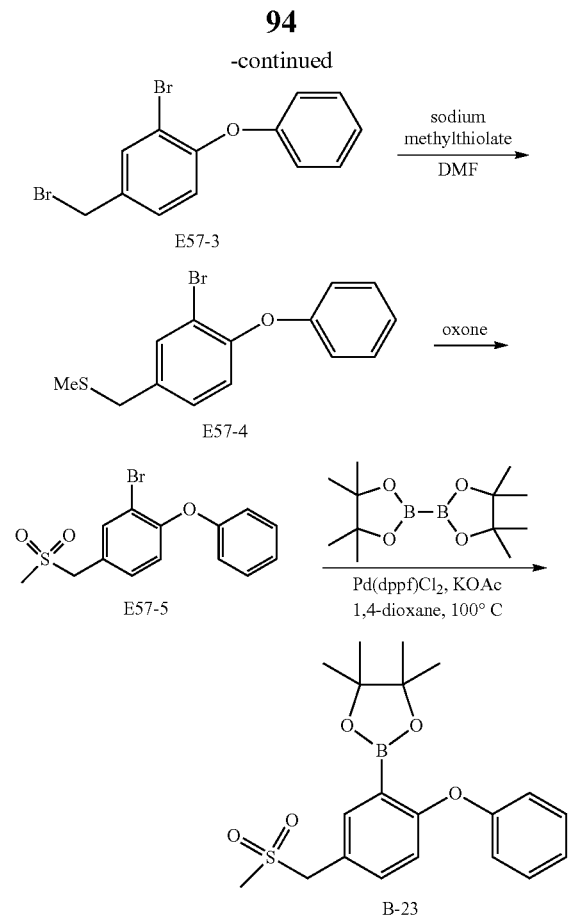

The same method as that in Example 56 was used to give borate B-23, except that phenol was used instead of 2,4-difluorophenol in Step 1.

Example 58: Synthesis of Borate B-24

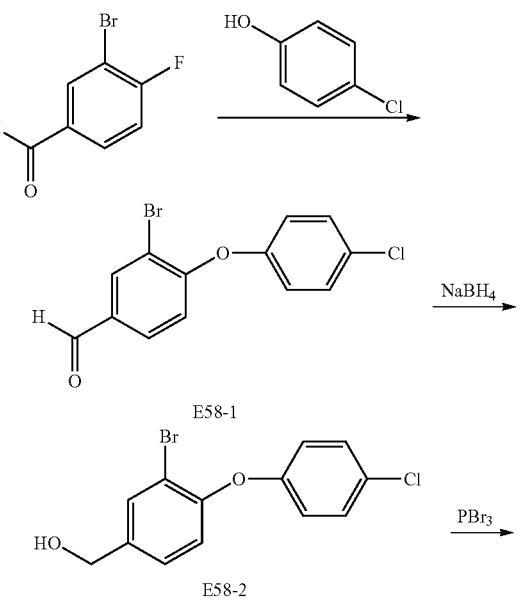

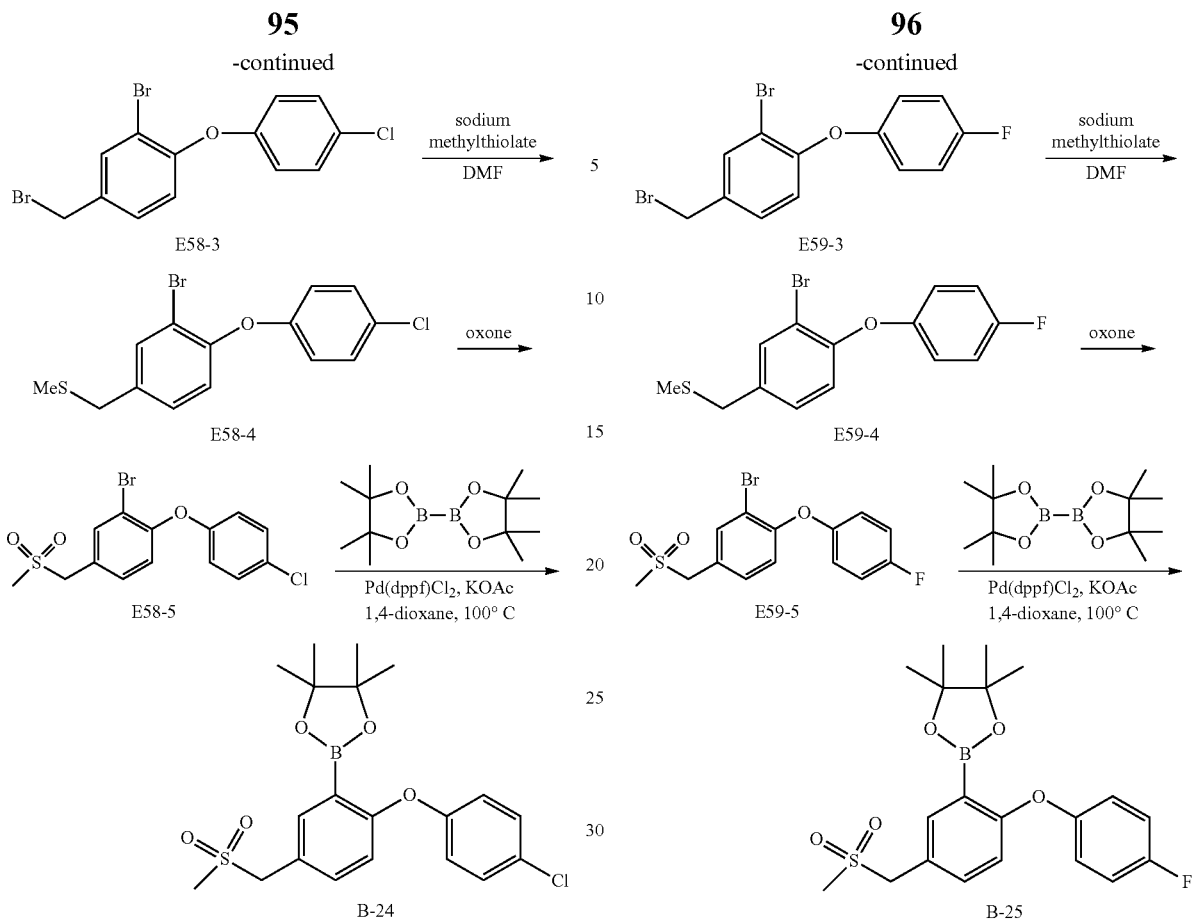
The same method as that in Example 56 was used to give borate B-24, except that p-chlorophenol (CAS: 106-48-9) was used instead of 2,4-difluorophenol in step 1.
Example 59: Synthesis of Borate B-25
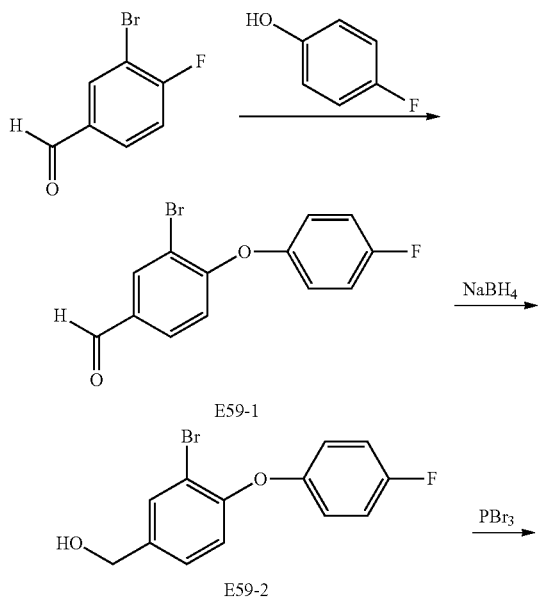
The same method as that in Example 56 was used to give borate B-25, except that p-fluorophenol (CAS: 371-41-5) was used instead of 2,4-difluorophenol in step 1.
Example 60: Synthesis of Borate B-26
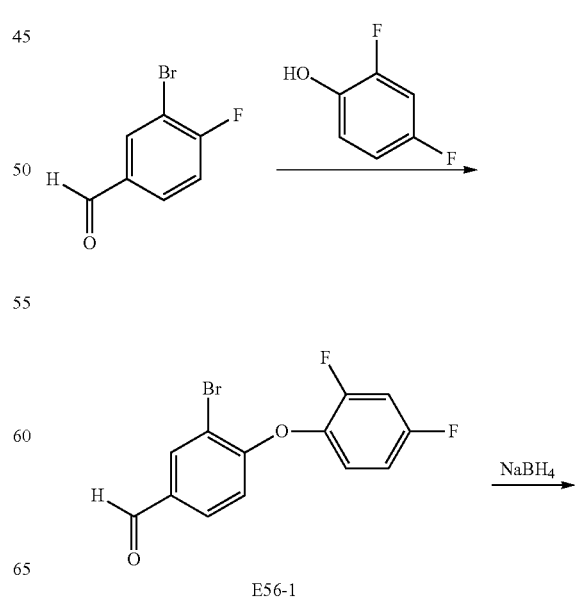

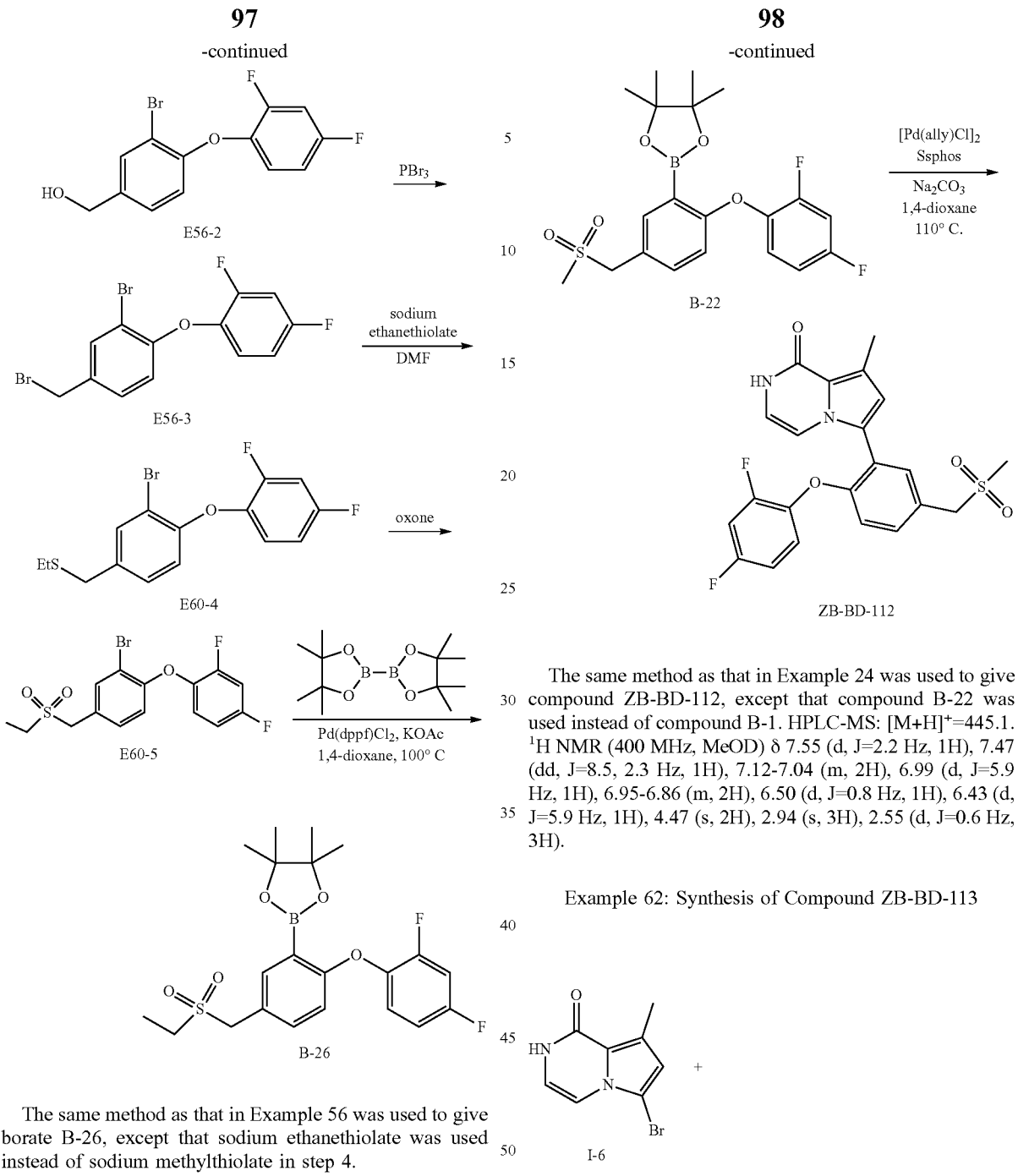
The same method as that in Example 24 was used to give compound ZB-BD-112, except that compound B-22 was used instead of compound B-1. HPLC-MS: [M+H]⁺=445.1. $^1$H NMR (400 MHz, MeOD) δ 7.55 (d, J=2.2 Hz, 1H), 7.47 (dd, J=8.5, 2.3 Hz, 1H), 7.12-7.04 (m, 2H), 6.99 (d, J=5.9 Hz, 1H), 6.95-6.86 (m, 2H), 6.50 (d, J=0.8 Hz, 1H), 6.43 (d, J=5.9 Hz, 1H), 4.47 (s, 2H), 2.94 (s, 3H), 2.55 (d, J=0.6 Hz, 3H).
Example 62: Synthesis of Compound ZB-BD-113
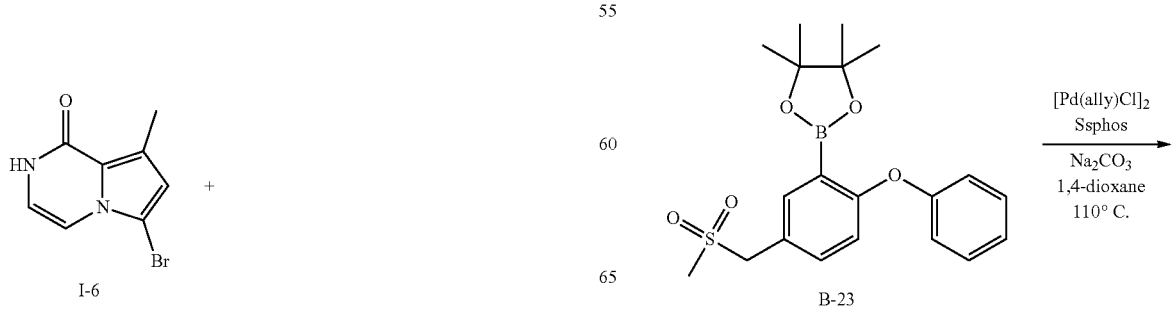

-continued

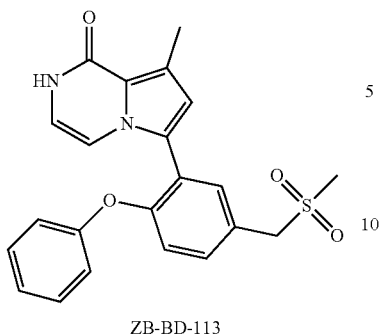

ZB-BD-113

The same method as that in Example 24 was used to give compound ZB-BD-113, except that compound B-23 was used instead of compound B-1. HPLC-MS: [M+H]⁺=409.1. ¹H NMR (400 MHz, DMSO-d₆) δ 10.27 (d, J=5.6 Hz, 1H), 7.52 (s, 1H), 7.46 (d, J=8.5 Hz, 1H), 7.35 (t, J=7.8 Hz, 2H), 7.13 (t, J=7.4 Hz, 1H), 6.99 (dd, J=8.3, 4.8 Hz, 3H), 6.90 (d, J=5.9 Hz, 1H), 6.48-6.36 (m, 2H), 4.53 (s, 2H), 2.94 (s, 3H), 2.44 (s, 3H).

Example 63: Synthesis of Compound ZB-BD-114

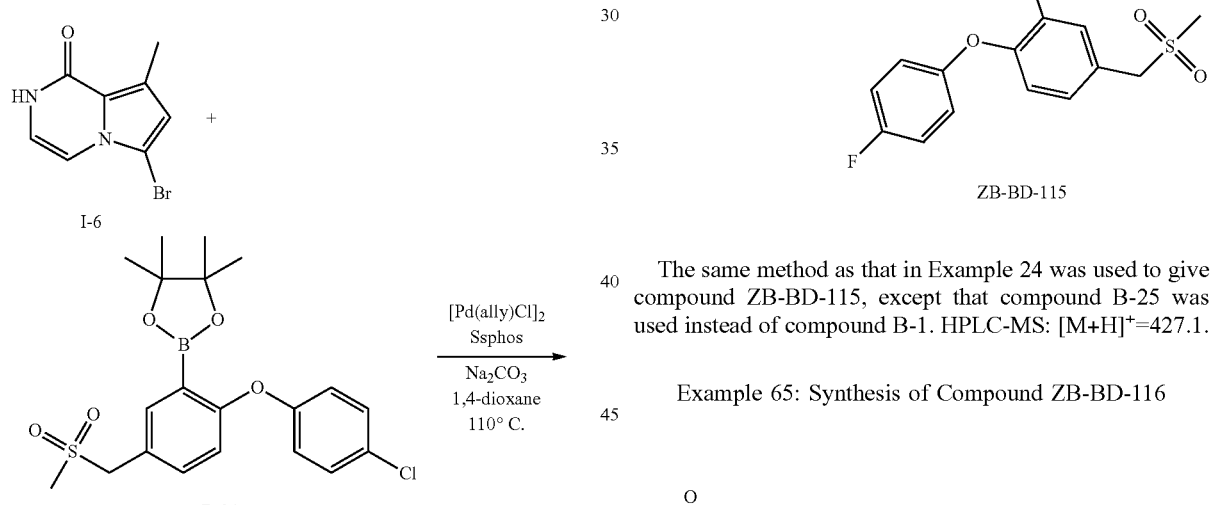

ZB-BD-114

The same method as that in Example 24 was used to give compound ZB-BD-114, except that compound B-24 was used instead of compound B-1. HPLC-MS: [M+H]⁺=443.1.

Example 64: Synthesis of Compound ZB-BD-116

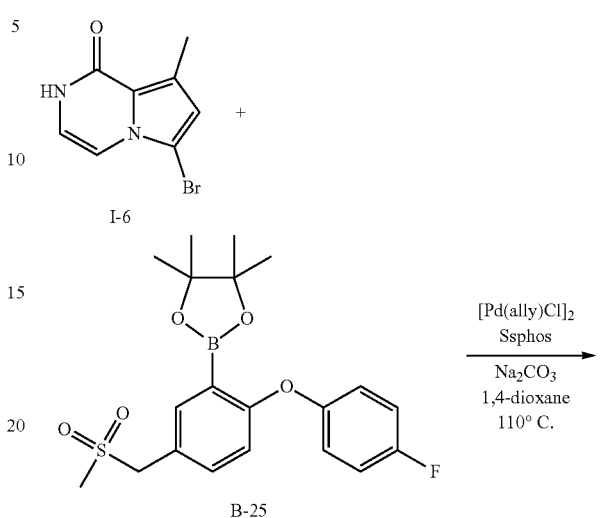

ZB-BD-115

The same method as that in Example 24 was used to give compound ZB-BD-115, except that compound B-25 was used instead of compound B-1. HPLC-MS: [M+H]⁺=427.1.

Example 65: Synthesis of Compound ZB-BD-116

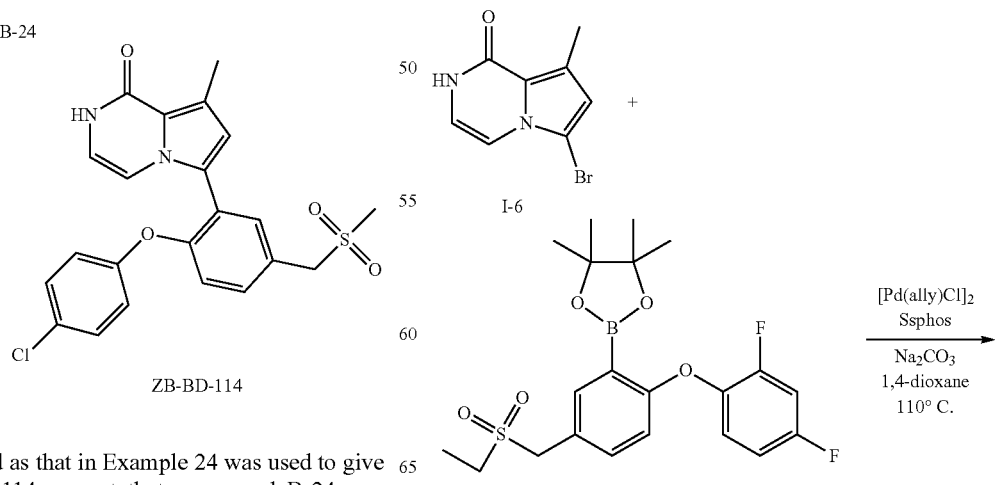

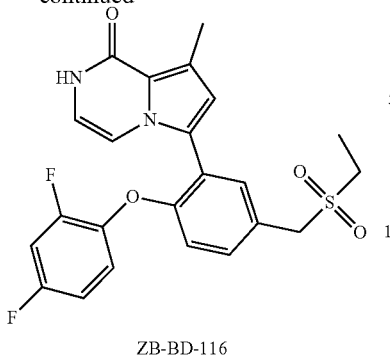

ZB-BD-116

The same method as that in Example 24 was used to give compound ZB-BD-116, except that compound B-26 was used instead of compound B-1. HPLC-MS: [M+H]⁺=459.1. ¹H NMR (400 MHz, MeOD) δ7.53 (d, J=2.2 Hz, 1H), 7.46 (dd, J=8.5, 2.3 Hz, 1H), 7.12-7.04 (m, 2H), 6.98 (d, J=5.9 Hz, 1H), 6.94-6.86 (m, 2H), 6.50 (d, J=0.7 Hz, 1H), 6.43 (d, J=5.9 Hz, 1H), 4.43 (s, 2H), 3.08 (q, J=7.5 Hz, 2H), 2.54 (s, 3H), 1.35 (t, J=7.5 Hz, 3H).

Example 66: Synthesis of Compound ZB-BD-117

Synthesis of Raw Material B-27

The same method as that in Example 48 was used to give borate B-27, except that Step 4 was omitted and Step 5 was directly carried out with compound E48-3.

Step 1

Compound I-6 (46 mg, 0.2 mmol) and borate B-27 (155 mg, 0.4 mmol) were dissolved in 9 mL of 1,4-dioxane, added with 3 mL of 2M aqueous sodium carbonate solution, followed by addition of allyl palladium (II) chloride dimer (7.3 mg, 0.02 mmol) and sodium 2'-dicyclohexylphosphino-2,6-dimethoxy-1,1'-biphenyl-3-sulfonate hydrate (21 mg, 0.04 mmol) under argon. The mixture was stirred at 110° C. for 2 h, diluted with water, extracted with ethyl acetate (20 mL×3), and purified by silica gel column chromatography to give compound E66-1 (12 mg). ¹H NMR (400 MHz, DMSO-d₆) δ 10.21 (d, J=5.1 Hz, 1H), 7.15 (dd, J=8.3, 2.0 Hz, 1H), 7.08 (d, J=1.9 Hz, 1H), 6.79 (d, J=8.3 Hz, 1H), 6.61 (d, J=5.7 Hz, 1H), 6.43 (t, J=5.7 Hz, 1H), 6.39 (s, 1H), 5.13 (s, 2H), 4.29 (s, 2H), 2.85 (s, 3H). HPLC-MS: [M+H]⁺= 332.1.

Step 2

Compound E66-1 (10 mg) was dissolved in 1 mL of dichloroethane, added with 0.5 mL of acetic acid, 10 mg of sodium cyanoborohydride and cyclopropylformaldehyde (5 μL, commercially available, CAS: 1489-69-6), and stirred at room temperature for 2 h. The solvent was removed and the

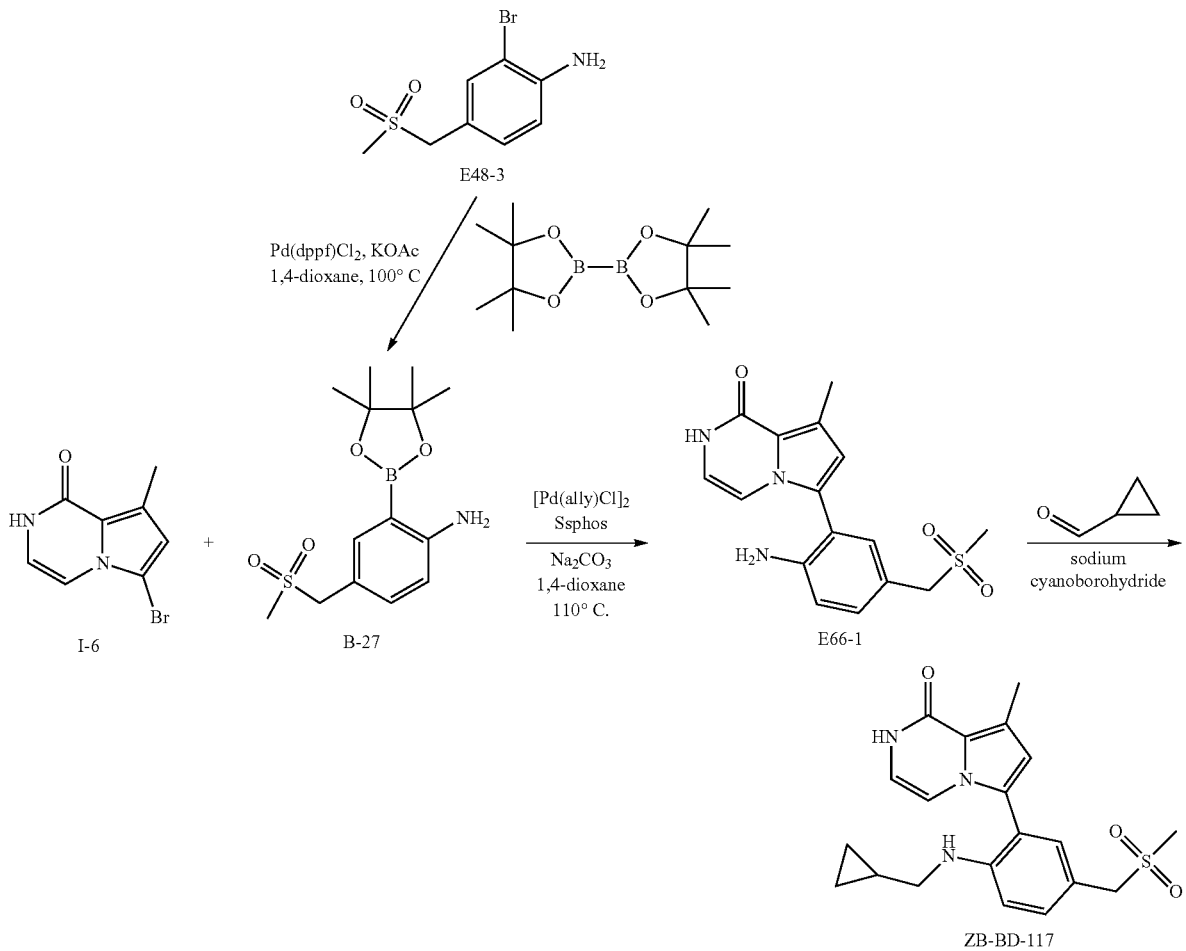

residue was purified by silica gel column chromatography to give compound ZB-BD-117 (5 mg). $^1$H NMR (400 MHz, DMSO-d$_6$) δ 10.24 (s, 1H), 7.27 (m, 1H), 7.10 (s, 1H), 6.80 (m, 1H), 6.56 (m, 1H), 6.41 (m, 2H), 4.87 (brs, 1H), 4.32 (s, 2H), 2.95 (m, 2H), 2.86 (s, 3H), 2.50 (s, 3H), 1.04 (m, 1H), 0.40 (m, 2H), 0.17 (m, 2H). HPLC-MS: [M+H]$^+$=386.2.

Example 67: Synthesis of Compound ZB-BD-118

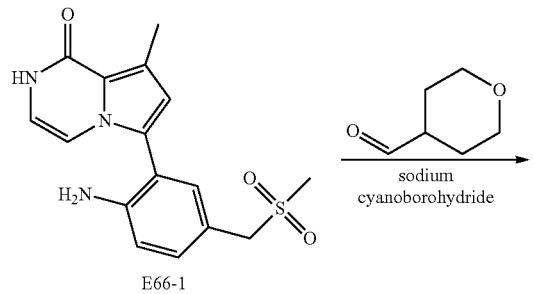

E66-1

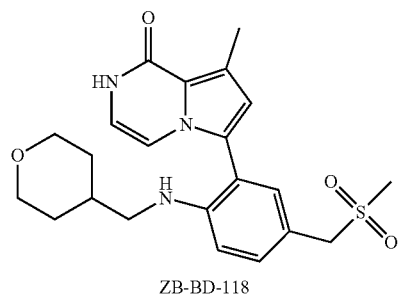

ZB-BD-118

Compound E66-1 (10 mg) was dissolved in 1 mL of dichloroethane, added with 0.5 mL of acetic acid, 10 mg of sodium cyanoborohydride and tetrahydropyran-4-carbaldehyde (10 μL, commercially available, CAS: 50675-18-8), and stirred at room temperature for 3 h. The solvent was removed and the residue was purified by silica gel column chromatography to give compound ZB-BD-118 (4 mg). $^1$H NMR (400 MHz, DMSO-d$_6$) δ 10.19 (d, J=4.8 Hz, 1H), 7.25 (d, J=7.7 Hz, 1H), 7.05 (s, 1H), 6.73 (d, J=8.6 Hz, 1H), 6.50 (d, J=5.5 Hz, 1H), 6.38 (m, 2H), 4.99 (s, 1H), 4.29 (s, 2H), 3.79 (d, J=8.9 Hz, 2H), 3.21 (t, J=11.2 Hz, 2H), 2.92 (m, 2H), 2.84 (s, 3H), 2.51 (s, 3H), 1.75 (m, 1H), 1.54 (m, 2H), 1.10 (m, 2H). HPLC-MS: [M+H]$^+$=430.2.

Example 68: Synthesis of Compound ZB-BD-119

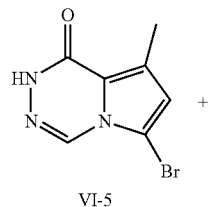

VI-5

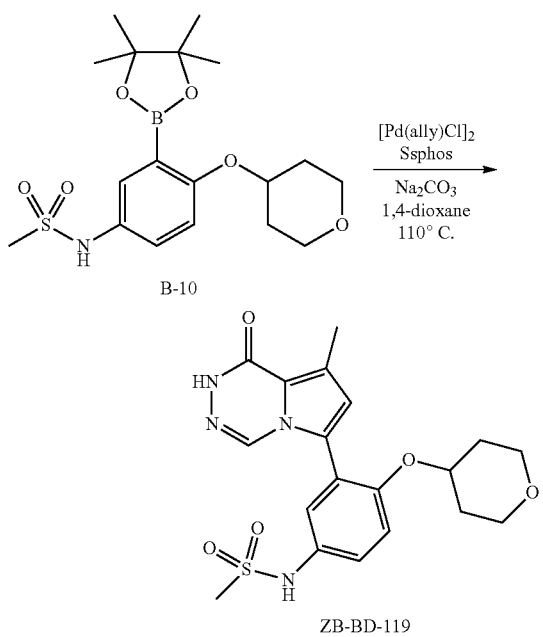

The same method as that in Example 24 was used to give compound ZB-BD-119, except that compound VI-5 was used instead of compound I-6 and compound B-10 was used instead of compound B-1. $^1$H NMR (400 MHz, DMSO-d$_6$) δ 11.55 (s, 1H), 9.60 (s, 1H), 7.89 (s, 1H), 7.33-7.19 (m, 3H), 6.59 (s, 1H), 4.65-4.51 (m, 1H), 3.58-3.48 (m, 2H), 3.40 (m, 2H), 2.98 (s, 3H), 2.50 (s, 3H), 1.95-1.76 (m, 2H), 1.42 (m, 2H). HPLC-MS: [M+H]$^+$=419.1.

Example 69: Synthesis of Compound ZB-BD-120

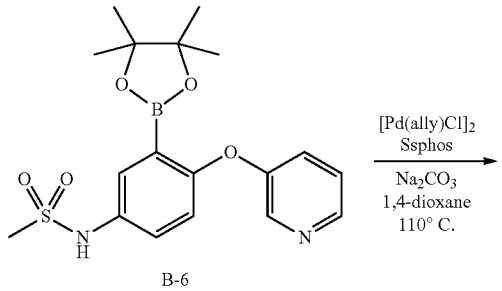

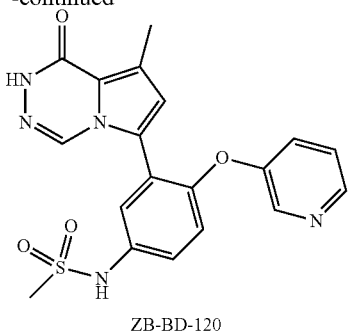

ZB-BD-120

The same method as that in Example 24 was used to give compound ZB-BD-120, except that compound VI-5 was used instead of compound I-6 and compound B-6 was used instead of compound B-1. $^1$H NMR (400 MHz, MeOD) δ 8.21 (m, 1H), 8.13 (s, 1H), 8.09 (s, 1H), 7.48 (m, 2H), 7.33 (m, 2H), 7.28-7.24 (m, 1H), 6.59 (s, 1H), 3.07 (s, 3H), 2.47 (s, 3H). HPLC-MS: [M+H]$^+$=412.1.

Example 70: Synthesis of Compound ZB-BD-121

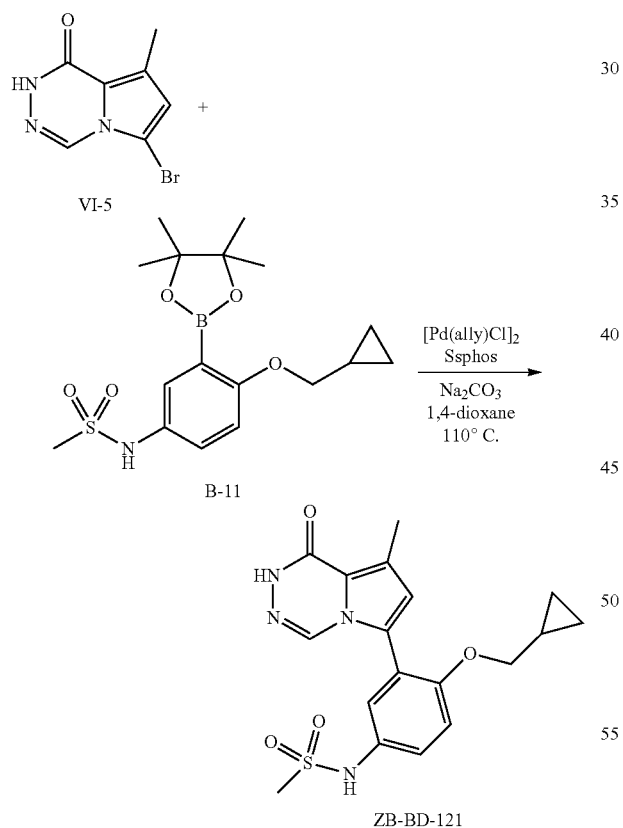

ZB-BD-121

The same method as that in Example 24 was used to give compound ZB-BD-121, except that compound VI-5 was used instead of compound I-6 and compound B-11 was used instead of compound B-1. $^1$H NMR (400 MHz, DMSO-d$_6$) δ 11.54 (s, 1H), 9.56 (s, 1H), 7.90 (s, 1H), 7.29 (dd, J=8.8, 2.6 Hz, 1H), 7.22 (d, J=2.6 Hz, 1H), 7.14 (d, J=8.9 Hz, 1H), 6.58 (s, 1H), 3.88 (d, J=6.9 Hz, 2H), 2.96 (s, 3H), 2.50 (s, 3H), 1.12-1.01 (m, 1H), 0.51-0.40 (m, 2H), 0.33-0.18 (m, 2H). HPLC-MS: [M+H]$^+$=389.1.

Example 71: Synthesis of Compound ZB-BD-122

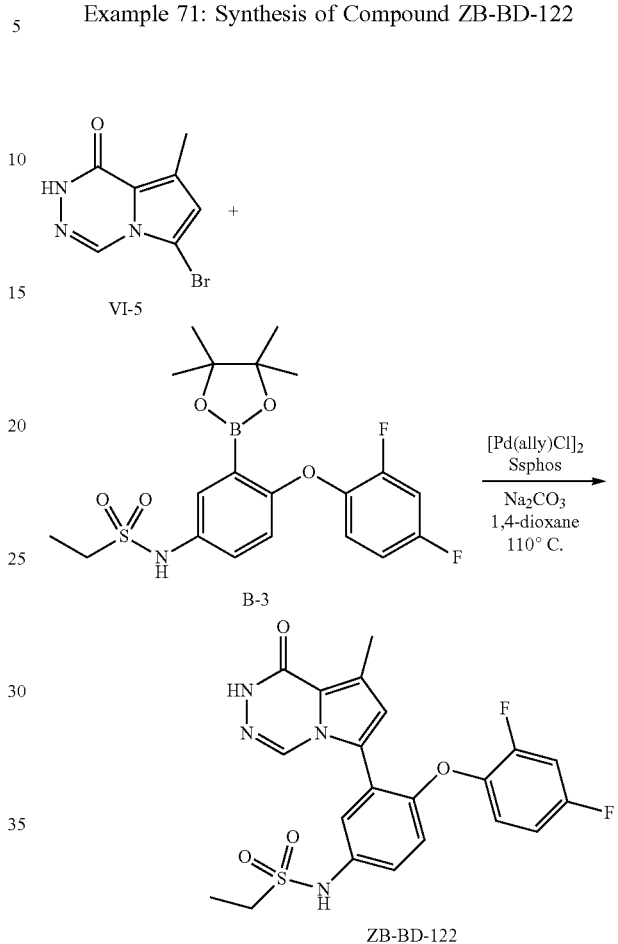

ZB-BD-122

The same method as that in Example 24 was used to give compound ZB-BD-122, except that compound VI-5 was used instead of compound I-6 and compound B-3 was used instead of compound B-1. HPLC-MS: [M+H]$^+$=461.1.

Example 72: Synthesis of Borate B-28

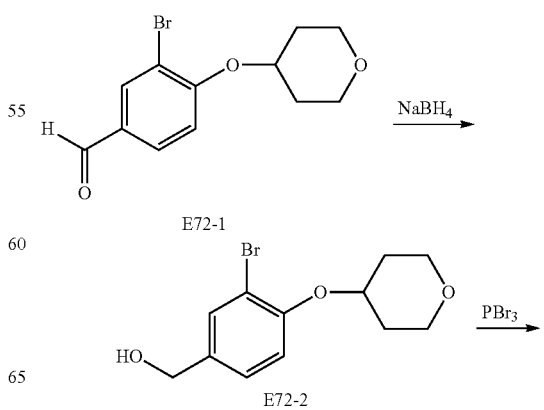

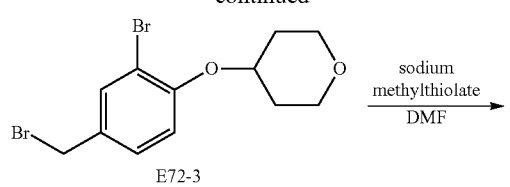
E72-3
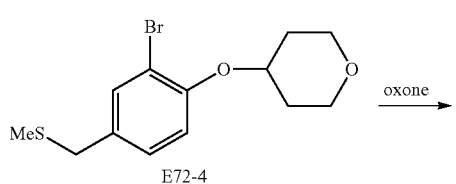
E72-4
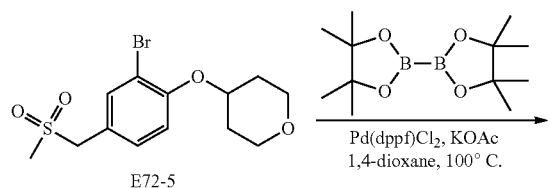
E72-5
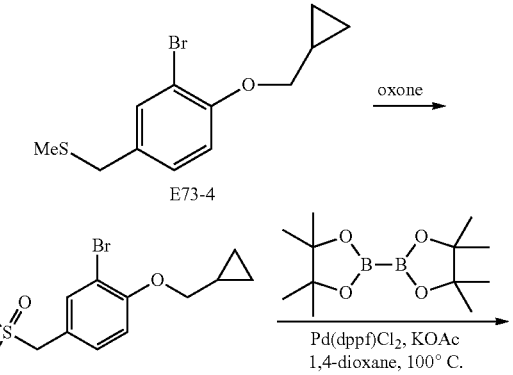
E73-3, E73-4, E73-5
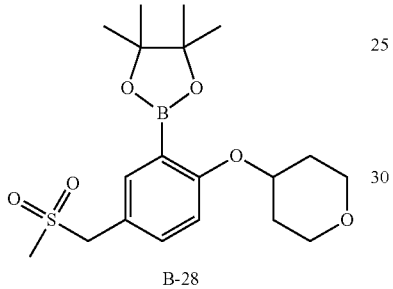
B-28
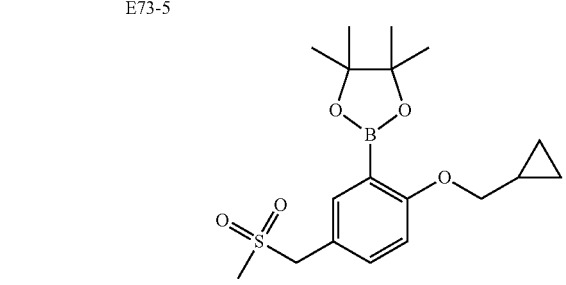
B-29
Borate B-28 was prepared in the same procedures as those in Steps 2-6 of Example 56, except that E72-1 was used instead of E56-1 as the raw material.
Borate B-29 was prepared in the same procedures as those in Steps 2-6 of Example 56 except that E73-1 was used instead of E56-1 as the raw material.
Example 73: Synthesis of Borate B-29
Example 74: Synthesis of Borate B-30
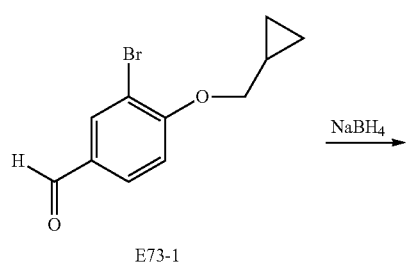
E73-1, E73-2
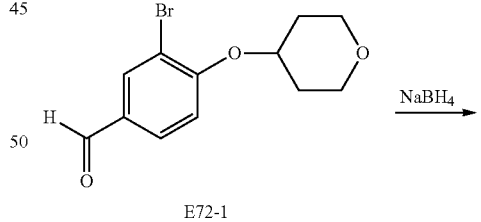
E72-1
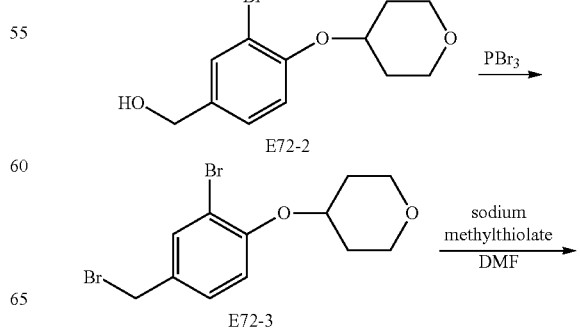
E72-2, E72-3
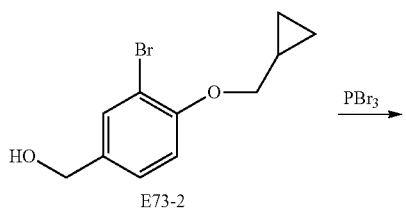

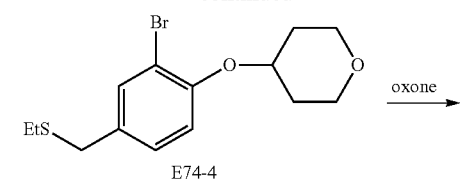

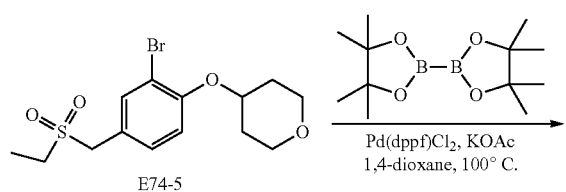

Borate B-30 was prepared in the same procedures as those in Steps 2-6 of Example 56, except that E72-1 was used instead of E56-1 as the raw material and sodium ethanethiolate was used instead of sodium methylthiolate.

Example 75: Synthesis of Compound ZB-BD-123

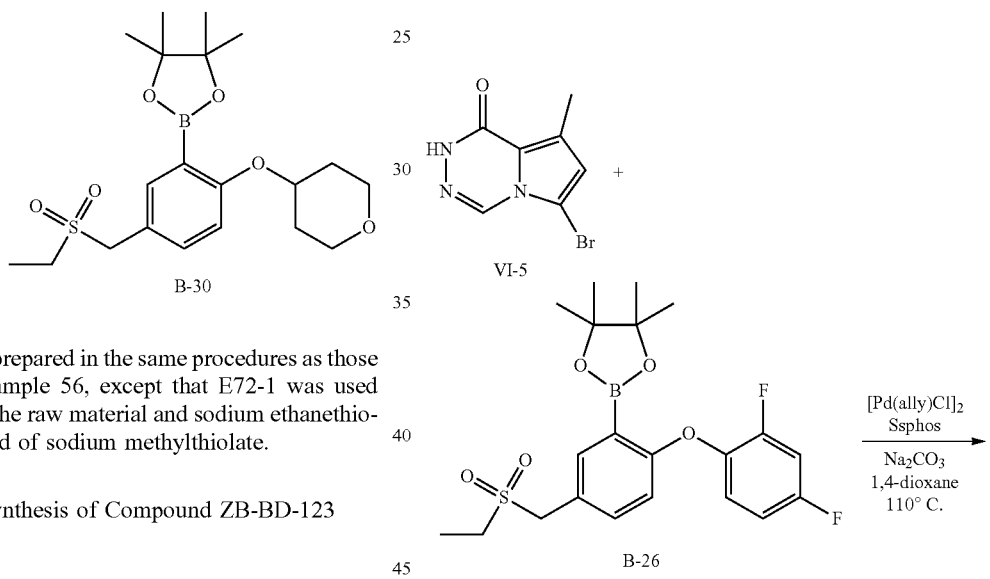

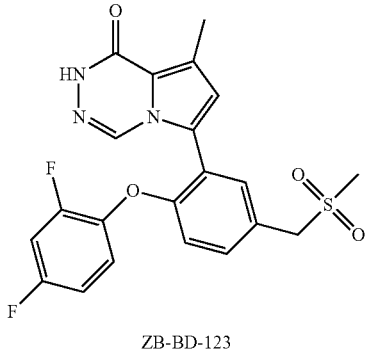

The same method as that in Example 24 was used to give compound ZB-BD-123, except that compound VI-5 was used instead of compound I-6 and compound B-22 was used instead of compound B-1. HPLC-MS: [M+H]$^+$=446.1.

Example 76: Synthesis of Compound ZB-BD-124

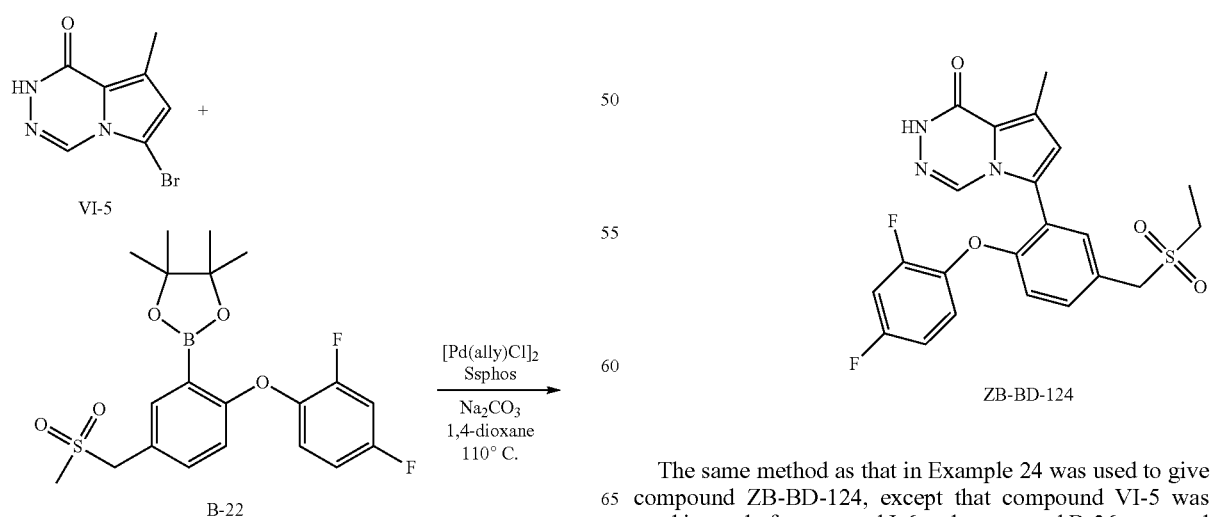

The same method as that in Example 24 was used to give compound ZB-BD-124, except that compound VI-5 was used instead of compound I-6 and compound B-26 was used instead of compound B-1. HPLC-MS: [M+H]$^+$=460.1.

Example 77: Synthesis of Compound ZB-BD-125

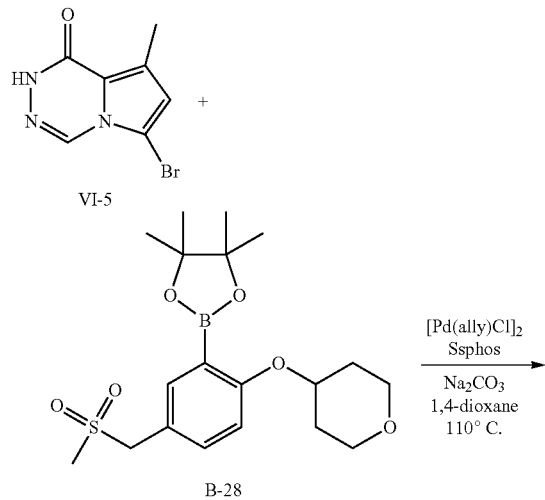

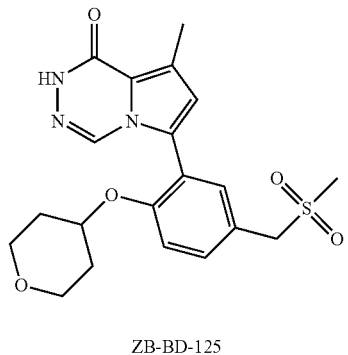

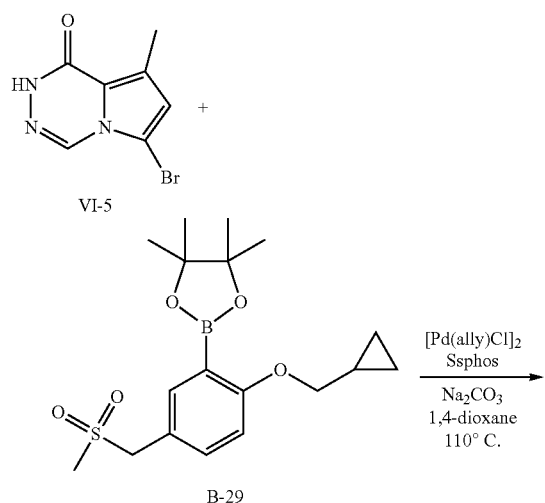

The same method as that in Example 24 was used to give compound ZB-BD-125, except that compound VI-5 was used instead of compound I-6 and compound B-28 was used instead of compound B-1. HPLC-MS: $[M+H]^+=418.1$.

Example 78: Synthesis of Compound ZB-RD-126

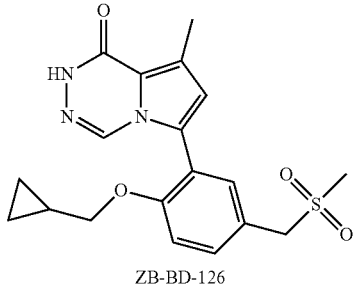

The same method as that in Example 24 was used to give compound ZD-BD-126, except that compound VI-5 was used instead of compound I-6 and compound B-29 was used instead of compound B-1. HPLC-MS: $[M+H]^+=388.1$.

Example 79: Synthesis of Compound ZB-BD-127

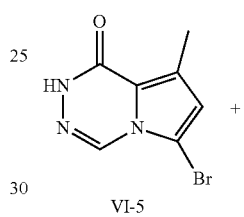

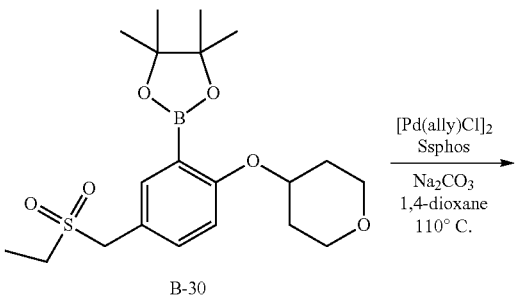

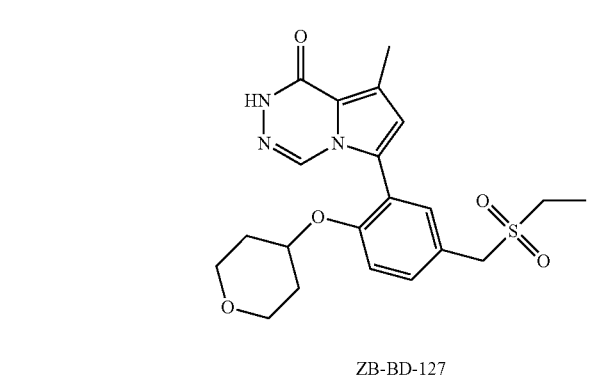

The same method as that in Example 24 was used to give compound ZB-BD-127, except that compound VI-5 was used instead of compound I-6 and compound B-30 was used instead of compound B-1. HPLC-MS: $[M+H]^+=432.1$.

Example 80: Synthesis of Compound ZB-BD-68

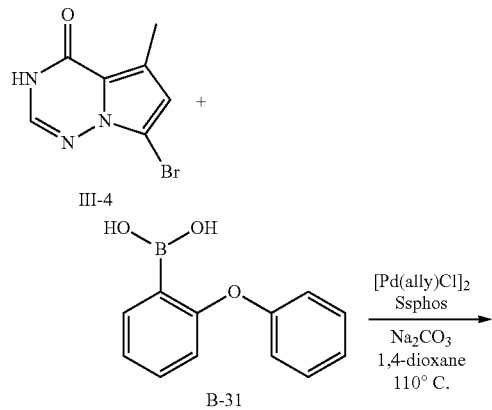

The same method as that in Example 24 was used to give compound ZB-BD-68, except that compound III-4 was used instead of compound I-6 and a commercially available boric acid B-31 (CAS: 108238-09-1) was used instead of compound B-1. $^1$H NMR (400 MHz, CDCl$_3$) δ 10.82 (s, 1H), 7.69 (dd, J=7.7, 1.7 Hz, 1H), 7.46 (d, J=3.3 Hz, 1H), 7.40-7.29 (m, 3H), 7.23 (td, J=7.6, 1.2 Hz, 1H), 7.09 (dd, J=10.6, 4.2 Hz, 1H), 7.01 (m, 3H), 6.55 (m, 1H), 2.57 (s, 3H). HPLC-MS: [M+H]$^+$=318.1.

Example 81: Synthesis of Compound ZB-BD-73

The same method as that in Example 24 was used to give compound ZB-BD-73, except that a commercially available boric acid B-31 (CAS: 108238-09-1) was used instead of compound B-1. $^1$H NMR (400 MHz, CDCl$_3$) δ 9.64 (s, 1H), 7.46 (dd, J=7.6, 1.7 Hz, 1H), 7.43-7.35 (m, 1H), 7.29-7.18 (m, 3H), 7.09-7.01 (m, 2H), 6.89 (m, 3H), 6.41 (s, 1H), 6.38 (m, 1H), 2.59 (s, 3H). HPLC-MS: [M+H]$^+$=317.1.

Example 82: Synthesis of Compound ZB-BD-128

The same method as that in Example 24 was used to give compound ZB-BD-128, except that compound B-28 was used instead of compound B-1. HPLC-MS: [M+H]$^+$*=417.1. $^1$H NMR (400 MHz, acetonitrile-d$_3$) δ 8.74 (s, 1H), 7.45 (dd, J=8.5, 2.3 Hz, 1H), 7.39 (d, J=2.3 Hz, 1H), 7.19 (d, J=8.6 Hz, 1H), 6.71 (d, J=5.9 Hz, 1H), 6.41 (s, 1H), 6.39-6.33 (m, 1H), 4.64-4.55 (m, 1H), 4.31 (s, 2H), 3.72-3.61 (m, 2H), 3.49-3.38 (m, 2H), 2.85 (s, 3H), 2.56 (s, 3H), 1.96-1.87 (m, 2H), 1.61-1.51 (m, 2H).

Example 83: Synthesis of Compound ZB-BD-129

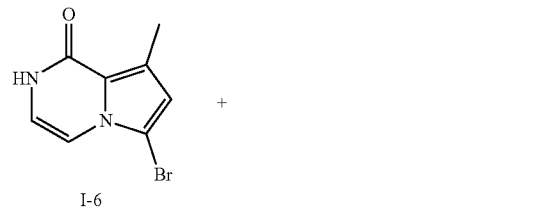

I-6

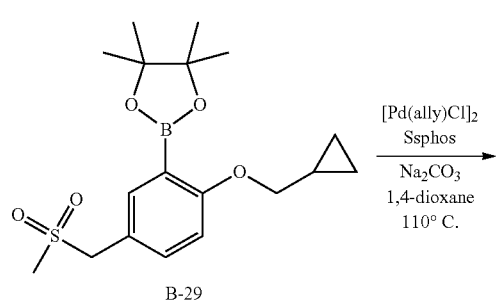

B-29

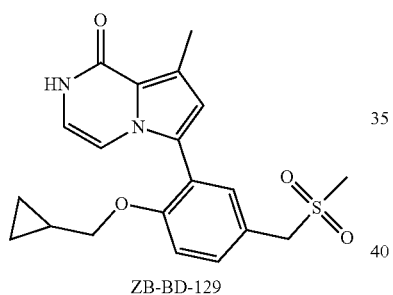

ZB-BD-129

The same method as that in Example 24 was used to give compound ZB-BD-129, except that compound B-29 was used instead of compound B-1. HPLC-MS: [M+H]⁺*=387.1. $^1$H NMR (400 MHz, DMSO-d$_6$) δ 10.22 (d, J=5.5 Hz, 1H), 7.43 (dd, J=8.5, 2.3 Hz, 1H), 7.34 (d, J=2.3 Hz, 1H), 7.17 (d, J=8.6 Hz, 1H), 6.68 (d, J=6.0 Hz, 1H), 6.41 (t, J=5.7 Hz, 1H), 6.37 (s, 1H), 4.44 (s, 2H), 3.90 (d, J=6.9 Hz, 2H), 2.89 (s, 3H), 2.50 (s, 3H), 1.16-1.06 (m, 1H), 0.50-0.41 (m, 2H), 0.29-0.21 (m, 2H).

Example 84: Synthesis of Compound ZB-BD-130

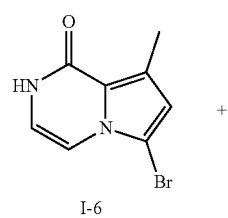

I-6

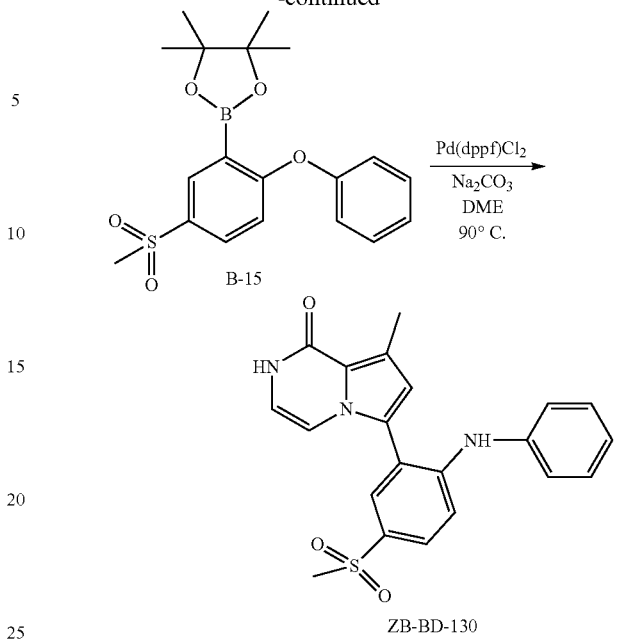

B-15

ZB-BD-130

The same method as that in Example 37 was used to give compound ZB-BD-130, except that compound B-15 was used instead of compound B-16. H NMR (400 MHz, DMSO-d) δ 10.23 (d, J=5.3 Hz, 1H), 7.94 (s, 1H), 7.74 (dd, J=8.8, 2.3 Hz, 1H), 7.66 (d, J=2.3 Hz, 1H), 7.34-7.23 (m, 3H), 7.19 (m, 2H), 7.04 (t, J=7.3 Hz, 1H), 6.68 (d, J=5.7 Hz, 1H), 6.52 (s, 1H), 6.40 (t, J=5.7 Hz, 1H), 3.18 (s, 3H), 2.50 (s, 3H). HPLC-MS: [M+H]⁺=394.1.

Example 85: Synthesis of Compound ZB-BD-131

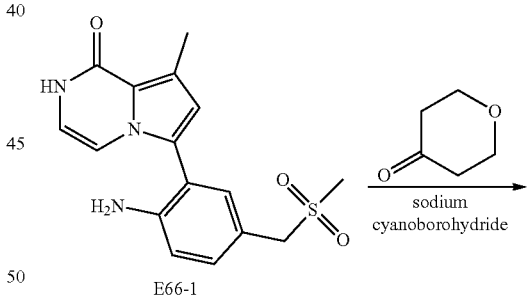

E66-1

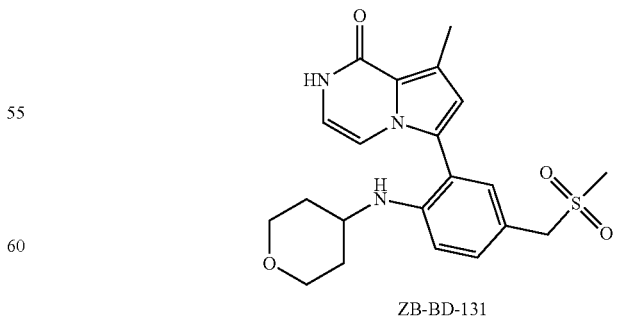

ZB-BD-131

Compound E66-1 (15 mg) was dissolved in 2 mL of dichloroethane, added with 1 mL of acetic acid, 50 mg of sodium cyanoborohydride and tetrahydropyrone (50 μL, commercially available, CAS: 29943-42-8), stirred at room temperature for 24 h. The solvent was removed and the residue was purified by silica gel column chromatography to give compound ZB-BD-131 (2 mg). $^1$H NMR (400 MHz, DMSO-d$_6$) δ 10.23 (d, J=5.2 Hz, 1H), 7.27 (d, J=8.3 Hz, 1H), 7.11 (d, J=2.1 Hz, 1H), 6.86 (d, J=8.7 Hz, 1H), 6.56 (d, J=5.8 Hz, 1H), 6.47-6.34 (m, 2H), 4.54 (d, J=8.1 Hz, 1H), 4.32 (s, 2H), 3.80 (m, 2H), 3.50 (m, 1H), 3.39 (m, 2H), 2.86 (s, 3H), 1.80 (m, 2H), 1.36 (m, 2H). HPLC-MS: [M+H]$^+$=416.2.

Example 86: Synthesis of Compound ZB-BD-132

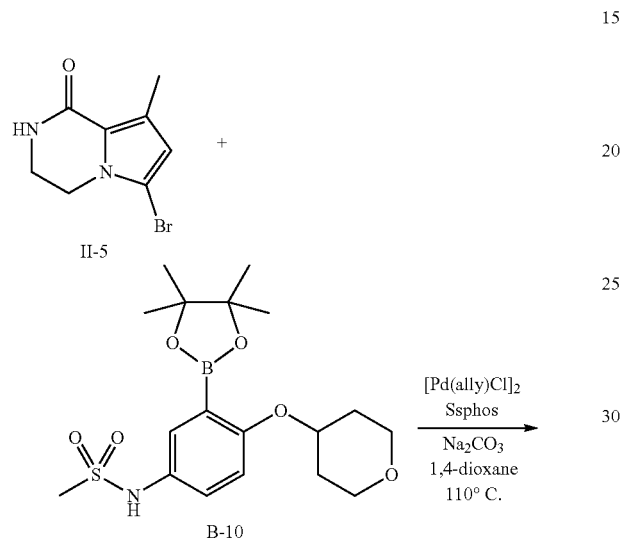

ZB-BD-132

The same method as that in Example 24 was used to give compound ZB-BD-132, except that compound II-5 was used instead of compound I-6 and compound B-10 was used instead of compound B-1. HPLC-MS: [M+H]$^+$=420.2.

Example 87: Synthesis of Compound ZB-BD-133

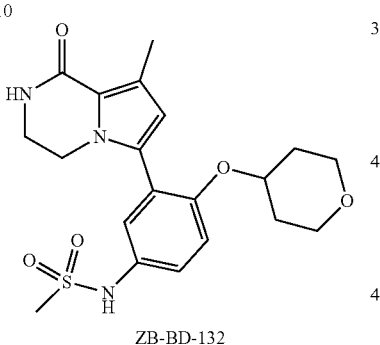

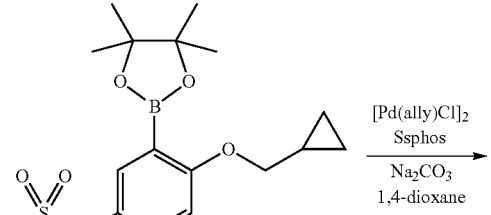

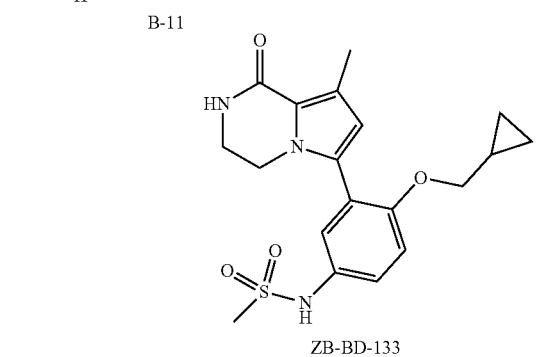

ZB-BD-133

The same method as that in Example 24 was used to give compound ZB-BD-133, except that compound II-5 was used instead of compound I-6 and compound B-11 was used instead of compound B-1. HPLC-MS: [M+H]$^+$=390.2.

Example 88: Synthesis of Compound ZB-BD-134

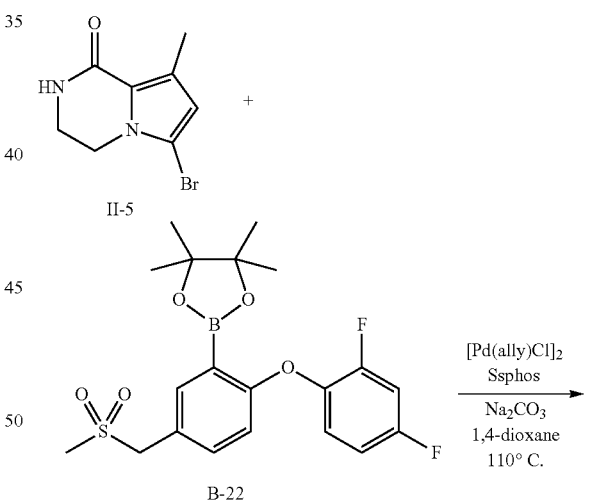

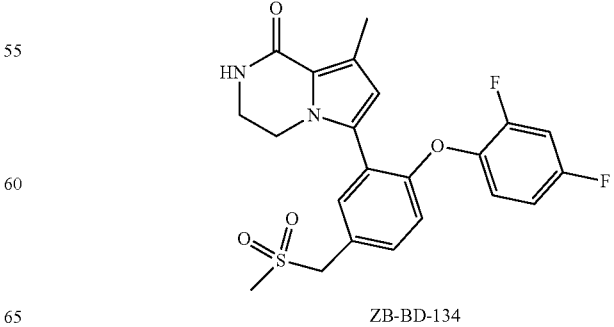

ZB-BD-134

The same method as that in Example 24 was used to give compound ZB-BD-134, except that compound II-5 was used instead of compound I-6 and compound B-22 was used instead of compound B-1. HPLC-MS: [M+H]⁺=447.2.

Example 89: Synthesis of Compound ZB-BD-135

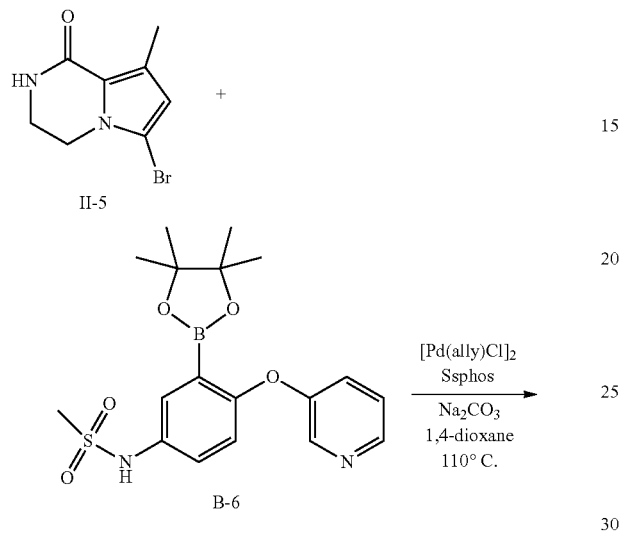

The same method as that in Example 24 was used to give compound ZB-BD-135, except that compound II-5 was used instead of compound I-6 and compound B-6 was used instead of compound B-1. HPLC-MS: [M+H]⁺=413.2.

Example 90: Synthesis of Compound ZB-BD-136

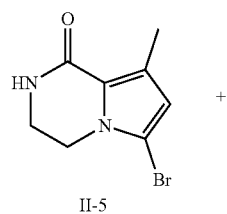

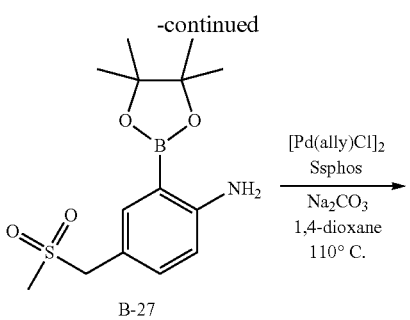

Step 1
Compound II-5 (46 mg) and borate B-27 (155 mg) were dissolved in 9 mL of 1,4-dioxane, added with 3 mL of 2M sodium carbonate aqueous solution, followed by addition of allyl palladium (II) chloride dimer (CAS: 12012-95-2) (7.3 mg, 0.02 mmol) and sodium 2'-dicyclohexylphosphino-2,6-dimethoxy-1,1'-biphenyl-3-sulfonate hydrate (21 mg, 0.04 mmol) under argon. The mixture was stirred at 110° C. for 2 h, diluted with water, extracted with ethyl acetate, and purified by silica gel column chromatography to give compound E90-1.

Step 2
Compound E90-1 (10 mg) was dissolved in 1 mL of dichloroethane, added with 0.5 mL of acetic acid, 10 mg of sodium cyanoborohydride and cyclopropylformaldehyde (5 μL, commercially available, CAS: 1489-69-6), stirred at room temperature for 2 h. The solvent was removed and the residue was purified by silica gel column chromatography to give compound ZB-BD-136 (4 mg). HPLC-MS: [M+H]⁺=388.2.

Example 91: Synthesis of Compound ZB-BD-137

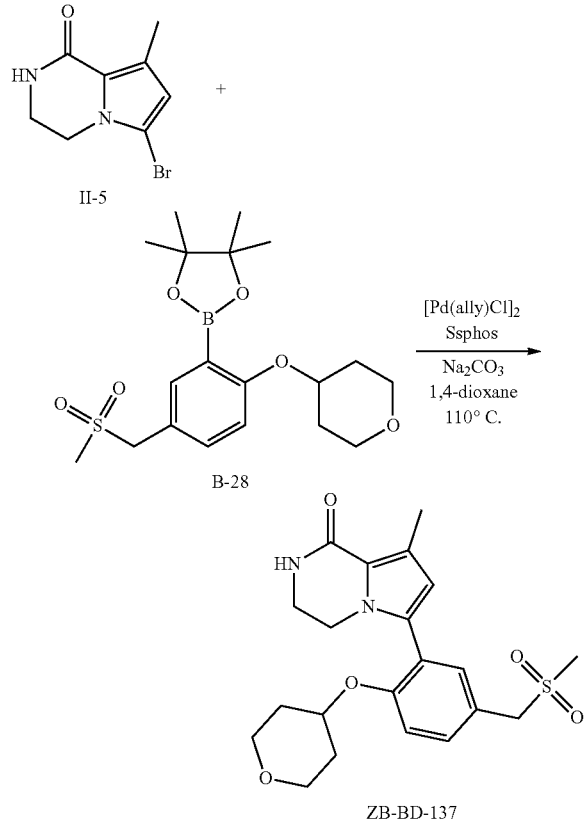

The same method as that in Example 24 was used to give compound ZB-BD-137, except that compound II-5 was used instead of compound I-6 and compound B-28 was used instead of compound B-1. HPLC-MS: [M+H]$^+$=419.2.

Example 92: Synthesis of Borate B-32

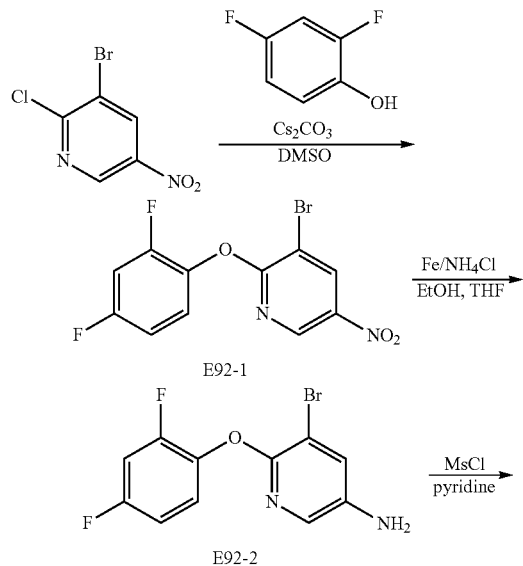

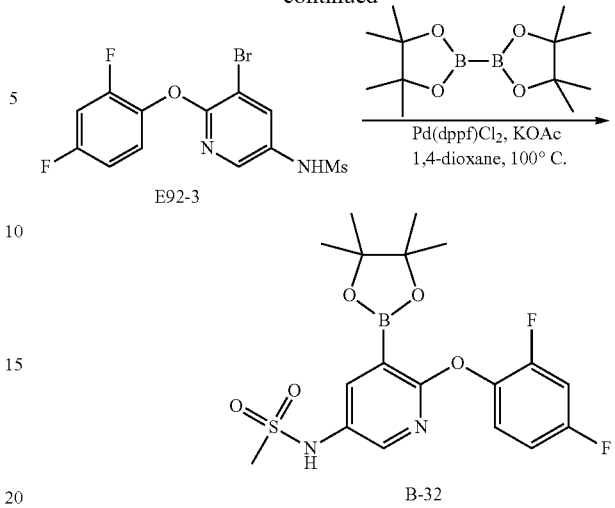

Compound B-32 was prepared with reference to the synthetic method described in WO 2015058160.

Step 1

2-chloro-3-bromo-5-nitropyridine (5.0 g, CAS: 5470-17-7), 2,4-difluorophenol (2.3 g) and cesium carbonate (8 g) were suspended in 100 mL of dimethyl sulfoxide, heated to 110° C. to react for 1 h, cooled to room temperature, filtered to remove the solid, and added with water and ethyl acetate for layering. The organic phase was washed with saturated saline, dried over anhydrous sodium sulfate, and concentrated to give intermediate E92-1 (7 g).

Step 2

E92-1 (7 g) was dissolved in 50 mL of ethanol and 50 mL of tetrahydrofuran, added with 20 mL of water, followed by batch addition of iron powder (7.1 g) and ammonium chloride (4.5 g) at room temperature. After completion of the addition, the temperature was slowly raised to 95° C. and the reaction was carried out under stirring for 2 h. The reaction solution was filtered through celite. The filtrate was poured into water and extracted twice with ethyl acetate. The combined organic phase was washed with saturated saline, dried over anhydrous sodium sulfate, and concentrated to give intermediate E92-2 (6.8 g). HPLC-MS: [M–H]$^+$=301.1/303.1.

Step 3

E92-2 (6.8 g) was dissolved in 50 mL of pyridine, cooled to 0° C., followed by slow dropwise addition of methanesulfonyl chloride (2.7 g). After completion of the dropwise addition, the mixture was warmed to room temperature to react for 6 h, and added with ice water and ethyl acetate for layering. The organic phase was washed with 2M dilute hydrochloric acid and saturated saline successively, dried over anhydrous sodium sulfate, concentrated to remove ethyl acetate, and slurried in petroleum ether to give intermediate E92-3 (5.3 g). HPLC-MS: [M–H]$^+$=379.1/380.1.

Step 4

E92-3 (6.4 g), potassium acetate (3.6 g) and bis(pinacolato)diboron (9.2 g) were dissolved in 100 mL of dioxane, added with [1,1'-bis(diphenylphosphino)ferrocene]palladium dichloride (0.7 g) under argon, heated to 100° C. to react for 12 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and slurried in diethyl ether to give borate B-32 (3.2 g). HPLC-MS: $[M+H]^+=427.1$.

Example 93: Synthesis of Borate B-33

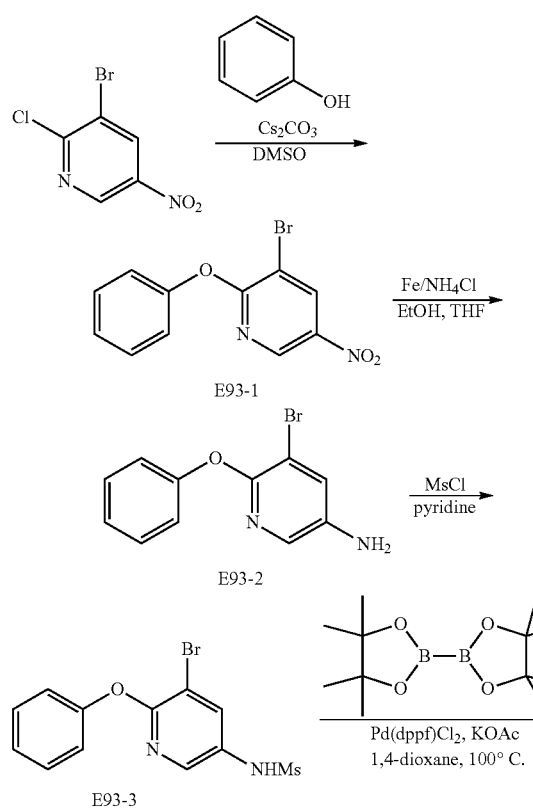

Borate B-33 was prepared in the same method as that in Example 92 except that phenol was used instead of 2,4-difluorophenol in Step 1. $^1$H NMR (400 MHz, DMSO-$d_6$) δ 9.68 (s, 1H), 8.08 (d, J=2.9 Hz, 1H), 7.92 (d, J=2.9 Hz, 1H), 7.42-7.32 (m, 2H), 7.16 (t, J=7.4 Hz, 1H), 7.04 (m, 2H), 2.99 (s, 3H), 1.27 (s, 12H). HPLC-MS: $[M+H]^+=391.1$.

Example 94: Synthesis of Borate B-34

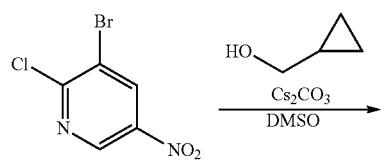

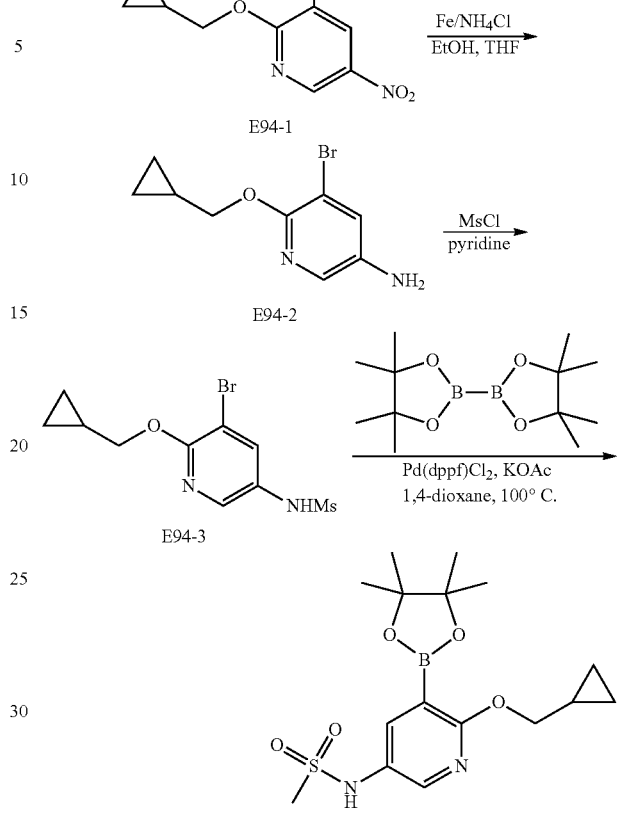

Borate B-34 was prepared in the same method as that in Example 92 except that hydroxymethylcyclopropane was used instead of 2,4-difluorophenol in Step 1. HPLC-MS: $[M+H]^+=369.1$.

Example 95: Synthesis of Borate B-35

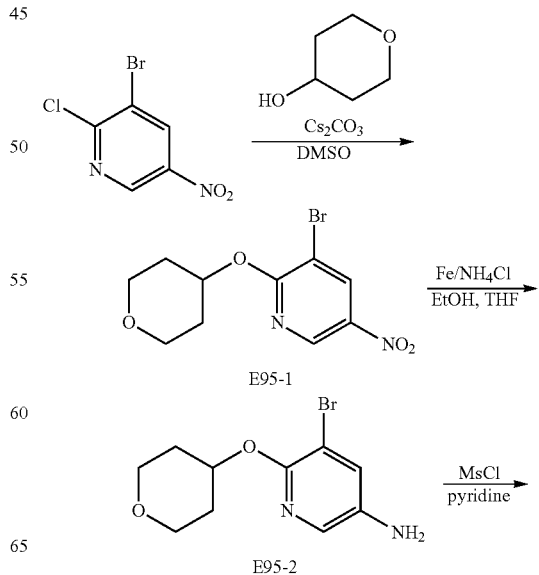

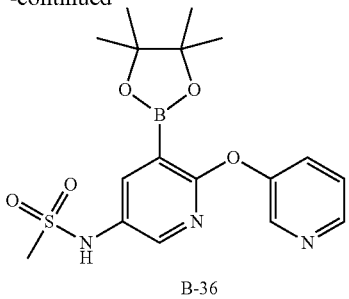

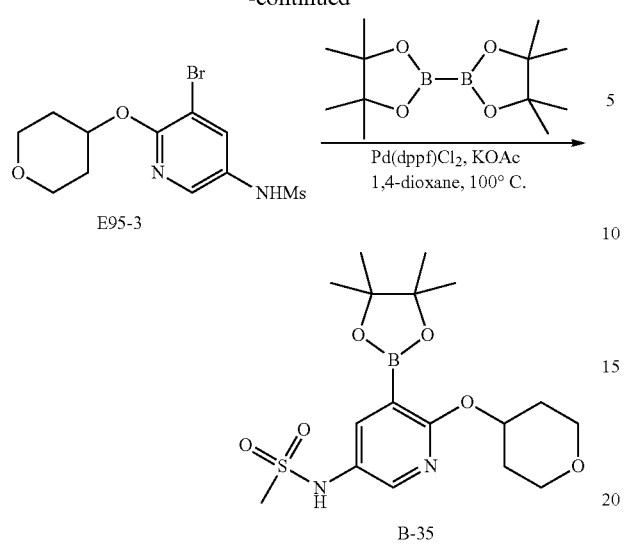

Borate B-35 was prepared in the same method as that in Example 92 except that tetrahydropyran-4-ol was used instead of 2,4-difluorophenol in Step 1. HPLC-MS: [M+H]$^+$=399.1.

Example 96: Synthesis of Borate B-36

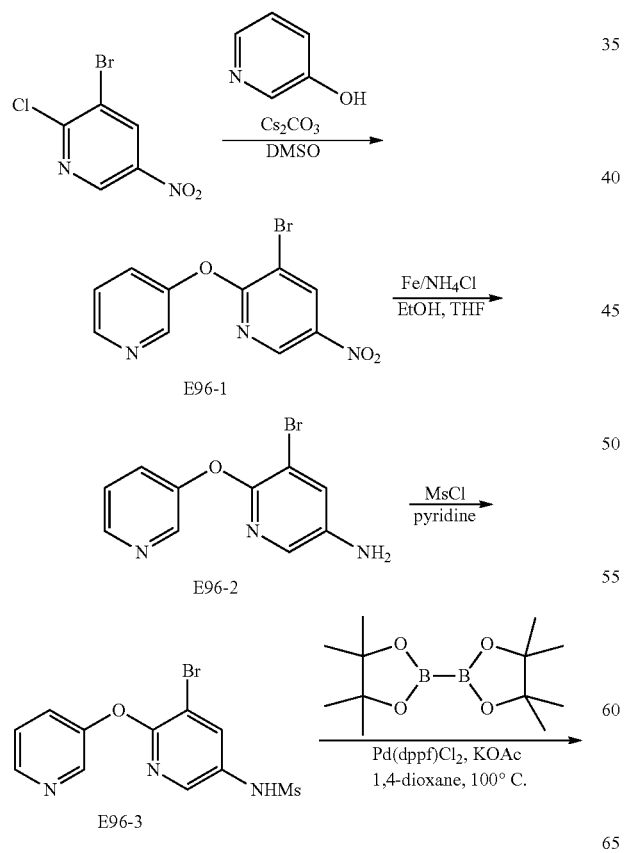

Borate B-36 was prepared in the same method as that in Example 92 except that 3-hydroxypyridine was used instead of 2,4-difluorophenol in Step 3. HPLC-MS: [M+H]$^+$=392.1.

Example 97: Synthesis of Borate B-37

Borate B-37 was prepared in the same method as that in Example 92, except that 3-bromo-4-fluoronitrobenzene (CAS: 701-45-1) was used as raw material and (S)-(+)-3-hydroxytetrahydrofuran (CAS: 86087-23-2) was used instead of 2,4-difluorophenol in Step 1. HPLC-MS: [M+H]⁺=384.1.

Example 98: Synthesis of Borate B-38

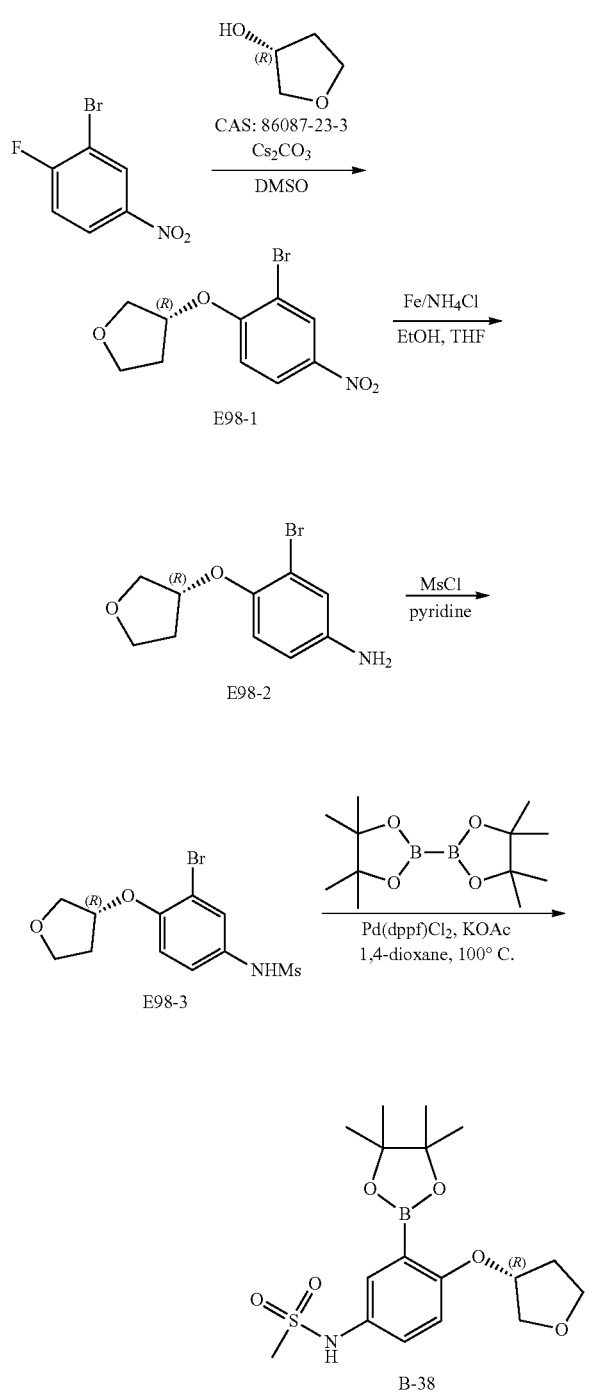

Borate B-38 was prepared in the same method as that in Example 92, except that 3-bromo-4-fluoronitrobenzene was used as raw material and (R)-(+)-3-hydroxytetrahydrofuran (CAS: 86087-24-3) was used instead of 2,4-difluorophenol in Step 1. HPLC-MS: [M+H]⁺+=384.1.

Example 99: Synthesis of Borate B-39

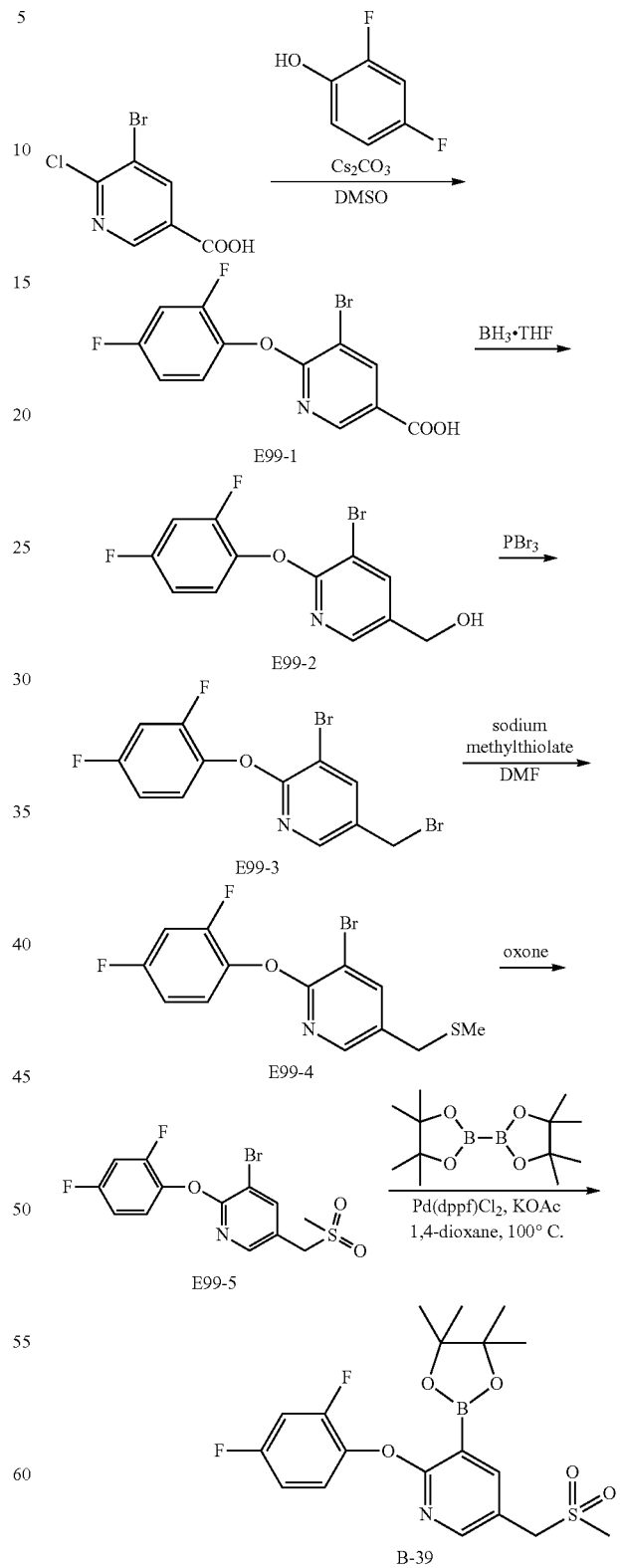

Borate B-39 was prepared with reference to the synthetic method described in WO 2013097601.

Step 1

5-Bromo-6-chloronicotinic acid (3.0 g, CAS: 29241-62-1), 2,4-difluorophenol (3.3 g) and cesium carbonate (16 g) were suspended in 30 mL of dimethyl sulfoxide, heated to 100° C. to react for 6 h, cooled to room temperature, added with water, adjusted pH to 3 with 12 M hydrochloric acid to precipitate a solid, which is filtered, washed with water, and dried to give the product E99-1 (2.8 g).

Step 2

E99-1 (2 g) was dissolved in 40 mL of tetrahydrofuran, added with borane tetrahydrofuran complex (12 mL, CAS: 14044-65-6), heated to 50° C. to react under stirring for 2 h, added with 20 mL of methanol, and kept at this temperature for another 1 h. After cooled, the reaction mixture was poured into water and extracted with ethyl acetate. The combined organic phase was washed with saturated saline, dried over anhydrous sodium sulfate, concentrated and passed through column chromatography to give intermediate E99-2 (0.68 g).

Step 3

E99-2 (0.7 g) was dissolved in 10 mL of dichloromethane, dropwise added with phosphorus tribromide (0.2 mL, CAS: 7789-60-8), and stirred at room temperature for 1 h. The reaction solution was poured into ice water, adjusted pH to 9 with sodium bicarbonate, and extracted with dichloromethane. The combined organic phase was washed with saturated saline, dried over anhydrous sodium sulfate, concentrated and passed through column chromatography to give intermediate E99-3 (0.65 g).

Step 4

Compound E99-3 (0.75 g) was dissolved in 5 mL of N,N-dimethylformamide, and added with sodium methylthiolate (0.14 g) to react at room temperature for 4 h. The mixture was dissolved with ethyl acetate, added with water, and extracted. The combined organic phase was washed three times with saturated saline, dried over anhydrous sodium sulfate, rotary evaporated under vacuum to remove the solvent to give compound E99-4 (0.62 g).

Step 5

Compound E99-4 (0.7 g) was dissolved in 7 mL of methanol, added with oxone (2.5 g, dissolved in 7 mL of water) at 0° C., and returned to room temperature to react for 2 h. The mixture was dissolved with ethyl acetate, added with water, and extracted. The combined organic phase was washed three times with saturated saline, dried over anhydrous sodium sulfate, rotary evaporated under vacuum to remove the solvent, and separated through column chromatography to give compound E99-5 (0.45 g).

Step 6

E99-5 (486 mg), potassium acetate (390 mg) and bis(pinacolato)diboron (680 mg) were dissolved in 15 mL of dioxane, added with [1,1'-bis(diphenylphosphino)ferrocene] palladium dichloride (47 mg) under argon, heated to 100° C. to react for 12 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give borate B-39 (110 mg).

Example 100: Synthesis of Borate B-40

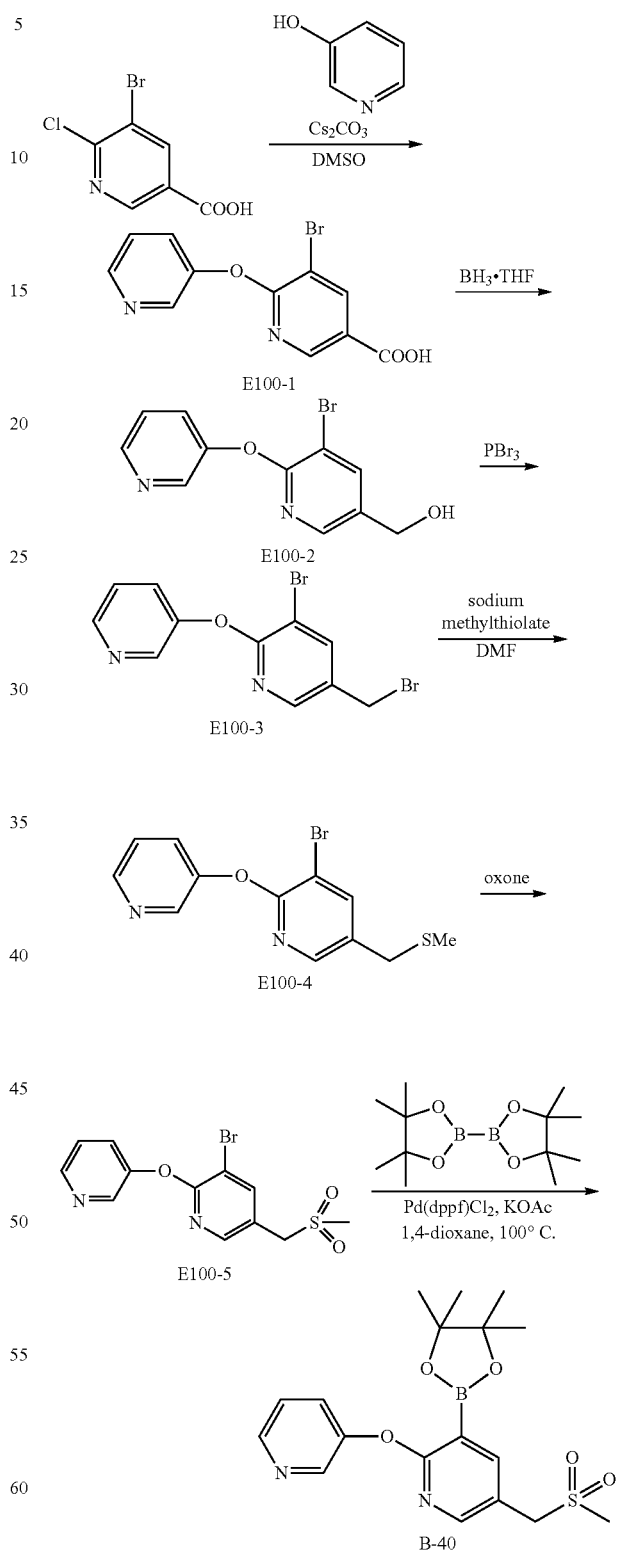

Borate B-40 was prepared in the same method as that in Example 99 except that 3-hydroxypyridine was used instead of 2,4-difluorophenol in Step 1.

Example 101: Synthesis of Borate B-41
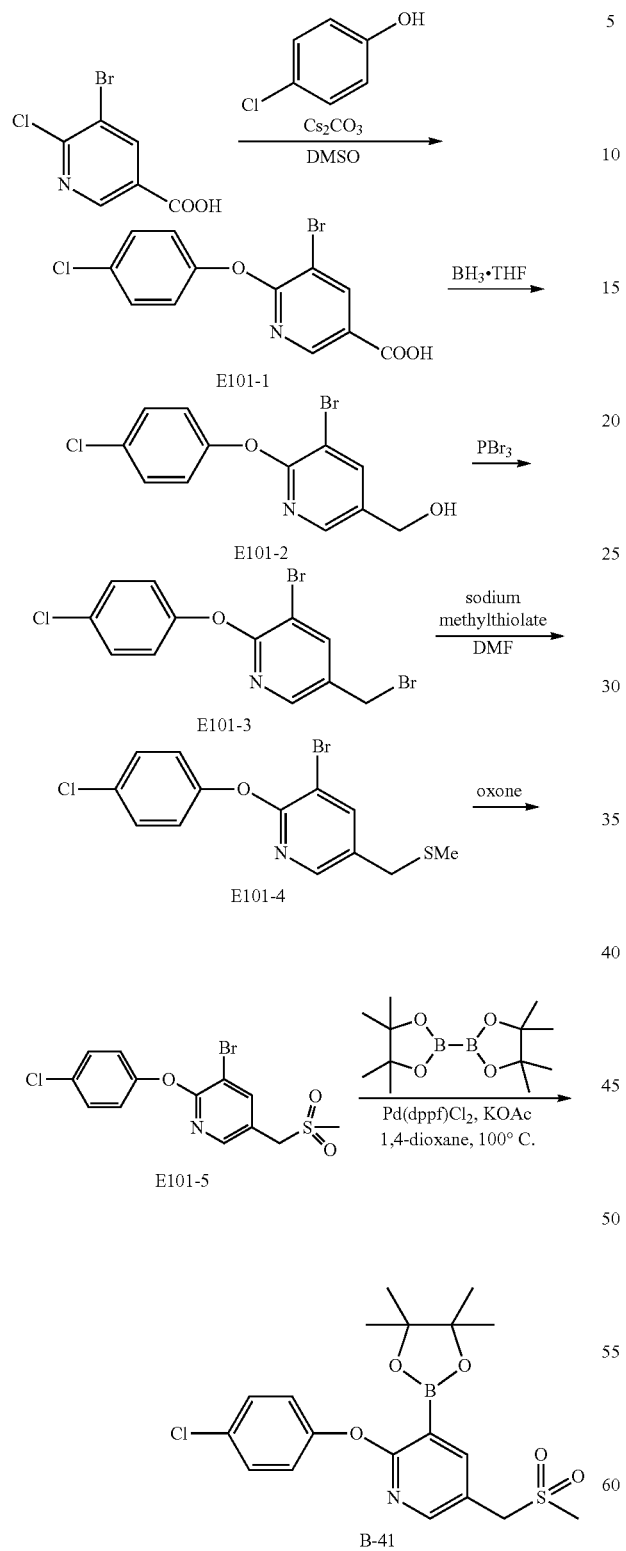
Example 102: Synthesis of Borate B-42
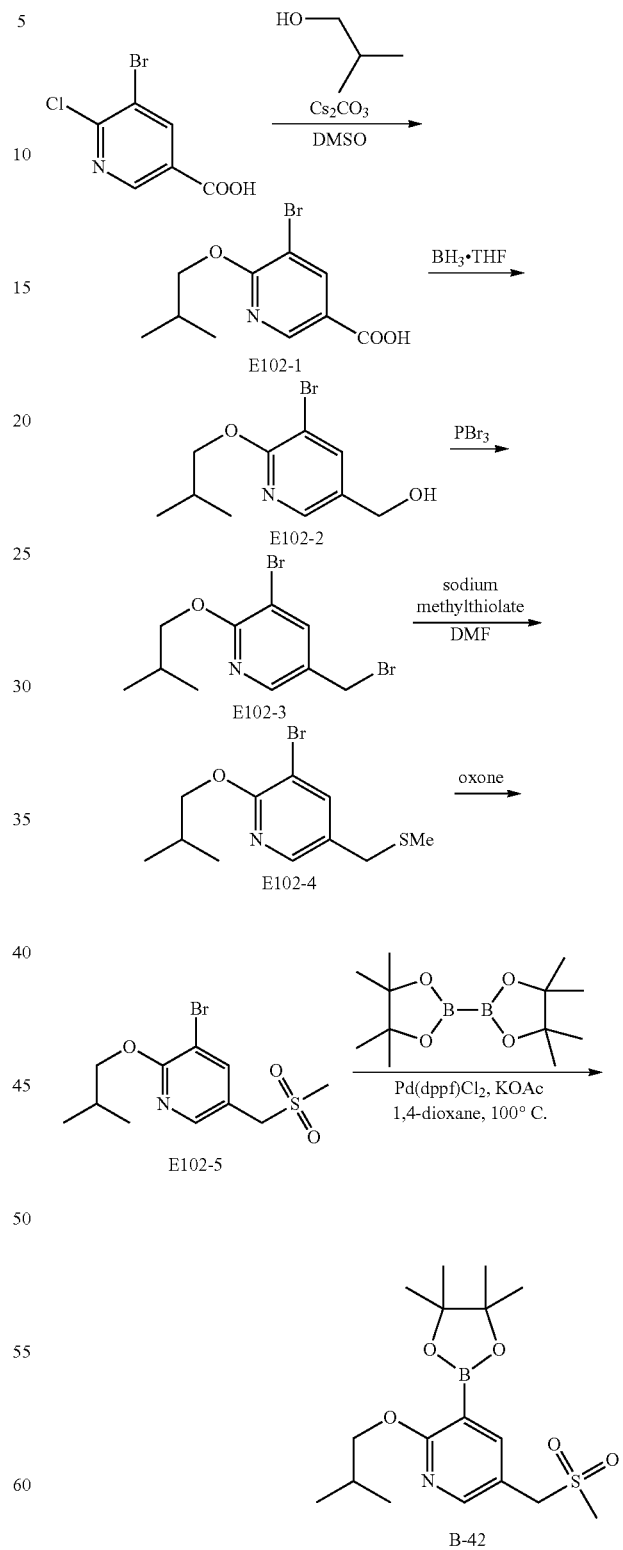
Borate B-41 was prepared in the same method as that in Example 99 except that p-chlorophenol was used instead of 2,4-difluorophenol in Step 1.
Borate B-42 was prepared in the same method as that in Example 99 except that isobutanol was used instead of 2,4-difluorophenol in Step 1.

Example 103: Synthesis of Borate B-43

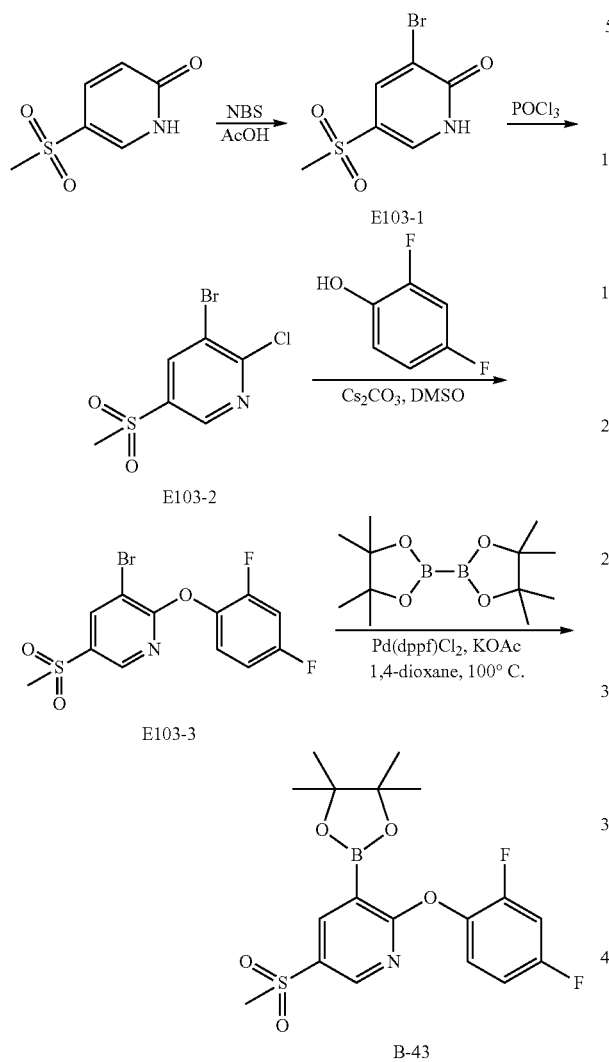

Borate B-43 was prepared with reference to the synthetic method described in WO 2013097601.

Step 1

5-methanesulfonyl-1H-pyridin-2-one (3.6 g, CAS. 18085-51-3) and sodium acetate (2 g) were dissolved in 50 mL of acetic acid, followed by slow dropwise addition of $Br_2$ (1.3 mL, dissolved in 10 mL of acetic acid in advance). The reaction was carried out at 40° C. for 5 h. After cooled to room temperature, the reaction was quenched by addition of 10% sodium thiosulfate. A solid was precipitated, filtered, washed with water, and dried in vacuo to give the product E103-1 (3.8 g).

Step 2

E103-1 (1.8 g) was dissolved in 30 mL of phosphorus oxychloride, and react at 110° C. for 4 h under stirring. The reaction solution was poured into ice water to precipitate a solid, which is filtered, washed with water, and dried in vacuo to give product E103-2 (0.66 g).

Step 3

E103-2 (0.4 g), 2,4-difluorophenol (0.1 g) and cesium carbonate (0.325 g) were suspended in 5 mL of dimethyl sulfoxide, heated to 100° C. for 2 h, cooled to room temperature, added with water, and extracted with ethyl acetate. The organic phase was washed with water, dried, and separated by column chromatography to give E103-3 (0.5 g).

Step 4

E103-3 (450 mg), potassium acetate (370 mg) and bis (pinacolato)diboron (650 mg) were dissolved in 15 mL of dioxane, added with [1,1'-bis (diphenylphosphino)ferrocene] palladium dichloride (40 mg) under argon, heated to 100° C. to react for 12 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give borate B-43 (80 mg).

Example 104: Synthesis of Borate B-44

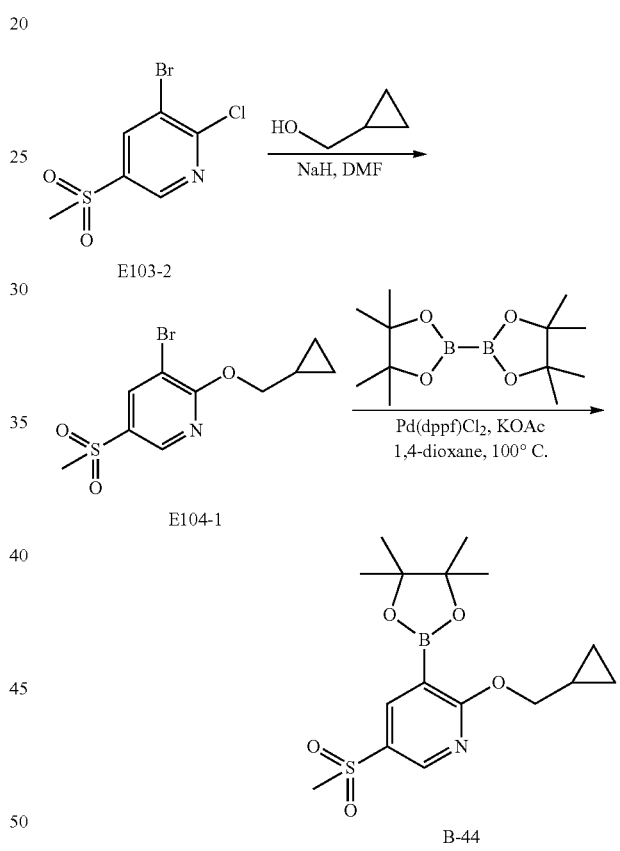

Borate B-44 was prepared with reference to the synthetic method described in WO 2013097601 and the method for borate B-43.

Step 1

E103-2 (0.4 g) and hydroxymethylcyclopropane (0.1 g, CAS: 2516-33-8) were dissolved in 3 mL DMF, added with 60% sodium hydrogen (0.5 g) at 0° C., returned to room temperature to react overnight, added with water, and extracted with ethyl acetate. The organic phase was washed with water, dried, and separated by column chromatography to give E104-1 (0.4 g).

Step 2

E104-1 (400 mg), potassium acetate (350 mg) and bis (pinacolato)diboron (600 mg) were dissolved in 10 mL of dioxane, added with [1,1'-bis (diphenylphosphino)ferrocene] palladium dichloride (30 mg) under argon, heated to 100° C. to react for 12 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give borate B-44 (95 mg).

Example 105: Synthesis of Borate B-45

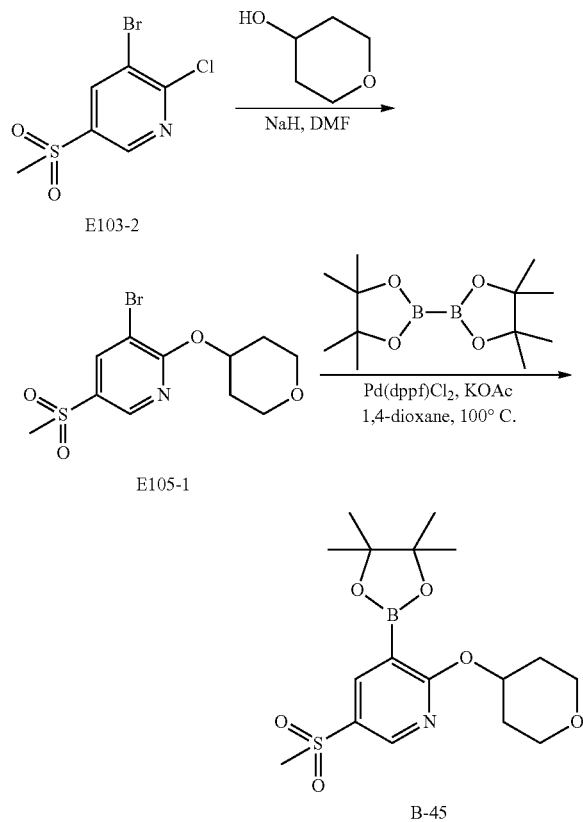

Borate B-45 was prepared in the same method as that in Example 104 except that tetrahydropyran-4-ol was used instead of hydroxymethylcyclopropane in Step 1.

Example 106: Synthesis of Borate B-46

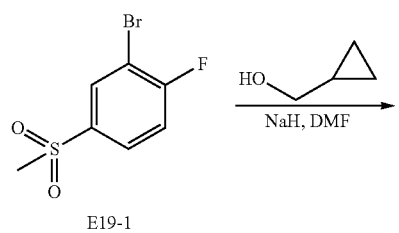

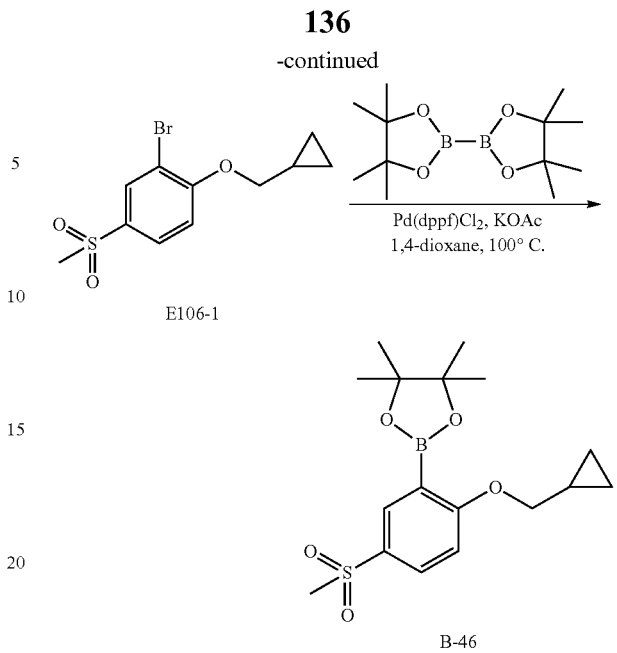

Borate B-46 was prepared with reference to the synthetic method described in WO 2013097601 and the method of borate B-13.

Step 1

E19-1 (0.35 g) and hydroxymethylcyclopropane (0.14 g, CAS: 2516-33-8) were dissolved in 3 mL DMF, added with 60% sodium hydrogen (0.5 g) at room temperature, heated to 60° C. to react overnight, added with water and extracted with ethyl acetate. The organic phase was washed with water, dried, and passed through column chromatography to give E106-1 (0.28 g).

Step 2

E106-1 (200 mg), potassium acetate (170 mg) and bis(pinacolato)diboron (300 mg) were dissolved in 5 mL of dioxane, added with [1,1'-bis(diphenylphosphino)ferrocene] palladium dichloride (15 mg) under argon, heated to 100° C. to react for 12 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give borate B-46 (60 mg).

Example 107: Synthesis of Borate B-47

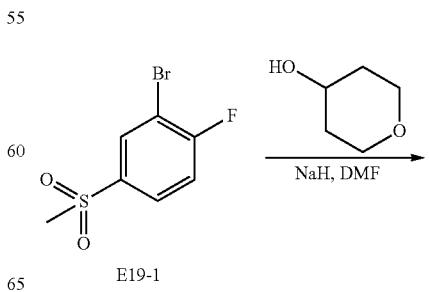

-continued

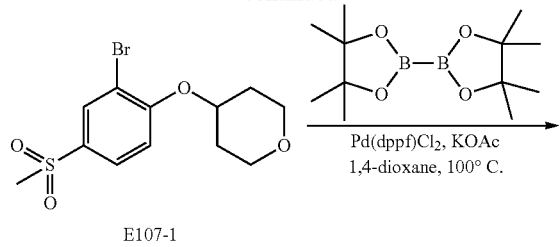

E107-1

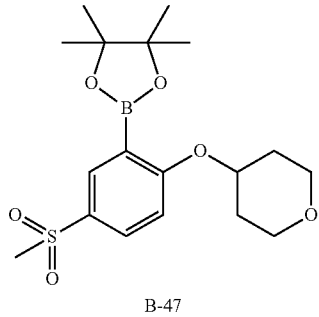

B-47

Borate B-47 was prepared in the same method as that in Example 106 except that tetrahydropyran-4-ol was used instead of hydroxymethylcyclopropane in Step 1.

Example 108: Synthesis of Compound ZB-BD-140

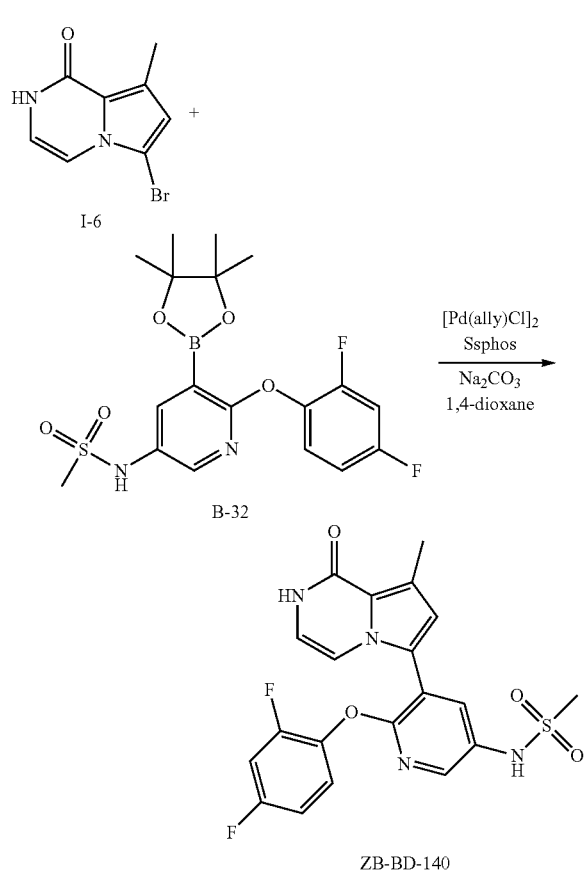

ZB-BD-140

Except that compound B-32 instead of compound B-1, the same method as that in Example 24 was used to give compound ZB-BD-140. HPLC-MS: [M+H]$^+$=447.1. $^1$H NMR (400 MHz, DMSO-d$_6$) δ 10.38 (d, J=5.6 Hz, 1H), 9.91 (s, 1H), 7.99 (d, J=2.6 Hz, 1H), 7.74 (d, J=2.7 Hz, 1H), 7.44 (tt, J=8.7, 4.4 Hz, 2H), 7.13 (td, J=8.4, 2.6 Hz, 1H), 6.98 (d, J=5.9 Hz, 1H), 6.62 (s, 1H), 6.52 (dt, J=5.7, 2.8 Hz, 1H), 3.07 (s, 3H), 2.50 (s, 3H).

Example 109: Synthesis of Compound ZB-BD-141

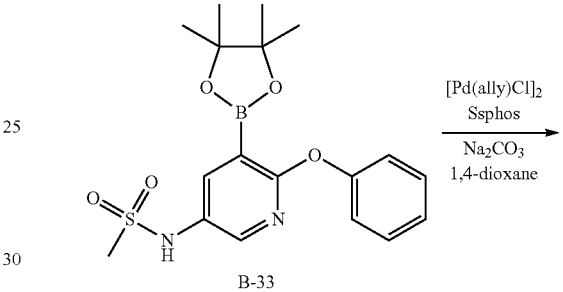

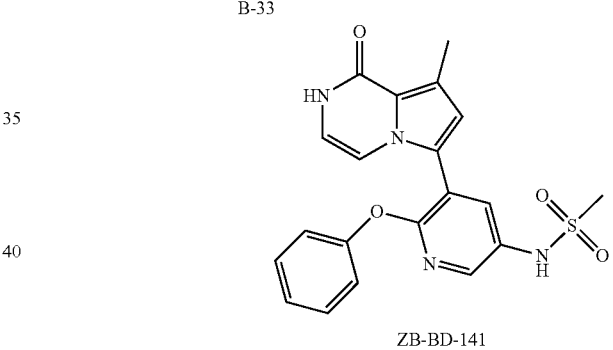

ZB-BD-141

The same method as that in Example 24 was used to give compound ZB-BD-141, except that compound B-33 was used instead of compound B-1. $^1$H NMR (400 MHz, MeOD) δ 8.07 (d, J=2.7 Hz, 1H), 7.84 (d, J=2.7 Hz, 1H), 7.37 (m, 2H), 7.18 (t, J=7.5 Hz, 1H), 7.09 (m, 3H), 6.60 (s, 1H), 6.50 (d, J=5.9 Hz, 1H), 3.04 (s, 3H), 2.59 (s, 3H). HPLC-MS: [M+H]$^+$=411.1.

Example 110: Synthesis of Compound ZB-BD-142

I-6

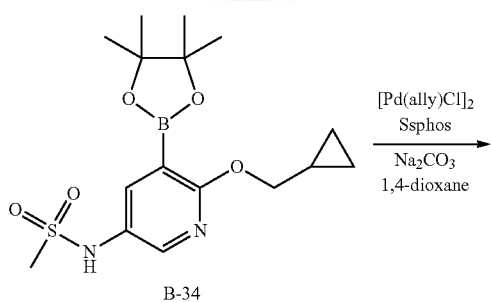

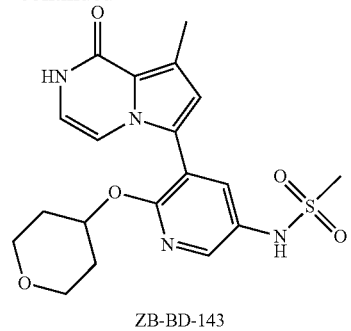

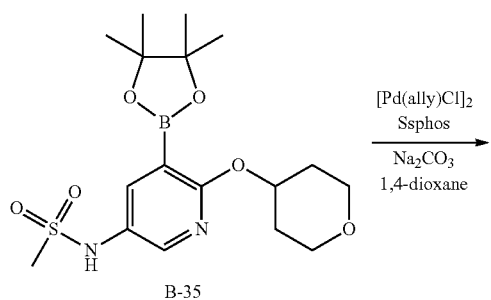

The same method as that in Example 24 was used to give compound ZB-BD-142, except that compound B-34 was used instead of compound B-1. HPLC-MS: [M+H]$^+$=389.1. $^1$H NMR (400 MHz, MeOD) δ 8.11 (d, J=2.7 Hz, 1H), 7.66 (d, J=2.8 Hz, 1H), 6.87 (d, J=5.9 Hz, 1H), 6.50 (s, 1H), 6.45 (d, J=5.9 Hz, 1H), 4.19 (d, J=7.1 Hz, 2H), 2.98 (s, 3H), 2.58 (s, 3H), 1.24-1.19 (m, 1H), 0.55-0.49 (m, 2H), 0.32-0.25 (m, 2H).

Example 111: Synthesis of Compound ZB-BD-143

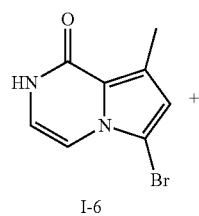

The same method as that in Example 24 was used to give compound ZB-BD-143, except that compound B-35 was used instead of compound B-1. HPLC-MS: [M+H]$^+$*=419.1. $^1$H NMR (400 MHz, MeOD-d$_4$) δ 8.13 (d, J=2.7 Hz, 1H), 7.68 (d, J=2.7 Hz, 1H), 6.87 (d, J=5.9 Hz, 1H), 6.50 (s, 1H), 6.47 (d, J=5.9 Hz, 1H), 5.37-5.30 (m, 1H), 3.80-3.72 (m, 2H), 3.60-3.52 (m, 2H), 2.99 (s, 3H), 2.58 (s, 3H), 2.07-1.99 (m, 2H), 1.73-1.63 (m, 2H).

Example 112: Synthesis of Compound ZB-BD-144

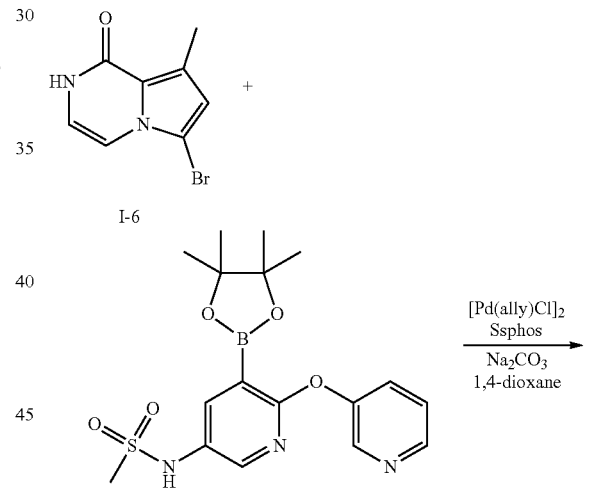

The same method as that in Example 24 was used to give compound ZB-BD-144, except that compound B-36 was used instead of compound B-1. HPLC-MS: [M+H]$^+$=412.1.

Example 113: Synthesis of Compound ZB-BD-145

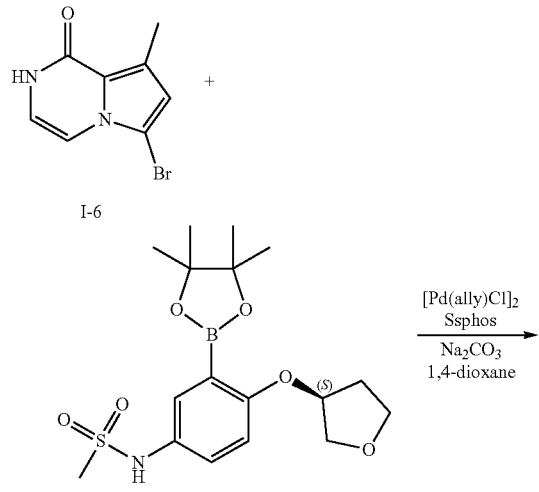

The same method as that in Example 24 was used to give compound ZB-BD-145, except that compound B-37 was used instead of compound B-1. HPLC-MS: [M+H]$^+$=404.1.

Example 114: Synthesis of Compound ZB-BD-146

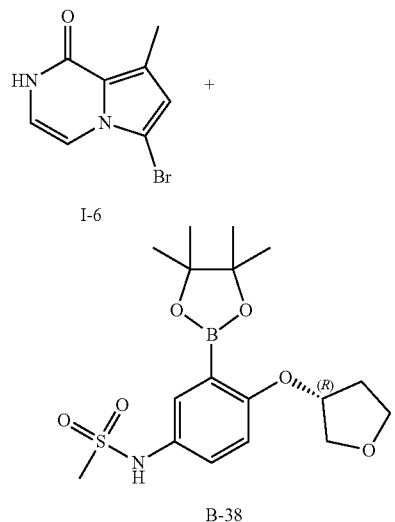

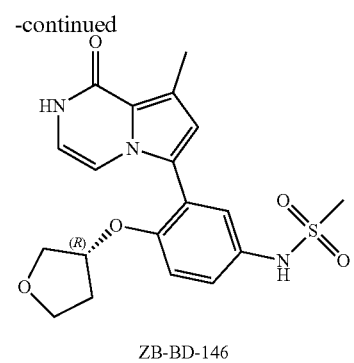

The same method as that in Example 24 was used to give compound ZB-BD-146, except that compound B-38 was used instead of compound B-1. HPLC-MS: [M+H]$^+$=404.1.

Example 115: Synthesis of Compound ZB-BD-147

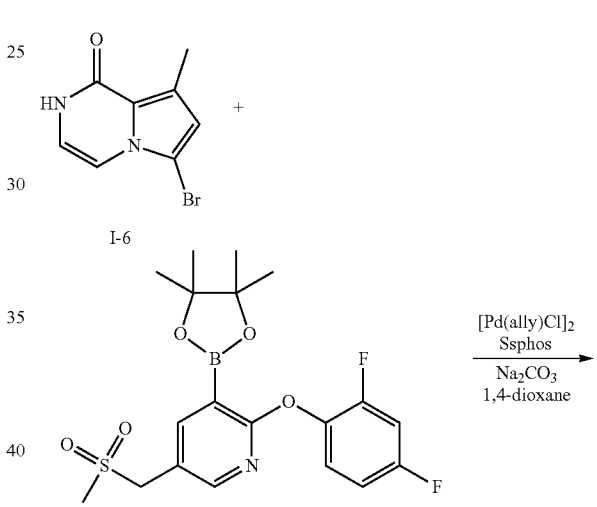

The same method as that in Example 24 was used to give compound ZB-BD-147, except that compound B-39 was used instead of compound B-1. HPLC-MS: [M+H]$^+$=446.1. H NMR (400 MHz, DMSO-d$_6$) δ 10.39 (d, J=5.3 Hz, 1H), 8.15 (d, J=2.3 Hz, 1H), 7.98 (d, J=2.3 Hz, 1H), 7.52-7.40 (m, 2H), 7.20-7.10 (m, 1H), 7.00 (d, J=5.8 Hz, 1H), 6.62 (s, 1H), 6.53 (t, J=5.7 Hz, 1H), 4.58 (s, 2H), 2.99 (s, 3H), 2.51 (s, 3H).

Example 116: Synthesis of Compound ZB-BD-148

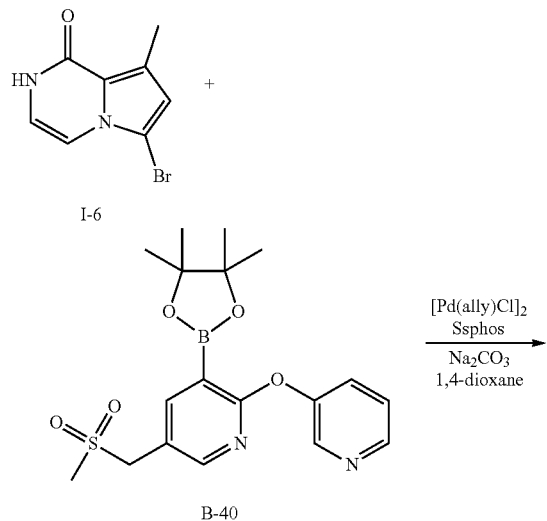

The same method as that in Example 24 was used to give compound ZB-BD-148, except that compound B-40 was used instead of compound B-1. HPLC-MS: [M+H]$^+$=411.1.

Example 117: Synthesis of Compound ZB-BD-149

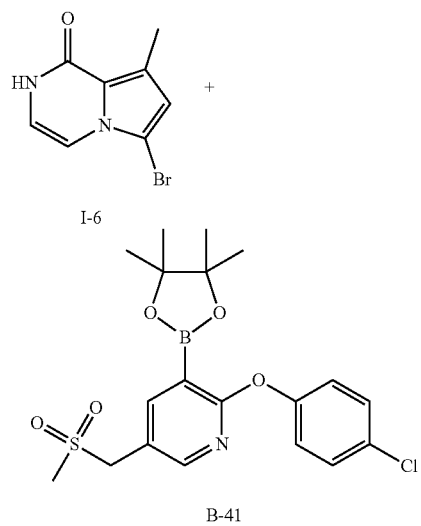

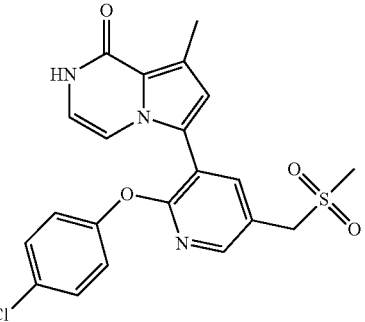

The same method as that in Example 24 was used to give compound ZB-BD-149, except that compound B-41 was used instead of compound B-1. HPLC-MS: [M+H]$^+$=444.1.

Example 118: Synthesis of Compound Z-BD-150

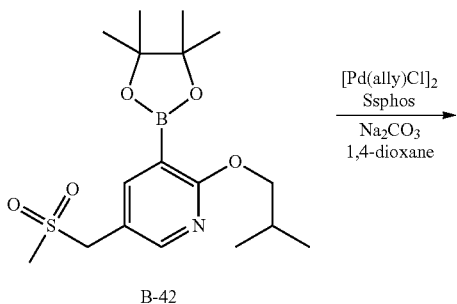

The same method as that in Example 24 was used to give compound ZB-BD-150, except that compound B-42 was used instead of compound B-1. HPLC-MS: [M+H]$^+$=390.2.

Example 119: Synthesis of Compound ZB-BD-151

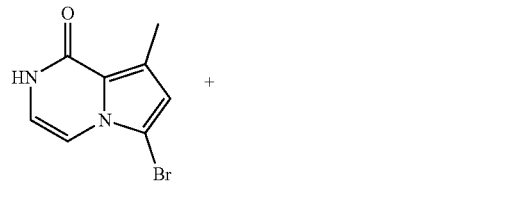

I-6

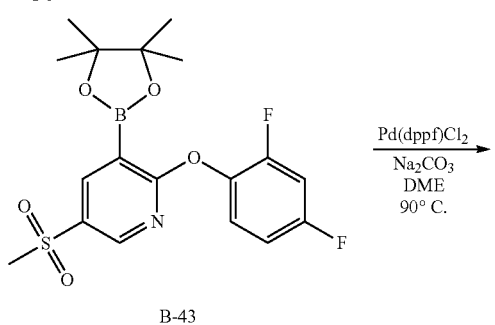

B-43

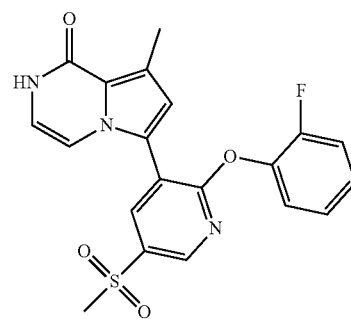

ZB-BD-151

The same method as that in Example 37 was used to give compound ZB-BD-151, except that compound B-43 was used instead of compound B-16. HPLC-MS: [M+H]⁺= 432.1. ¹H NMR (400 MHz, DMSO-d₆) δ 10.43 (d, J=5.2 Hz, 1H), 8.66 (d, J=2.4 Hz, 1H), 8.39 (d, J=2.4 Hz, 1H), 7.58-7.44 (m, 2H), 7.18 (t, J=8.5 Hz, 1H), 7.06 (d, J=5.8 Hz, 1H), 6.73 (s, 1H), 6.55 (t, J=5.6 Hz, 1H), 3.36 (s, 3H), 2.52 (s, 3H).

Example 120: Synthesis of Compound ZB-BD-152

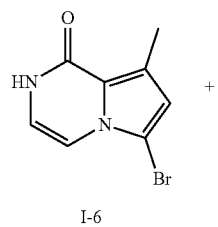

I-6

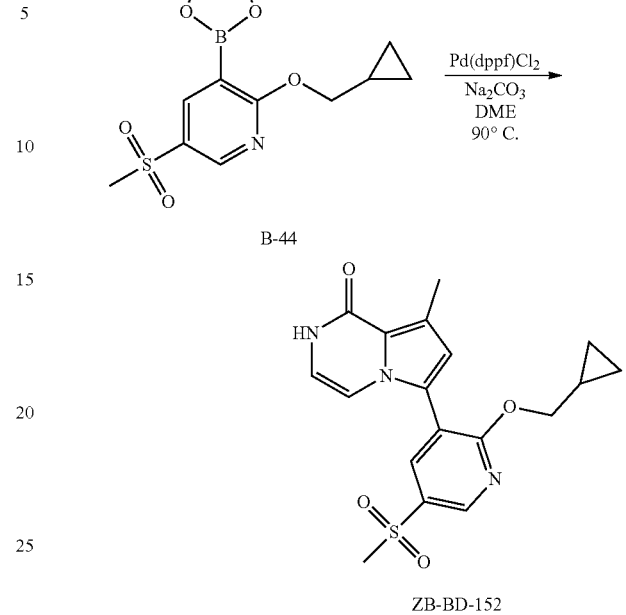

B-44

ZB-BD-152

The same method as that in Example 37 was used to give compound ZB-BD-152, except that compound B-44 was used instead of compound B-16. HPLC-MS: [M+H]⁺= 374.1. ¹H NMR (400 MHz, DMSO-d₆) δ 10.37 (d, J=5.1 Hz, 1H), 8.71 (d, J=2.5 Hz, 1H), 8.18 (d, J=2.5 Hz, 1H), 6.84 (d, J=5.7 Hz, 1H), 6.60 (s, 1H), 6.49 (t, J=5.7 Hz, 1H), 4.29 (d, J=7.2 Hz, 2H), 3.32 (s, 3H), 2.51 (s, 3H), 1.26-1.22 (m, 1H), 0.54-0.48 (m, 2H), 0.36-0.29 (m, 2H).

Example 121: Synthesis of Compound ZB-BD-153

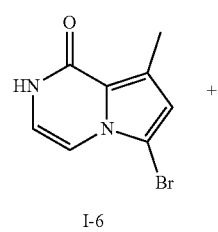

I-6

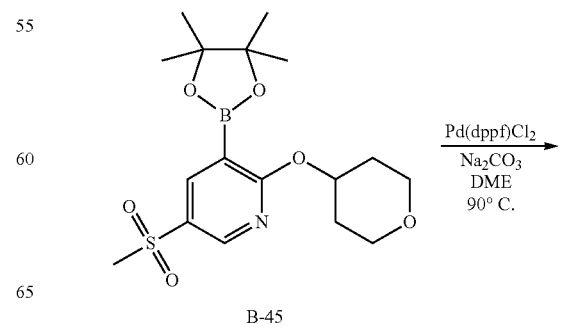

B-45

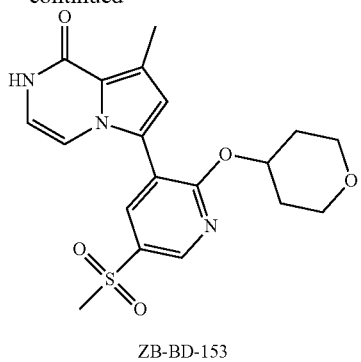

ZB-BD-153

The same method as that in Example 37 was used to give compound ZB-BD-153, except that compound B-45 was used instead of compound B-16. HPLC-MS: [M+H]⁺= 404.1. $^1$H NMR (400 MHz, DMSO-d$_6$) δ 10.37 (d, J=5.2 Hz, 1H), 8.72 (d, J=2.5 Hz, 1H), 8.20 (d, J=2.5 Hz, 1H), 6.84 (d, J=5.7 Hz, 1H), 6.59 (s, 1H), 6.50 (t, J=5.7 Hz, 1H), 5.49-5.35 (m, 1H), 3.77-3.65 (m, 2H), 3.54-3.43 (m, 2H), 3.33 (s, 3H), 2.51 (s, 3H), 2.02 (dd, J=9.3, 4.0 Hz, 2H), 1.69-1.51 (m, 2H).

Example 122: Synthesis of Compound ZB-BD-154

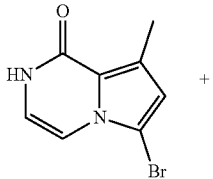

I-6

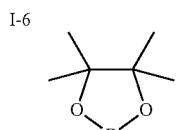

B-46

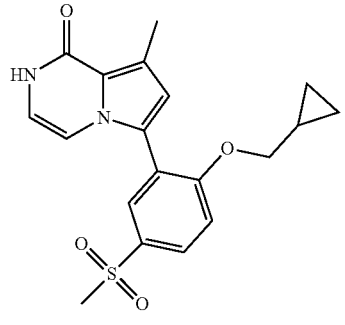

ZB-BD-154

The same method as that in Example 37 was used to give compound ZB-BD-154, except that compound B-46 was used instead of compound B-16. HPLC-MS: [M+H]⁺= 373.1.

Example 123: Synthesis of Compound ZB-BD-155

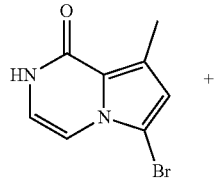

I-6

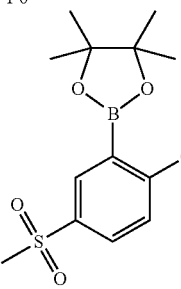

B-47

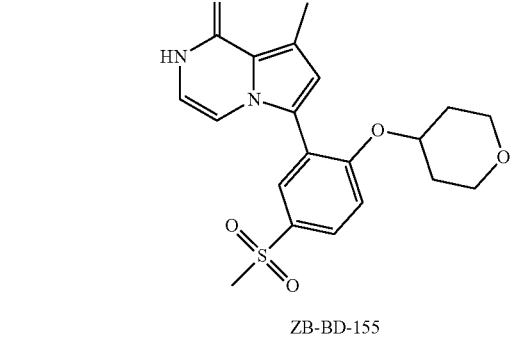

ZB-BD-155

The same method as that in Example 37 was used to give compound ZB-BD-155, except that compound B-47 was used instead of compound B-16. HPLC-MS: [M+H]⁺= 403.1.

Example 124: Synthesis of Compound VII-1

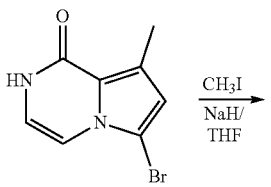
I-6

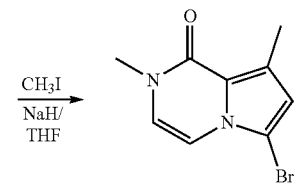
VII-1

Compound I-6 (113 mg) and methyl iodide (78 mg) were dissolved in 5 mL of anhydrous tetrahydrofuran, added with 60% sodium hydride (60 mg) to react at room temperature for 2 h, rotary evaporated under vacuum to remove the solvent and purified by silica gel column chromatography to give compound VII-1 (120 mg). HPLC-MS: [M+H]⁺=241.1/243.1.

Example 125: Synthesis of Compound ZB-BD-156

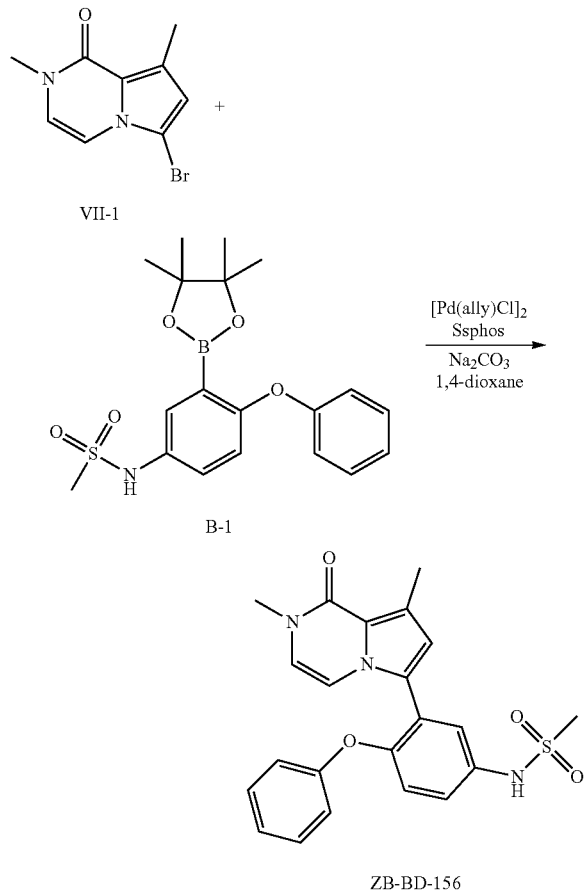

The same method as that in Example 24 was used to give compound ZB-BD-156, except that compound VII-1 was used instead of compound I-6. $^1$H NMR (400 MHz, MeOD) δ 7.36 (dd, J=6.4, 2.3 Hz, 2H), 7.24-7.17 (m, 3H), 7.01-6.94 (m, 2H), 6.80 (m, 2H), 6.52 (d, J=6.0 Hz, 1H), 6.40 (s, 1H), 3.36 (s, 3H), 3.01 (s, 3H), 2.48 (s, 3H). HPLC-MS: [M+H]⁺= 424.1.

Example 126: Synthesis of Borate M-1

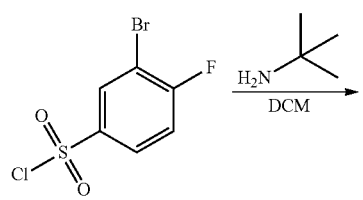

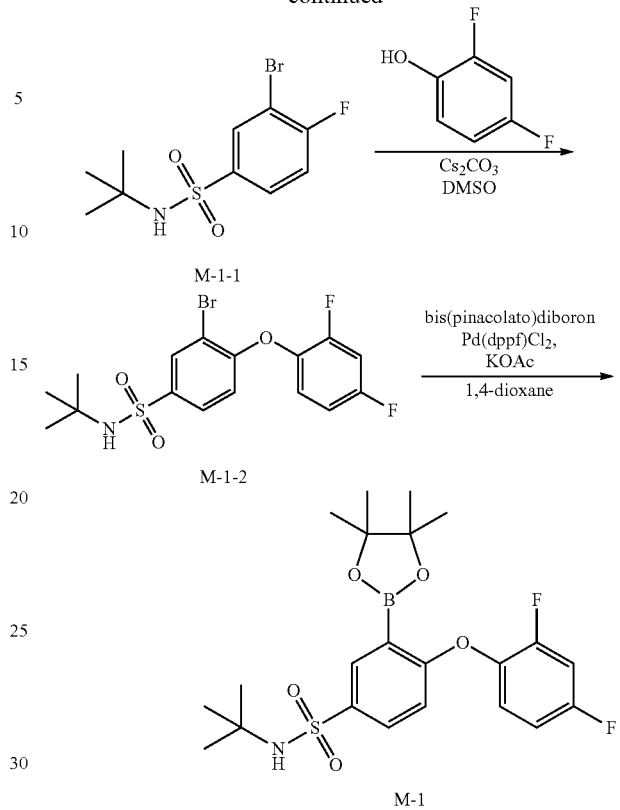

Step 1

3-Bromo-4-fluorobenzenesulfonyl chloride (0.96 g, 3.5 mmol, CAS: 631912-19-1) was dissolved in 8 ml of dichloromethane (DCM), added with triethylamine (0.71 g, 7.1 mmol) and tert-butylamine (0.28 g, 3.9 mmol) under ice bath, and stirred at room temperature for 3 h. TLC detection showed the reaction was complete. The reaction solution was poured into water and extracted with DCM. The organic layer was washed with saline, dried and concentrated to give 1.01 g of M-1-1.

Step 2

In 15 ml of dimethyl sulfoxide (DMSO), M-1-1 (1.01 g, 3.3 mmol), 2,4-difluorophenol (0.47 g, 3.6 mmol) and cesium carbonate (1.38 g, 4.25 mmol) were stirred at 110° C. for 2 h under nitrogen. TLC detection showed the reaction was complete. The reaction solution was cooled to room temperature, poured into water and extracted with EA. The organic layer was washed with water and saline, dried and concentrated to give M-1-2.

Step 3

M-1-2 (2.1 g, 4.9 mmol), potassium acetate (1.1 g, 11.3 mmol) and bis(pinacolato)diboron (2.5 g, 9.8 mmol, CAS: 73183-34-3) were dissolved in 30 mL of dioxane (1,4-dioxane), added with [1,1'-bis(diphenylphosphino)ferrocene]palladium dichloride (Pd(dppf)Cl₂, 0.18 g, 0.25 mmol, CAS: 72287-26-4) under argon, heated to 90° C. to react overnight, cooled to room temperature and filtered through celite. The filtrate was added with water and ethyl acetate for layering. The organic layer was washed with saturated saline, dried over anhydrous sodium sulfate, rotary evaporated under vacuum to remove the solvent, passed through silica gel chromatography and slurried in petroleum ether to give borate M-1. $^1$H NMR (400 MHz, CDCl₃) δ 8.28 (d, J=2.8 Hz, 1H), 7.86 (dd, J=8.4, 2.4 Hz, 1H), 7.00-6.92 (m, 2H), 6.86-6.80 (m, 2H), 4.47 (s, 1H), 1.29 (s, 12H), 1.24 (s, 9H).

Example 127: Synthesis of Borate M-2

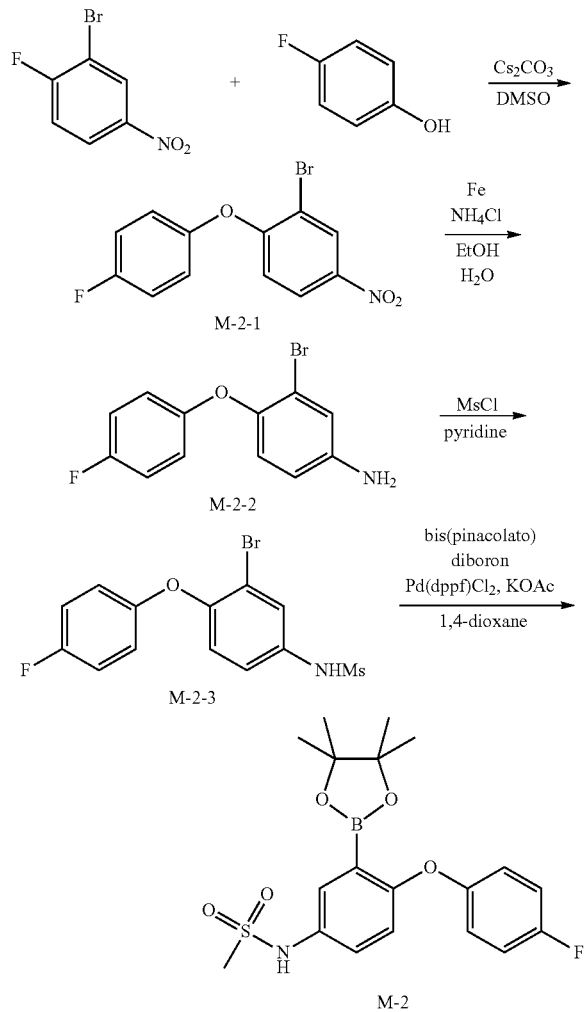

The same procedure as the synthetic method in Example 7 was used to give borate M-2, except that p-fluorophenol was used instead of phenol in Step 1.

$^1$H NMR (400 MHz, CDCl$_3$) δ 7.51 (d, J=2.4 Hz, 1H), 7.42 (dd, J=8.8, 2.8 Hz, 1H), 6.98-6.93 (m, 3H), 6.85-6.81 (m, 2H), 6.54 (s, 1H), 3.01 (s, 3H), 1.20 (s, 12H).

Example 128: Synthesis of Borate M-3

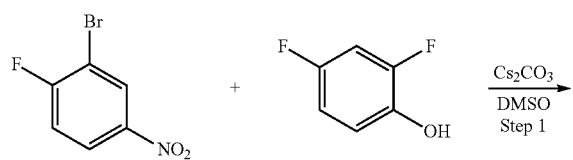

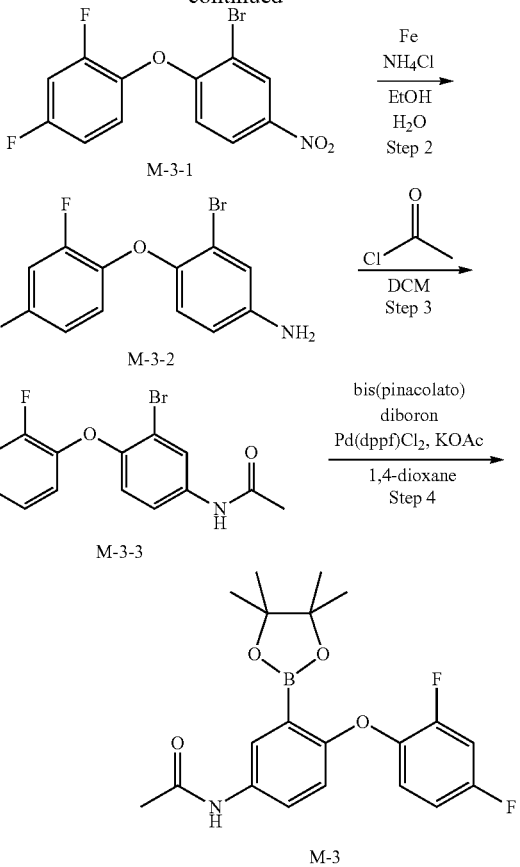

Step 1
3-Bromo-4-fluoronitrobenzene (5.0 g, 22.7 mmol, CAS: 701-45-1), 2,4-difluorophenol (3.0 g, 23.1 mmol) and cesium carbonate (9.5 g, 29.2 mmol) were suspended in 6 mL of dimethyl sulfoxide, heated to 100° C. to react overnight, cooled to room temperature, and added with water and ethyl acetate for layering. The organic phase was washed with saturated saline, dried over anhydrous sodium sulfate, and rotary evaporated under vacuum to give intermediate M-3-1.

Step 2
M-3-1 (7.2 g, 21.8 mmol) was dissolved in 50 mL of ethanol and 30 mL of water, followed by batch addition of iron powder (5.0 g) and ammonium chloride (9.6 g) at room temperature. After completion of the addition, the mixture was slowly raised to 80° C. to react under stirring for 2 h and filtered through celite. The filtrate was poured into water, and extracted twice with ethyl acetate. The combined organic phase was washed with saturated saline, dried over anhydrous sodium sulfate, and concentrated to give crude intermediate M-3-2 (6.3 g).

Step 3
M-3-2 (8.0 g, 26.7 mmol) and triethylamine (5.4 g, 53.3 mmol) were dissolved in DCM (50 mL), followed by dropwise addition of acetyl chloride (2.7 g, 34.7 mmol) under ice bath. The mixture was stirred at room temperature for 1 h. TLC showed that the reaction was complete. The mixture was concentrated, added with water, and extracted with EA. The organic phase was dried over anhydrous sodium sulfate, concentrated, and slurried in PE/A to give 6.9 g of M-3-3 as a solid.

Step 4

M-3-3 (6.9 g, 20.2 mmol), potassium acetate (5.9 g, 60.5 mmol) and bis(pinacolato)diboron (10.2 g, 40.4 mmol, CAS: 73183-34-3) were dissolved in 50 mL of dioxane, added with [1,1'-bis(diphenylphosphino)ferrocene]palladium dichloride (0.8 g, 1.1 mmol, CAS: 72287-26-4) under argon, heated to 100° C. to react for 3 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, passed through silica gel chromatography and slurried in ethyl acetate and petroleum ether to give borate M-3 (1.7 g).

$^1$H NMR (400 MHz, CDCl$_3$) δ 7.85 (dd, J=8.8, 2.8 Hz, 1H), 7.61 (d, J=2.8 Hz, 1H), 7.31 (s, 1H), 6.93-6.81 (m, 2H), 6.70-6.65 (m, 2H), 2.15 (s, 3H), 1.18 (s, 12H). HPLC-MS: [M+H]$^+$=390.1

Example 129: Synthesis of Borate M-4

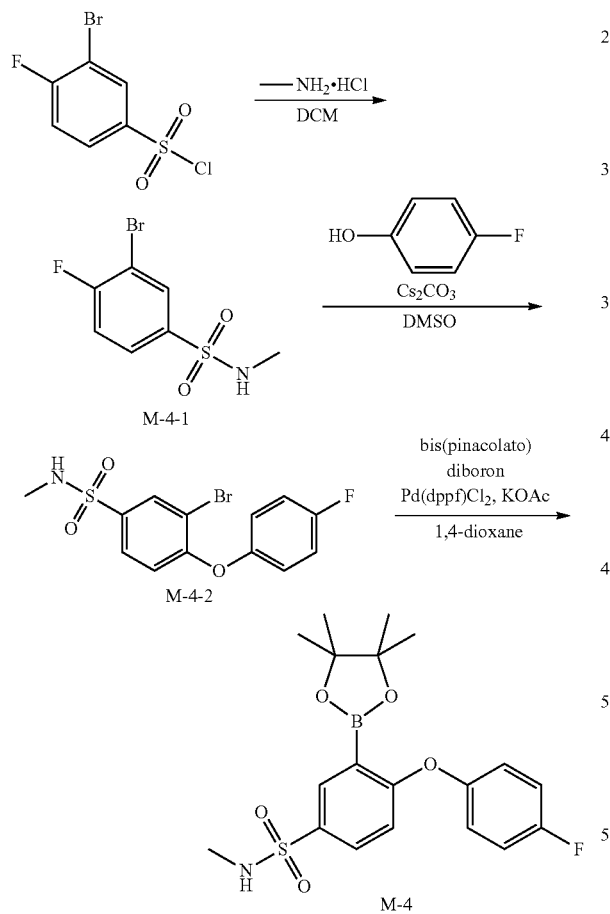

Step 1

Methylamine hydrochloride (1.1 g, 16.3 mmol) and triethylamine (3.3 g, 32.6 mol) were dissolved in 40 mL of DCM, added dropwisely with 3-bromo-4-fluorobenzenesulfonyl chloride (3.0 g, 11.0 mmol, CAS: 631912-19-1) under ice bath, and stirred at room temperature for 2 h. TLC detection showed the reaction was complete. The reaction solution was poured into water and extracted with EA. The organic layer was washed with saline, dried and concentrated to give 2.8 g of M-4-1.

Step 2

M-4-1 (2.8 g, 10.4 mmol), p-fluorophenol (1.3 g, 11.5 mmol) and cesium carbonate (4.4 g, 13.5 mmol) were dissolved in DMSO (35 mL), heated to 110° C. under nitrogen, and stirred for 2 h. TLC detection showed the reaction was complete. The reaction solution was cooled to room temperature, poured into water and extracted with EA. The organic layer was washed with water and saline, dried, concentrated and purified by column chromatography to give 2.7 g of M-4-2.

Step 3

M-4-2 (2.6 g, 7.2 mmol), potassium acetate (1.6 g, 16.7 mmol) and bis(pinacolato)diboron (3.7 g, 14.4 mmol, CAS: 73183-34-3) were dissolved in 35 mL of dioxane, added with [1,1'-bis(diphenylphosphino)ferrocene]palladium dichloride (0.3 g, 0.4 mmol, CAS: 72287-26-4) under argon, heated to 100° C. to react for 2 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, passed through silica gel chromatography and slurried in petroleum ether to give borate M-4 (1.4 g).

$^1$H NMR (400 MHz, CDCl$_3$) δ 8.23 (d, J=2.4 Hz, 1H), 7.84 (dd, J=8.4, 2.4 Hz, 1H), 7.07-7.02 (m, 2H), 6.97-6.94 (m, 2H), 6.89 (d, J=8.8 Hz, 1H), 4.35 (q, J=5.6 Hz, 1H), 2.67 (d, J=5.2 Hz, 3H), 1.27 (s, 12H). HPLC-MS: [M+H]$^+$=408.2

Example 130: Synthesis of Borate M-5

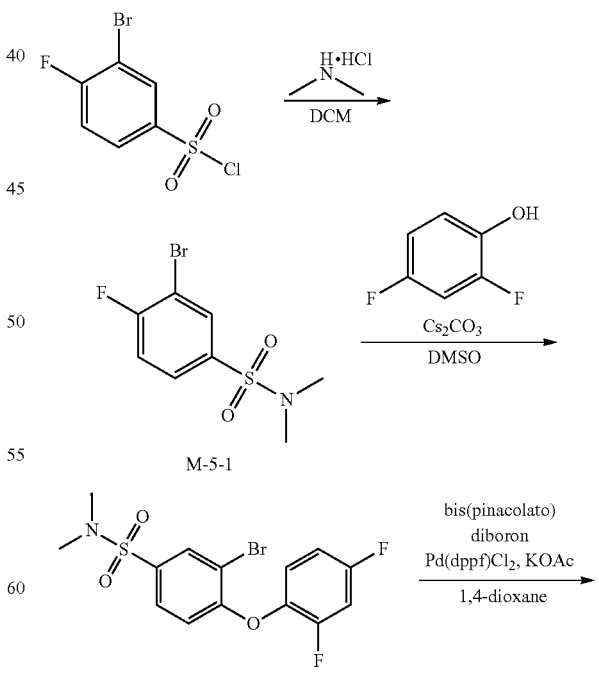

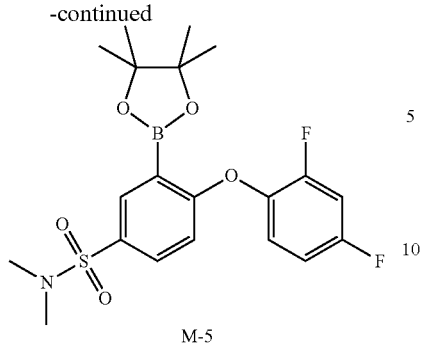

M-5

Step 1

Dimethylamine hydrochloride (1.3 g, 15.4 mmol) and triethylamine (3.1 g, 30.0 mmol) were dissolved in 30 ml of DCM, added dropwisely with 3-bromo-4-fluorobenzenesulfonyl chloride (2.8 g, 10.3 mmol, CAS: 631912-19-1) in an ice bath, and then stirred at room temperature for 2 h. TLC detection showed the reaction was complete. The reaction solution was poured into water and extracted with EA. The organic layer was washed with saline, dried and concentrated to give 2.9 g of M-5-1 as a yellowish solid.

Step 2

M-5-1 (2.9 g, 10.4 mmol), 2,4-difluorophenol (1.5 g, 11.5 mmol), cesium carbonate (4.4 g, 13.5 mmol) were dissolved in DMSO (35 mL), heated to 110° C. under nitrogen, and stirred for 3 h. TLC detection showed the reaction was complete. The reaction solution was cooled to room temperature, poured into water and extracted with EA. The organic layer was washed with water and saline, dried, concentrated and purified by column chromatography to give 3.8 g of M-5-2 as a white solid.

Step 3

M-5-2 (3.8 g, 9.8 mmol), potassium acetate (1.8 g, 18.4 mmol) and bis(pinacolato)diboron (5.0 g, 19.6 mmol, CAS: 73183-34-3) were dissolved in 50 mL of dioxane, added with [1,1'-bis(diphenylphosphino)ferrocene] palladium dichloride (0.4 g, 0.6 mmol, CAS: 72287-26-4) under argon, heated to 100° C. to react for 3 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, passed through silica gel chromatography and slurried in petroleum ether to give borate M-5 (0.8 g) as a pale white solid.

$^1$H NMR (400 MHz, CDCl$_3$) δ 8.17 (d, J=2.4 Hz, 1H), 7.75 (dd, J=8.8, 2.4 Hz, 1H), 7.05-6.94 (m, 2H), 6.88-6.82 (m, 2H), 2.72 (s, 6H), 1.30 (s, 12H).

Example 131: Synthesis of Borate M-6

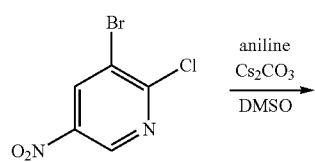

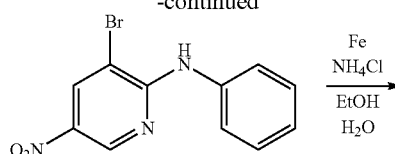

M-6-1

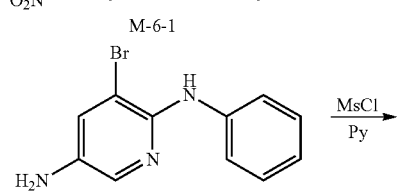

M-6-2

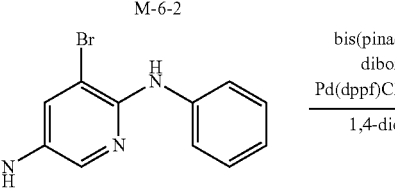

M-6-3

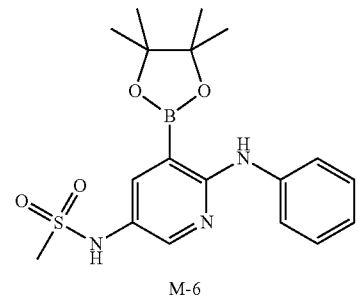

M-6

Step 1

2-Chloro-3-bromo-5-nitropyridine (10.0 g, 42.1 mmol, CAS: 5470-17-7), aniline (4.3 g, 46.2 mmol, CAS: 62-53-3) and cesium carbonate (18.0 g, 55.2 mmol) were suspended in 100 mL of dimethyl sulfoxide, heated to 80° C. to react for 2 h, cooled to room temperature, and added with water and ethyl acetate for layering. The organic phase was washed with saturated saline, dried over anhydrous sodium sulfate, rotary evaporated under vacuum, and purified by column chromatography to give intermediate M-6-1 (5.4 g).

Step 2

M-6-1 (5.4 g, 18.4 mmol) was dissolved in 100 mL of ethanol and 30 mL of water, added in batches with iron powder (5.1 g) and ammonium chloride (9.8 g) at room temperature, and then slowly raised to 100° C. to react under stirring for 2 h and filtered through celite. The filtrate was poured into water and extracted twice with ethyl acetate. The combined organic phase was washed with saturated saline, dried over anhydrous sodium sulfate, and concentrated to give a crude intermediate M-6-2 (4.7 g).

Step 3

M-6-2 (4.7 g, 17.8 mmol) was dissolved in 20 mL of pyridine (Py), cool to 0° C., added slowly and dropwisely with methylsulfonyl chloride (2.5 g, 21.8 mmol), and then warmed to room temperature to react for 1 h, and added with ice water and ethyl acetate for layering. The organic phase was washed with 2M diluted hydrochloric acid and saturated saline successively, dried over anhydrous sodium sulfate, rotary evaporated under vacuum to remove ethyl acetate, and purified by column chromatography to give intermediate M-6-3 (4.0 g).

Step 4

M-6-3 (4.0 g, 11.7 mmol), potassium acetate (2.3 g, 23.4 mmol) and bis(pinacolato)diboron (6.0 g, 23.6 mmol, CAS: 73183-34-3) were dissolved in 50 mL of dioxane, added with [1,1'-bis(diphenylphosphino)ferrocene]palladium dichloride (240 mg, 0.3 mmol, CAS: 72287-26-4) under argon, heated to 100° C. to react overnight, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give borate M-6 (0.94 g) as an off-white solid.

$^1$H NMR (400 MHz, DMSO-$d_6$) δ 9.36 (s, 1H), 8.51 (s, 1H), 8.18 (d, J=2.8 Hz, 1H), 7.75 (d, J=2.8 Hz, 1H), 7.65 (d, J=8.4 Hz, 2H), 7.30 (t, J=7.8 Hz, 2H), 6.96 (t, J=8.0 Hz, 1H), 2.93 (s, 3H), 1.38 (s, 12H).

Example 132: Synthesis of Borate M-7

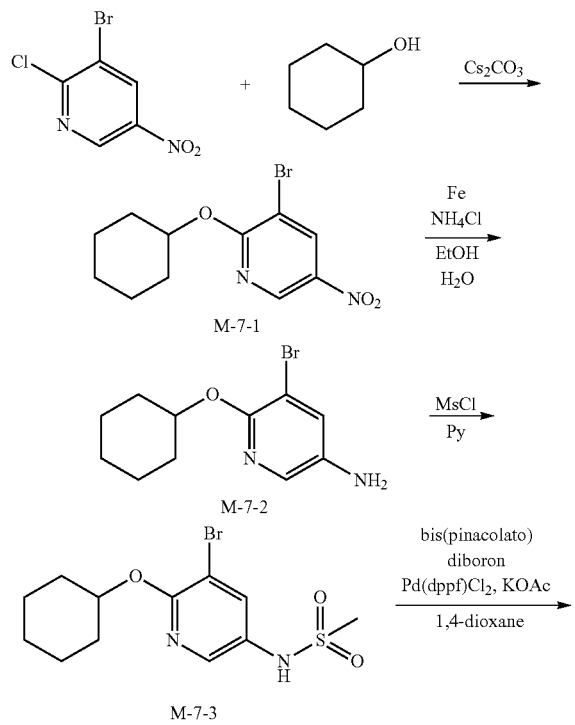

Step 1

2-Chloro-3-bromo-5-nitropyridine (3.0 g, 12.6 mmol, CAS: 5470-17-7) and cesium carbonate (8.4 g, 25.8 mmol) were suspended in cyclohexanol (10 mL, CAS: 108-93-0), heated to 100° C. to react for 4 h, cooled to room temperature, and added with water and ethyl acetate for layering. The organic phase was washed with saturated saline, dried over anhydrous sodium sulfate, and concentrated by rotary evaporation under vacuum to give intermediate M-7-1 (3.5 g).

Step 2

M-7-1 (3.5 g, 11.6 mmol) was dissolved in 60 mL ethanol and 20 mL water, added in batches with iron powder (3.3 g) and ammonium chloride (6.5 g) at room temperature, and then slowly raised to 100° C. to react under stirring for 2 h and filtered through celite. The filtrate was poured into water and extracted twice with ethyl acetate. The combined organic phase was washed with saturated saline, dried over anhydrous sodium sulfate, and concentrated to give intermediate M-7-2 (3.0 g).

Step 3

M-7-2 (3.0 g, 11.1 mmol) was dissolved in 5 mL of pyridine and 10 mL of dichlorohexane, cool to 0° C., added slowly and dropwises with methylsulfonyl chloride (1.5 g, 13.1 mmol), and then warmed to room temperature to react for 1 h, and added with ice water and ethyl acetate for layering. The organic phase was washed with 2M dilute hydrochloric acid and saturated saline successively, dried over anhydrous sodium sulfate, rotary evaporated under vacuum to remove ethyl acetate, and purified by column chromatography to give intermediate M-7-3 (1.5 g).

Step 4

M-7-3 (1.5 g, 4.3 mmol), potassium acetate (0.8 g, 8.2 mmol) and bis(pinacolato)diboron (2.1 g, 8.3 mmol, CAS: 73183-34-3) were dissolved in 30 mL of dioxane, added with [1,1'-bis(diphenylphosphino)ferrocene]palladium dichloride (170 mg, 0.2 mmol, CAS: 72287-26-4) under argon, heated to 100° C. to react for 4 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give borate M-7 (0.67 g) as a yellowish oil.

$^1$H NMR (400 MHz, CDCl$_3$) δ 8.12 (d, J=2.8 Hz, 1H), 7.80 (d, J=2.8 Hz, 1H), 6.39 (s, TH), 6.12 (t, J=7.6 Hz, 1H), 2.97 (s, 3H), 1.84-1.79 (m, 4H), 1.71-1.64 (m, 2H), 1.48-1.38 (m, 4H), 1.34 (s, 12H). HPLC-MS: [M+H]$^+$=397.2

Example 133: Synthesis of Borate M-8

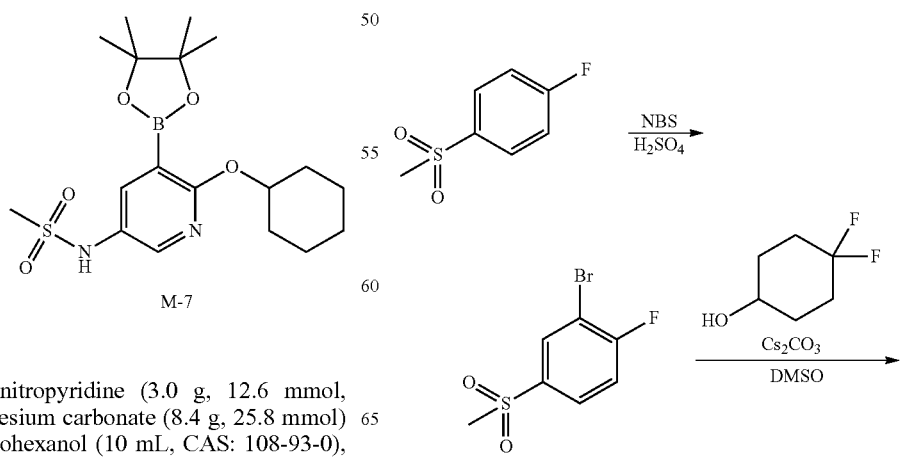

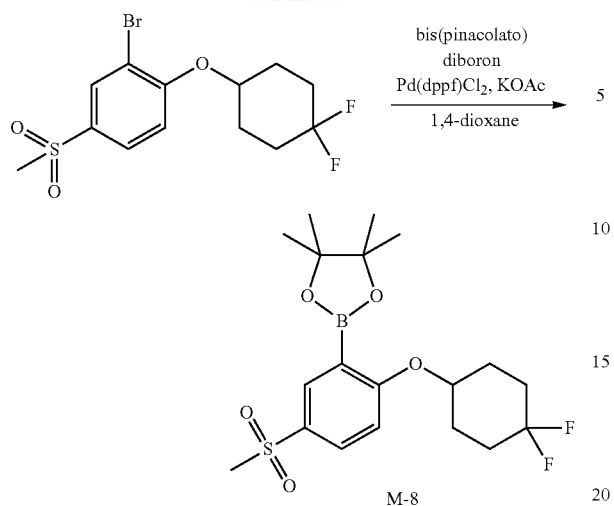

The same procedure as the synthetic method in Example 19 was used to give the borate M-8, except that 4,4-difluorocyclohexanol (CAS: 22419-35-8) was used instead of 2,4-difluorophenol in Step 2.

$^1$H NMR (400 MHz, CDCl$_3$) δ 8.28 (d, J=2.4 Hz, 1H), 7.95 (dd, J=8.8 Hz, 2.4 Hz, TH), 7.00 (d, J=8.8 Hz, 1H), 4.78 (m, 1H), 3.05 (s, 3H), 2.42-2.30 (m, 2H), 2.09 (d, J=13.6 Hz, 2H), 1.93-1.82 (m, 4H), 1.33 (s, 12H).

Example 134: Synthesis of Borate M-9

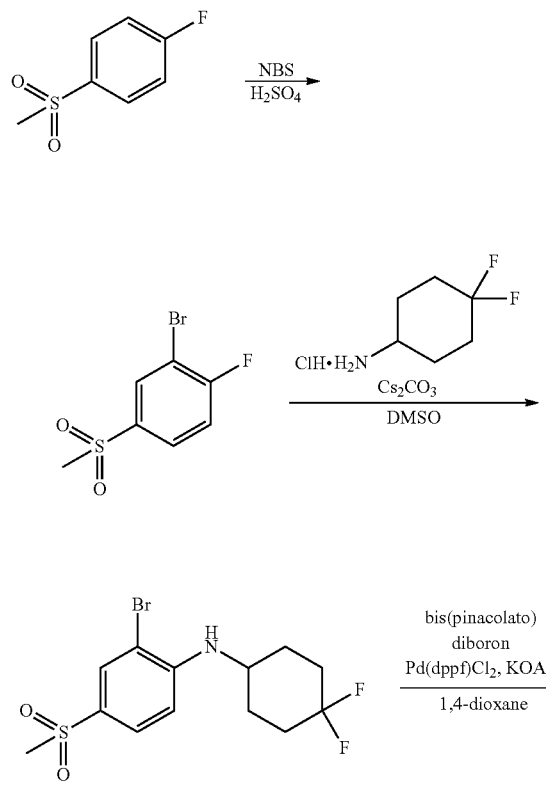

Borate M-9 was prepared in the same method as that in Example 19, except that 4,4-difluorocyclohexylamine hydrochloride (CAS: 675112-70-6) was used instead of 2,4-difluorophenol in step 2.

$^1$H NMR (400 MHz, CDCl$_3$) δ 8.18 (d, J=2.4 Hz, 1H), 7.80 (dd, J=8.8 Hz, 2.4 Hz, 1H), 6.65-6.59 (m, 2H), 3.65-3.61 (m, 1H), 3.02 (s, 3H), 2.15-1.95 (m, 6H), 1.78-1.74 (m, 2H), 1.38 (s, 12H). HPLC-MS: [M+H]$^+$=416.1

Example 135: Synthesis of Borate M-10

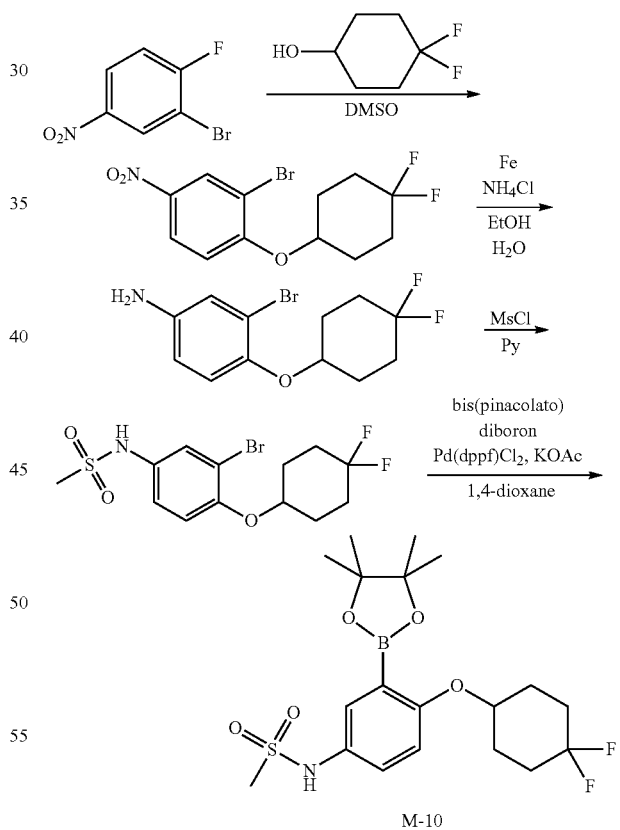

Borate M-10 was prepared in the same method as that in Example 7, except that 4,4-difluorocyclohexanol (CAS: 22419-35-8) was used instead of phenol in Step 1.

$^1$H NMR (400 MHz, CDCl$_3$) 7.46 (d, J=3.2 Hz, 1H), 7.41 (dd, J=8.4 Hz, 2.8 Hz, 1H), 6.90 (d, J=8.8 Hz, 1H), 6.34 (s, 1H), 4.64 (s, 1H), 2.97 (s, 3H), 2.45-2.30 (m, 2H), 2.08 (d, J=14.0 Hz, 2H), 1.93-1.77 (m, 4H), 1.33 (s, 12H).

Example 136: Synthesis of Borate M-11

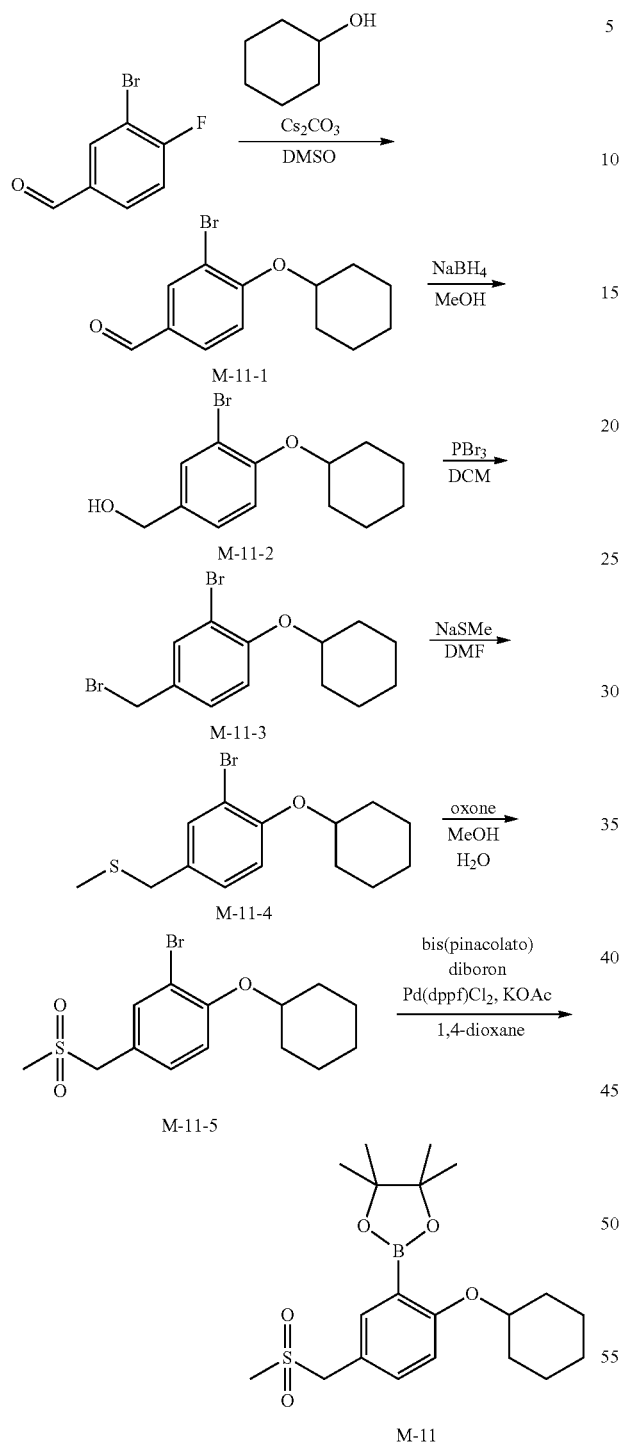

Example 137: Synthesis of Borate M-12

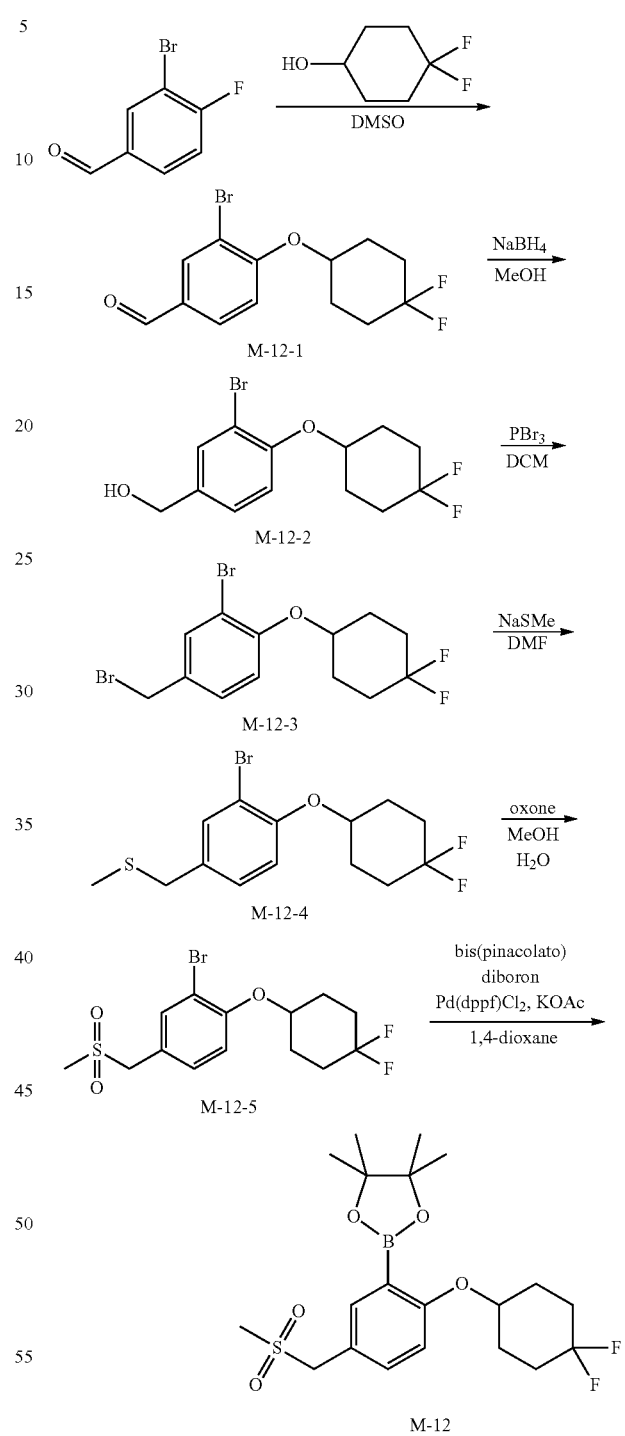

The same method as that in Example 56 was used to give borate M-11, except that cyclohexanol was used instead of 2,4-difluorophenol in Step 1.

$^1$H NMR (400 MHz, CDCl$_3$) δ 7.57 (d, J=2.4 Hz, 1H), 7.43 (dd, J=8.8 Hz, 2.8 Hz, 1H), 6.91 (d, J=8.4 Hz, 1H), 4.34 (m, 1H), 4.16 (s, 2H), 2.71 (s, 3H), 1.84-1.76 (m, 4H), 1.70-1.57 (m, 4H), 1.50-1.41 (m, 2H), 1.34 (s, 12H).

The same method as that in Example 56 was used to give borate M-12, except that 4,4-difluorocyclohexanol was used instead of 2,4-difluorophenol in Step 1.

$^1$H NMR (400 MHz, CDCl$_3$) δ 7.68 (d, J=2.4 Hz, 1H), 7.49 (dd, J=8.8 Hz, 2.8 Hz, 1H), 6.93 (d, J=8.4 Hz, 1H), 4.69 (m, 1H), 4.18 (s, 2H), 2.76 (s, 3H), 2.43-2.31 (m, 2H), 2.10 (d, J=14.0 Hz, 2H), 1.93-1.78 (m, 4H), 1.30 (s, 12H).

Example 138: Synthesis of Borate M-13

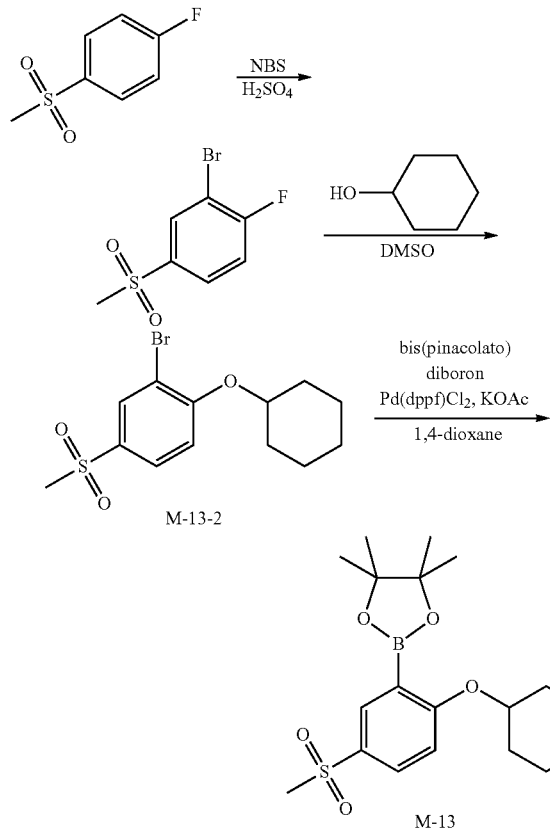

Borate M-13 was prepared in the same method as that in Example 19, except that cyclohexanol was used instead of 2,4-difluorophenol in Step 2.

$^1$H NMR (400 MHz, CDCl$_3$) 8.17 (d, J=2.8 Hz, 1H), 7.89 (dd, J=8.8 Hz, 2.4 Hz, 1H), 6.96 (d, J=8.8 Hz, 1H), 4.49-4.45 (m, 1H), 3.02 (s, 3H), 1.86-1.81 (m, 4H), 1.74-1.67 (m, 2H), 1.50-1.38 (m, 4H), 1.35 (s, 12H).

Example 139: Synthesis of Borate M-14

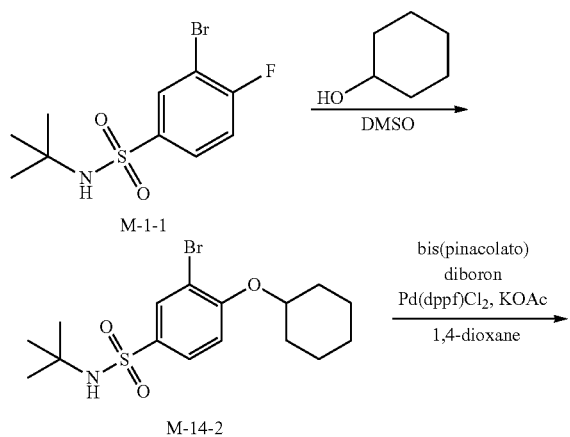

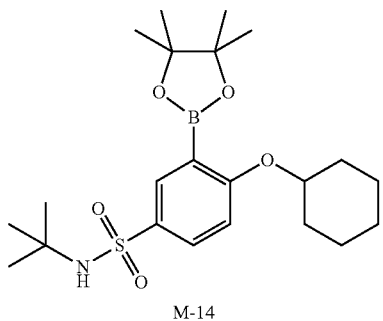

Cyclohexanol (2.7 g, 27.0 mmol) was added to THF (30 mL), added with sodium hydride (0.5 g, 12.5 mmol, 60% content attached to mineral oil) in an ice bath under nitrogen, and then stirred for 30 min, added with M-1-1 (1.7 g, 5.5 mmol), and heated to 60° C. to react overnight. The reaction mixture was added with water (50 mL) and extracted with EA. The combined organic phase was washed with saturated saline, dried, rotary evaporated to dryness and purified by column chromatography to give a colorless oil M-14-2 (2.3 g).

M-14-2 (2.3 g, 5.9 mmol), potassium acetate (1.0 g, 11.2 mmol), bis(pinacolato)diboron (2.4 g, 9.5 mmol, CAS: 73183-34-3) were dissolved in 30 mL of dioxane, added with [1,1'-bis(diphenylphosphino)ferrocene]palladium dichloride (220 mg, 0.3 mmol, CAS: 72287-26-4) under argon, heated to 95° C. to react for 4 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, passed through silica gel chromatography and slurried in petroleum ether to give 0.7 g of borate M-14 as a white solid.

$^1$H NMR (400 MHz, CDCl$_3$) δ 8.11 (d, J=2.4 Hz, 1H), 7.84 (dd, J=8.8, 2.8 Hz, 1H), 6.90 (d, J=8.8 Hz, 1H), 4.44-4.41 (m, 1H), 1.86-1.80 (m, 4H), 1.72-1.66 (m, 2H), 1.52-1.40 (m, 4H), 1.34 (s, 12H), 1.22 (s, 9H).

Example 140: Synthesis of Borate M-15

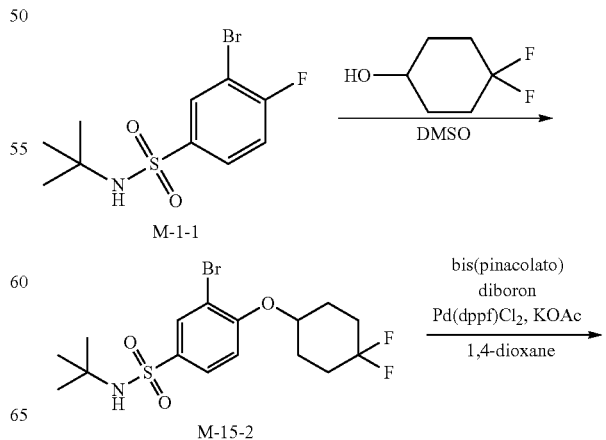

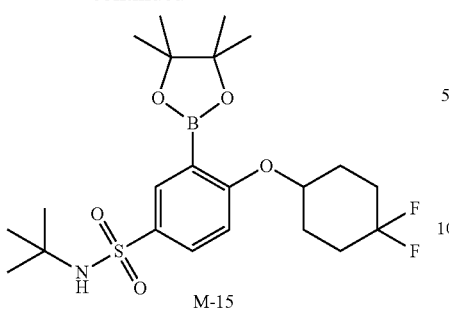

M-1-1 (1.4 g, 4.5 mmol), 4,4-difluorocyclohexanol (0.9 g, 6.6 mmol) and cesium carbonate (2.2 g, 6.8 mmol) were suspended in 10 mL of dimethyl sulfoxide, heated to 100° C. to react for 48 h, cooled to room temperature, and added with water and ethyl acetate for layering. The organic phase was washed with saturated saline, dried over anhydrous sodium sulfate, concentrated by rotary evaporation under vacuum, and purified by column chromatography to give intermediate M-15-2 (1.2 g).

M-15-2 (1.2 g, 2.8 mmol), potassium acetate (0.6 g, 6.1 mmol) and bis(pinacolato)diboron (1.8 g, 7.1 mmol, CAS: 73183-34-3) were dissolved in 20 mL of dioxane, added with [1,1'-bis(diphenylphosphino)ferrocene]palladium dichloride (118 mg, 0.2 mmol, CAS: 72287-26-4) under argon, heated to 95° C. to react for 4 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give 1.1 g of borate M-15. $^1$H NMR (400 MHz, CDCl$_3$) δ 8.22 (d, J=2.4 Hz, 1H), 7.89 (dd, J=8.8, 2.8 Hz, 1H), 6.92 (d, J=8.8 Hz, 1H), 4.75 (s, 1H), 4.42 (s, 1H), 2.46-2.30 (m, 2H), 2.12-2.07 (m, 2H), 1.91-1.80 (m, 4H), 1.33 (s, 12H), 1.23 (s, 9H).

Example 141: Synthesis of Borate M-16

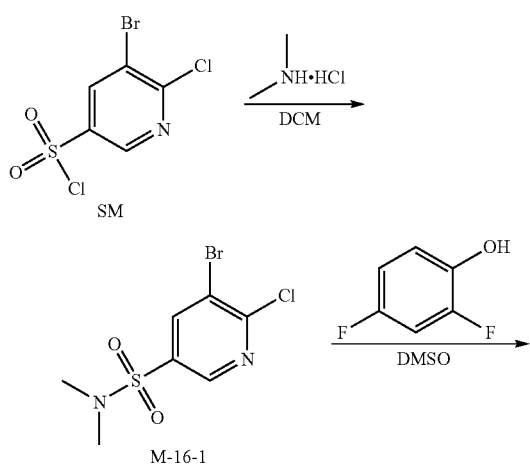

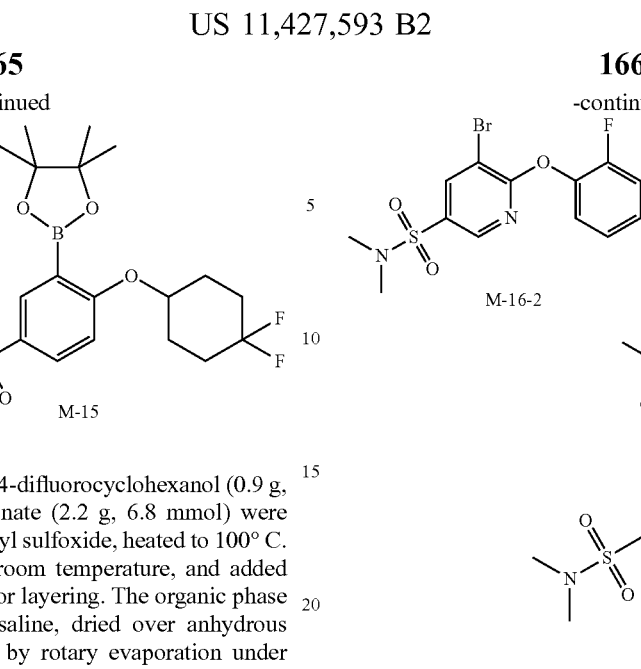

Step 1

Dimethylamine hydrochloride (2.1 g, 25.8 mmol) and triethylamine (5.5 g, 54.4 mmol) were dissolved in 50 ml of dichloromethane (DCM), stirred under ice bath for 15 min, added dropwisely with a solution of 3-bromo-2-chloropyridine-5-sulfonyl chloride (5.0 g, 17.2 mmol, CAS: 216394-05-7) in 40 mL of DCM, and then kept at this temperature to react for 0.5 h. TLC showed the reaction was complete. The reaction mixture was added with 50 mL of water for layering. The aqueous phase was extracted with DCM again. The combined organic phase was washed with saturated saline, dried, and rotary evaporated to dryness to give 5.0 g of M-16-1 as a white solid.

Step 2

M-16-1 (1.9 g, 6.3 mmol), 2,4-difluorophenol (1.0 g, 8.5 mmol) and cesium carbonate (2.7 g, 8.3 mmol) were suspended in 15 mL of dimethyl sulfoxide, heated to 100° C. to react for 2 h, cooled to room temperature, and added with water and ethyl acetate for layering. The organic phase was washed with saturated saline, dried over anhydrous sodium sulfate, concentrated by rotary evaporation under vacuum, and purified by column chromatography to give intermediate M-16-2 (1.5 g).

Step 3

M-16-2 (1.5 g, 3.8 mmol), potassium acetate (0.7 g, 7.1 mmol) and bis(pinacolato)diboron (1.8 g, 7.1 mmol, CAS: 73183-34-3) were dissolved in 20 mL of dioxane, added with [1,1'-bis(diphenylphosphino)ferrocene]palladium dichloride (150 mg, 0.2 mmol, CAS: 72287-26-4) under argon, heated to 95° C. to react for 4 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give 0.9 g of borate M-16. $^1$H NMR (400 MHz, CDCl$_3$) δ 8.52 (d, J=2.8 Hz, 1H), 8.43 (d, J=2.8 Hz, 1H), 7.27-7.21 (m, 1H), 6.98-6.89 (m, 2H), 2.74 (s, 6H), 1.37 (s, 12H).

Example 142: Synthesis of Borate M-17

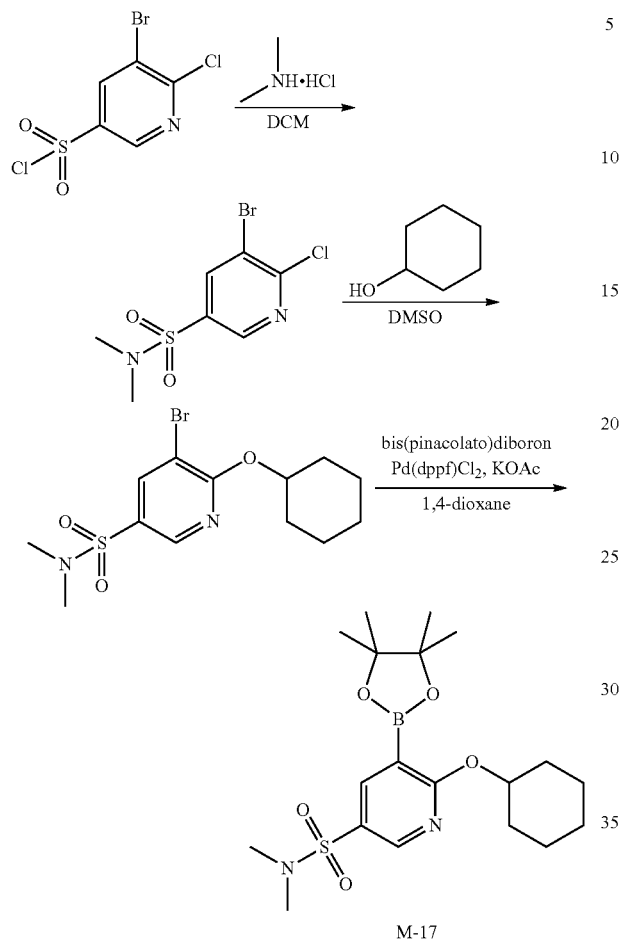

Borate M-17 was prepared in the same method as that in Example 141, except that cyclohexanol was used instead of 2,4-difluorophenol in Step 2. $^1$H NMR (400 MHz, CDCl$_3$) δ 8.57 (d, =2.8 Hz, 1H), 8.18 (d, J=2.8 Hz, 1H), 5.25-5.21 (m, 1H), 2.72 (s, 6H), 1.90-1.77 (m, 4H), 1.78-1.65 (s, 2H), 1.52-1.48 (m, 4H), 1.34 (s, 12H).

Example 143: Synthesis of Borate M-18

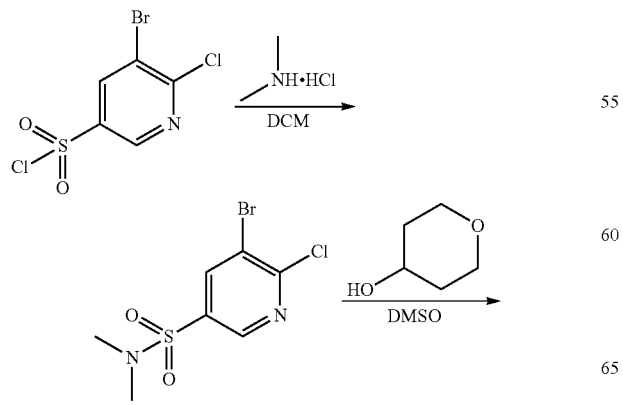

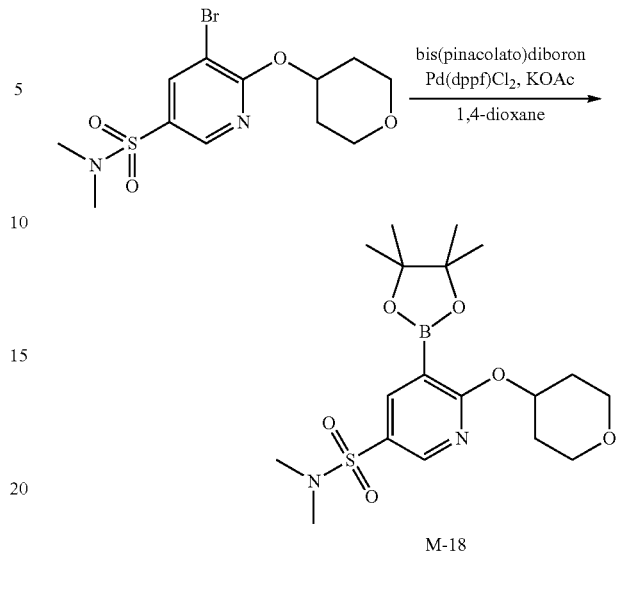

Borate M-18 was prepared in the same method as that in Example 141, except that tetrahydropyran-4-ol was used instead of 2,4-difluorophenol in step 2. $^1$H NMR (400 MHz, CDCl$_3$) δ 8.57 (d, J=2.8 Hz, 1H), 8.24 (d, J=2.4 Hz, 1H), 5.47-5.43 (m, 1H), 4.05-3.99 (n, 2H), 3.72-3.67 (m, 2H), 2.73 (s, 6H), 2.07-2.02 (m, 2H), 1.87-1.81 (m, 2H), 1.35 (s, 12H).

Example 144: Synthesis of Borate M-19

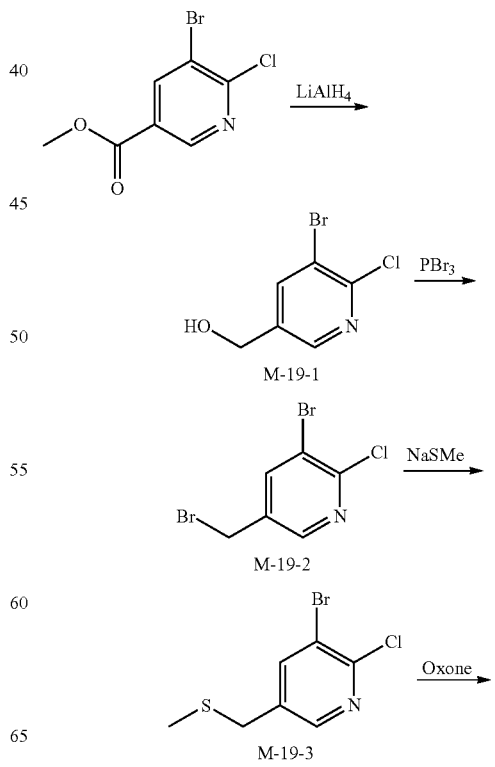

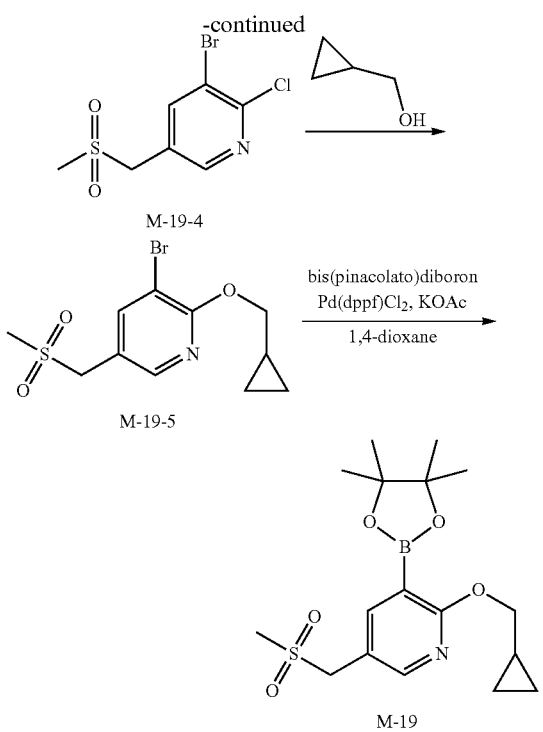

Step 5

M-19-4 (4.0 g, 14.1 mmol) and cesium carbonate (9.2 g, 28.2 mmol) were stirred in 20 mL of hydroxymethylcyclopropane under nitrogen at 90° C. overnight. TLC detection showed the reaction was complete. The reaction solution was cooled to room temperature, poured into water and extracted with EA. The organic layer was washed with water and saline, dried, concentrated, and passed through column chromatography to give 2.5 g of M-19-5.

Step 6

M-19-5 (2.5 g), potassium acetate (3.5 g, 35.7 mmol) and bis(pinacolato)diboron (6.0 g, 23.6 mmol, CAS: 73183-34-3) were dissolved in 20 mL of dioxane, added with [1,1'-bis(diphenylphosphino)ferrocene]palladium dichloride (0.4 g, CAS: 72287-26-4) under argon, heated to 90° C. to react for 4 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give borate M-19.

$^1$H NMR (400 MHz, CDCl$_3$) δ 8.17 (d, J=2.4 Hz, 1H), 7.95 (d, J=2.4 Hz, 1H), 4.22 (d, J=6.4 Hz, 2H), 4.14 (s, 2H), 2.77 (s, 3H), 1.35 (s, 12H), 1.29-1.23 (m, 1H), 0.57-0.52 (m, 2H), 0.43-0.39 (m, 2H). HPLC-MS: [M+H]$^+$=368.2

Example 145: Synthesis of Borate M-20

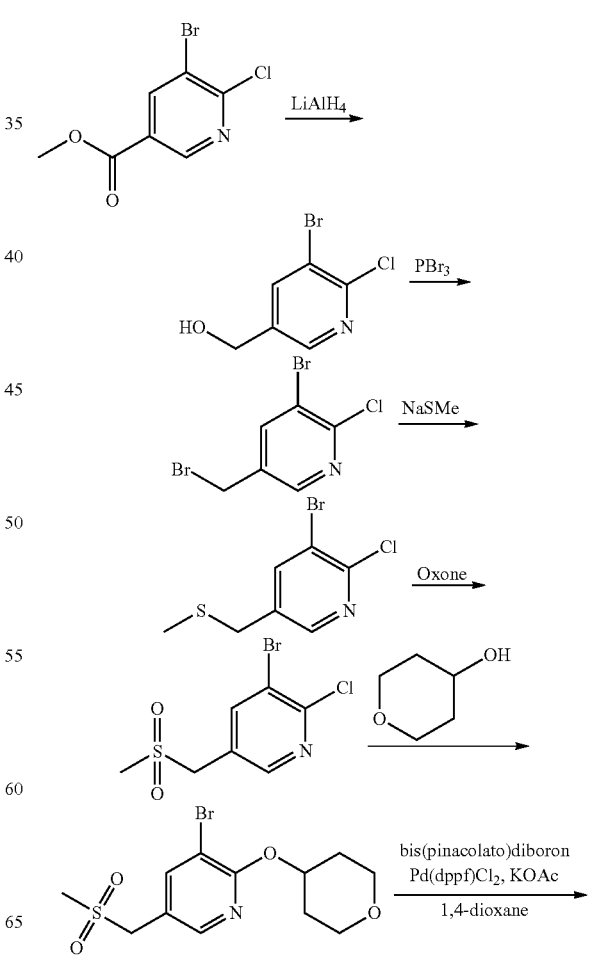

Step 1

Methyl 5-bromo-6-chloronicotinate (30.0 g, 0.12 mol, CAS: 78686-77-8) was dissolved in 300 mL of ethanol, added with sodium borohydride (5.4 g, 0.14 mol) at room temperature, and heated to reflux for 2 h. TLC showed the reaction was complete. The mixture was quenched with water, concentrated and passed through column chromatography to give 10.0 g of M-19-1.

Step 2

M-19-1 (10.0 g, 44.9 mmol) was dissolved in 50 mL of DCM, added with phosphine tribromide (12.2 g, 45.1 mmol) in an ice bath, and stirred at 0° C. for 1 h. TLC showed the reaction was complete. The reaction mixture was added with water and extracted with EA. The organic phase was washed with saline, dried and concentrated to give M-19-2, which was used directly in the next step.

Step 3

M-19-2 (calculated according to the theoretical yield in the previous step) was dissolved in 50 mL of DMF, added with sodium methylthiolate (3.8 g, 54.2 mmol), and stirred at room temperature for 2 h. TLC showed that M-19-2 was completely reacted. The mixture was diluted with water and extracted with EA. The organic phase was washed with saline, dried and concentrated to give M-19-3, which was used directly in the next step.

Step 4

M-19-3 (calculated according to the theoretical yield of the previous step) was dissolved in 100 mL of methanol, added with potassium peroxymonosulfonate (Oxone) (15.9 g, 94.5 mmol) under an ice bath, and stirred at room temperature for 1 h. TLC showed that M-19-3 was completely reacted. The mixture was diluted with water and extracted with EA. The organic phase was washed with saturated aqueous sodium thiosulfate solution and then with saturated saline, dried, concentrated and passed through column chromatography to give 8.2 g of M-19-4.

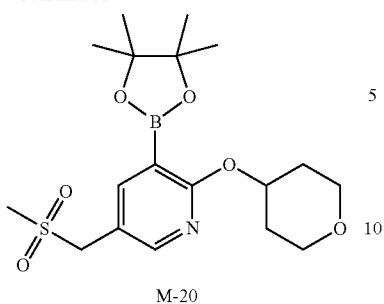

M-20

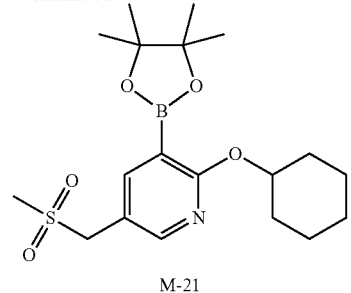

M-21

Borate M-20 was prepared in the same method as that in Example 144, except that tetrahydropyran-4-ol was used instead of hydroxymethylcyclopropane in Step 5. $^1$H NMR (400 MHz, CDCl$_3$) δ 8.18 (d, J=2.4 Hz, 1H), 7.97 (d, J=2.8 Hz, 1H), 5.40-5.35 (m, 1H), 4.14 (s, 2H), 4.04-3.99 (m, 2H), 3.71-3.66 (m, 2H), 2.80 (s, 3H), 2.05-1.98 (m, 2H), 1.85-1.78 (m, 2H), 1.34 (s, 12H). HPLC-MS: [M+H]$^+$=398.2.

Example 146: Synthesis of Borate M-21

Borate M-21 was prepared in the same method as that in Example 144, except that cyclohexanol was used instead of hydroxymethylcyclopropane in Step 5. $^1$H NMR (400 MHz, CDCl$_3$) δ 8.17 (d, J=2.8 Hz, 1H), 7.93 (d, J=2.8 Hz, 1H), 5.17-5.13 (m, 1H), 4.13 (s, 2H), 2.77 (s, 3H), 1.87-1.78 (m, 4H), 1.71-1.65 (m, 2H), 1.50-1.41 (m, 4H), 1.34 (s, 12H).

Example 147: Synthesis of Borate M-23

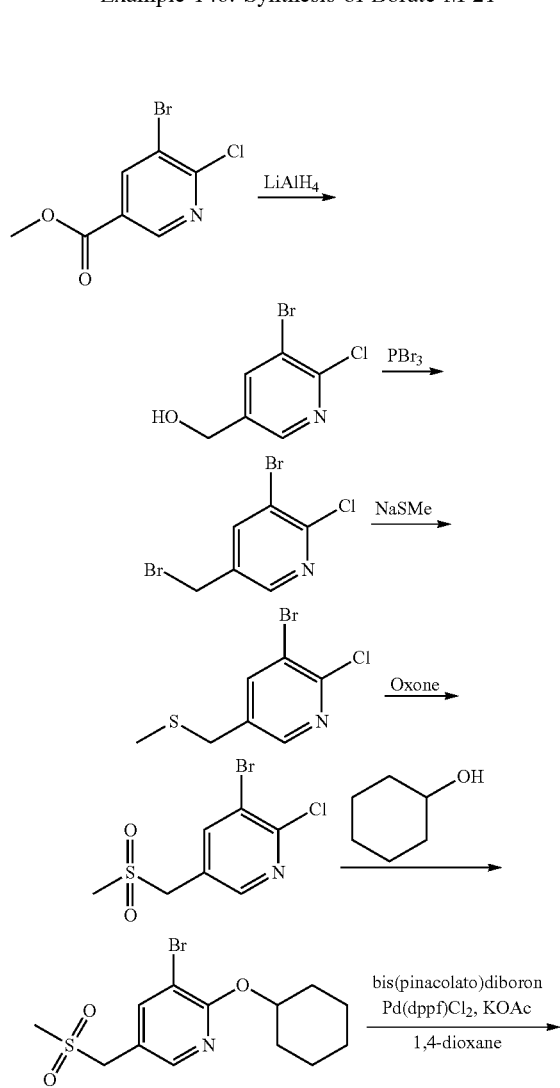

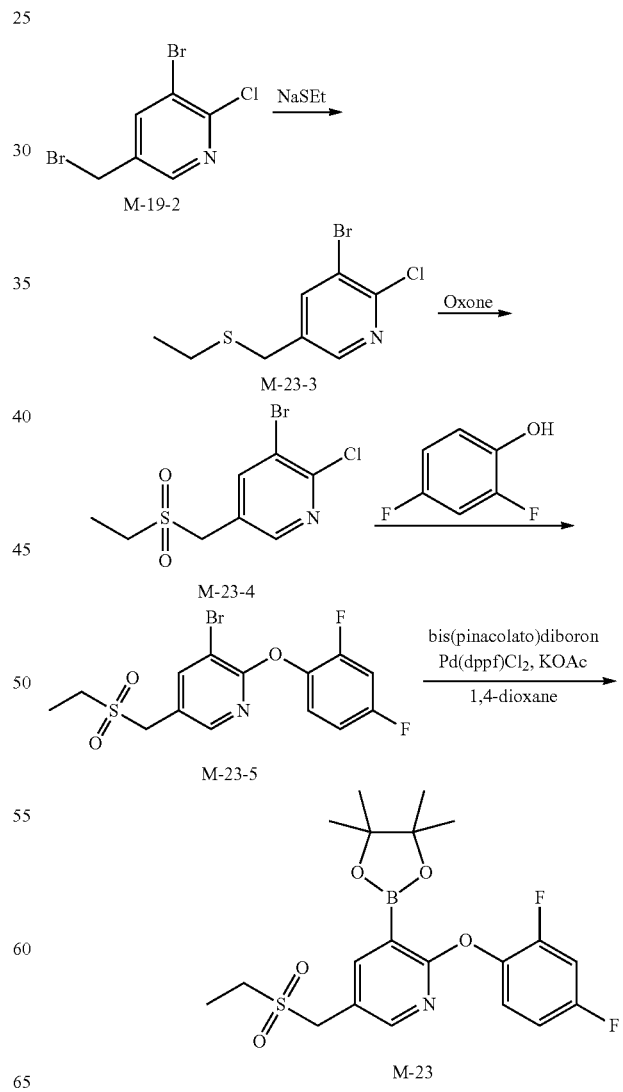

Step 1

M-19-2 (8.0 g, 28.0 mmol) was dissolved in 30 mL of DMF, added with sodium ethanethiolate (3.4 g, 40.4 mmol), and stirred at room temperature for 1 h. TLC showed the reaction was complete. The mixture was diluted with water and extracted with EA. The organic phase was washed with saline, dried and concentrated to give M-23-3 (4.0 g).

Step 2

M-23-3 (4.0 g, 15.0 mmol) was dissolved in 50 mL of methanol and 20 mL of water, added with potassium peroxymonosulfonate (Oxone, 12.0 g, 71.4 mmol) under an ice bath, and stirred at room temperature for 2 h. TLC showed the reaction was complete. The mixture was diluted with water and extracted with EA. The organic phase was washed with saturated aqueous sodium thiosulfate solution and then with saturated saline, dried and concentrated, and passed through column chromatography to give M-23-4 (0.9 g).

Step 3

M-23-4 (5.3 g, 17.8 mmol), 2,4-difluorophenol (3.5 g, 26.9 mmol) and cesium carbonate (11.6 g, 35.6 mmol) were stirred in 20 ml of dimethyl sulfoxide (DMSO) at 95° C. for 2 h under nitrogen. TLC detection showed the reaction was complete. The reaction solution was cooled to room temperature, poured into water and extracted with EA. The organic layer was washed with water and saline, dried and concentrated, and passed through column chromatography to give M-23-5.

Step 4

M-23-5 (4.7 g, 12.0 mmol), potassium acetate (3.5 g, 35.7 mmol) and bis(pinacolato)diboron (6.0 g, 23.6 mmol, CAS: 73183-34-3) were dissolved in 20 mL of dioxane, added with [1,1'-bis(diphenylphosphino)ferrocene] palladium dichloride (0.4 g, 0.5 mmol, CAS: 72287-26-4) under argon, heated to 95° C. to react for 2 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give 3.2 g of borate M-23.

¹H NMR (400 MHz, CDCl₃) δ 8.17 (d, J=2.4 Hz, 1H), 8.12 (d, J=2.4 Hz, 1H), 7.24-7.19 (m, 1H), 6.95-6.87 (m, 2H), 4.13 (s, 2H), 2.90 (q, J=7.6 Hz, 2H), 1.38 (t, J=7.6 Hz, 3H), 1.36 (s, 12H).

Example 148: Synthesis of Borate M-24

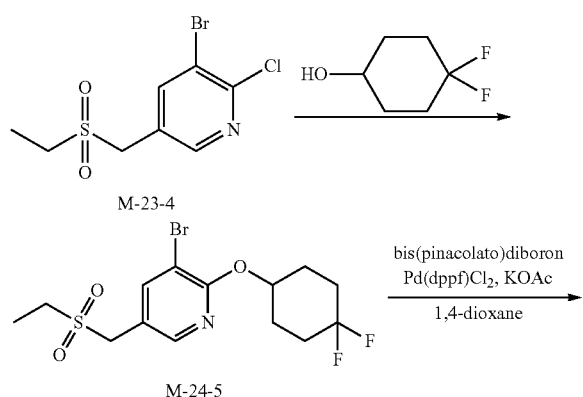

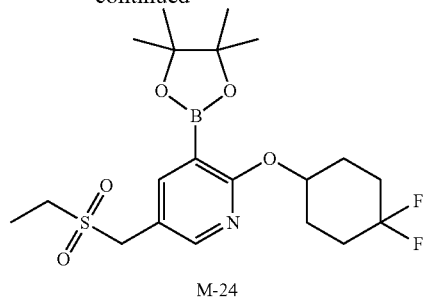

M-24

M-23-4 (2.4 g, 8.0 mmol), 4,4-difluorocyclohexanol (2.2 g, 16.2 mmol) and cesium carbonate (5.3 g, 16.3 mmol) were stirred in 20 mL of dimethyl sulfoxide (DMSO) at 95° C. for 2 h under nitrogen. TLC detection showed the reaction was complete. The reaction solution was cooled to room temperature, poured into water and extracted with EA. The organic layer was washed with water and saline, dried and concentrated, and passed through column chromatography to give intermediate M-24-5.

M-24-5 (0.7 g, 1.8 mmol), potassium acetate (0.5 g, 5.1 mmol) and bis(pinacolato)diboron (0.9 g, 3.5 mmol, CAS: 73183-34-3) were dissolved in 20 mL of dioxane, added with [1,1'-bis(diphenylphosphino)ferrocene]palladium dichloride (75 mg, 0.1 mmol, CAS: 72287-26-4) under argon, heated to 95° C. to react for 2 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, passed through silica gel chromatography and slurried in diethyl ether to give 0.4 g of borate M-24.

¹H NMR (400 MHz, CDCl₃) δ 8.19 (d, J=2.4 Hz, 1H), 8.01 (d, J=2.4 Hz, 1H), 5.43 (m, 1H), 4.11 (s, 2H), 2.91 (q, J=7.6 Hz, 2H), 2.40-2.25 (m, 2H), 2.08-1.80 (m, 6H), 1.40 (t, J=7.2 Hz, 3H), 1.32 (s, 12H). HPLC-MS: [M+H]⁺=446.2

Example 149: Synthesis of Borate M-25

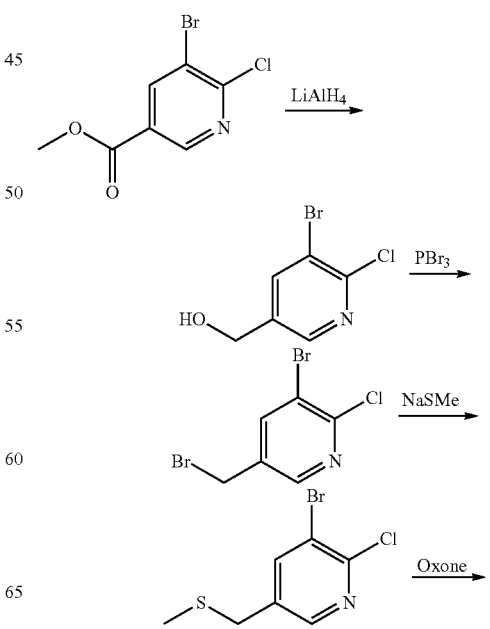

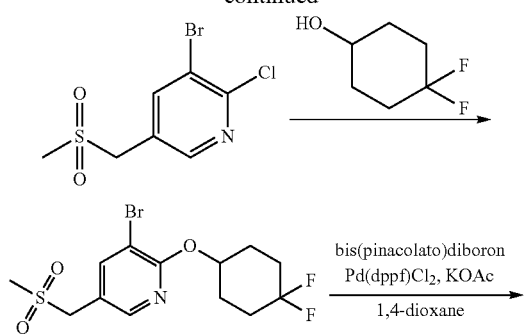

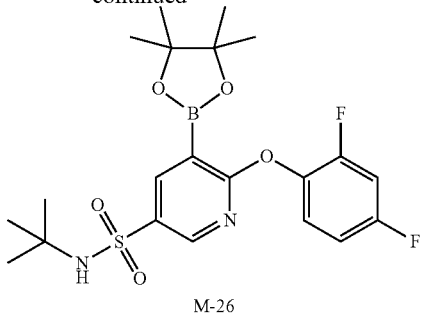

Borate M-25 was prepared in the same method as that in Example 144, except that 4,4-difluorocyclohexanol was used instead of hydroxymethylcyclopropane in Step 5.

$^1$H NMR (400 MHz, CDCl$_3$) δ 8.20 (d, J=2.8 Hz, 1H), 8.01 (d, J=2.8 Hz, 1H), 5.44-5.43 (m, 1H), 4.15 (s, 2H), 2.82 (s, 3H), 2.40-2.25 (m, 2H), 2.06 (d, J=13.6 Hz, 2H), 1.95-1.81 (m, 4H), 1.33 (s, 12H). HPLC-MS: [M+H]$^+$=432.2.

Example 150: Synthesis of Borate M-26

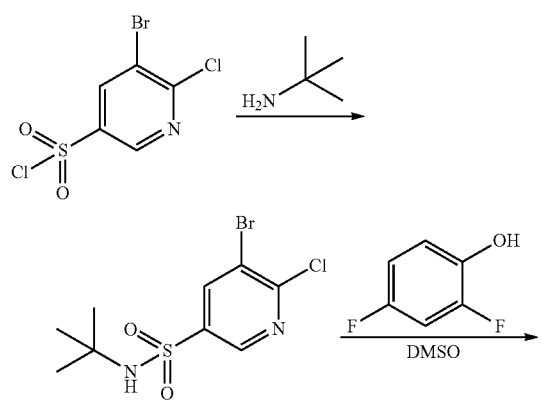

Tert-butylamine (0.8 g, 10.9 mmol) and triethylamine (2.1 g, 20.8 mmol) were dissolved in 50 ml of dichloromethane (DCM), stirred for 15 minutes under ice bath, added dropwisely with a solution of 3-bromo-2-chloropyridine-5-sulfonyl chloride (3.0 g, 10.3 mmol, CAS: 216394-05-7) in 20 mL of DCM, and then stirred for 0.5 h. TLC showed the reaction was complete. The mixture was added with 50 mL of water for layering. The aqueous phase was extracted with DCM again. The combined organic phase was washed with saturated saline, dried, and rotary evaporated to dryness to give 3.0 g of M-26-1 as a white solid.

Step 2

M-26-1 (3.0 g, 6.3 mmol), 2,4-difluorophenol (1.3 g, 10.0 mmol) and cesium carbonate (3.9 g, 12.0 mmol) were suspended in 20 mL of dimethyl sulfoxide, heated to 80° C. to react for 1 h, cooled to room temperature, and added with water and ethyl acetate for layering. The organic phase was washed with saturated saline, dried over anhydrous sodium sulfate, concentrated by rotary evaporation in vacuo, and purified by column chromatography to give intermediate M-26-2 (3.3 g).

Step 3

M-26-2 (3.3 g, 7.8 mmol), potassium acetate (1.5 g, 15.3 mmol) and bis(pinacolato)diboron (4.0 g, 15.8 mmol, CAS: 73183-34-3) were dissolved in 20 mL of dioxane, added with [1,1'-bis(diphenylphosphino)ferrocene]palladium dichloride (318 mg, 0.4 mmol, CAS: 72287-26-4) under argon, heated to 95° C. to react for 5 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, passed through silica gel chromatography and slurried in petroleum ether to give 1.4 g of borate M-26.

$^1$H NMR (400 MHz, CDCl$_3$) δ 8.61 (d, J=2.4 Hz, 1H), 8.52 (d, J=2.4 Hz, 1H), 7.25-7.21 (m, 1H), 6.97-6.89 (m, 2H), 1.37 (s, 12H), 1.26 (s, 9H).

Example 151: Synthesis of Borate M-27

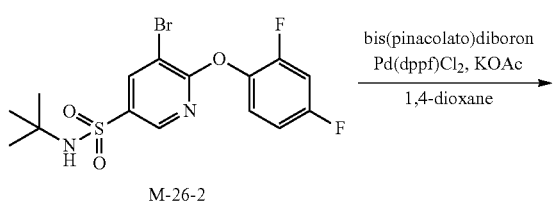

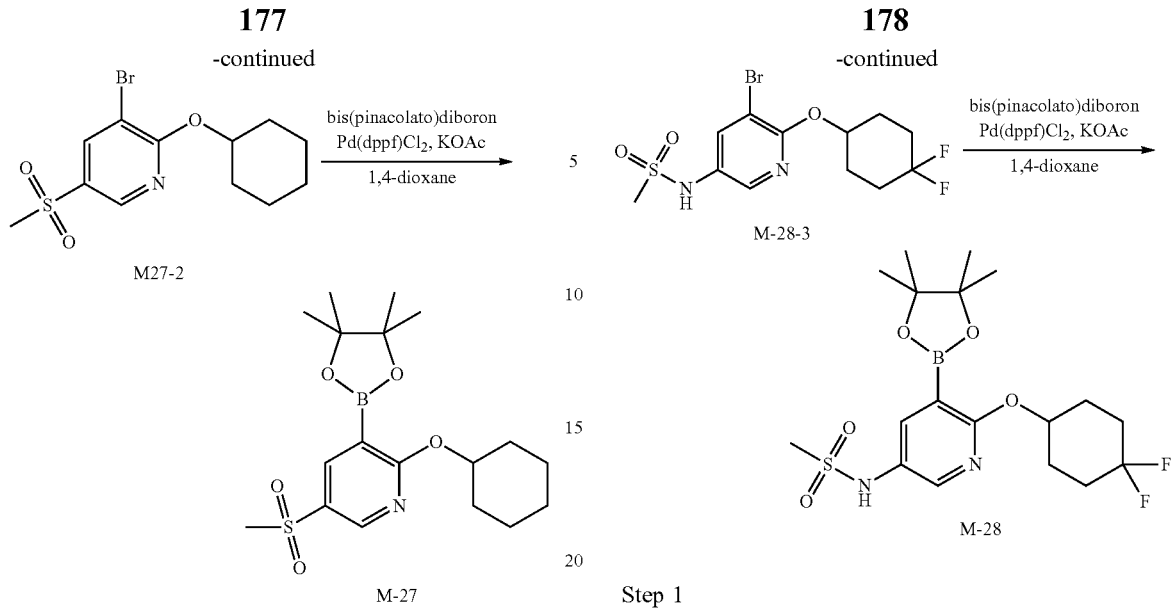

Step 1

Cyclohexanol (0.4 g, 4.1 mmol) was dissolved in DMF (10 mL), added with sodium hydride (0.18 g, 60% content) under ice bath, stirred for 0.5 h, added with E103-2 (1.0 g, 3.7 mmol), stirred at room temperature overnight, quenched with water, and extracted with ethyl acetate. The organic phase was washed with saturated saline, dried over anhydrous sodium sulfate, and purified by column chromatography to give 1.2 g of product M27-2 as a white solid.

Step 2

A mixture of M27-2 (1.1 g, 3.3 mmol), bis(pinacolato) diboron (1.7 g, 6.5 mmol), Pd(dppf)Cl$_2$ (120 mg, 0.16 mmol), potassium acetate (0.64 g, 6.5 mmol) and 1,4-dioxane (25 mL) was heated at 95° C. for 4 h under argon, and then concentrated and passed through column chromatography, slurried with a mixed solvent of ethyl acetate and petroleum ether to give 0.3 g of product M-27. $^1$H NMR (400 MHz, CDCl$_3$) δ 8.71 (d, J=2.8 Hz, 1H), 8.34 (d, J=2.8 Hz, 1H), 5.28-5.24 (m, 1H), 3.05 (s, 3H), 1.86-1.81 (m, 4H), 1.73-1.66 (m, 2H), 1.50-1.44 (m, 4H), 1.34 (s, 12H).

Example 152: Synthesis of Borate M-28

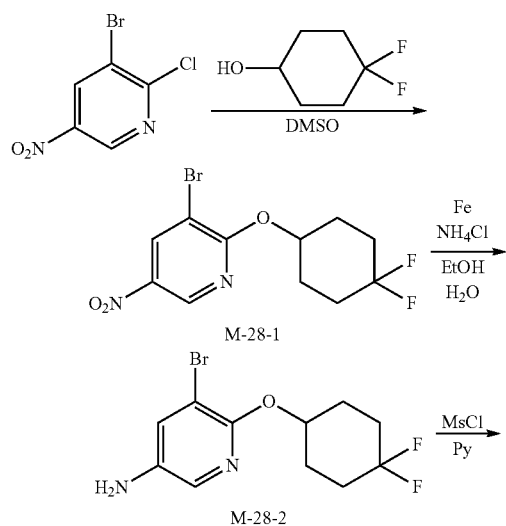

Step 1

2-Chloro-3-bromo-5-nitropyridine (5.8 g, 24.4 mmol, CAS: 5470-17-7) and cesium carbonate (9.6 g, 29.5 mmol) were suspended in 20 mL of dimethyl sulfoxide, added with 4,4-difluorocyclohexanol (4.0 g, 29.4 mmol), heated to 80° C. to react for 1 h, cooled to room temperature, and added with water and ethyl acetate for layering. The organic phase was washed with saturated saline, dried over anhydrous sodium sulfate, concentrated by rotary evaporation in vacuo to give intermediate M-28-1 (3.5 g).

Step 2

M-28-1 (3.5 g, 8.7 mmol) was dissolved in 60 mL of ethanol and 20 mL of water, added in batches with iron powder (3.3 g) and ammonium chloride (6.5 g) at room temperature, slowly heated to 100° C. to react for 1 h and filtered through celite. The filtrate was poured into water and extracted twice with ethyl acetate. The combined organic phase was washed with saturated saline, dried over anhydrous sodium sulfate, and concentrated to give intermediate M-28-2 (3.5 g).

Step 3

M-28-2 (3.5 g, 11.4 mmol) was dissolved in 15 mL of pyridine, cool to 0° C., added slowly and dropwisely with methylsulfonyl chloride (1.5 g, 13.1 mmol), heated to 100° C. to react for 1 h, and added with ice water and ethyl acetate for layering. The organic phase was washed with 2M dilute hydrochloric acid and saturated saline successively, dried over anhydrous sodium sulfate, rotary evaporated under vacuum to remove ethyl acetate to give intermediate M-28-3 (4.0 g).

Step 4

M-28-3 (4.0 g, 10.4 mmol), potassium acetate (3.1 g, 31.6 mmol) and bis(pinacolato)diboron (5.3 g, 20.9 mmol, CAS: 73183-34-3) were dissolved in 30 mL of dioxane, added with [1,1'-bis(diphenylphosphino)ferrocene]palladium dichloride (0.8 g, 1.1 mmol, CAS: 72287-26-4) under argon, heated to 100° C. to react for 8 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, passed through silica gel chromatography and slurried in diethyl ether to give 1.4 g of borate M-28 (1.1 g).

$^1$H NMR (400 MHz, CDCl$_3$) δ 8.16 (d, J=2.8 Hz, 1H), 7.88 (d, J=2.8 Hz, 1H), 6.33 (s, 1H), 5.40-5.38 (m, 1H), 3.00

(s, 3H), 2.39-2.24 (m, 2H), 2.06 (d, J=12.0 Hz, 2H), 1.97-1.80 (m, 4H), 1.33 (s, 12H). HPLC-MS: [M+H]$^+$=433.2

Example 153: Synthesis of Borate M-29

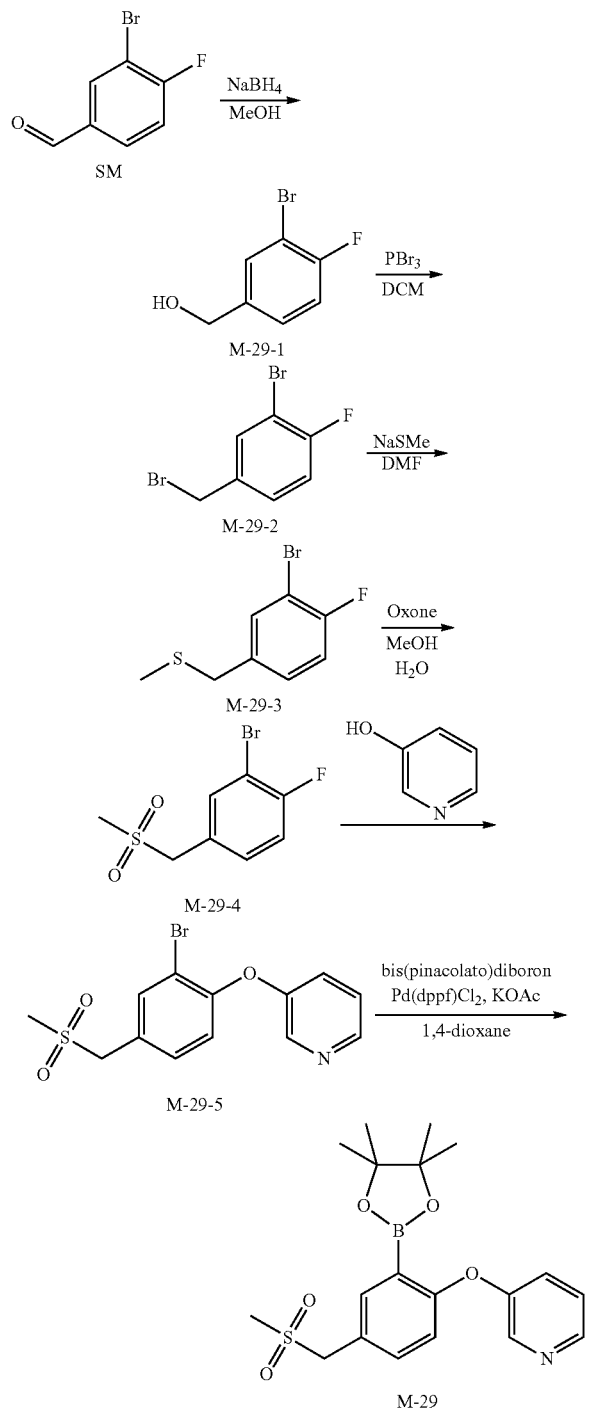

Step 1

3-Bromo-4-fluorobenzaldehyde (15.0 g, 7.4 mmol, CAS: 77771-02-9) was dissolved in 100 mL of methanol, added with sodium borohydride (3.4 g, 89.9 mmol) under an ice bath, stirred for 1 h, added with water and extracted with ethyl acetate. The combined organic phase was washed three times with saturated saline, dried over anhydrous sodium sulfate, and rotary evaporated under vacuum to give intermediate M-29-1 (15.1 g).

Step 2

Compound M-29-1 (15.1 g, 7.4 mmol) was dissolved in 50 mL of dichloromethane, added dropwisely with phosphorus tribromide (19.9 g, 7.4 mmol) under ice bath, reacted for 1 h, added with water and extracted with dichloromethane. The combined organic phase was washed with saturated saline three times, dried over anhydrous sodium sulfate, rotary evaporated under vacuum to remove the solvent to give compound M-29-2 (19.7 g).

Step 3

Compound M-29-2 (19.7 g, 7.4 mmol) was dissolved in 30 mL of N,N-dimethylformamide (DMF), added with sodium methylthiolate (10.3 g, 0.15 mol) to react at room temperature for 2 h, added with water and extracted with ethyl acetate. The organic phase was washed three times with saturated saline, dried over anhydrous sodium sulfate, rotary evaporated under vacuum to remove the solvent to give compound M-29-3 (17.3 g).

Step 4

Compound M-29-3 (17.3 g, 7.4 mmol) was dissolved in 40 mL of methanol, added with potassiumhydrogenperoxymonosulfate (Oxone, CAS: 70693-62-8, 26.0 g, 0.15 mol) under an ice bath, reacted at room temperature for 1 h, added with water and extracted with ethyl acetate. The combined organic phase was washed with saturated saline, dried over anhydrous sodium sulfate, rotary evaporated under vacuum, and purified by column chromatography to give compound M-29-4 (10.0 g).

Step 5

Compound M-29-4 (10.0 g, 37.4 mmol) was dissolved in 50 mL of dimethyl sulfoxide, added with 3-hydroxypyridine (7.1, 74.7 mmol) and cesium carbonate (24.3 g, 74.6 mmol), heated at 100° C. overnight, cooled to room temperature, added with water and extracted with ethyl acetate. The combined organic phase was washed with saturated saline, dried over anhydrous sodium sulfate, rotary evaporated under vacuum to remove the solvent, and purified by column chromatography to give compound M-29-5.

Step 6

M-29-5 (3.0, 8.8 mmol), potassium acetate (1.7 g, 17.3 mmol), bis(pinacolato)diboron (4.4 g, 17.3 mmol) were dissolved in 20 mL of dioxane, added with [1,1'-bis(diphenylphosphino)ferrocene]palladium dichloride (0.3 g, 0.4 mmol) under argon, heated to 100° C. to react for 5 h, cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography to give borate M-29. $^1$H NMR (400 MHz, CDCl$_3$) δ 8.33 (d, J=2.8 Hz, 1H), 8.29 (d, J=4.4 Hz, 1H), 7.80 (d, J=2.4 Hz, 1H), 7.57 (dd, J=8.4 Hz, 2.8 Hz, 1H), 7.21-7.18 (m, 1H), 7.12-7.09 (m, 1H), 7.06 (d, J=8.4 Hz, 1H), 4.26 (s, 2H), 2.81 (s, 3H), 1.17 (s, 12H). HPLC-MS: [M+H]$^+$=390.1.

Example 154: Synthesis of Compound ZB-BD-162

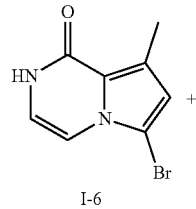

I-6

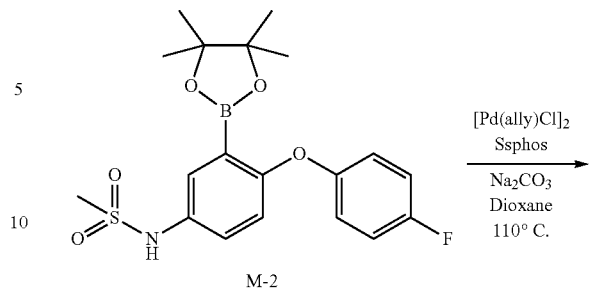

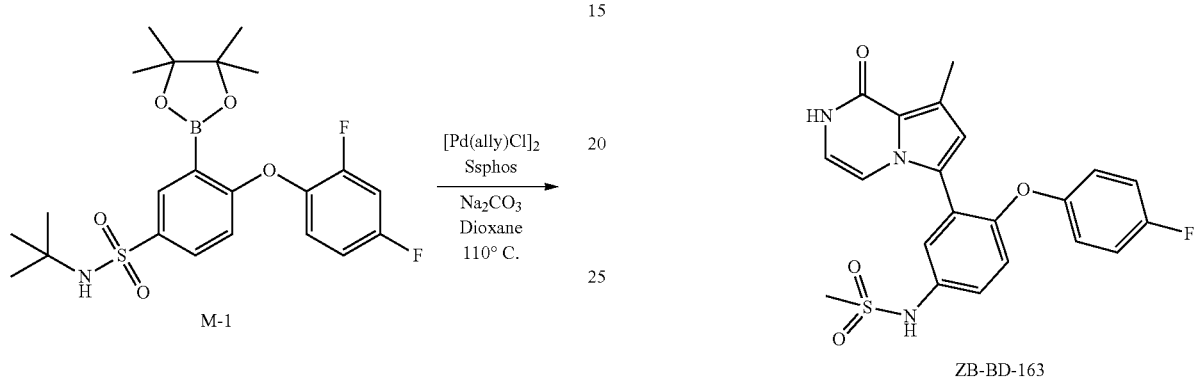

The same method as that in Example 24 was used to give compound ZB-BD-162, except that compound M-1 was used instead of compound B-1. $^1$H NMR (400 MHz, MeOD) δ 7.95 (d, J=2.4 Hz, 1H), 7.91 (dd, J=8.7, 2.4 Hz, 1H), 7.27-7.12 (m, 2H), 7.04-6.90 (m, 3H), 6.54 (s, 1H), 6.50 (d, J=5.9 Hz, 1H), 2.59 (s, 3H), 1.23 (s, 9H). HPLC-MS: [M+H]$^+$=488.3

Example 155: Synthesis of Compound ZB-BD-163

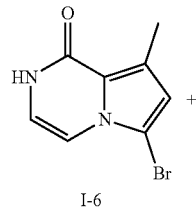

I-6

The same method as that in Example 24 was used to give compound ZB-BD-163, except that compound M-2 was used instead of compound B-1. $^1$H NMR (400 MHz, MeOD) δ 7.38-7.31 (m, 2H), 7.08-7.02 (m, 1H), 6.99-6.89 (m, 3H), 6.84-6.76 (m, 2H), 6.45 (d, J=5.9 Hz, 1H), 6.38 (s, 1H), 3.00 (s, 3H), 2.48 (s, 3H). HPLC-MS: [M+H]$^+$=428.1

Example 156: Synthesis of Compound ZB-BD-164

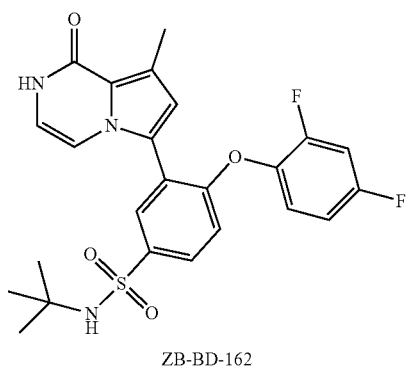

I-6

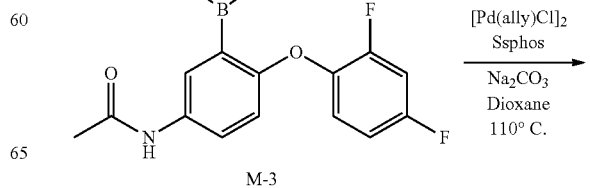

M-3

-continued

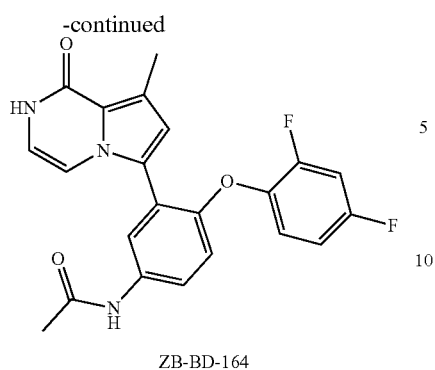

ZB-BD-164

The same method as that in Example 24 was used to give compound ZB-BD-164, except that compound M-3 was used instead of compound B-1. $^1$H NMR (400 MHz, MeOD) δ 7.66 (d, J=2.6 Hz, 1H), 7.57 (dd, J=8.9, 2.7 Hz, 1H), 7.04-6.90 (m, 3H), 6.88 (d, J=9.0 Hz, 1H), 6.85-6.78 (m, 1H), 6.44-6.38 (m, 2H), 2.52 (s, 3H), 2.13 (s, 3H). HPLC-MS: [M+H]$^+$=410.3

Example 157: Synthesis of Compound ZB-BD-166

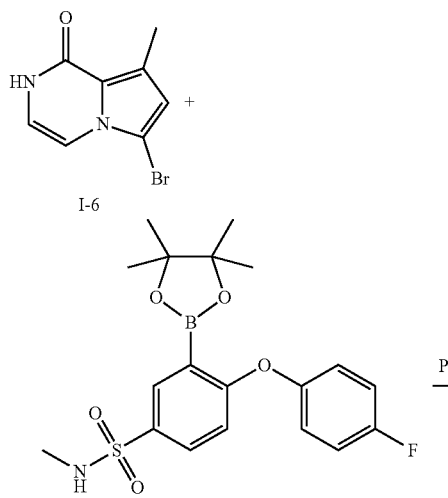

ZB-BD-166

The same method as that in Example 37 was used to give compound ZB-BD-166, except that compound M-4 was used instead of compound B-16. $^1$H NMR (400 MHz, MeOD) δ 7.88 (d, J=2.3 Hz, 1H), 7.84 (dd, J=8.7, 2.4 Hz, 1H), 7.11-6.98 (m, 5H), 6.95 (d, J=5.9 Hz, 1H), 6.50-6.45 (m, 2H), 2.57 (s, 3H), 2.53 (s, 3H). HPLC-MS: [M+H]$^+$=428.2

Example 158: Synthesis of Compound ZB-BD-167

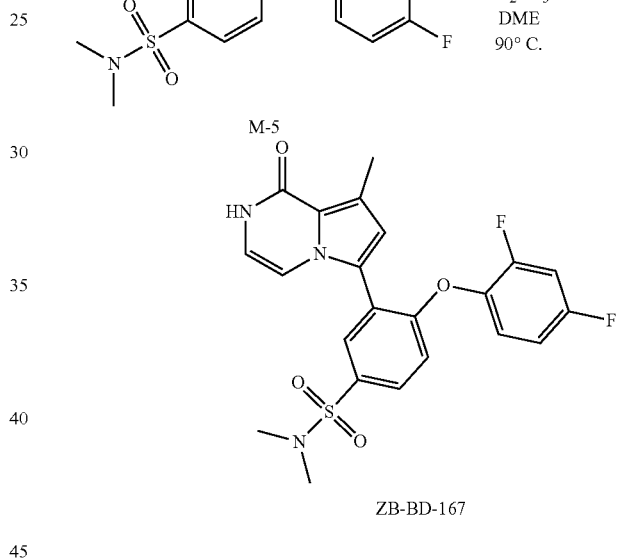

ZB-BD-167

The same method as that in Example 37 was used to give compound ZB-BD-167, except that compound M-5 was used instead of compound B-16. $^1$H NMR (400 MHz, MeOD) δ 7.83-7.80 (m, 2H), 7.29-7.14 (m, 2H), 7.04-7.00 (m, 2H), 6.96 (d, J=5.9 Hz, 1H), 6.56 (s, 1H), 6.49 (d, J=5.9 Hz, 1H), 2.72 (s, 6H), 2.58 (s, 3H). HPLC-MS: [M+H]$^+$=460.3

Example 159: Synthesis of Compound ZB-BD-172

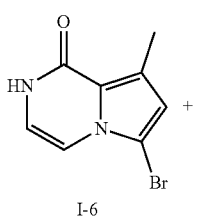

I-6

-continued

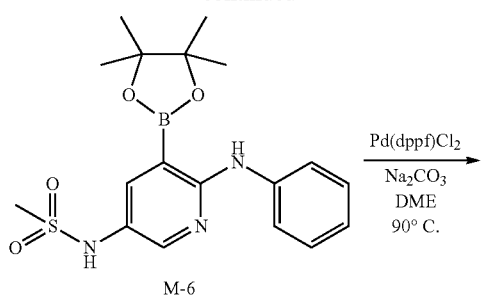 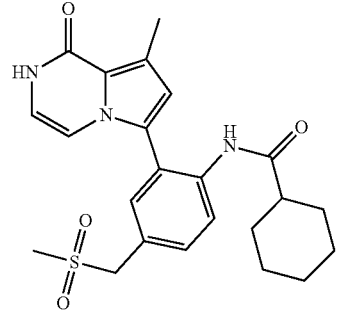

M-6

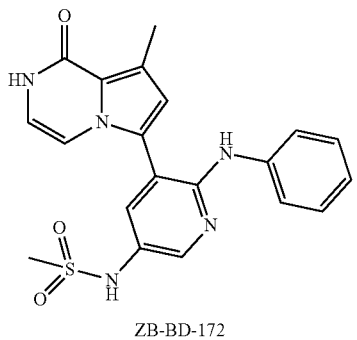

ZB-BD-172

The same method as that in Example 37 was used to give compound ZB-BD-172, except that compound M-6 was used instead of compound B-16. $^1$H NMR (400 MHz, DMSO-$d_6$) δ 10.28 (s, 1H), 9.52 (d, J=2.1 Hz, 1H), 8.09 (d, J=2.6 Hz, 1H), 7.93 (d, J=3.2 Hz, 1H), 7.55-7.47 (m, 2H), 7.41 (d, J=2.6 Hz, 1H), 7.20 (dd, J=8.6, 7.2 Hz, 2H), 6.89 (t, J=7.3 Hz, 1H), 6.71-6.64 (m, 1H), 6.53 (s, 1H), 6.43 (t, J=5.7 Hz, 1H), 2.99 (s, 3H), 2.52 (s, 3H). HPLC-MS: [M+H]$^+$= 410.3

Example 160: Synthesis of Compound ZB-BD-173

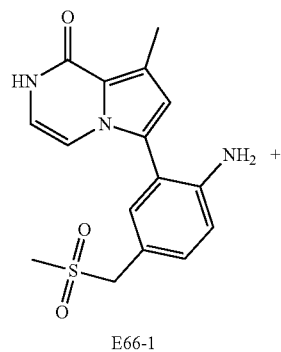

E66-1

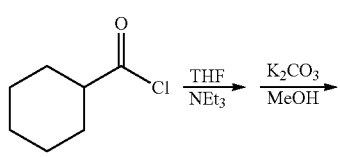

-continued

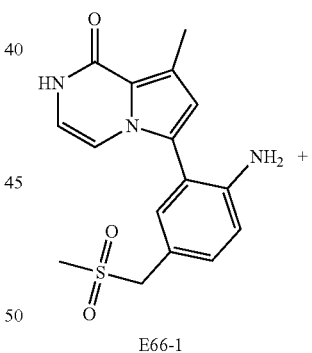

ZB-BD-173

Intermediate E66-1 (33 mg, 0.1 mmol) was dissolved in 1 mL of tetrahydrofuran, added with 0.5 mL of triethylamine, followed by addition at 0° C. of 0.05 mL of cyclohexylformyl chloride. The mixture was stirred at room temperature overnight, rotary evaporated under vacuum to remove the solvent, dissolved in 1 mL of methanol, added with potassium carbonate (69 mg, 0.5 mmol), stirred at room temperature for 2 h and then filtered. The filtrate was rotary evaporated under vacuum to remove the solvent, and purified by HPLC to give compound ZB-BD-173. $^1$H NMR (400 MHz, CDCl$_3$) δ 8.52 (d, J=8.5 Hz, 1H), 7.46 (dd, J=8.5, 2.2 Hz, 1H), 7.42 (d, J=2.2 Hz, 1H), 7.38 (s, 1H), 6.71 (d, J=5.9 Hz, 1H), 6.49 (s, 1H), 6.39 (t, J=5.6 Hz, 1H), 4.26 (s, 2H), 2.86 (s, 3H), 2.68 (s, 3H), 1.81 (t, J=15.4 Hz, 4H), 1.44-1.20 (m, 7H). HPLC-MS: [M+H]$^+$=442.3

Example 161: Synthesis of Compound ZB-BD-174

E66-1

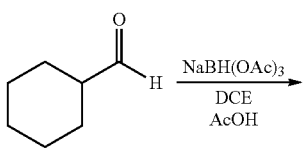

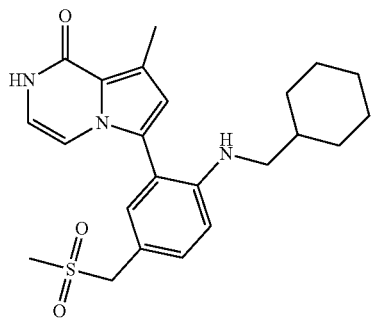

ZB-BD-174

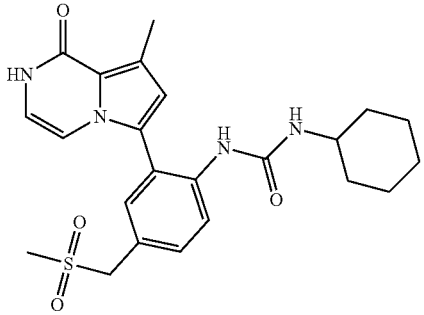

ZB-BD-175

Intermediate E66-1 (9 mg, 0.027 mmol) and cyclohexyl formaldehyde (CAS: 2043-61-0) (15 mg, 0.136 mmol) were dissolved in 1 mL of 1,2-dichloroethane, added with 0.5 mL of glacial acetic acid, followed by addition at 0° C. of sodium triacetoxyborohydride (30 mg, 0.136 mmol). After reacted at room temperature overnight, the mixture was added with 20 mL of water and extracted with ethyl acetate (20 mL×3). The organic layers were combined, dried over anhydrous sodium sulfate, rotary evaporated under vacuum to remove ethyl acetate, and purified by HPLC to give ZB-BD-174. $^1$H NMR (400 MHz, DMSO-$d_6$) δ 10.21 (d, J=5.5 Hz, 1H), 7.25 (d, J=8.9 Hz, 1H), 7.06 (d, J=2.2 Hz, 1H), 6.70 (d, J=8.6 Hz, 1H), 6.52 (d, J=5.9 Hz, 1H), 6.44-6.33 (m, 2H), 4.95-4.86 (m, 1H), 4.30 (s, 2H), 3.34 (s, 3H), 2.86 (d, J=9.6 Hz, 5H), 1.99 (d, J=8.0 Hz, 1H), 1.65 (s, 4H), 1.20-1.01 (m, 4H), 0.84 (d, J=11.6 Hz, 2H). HPLC-MS: [M+H]$^+$=428.2

Intermediate E66-1 (9 mg, 0.027 mmol) and cyclohexyl isocyanate (3.5 μL, 0.027 mmol) were dissolved in 1 mL of tetrahydrofuran, added with 0.5 mL of triethylamine, heated to 60° C. to react for 2 h, rotary evaporated under vacuum to remove the solvent, and purified by HPLC to give compound ZB-BD-175. $^1$H NMR (400 MHz, DMSO-$d_6$) δ 9.85 (d, J=7.5 Hz, 1H), 7.39 (d, J=6.5 Hz, 1H), 7.18 (d, J=8.4 Hz, 1H), 7.09 (s, 1H), 6.79 (d, J=7.4 Hz, 2H), 6.51 (s, 1H), 5.25 (s, 2H), 4.29 (s, 2H), 3.69 (s, 1H), 2.85 (s, 3H), 2.53 (s, 3H), 1.94-1.82 (m, 2H), 1.72-1.61 (m, 2H), 1.42-1.30 (m, 4H), 1.26-1.21 (m, 2H). HPLC-MS: [M+H]$^+$=457.2

Example 162: Synthesis of Compound ZB-BD-175

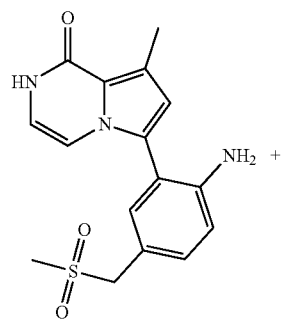

E66-1

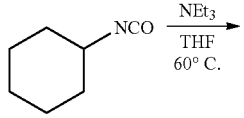

Example 163: Synthesis of Compound ZB-BD-179

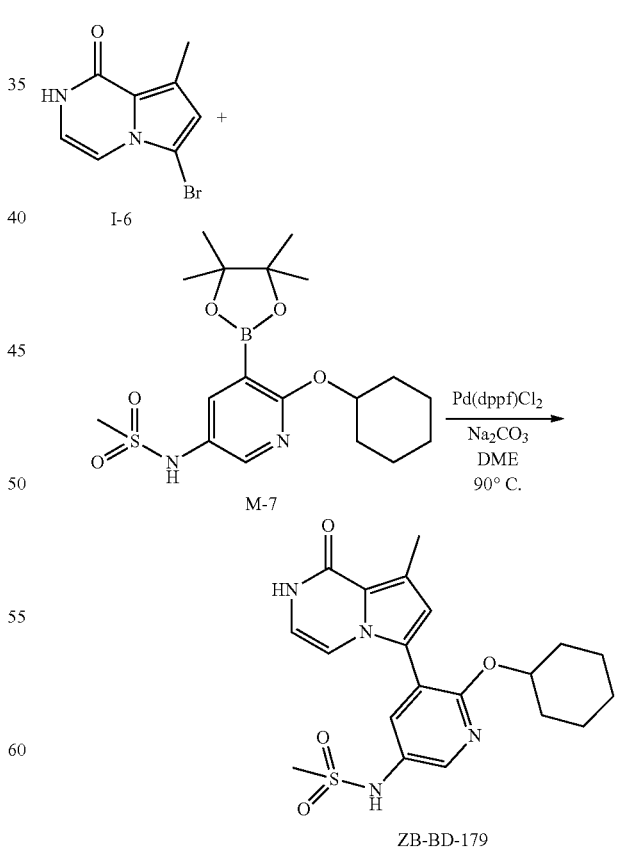

The same method as that in Example 37 was used to give compound ZB-BD-179, except that compound M-7 was used instead of compound B-16. $^1$H NMR (400 MHz, MeOD) δ 8.11 (d, J=2.7 Hz, 1H), 7.65 (d, J=2.8 Hz, 1H), 6.84 (d, J=5.9 Hz, 1H), 6.48 (s, 1H), 6.44 (d, J=5.9 Hz, 1H), 5.12 (tt, J=8.4, 3.7 Hz, 1H), 2.99 (s, 3H), 2.57 (s, 3H), 1.97-1.86 (m, 2H), 1.68-1.56 (m, 2H), 1.55-1.31 (m, 6H). HPLC-MS: [M+H]$^+$=417.4

Example 164: Synthesis of Compound ZB-BD-183

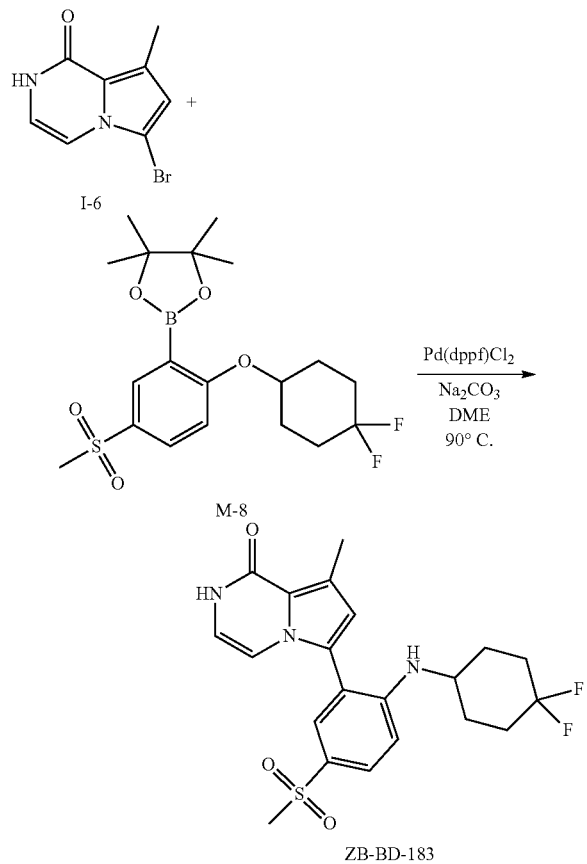

The same method as that in Example 37 was used to give compound ZB-BD-183, except that compound M-8 was used instead of compound B-16. $^1$H NMR (400 MHz, MeOD) δ 8.00 (dd, J=8.8, 2.4 Hz, 1H), 7.91 (d, J=2.4 Hz, 1H), 7.40 (d, J=8.9 Hz, 1H), 6.77 (d, J=5.9 Hz, 1H), 6.47 (s, 1H), 6.44 (d, J=5.9 Hz, 1H), 4.82-4.75 (m, 1H), 3.14 (s, 3H), 2.58 (s, 3H), 1.94-1.57 (m, 8H). HPLC-MS: [M+H]$^+$=437.3

Example 165: Synthesis of Compound ZB-BD-184

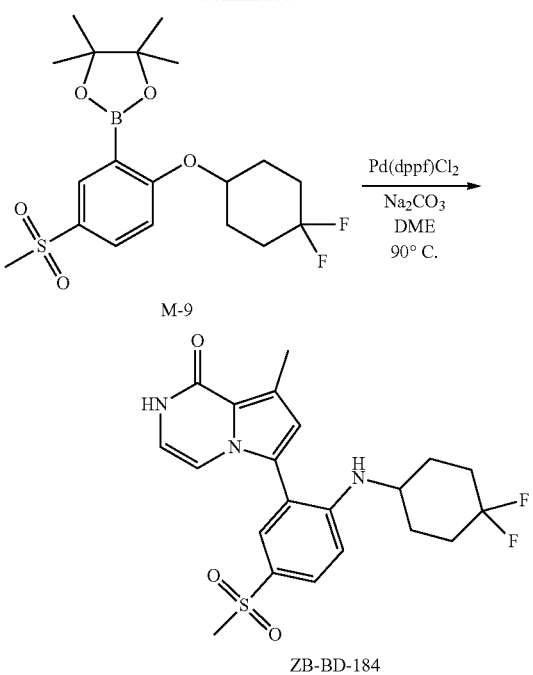

The same method as that in Example 37 was used to give compound ZB-BD-184, except that compound M-9 was used instead of compound B-16. $^1$H NMR (400 MHz, DMSO-d$_6$) δ 10.25 (d, J=4.1 Hz, 1H), 7.72 (d, J=7.7 Hz, 1H), 7.50 (s, 1H), 7.00 (d, J=8.9 Hz, 1H), 6.59-6.33 (m, 3H), 5.53 (d, J=8.1 Hz, 1H), 3.73-3.57 (m, 1H), 3.08 (s, 3H), 2.52 (s, 3H), 2.09-1.79 (m, 6H), 1.63-1.42 (m, 2H). HPLC-MS: [M+H]$^+$=436.2

Example 166: Synthesis of Compound ZB-BD-185

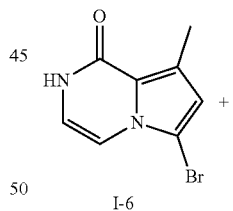

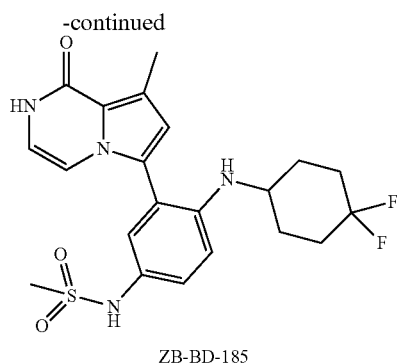

ZB-BD-185

The same method as that in Example 37 was used to give compound ZB-BD-185, except that compound M-10 was used instead of compound B-16. ¹H NMR (400 MHz, DMSO-d₆) δ 10.23 (d, J=5.2 Hz, 1H), 9.59 (s, 1H), 7.32-7.21 (m, 2H), 7.18 (d, J=2.4 Hz, 1H), 6.67 (d, J=5.4 Hz, 1H), 6.42 (t, J=5.7 Hz, 1H), 6.37 (d, J=8.4 Hz, 1H), 4.53 (s, 1H), 2.97 (s, 3H), 2.48 (s, 3H), 1.85-1.52 (m, 8H). HPLC-MS: [M+H]⁺=452.3

Example 167: Synthesis of Compound ZB-BD-187

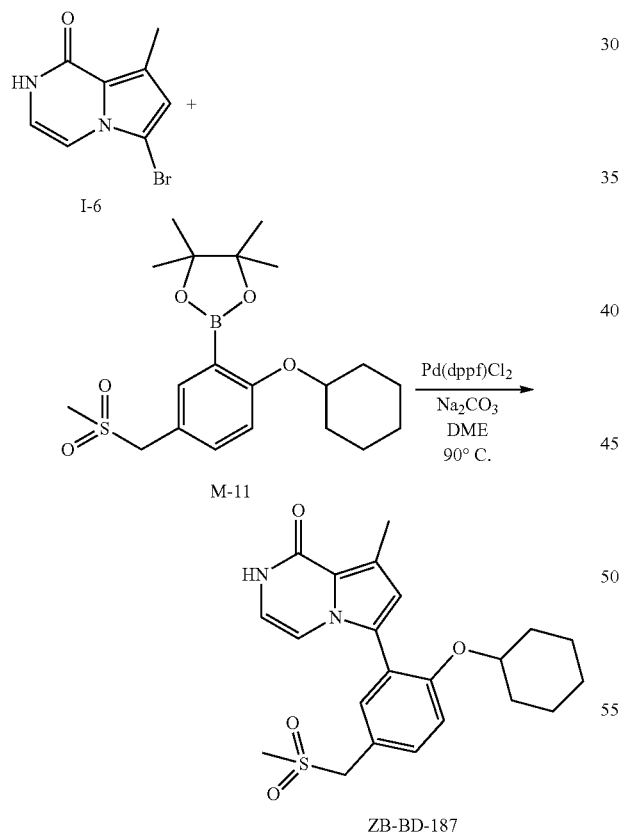

ZB-BD-187

The same method as that in Example 37 was used to give compound ZB-BD-187, except that compound M-11 was used instead of compound B-16. ¹H NMR (400 MHz, DMSO-d₆) δ 10.22 (d, J=5.0 Hz, 1H), 7.43 (dd, J=8.5, 1.9 Hz, 1H), 7.36 (d, J=1.9 Hz, 1H), 7.21 (d, J=8.6 Hz, 1H), 6.66 (d, J=5.7 Hz, 1H), 6.43 (t, J=5.6 Hz, 1H), 6.37 (s, 1H), 4.51-4.32 (m, 3H), 2.91 (s, 3H), 2.50 (s, 3H), 1.88-1.78 (m, 2H), 1.58-1.47 (m, 2H), 1.43-1.20 (m, 6H). HPLC-MS: [M+H]⁺=415.2

Example 168: Synthesis of Compound ZB-BD-188

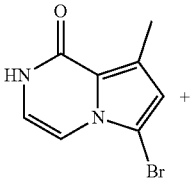

I-6

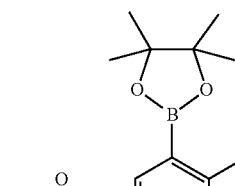

M-12

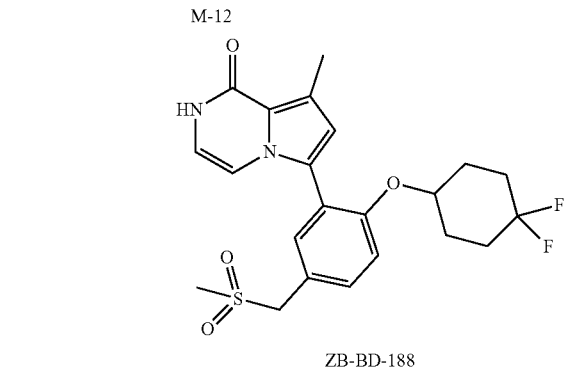

ZB-BD-188

The same method as that in Example 37 was used to give compound ZB-BD-188, except that compound M-12 was used instead of compound B-16. ¹H NMR (400 MHz, Acetonitrile-d₃) δ 8.74 (s, 1H), 7.44 (dd, J=8.5, 2.3 Hz, 1H), 7.38 (d, J=2.3 Hz, 1H), 7.17 (d, J=8.8 Hz, 1H), 6.69 (d, J=5.9 Hz, 1H), 6.38 (s, 1H), 6.34 (t, J=4.5 Hz, 1H), 4.62-4.54 (m, 1H), 4.28 (s, 2H), 2.83 (s, 3H), 2.53 (s, 3H), 1.84-1.63 (m, 8H). HPLC-MS: [M+H]⁺=451.2

Example 169: Synthesis of Compound ZB-BD-189

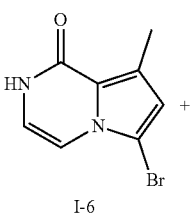

I-6

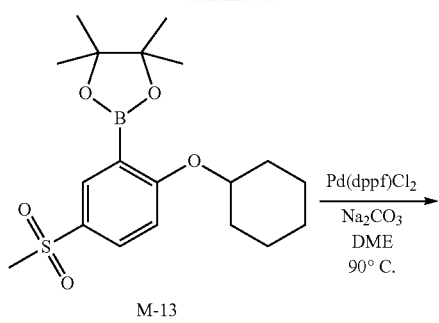

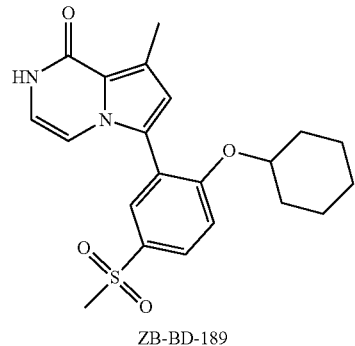

ZB-BD-189

The same method as that in Example 37 was used to give compound ZB-BD-189, except that compound M-13 was used instead of compound B-16. $^1$H NMR (400 MHz, DMSO-d$_6$) δ 10.28 (d, J=5.0 Hz, 1H), 7.92 (dd, J=8.7, 2.0 Hz, 1H), 7.81 (d, J=2.0 Hz, 1H), 7.43 (d, J=8.9 Hz, 1H), 6.66 (d, J=5.8 Hz, 1H), 6.54-6.39 (m, 2H), 4.59 (s, 1H), 3.23 (s, 3H), 2.50 (s, 3H), 1.96-1.79 (m, 2H), 1.58-1.12 (m, 8H). HPLC-MS: [M+H]$^+$=401.3

Example 170: Synthesis of Compound ZB-BD-190

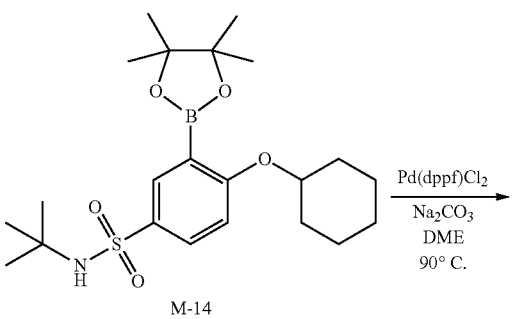

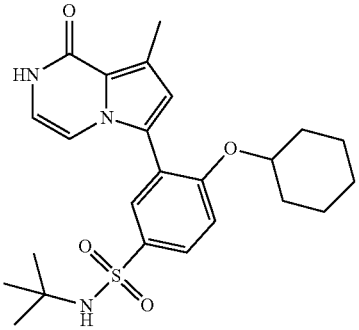

ZB-BD-190

The same method as that in Example 37 was used to give compound ZB-BD-190, except that compound M-14 was used instead of compound B-16. $^1$H NMR (400 MHz, DMSO-d$_6$) δ 10.27 (d, J=5.3 Hz, 1H), 7.83 (dd, J=8.8, 2.4 Hz, 1H), 7.72 (d, J=2.4 Hz, 1H), 7.42 (s, 1H), 7.35 (d, J=9.0 Hz, 1H), 6.59 (d, J=5.8 Hz, 1H), 6.46 (t, J=5.7 Hz, 1H), 6.39 (s, 1H), 4.60-4.46 (m, 1H), 2.50 (s, 3H), 1.91-1.82 (m, 2H), 1.57-1.48 (m, J=6.0 Hz, 2H), 1.44-1.19 (m, J=19.6, 10.7 Hz, 6H), 1.10 (s, 9H). HPLC-MS: [M+H]$^+$=458.4

Example 171: Synthesis of Compound ZB-BD-191

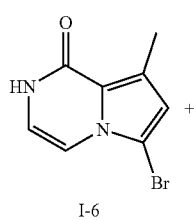

I-6

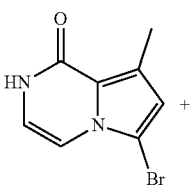

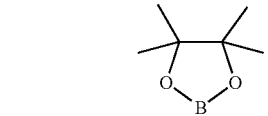

M-15

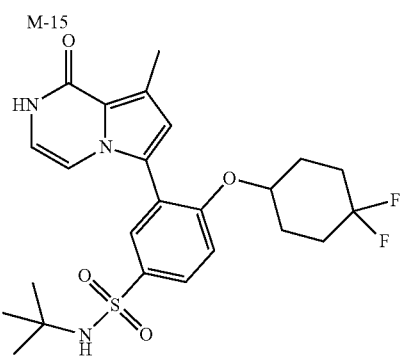

ZB-BD-191

The same method as that in Example 37 was used to give compound ZB-BD-191, except that compound M-15 was used instead of compound B-16. $^1$H NMR (400 MHz, DMSO-$d_6$) δ 10.29 (d, J=5.2 Hz, 1H), 7.86 (dd, J=8.8, 2.3 Hz, 1H), 7.76 (d, J=2.3 Hz, 1H), 7.52-7.34 (m, 2H), 6.64 (d, J=5.8 Hz, 1H), 6.45 (t, J=5.7 Hz, 1H), 6.41 (s, 1H), 4.84-4.70 (m, 1H), 2.50 (s, 3H), 1.93-1.61 (m, 8H), 1.11 (s, 9H). HPLC-MS: [M+H]$^+$=494.4

Example 172: Synthesis of Compound ZB-BD-194

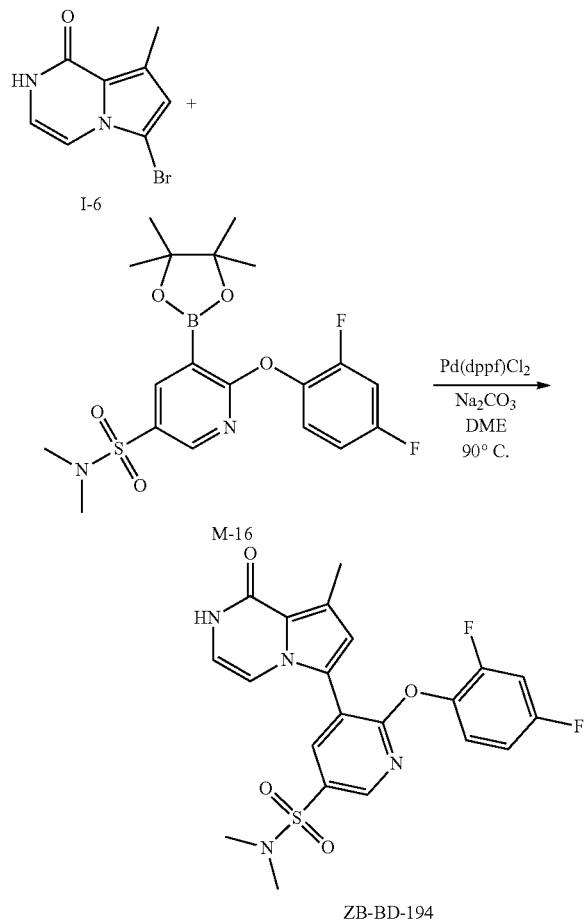

The same method as that in Example 37 was used to give compound ZB-BD-194, except that compound M-16 was used instead of compound B-16. $^1$H NMR (400 MHz, DMSO-$d_6$) δ 10.42 (d, J=5.2 Hz, 1H), 8.56 (d, J=2.4 Hz, 1H), 8.17 (d, J=2.4 Hz, 1H), 7.59-7.44 (m, 2H), 7.23-7.13 (m, 1H), 7.05 (d, J=5.8 Hz, 1H), 6.72 (s, 1H), 6.55 (t, J=5.6 Hz, 1H), 2.70 (s, 6H), 2.51 (s, 3H). HPLC-MS: [M+H]$^+$=461.3

Example 173: Synthesis of Compound ZB-BD-195

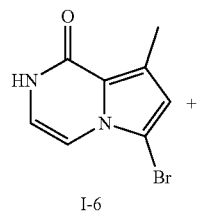

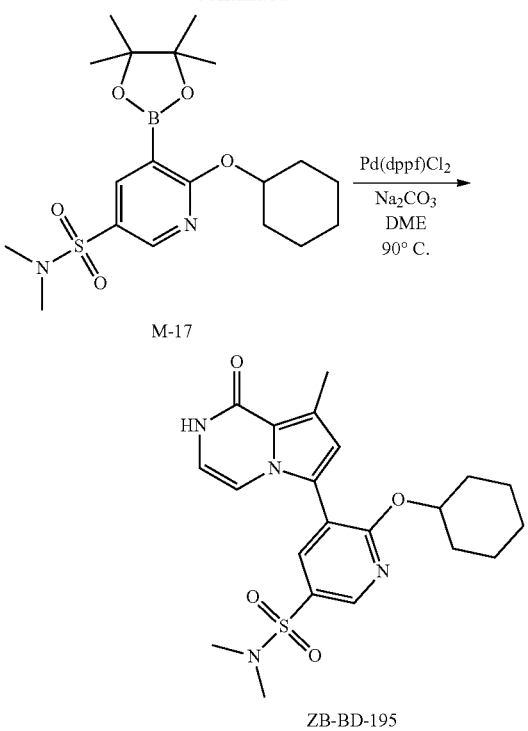

The same method as that in Example 37 was used to give compound ZB-BD-195, except that compound M-17 was used instead of compound B-16. $^1$H NMR (400 MHz, DMSO-$d_6$) δ 10.34 (d, J=5.2 Hz, 1H), 8.58 (d, J=2.5 Hz, 1H), 7.93 (d, J=2.5 Hz, 1H), 6.79 (d, J=5.6 Hz, 1H), 6.54 (s, 1H), 6.48 (t, J=5.7 Hz, 1H), 5.26-5.17 (m, 1H), 2.67 (s, 6H), 2.49 (s, 3H), 1.99-1.88 (m, 2H), 1.65-1.53 (m, 2H), 1.47-1.19 (m, 6H). HPLC-MS: [M+H]$^+$=431.2

Example 174: Synthesis of Compound ZB-BD-196

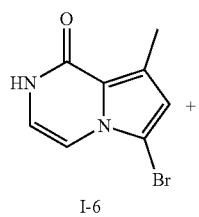

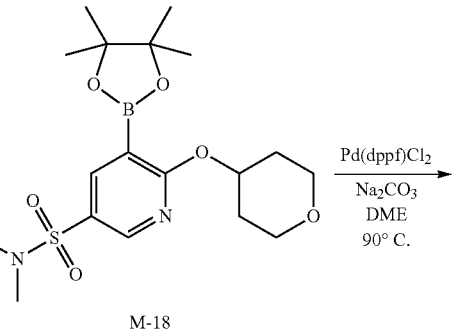

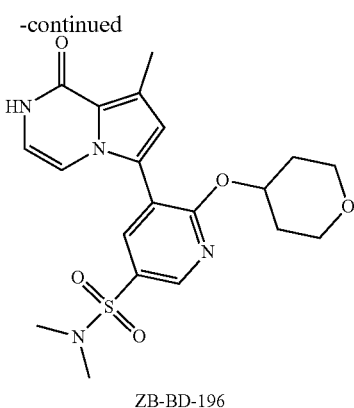

ZB-BD-196

The same method as that in Example 37 was used to give compound ZB-BD-196, except that compound M-18 was used instead of compound B-16. ¹H NMR (400 MHz, DMSO-d₆) δ 10.37 (s, 1H), 8.60 (s, 1H), 7.97 (s, 1H), 6.84 (d, J=4.5 Hz, 1H), 6.57 (s, 1H), 6.50 (s, 1H), 5.40 (s, 1H), 3.80-3.64 (m, 2H), 3.55-3.40 (m, 2H), 2.68 (s, 6H), 2.50 (s, 3H), 2.11-1.91 (m, 2H), 1.67-1.50 (m, 2H). HPLC-MS: [M+H]⁺=433.3

Example 175: Synthesis of Compound ZB-BD-197

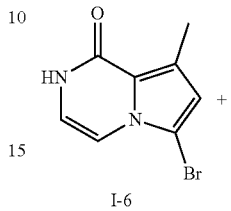

I-6

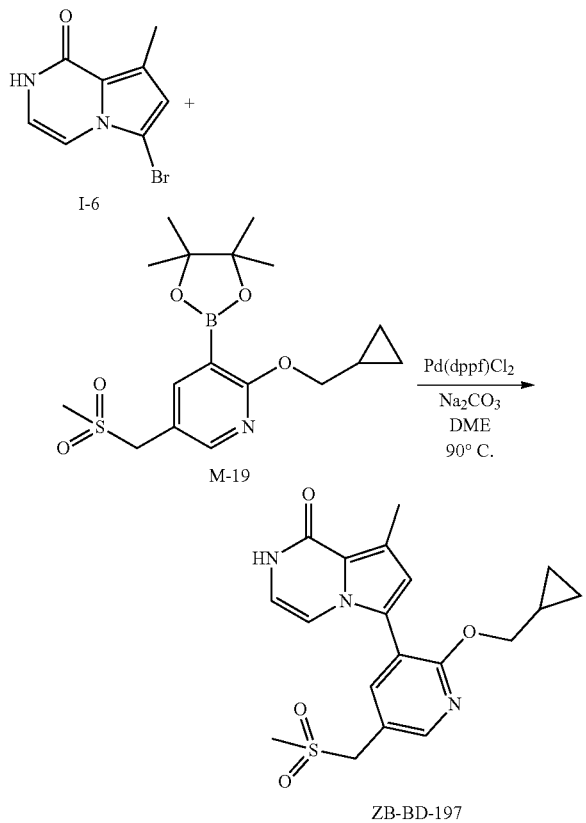

ZB-BD-197

The same method as that in Example 37 was used to give compound ZB-BD-197, except that compound M-19 was used instead of compound B-16. ¹H NMR (400 MHz, DMSO-d₆) δ 10.32 (d, J=5.0 Hz, 1H), 8.23 (d, J=2.2 Hz, 1H), 7.79 (d, J=2.2 Hz, 1H), 6.79 (d, J=5.7 Hz, 1H), 6.49-6.45 (m, 2H), 4.52 (s, 2H), 4.19 (d, J=7.1 Hz, 2H), 2.97 (s, 3H), 2.50 (s, 3H), 1.28-1.20 (m, 1H), 0.49 (q, J=4.7 Hz, 2H), 0.30 (q, J=4.7 Hz, 2H). HPLC-MS: [M+H]⁺=388.4

Example 176: Synthesis of Compound ZB-BD-198

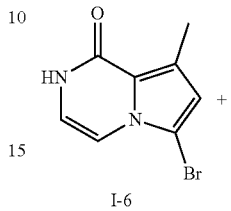

I-6

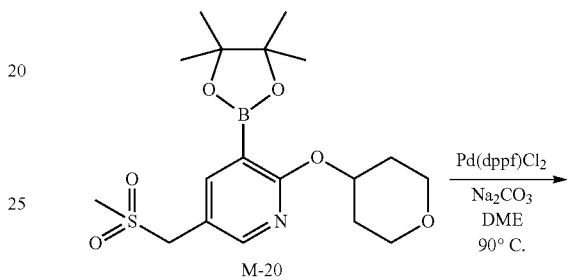

M-20

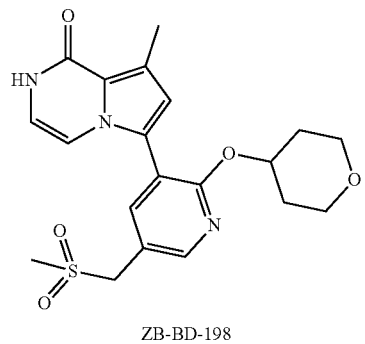

ZB-BD-198

The same method as that in Example 37 was used to give compound ZB-BD-198, except that compound M-20 was used instead of compound B-16. ¹H NMR (400 MHz, DMSO-d₆) δ 10.32 (d, J=5.1 Hz, 1H), 8.23 (d, J=2.1 Hz, 1H), 7.80 (d, J=2.1 Hz, 1H), 6.79 (d, J=5.8 Hz, 1H), 6.53-6.41 (m, 2H), 5.36-5.26 (m, 1H), 4.53 (s, 2H), 3.78-3.64 (m, 2H), 3.53-3.39 (m, 2H), 2.98 (s, 3H), 2.50 (s, 3H), 2.05-1.93 (m, 2H), 1.64-1.50 (m, 2H). HPLC-MS: [M+H]⁺=418.2

Example 177: Synthesis of Compound ZB-BD-202

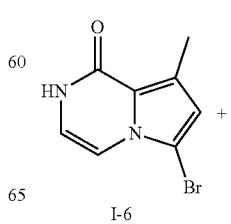

I-6

-continued

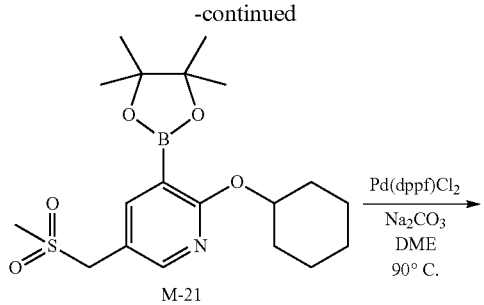

M-21

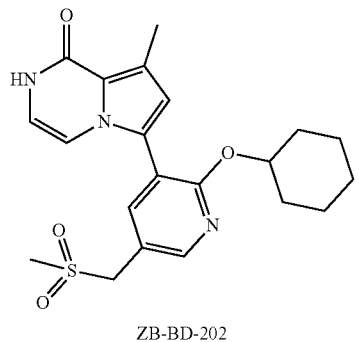

ZB-BD-202

The same method as that in Example 37 was used to give compound ZB-BD-202, except that compound M-21 was used instead of compound B-16. $^1$H NMR (400 MHz, DMSO-d$_6$) δ 10.29 (d, J=5.3 Hz, 1H), 8.21 (d, J=2.3 Hz, 1H), 7.77 (d, J=2.3 Hz, 1H), 6.76 (d, J=5.8 Hz, 1H), 6.50-6.42 (m, 2H), 5.20-5.04 (m, 1H), 4.51 (s, 2H), 2.97 (s, 3H), 2.49 (s, 3H), 1.97-1.86 (m, 2H), 1.66-1.53 (m, 2H), 1.45-1.30 (m, 4H), 1.26-1.13 (m, 2H). HPLC-MS: [M+H]$^+$= 416.3

Example 178: Synthesis of Compound ZB-BD-216

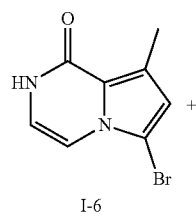

I-6

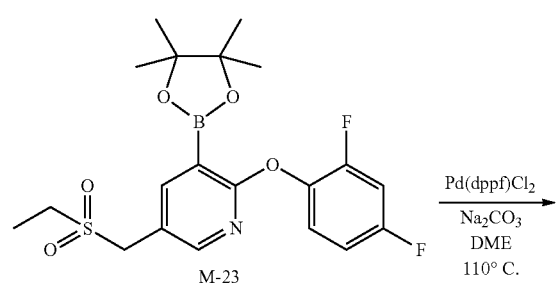

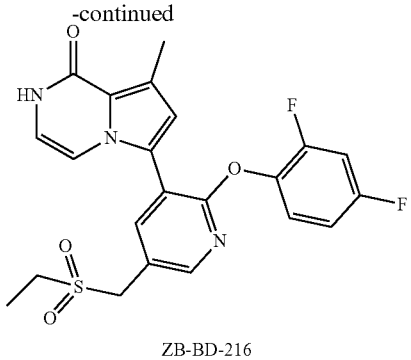

ZB-BD-216

Compound I-6 (46 mg, 0.2 mmol) and borate M-23 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-216. $^1$H NMR (400 MHz, DMSO-d$_6$) δ 10.38 (d, J=5.6 Hz, 1H), 8.15 (d, J=2.0 Hz, 1H), 7.97 (d, J=2.1 Hz, 1H), 7.52-7.42 (m, 2H), 7.19-7.12 (m, 1H), 7.00 (d, J=5.7 Hz, 1H), 6.62 (s, 1H), 6.53 (t, J=5.8 Hz, 1H), 4.56 (s, 2H), 3.12 (q, J=7.5 Hz, 2H), 2.52 (s, 3H), 1.25 (t, J=7.4 Hz, 3H). HPLC-MS: [M+H]$^+$=460.3

Example 179: Synthesis of Compound ZB-BD-217

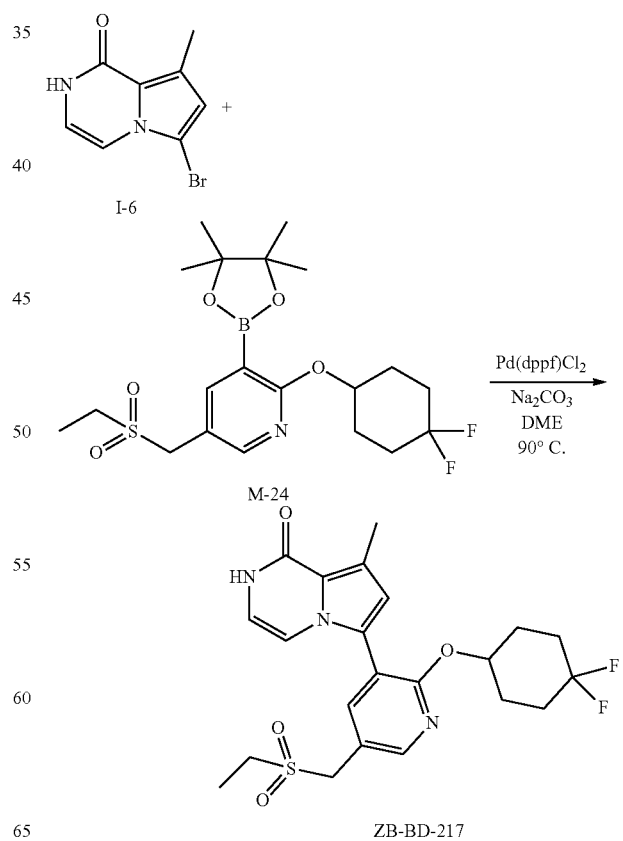

Compound I-6 (46 mg, 0.2 mmol) and borate M-24 (156 mg) were dissolved in 3 mL of 1,4-dioxane, added with 1 mL of 2M sodium carbonate solution, followed by addition of [1,1'-bis (diphenylphosphino)ferrocene] palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-217. $^1$H NMR (400 MHz, DMSO-d$_6$) δ 10.30 (d, J=5.3 Hz, 1H), 8.24 (d, J=2.1 Hz, 1H), 7.81 (d, J=2.2 Hz, 1H), 6.83 (d, J=5.8 Hz, 1H), 6.50-6.39 (m, 2H), 5.36-5.27 (m, 1H), 4.52 (s, 2H), 3.10 (q, J=7.4 Hz, 2H), 2.50 (s, 3H), 2.05-1.71 (m, J=20.5 Hz, 8H), 1.25 (t, J=7.4 Hz, 3H). HPLC-MS: [M+H]$^+$=466.3

Example 180: Synthesis of Compound ZB-BD-220

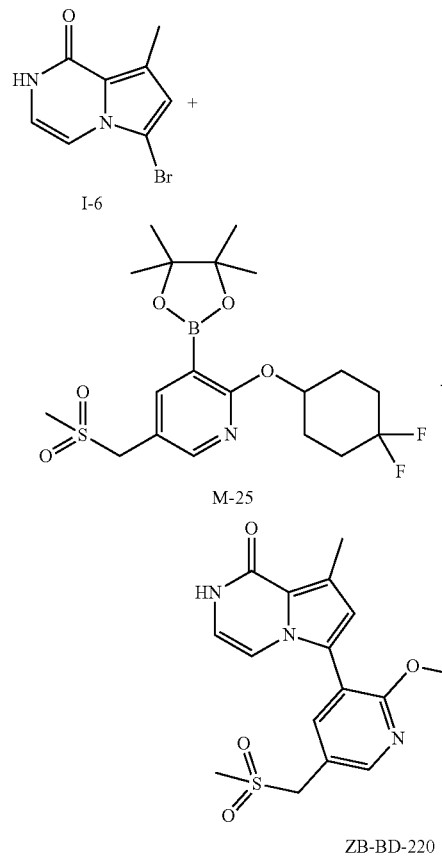

Compound I-6 (46 mg, 0.2 mmol) and borate M-25 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-220. $^1$H NMR (400 MHz, DMSO-d$_6$) δ 10.30 (d, J=5.2 Hz, 1H), 8.25 (d, J=1.7 Hz, 1H), 7.82 (d, J=1.8 Hz, 1H), 6.83 (d, J=5.9 Hz, 1H), 6.53-6.37 (m, 2H), 5.32 (s, 1H), 4.53 (s, 2H), 2.98 (s, 3H), 2.50 (s, 3H), 1.99-1.78 (m, 8H). HPLC-MS: [M+H]$^+$= 452.2

Example 181: Synthesis of Compound ZB-BD-199

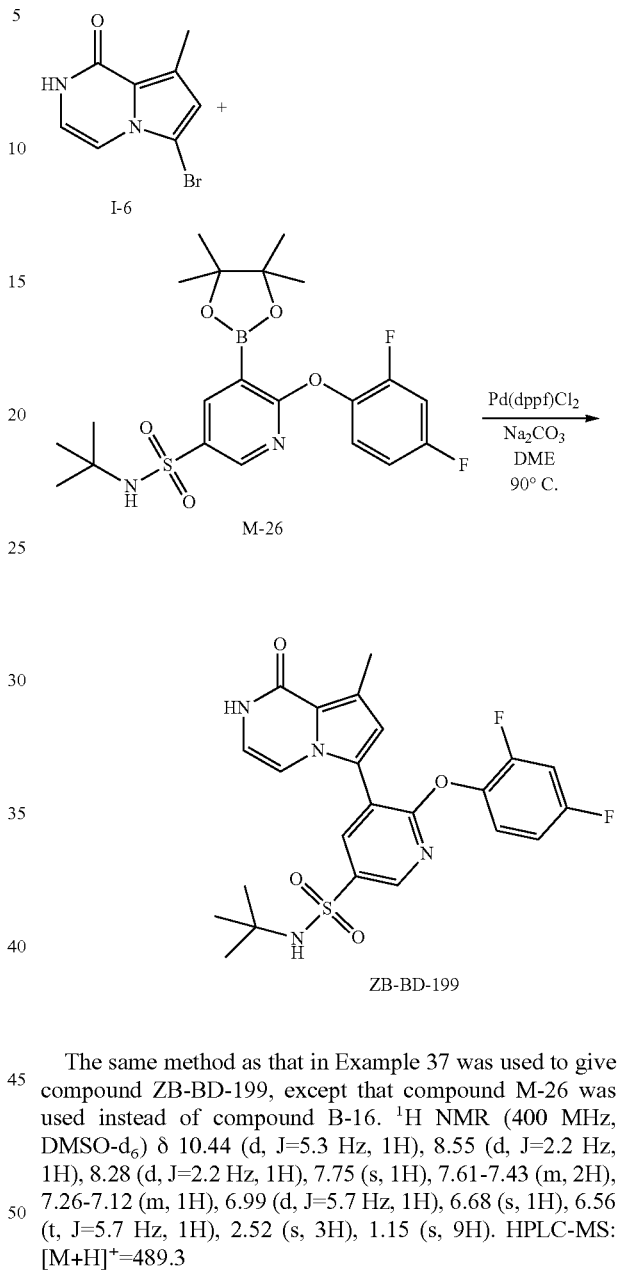

The same method as that in Example 37 was used to give compound ZB-BD-199, except that compound M-26 was used instead of compound B-16. $^1$H NMR (400 MHz, DMSO-d$_6$) δ 10.44 (d, J=5.3 Hz, 1H), 8.55 (d, J=2.2 Hz, 1H), 8.28 (d, J=2.2 Hz, 1H), 7.75 (s, 1H), 7.61-7.43 (m, 2H), 7.26-7.12 (m, 1H), 6.99 (d, J=5.7 Hz, 1H), 6.68 (s, 1H), 6.56 (t, J=5.7 Hz, 1H), 2.52 (s, 3H), 1.15 (s, 9H). HPLC-MS: [M+H]$^+$=489.3

Example 182: Synthesis of Compound ZB-BD-203

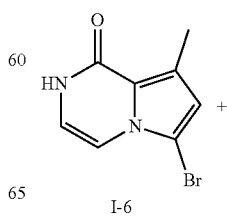

-continued

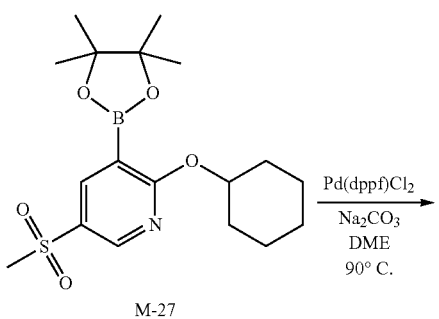

M-27

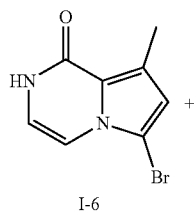

ZB-BD-203

The same method as that in Example 37 was used to give compound ZB-BD-203, except that compound M-27 was used instead of compound B-16. ¹H NMR (400 MHz, DMSO-d₆) δ 10.36 (d, J=5.2 Hz, 1H), 8.70 (d, J=2.4 Hz, 1H), 8.17 (d, J=2.4 Hz, 1H), 6.80 (d, J=5.8 Hz, 1H), 6.57 (s, 1H), 6.49 (t, J=5.7 Hz, 1H), 5.28-5.19 (m, 1H), 3.32 (s, 3H), 2.50 (s, 3H), 1.99-1.89 (m, 2H), 1.65-1.53 (m, 2H), 1.47-1.22 (m, 6H). HPLC-MS: [M+H]⁺=402.4

Example 183: Synthesis of Compound ZB-BD-218

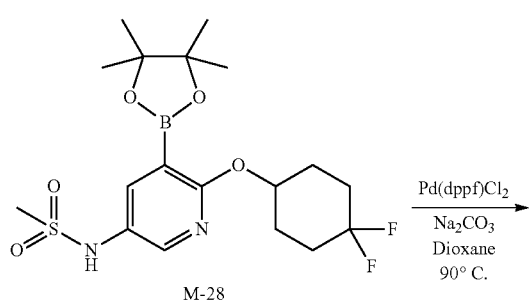

M-28

-continued

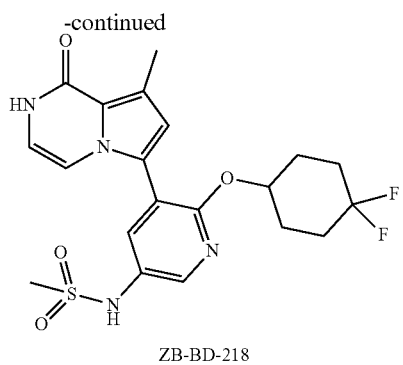

ZB-BD-218

Compound I-6 (46 mg, 0.2 mmol) and borate M-28 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl₂) (29 mg, 0.04 mmol) under Ar. The mixture was stirred at 90° C. for 2 h, diluted with water, extracted with ethyl acetate, and purified by silica gel column chromatography to give compound ZB-BD-218. ¹H NMR (400 MHz, DMSO-d₆) δ 10.30 (d, J=5.1 Hz, 1H), 9.71 (s, 1H), 8.11 (d, J=2.3 Hz, 1H), 7.62 (d, J=2.2 Hz, 1H), 6.81 (d, J=5.7 Hz, 1H), 6.54-6.38 (m, 2H), 5.32-5.15 (m, 1H), 3.03 (s, 3H), 2.50 (s, 3H), 2.02-1.76 (m, J=19.6, 8.3 Hz, 8H). HPLC-MS: [M+H]⁺=453.3

Example 184: Synthesis of Compound ZB-BD-214

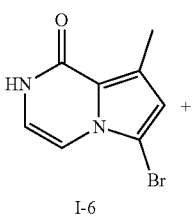

I-6

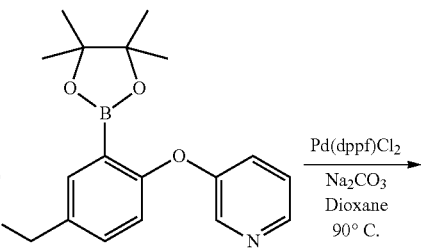

M-29

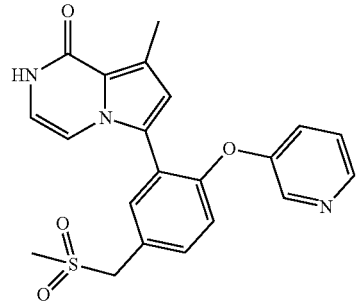

ZB-BD-214

Compound I-6 (46 mg, 0.2 mmol) and borate M-29 (156 mg) were dissolved in 3 mL of 1,4-dioxane, added with 1 mL of 2M sodium carbonate solution, followed by addition of [1,1'-bis (diphenylphosphino)ferrocene] palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-214. $^1$H NMR (400 MHz, DMSO) δ 10.28 (d, J=5.2 Hz, 1H), 8.35 (s, 2H), 7.56 (d, J=2.0 Hz, 1H), 7.51 (dd, J=8.5, 2.1 Hz, 1H), 7.46-7.37 (m, 2H), 7.10 (d, J=8.4 Hz, 1H), 6.91 (d, J=5.8 Hz, 1H), 6.46 (t, J=5.7 Hz, 1H), 6.42 (s, 1H), 4.56 (s, 2H), 2.96 (s, 3H), 2.43 (s, 3H). HPLC-MS: [M+H]$^+$=410.2

Example 185: Synthesis of Borate M-88

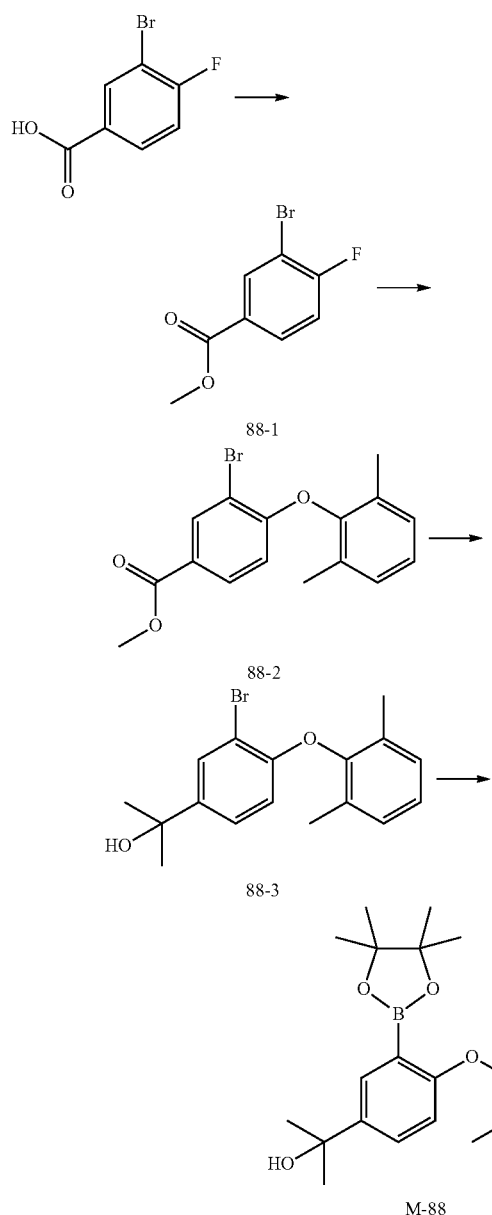

Step 1

3-Bromo-4-fluorobenzoic acid (11.0 g, 50.2 mmol) was dissolved in DCM (100 mL), cooled to 0° C., added slowly and dropwises with oxalyl chloride (5.1 mL, 60.3 mmol), and stirred at room temperature for 3 h. The mixture was rotary evaporated, added with methanol (40 mL), and stirred at room temperature for 3 h. The resultant was rotary evaporated to dryness to give 88-1 (10.8 g) as a brown liquid.

Step 2

88-1 (10.8 g, 46.3 mmol), 2,6-dimethylphenol (6.8 g, 55.7 mmol) and cesium carbonate (18.1 g, 55.6 mmol) were heated in DMSO (40 mL) at 90° C. for 4 h. TLC showed that the reaction was complete. The mixture was cooled and added with water and ethyl acetate for layering. The organic phase was washed several times with saturated saline, dried over anhydrous sodium sulfate, and rotary evaporated to dryness to give 88-2 (13.0 g) as a brown liquid.

Step 3

88-2 (10.5 g, 31.3 mmol) was dissolved in THF (100 mL), cooled to 0° C., added slowly and dropwisely with MeMgBr (3.0 M, 52.2 mL), quenched with saturated aqueous ammonium chloride solution, and extracted with ethyl acetate. The organic phase was dried over anhydrous sodium sulfate, and purified by column chromatography (PE/EA=20/1) to give 88-3 (7.0 g).

Step 4

88-3 (6.7 g, 20.0 mmol), palladium acetate (0.45 g, 2.0 mmol), triphenylphosphine (1.05 g, 4.0 mmol), potassium acetate (5.88 g, 60.0 mmol) and bis(pinacolato)diboron (15.2 g, 60.0 mmol) were mixed in dioxane (100 mL), heated at 85° C. overnight under argon, and filtered through celite. The filtrate was rotary evaporated to dryness and passed through column chromatography (PE/EA=40/1-10/1) to give M-88 (2.9 g). $^1$H NMR (400 MHz, CDCl$_3$) δ 7.80 (d, J=2.4 Hz, 1H), 7.33 (dd, J=8.4, 2.4 Hz, 1H), 7.14-7.02 (m, 3H), 6.16 (d, J=8.8 Hz, 1H), 4.93 (s, 1H), 2.04 (s, 6H), 1.38 (s, 6H), 1.31 (s, 12H).

Example 186: Synthesis of Borate M-86

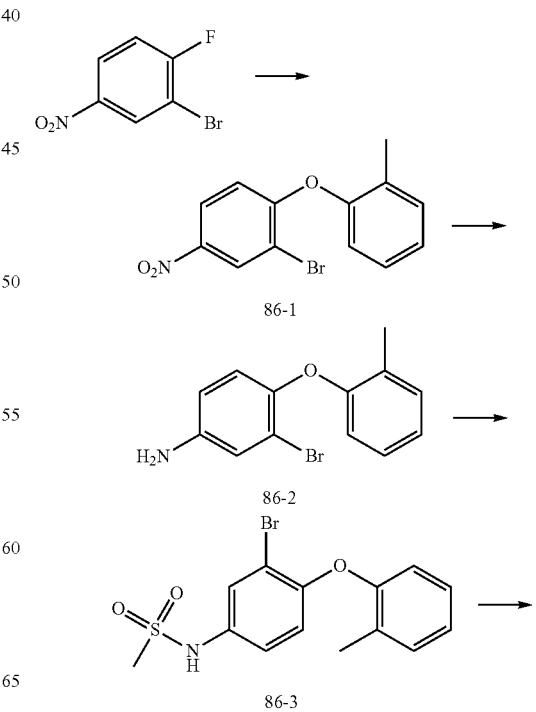

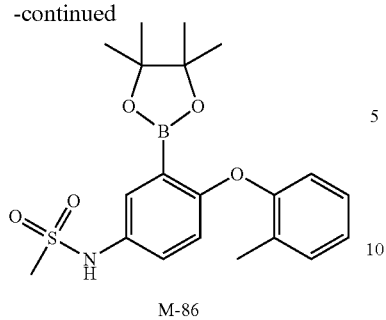

M-86

Step 1

3-Bromo-4-fluoronitrobenzene (5.0 g, 22.7 mmol), o-methylphenol (2.7 g, 25.0 mmol) and cesium carbonate (8.9 g, 27.3 mmol) were added to DMSO (30 mL) and stirred at 85° C. overnight. TLC detection showed that the raw material reacted completely. The reaction solution was poured into water (100 mL) and extracted with EA. The organic layer was washed with water and saline, dried over anhydrous sodium sulfate, concentrated by rotary evaporation to dryness to give 86-1 (6.5 g) as a yellow oil.

Step 2

86-1 (6.5 g, 21.1 mmol) was dissolved in ethanol (100 mL) and water (30 mL), added with iron powder (5.9 g, 0.1 mol) and ammonium chloride (11.3 g, 0.2 mol) and stirred at 80° C. for 3 h. TLC showed that the raw material reacted completely. The reaction mixture was cooled, added with celite, stirred for 5 min and suction filtered. The filtered cake was washed with EtOH. The filtrate was distilled under reduced pressure to remove ethanol, added with water (50 mL) and extracted with EA. The organic layer was washed with water and saturated saline respectively, dried over anhydrous sodium sulfate, and rotary evaporated to dryness to give 86-2 (5.6 g) as a brown oil.

Step 3

86-2 (5.6 g, 20.1 mmol) was dissolved in pyridine, added dropwisely with methanesulfonyl chloride (2.8 g, 24.5 mmol) under ice bath and stirred at room temperature for 1 h. TLC showed that the reaction was complete. The reaction solution was poured into ice water (100 mL) and extracted with EA. The organic layer was washed with water and saturated saline respectively, dried over anhydrous sodium sulfate and passed through column chromatography to give 86-3 (6.1 g) as a white solid.

Step 4

86-3 (6.1 g, 17.1 mmol), potassium acetate (3.4 g, 34.6 mmol), bis(pinacolato)diboron (8.7 g, 34.6 mmol) were dissolved in 100 mL of dioxane, added with [1,1'-bis(diphenylphosphino)ferrocene]palladium dichloride (0.7 g, 0.9 mmol) under argon, heated to 100° C. to react overnight. LCMS detection showed the reaction was complete. The reaction mixture was cooled to room temperature and filtered through celite. The filtrate was added with water and ethyl acetate for layering. The organic layer was washed with saturated saline, dried over anhydrous sodium sulfate, rotary evaporated under vacuum to remove the solvent, passed through silica gel chromatography and slurried in diethyl ether to give M-86 (2.1 g) as a white solid. LCMS: [M−H]−=402.1; $^1$H NMR (400 MHz, CDCl$_3$) δ 7.52 (d, J=2.8 Hz, 1H), 7.39 (dd, J=8.8, 2.8 Hz, 1H), 7.21 (d, J=7.6 Hz, 1H), 7.06 (t, J=6.4 Hz, 1H), 6.95 (t, J=7.4 Hz, 1H), 6.87 (d, J=8.8 Hz, 1H), 6.60 (d, J=7.6 Hz, 1H), 6.59 (s, 1H), 3.01 (s, 3H), 2.33 (s, 3H), 1.20 (s, 12H).

Example 187: Synthesis of Borate M-87

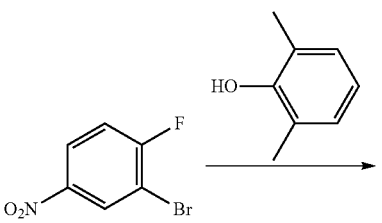

87-1

87-2

87-3

M-87

Borate M-87 was prepared in the same method as that in Example 186, except that 2,6-dimethylphenol was used instead of o-methylphenol in Step 1. LCMS: borate, [M−H]−= 416.2; $^1$H NMR (400 MHz, CDCl$_3$) δ 7.50 (d, J=2.8 Hz, 1H), 7.21 (dd, J=8.8, 2.8 Hz, 1H), 7.19-7.05 (m, 3H), 6.31 (d, J=8.8 Hz, 1H), 6.23 (s, 1H), 2.96 (s, 3H), 2.13 (s, 6H), 1.36 (s, 12H).

Example 188: Synthesis of Borate M-85

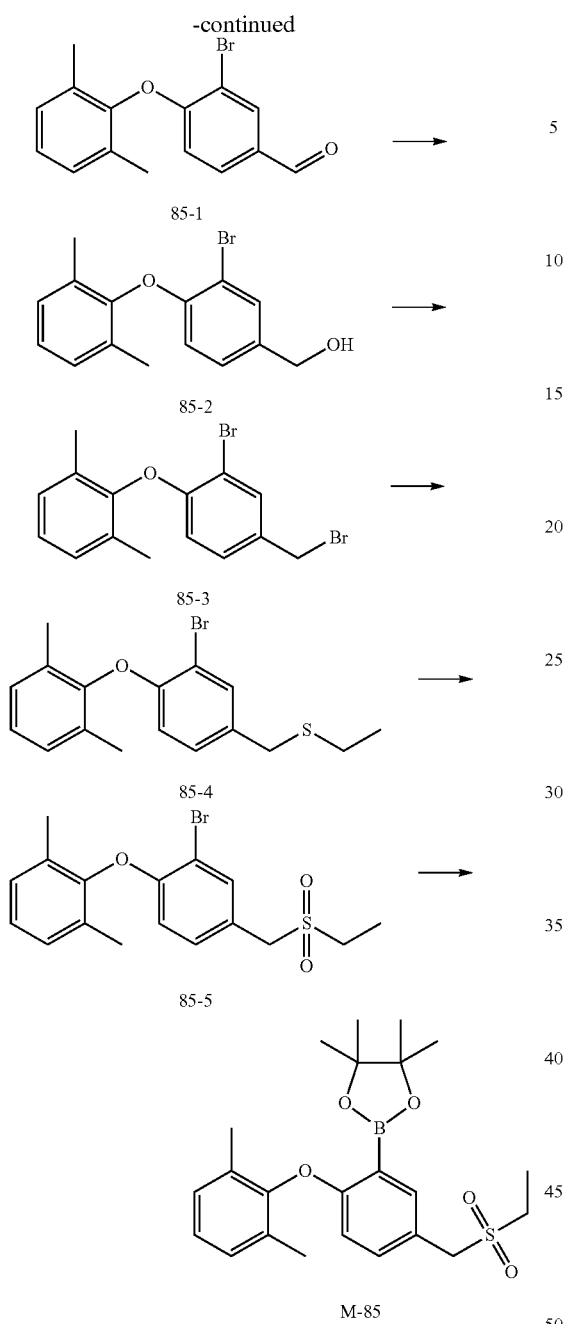

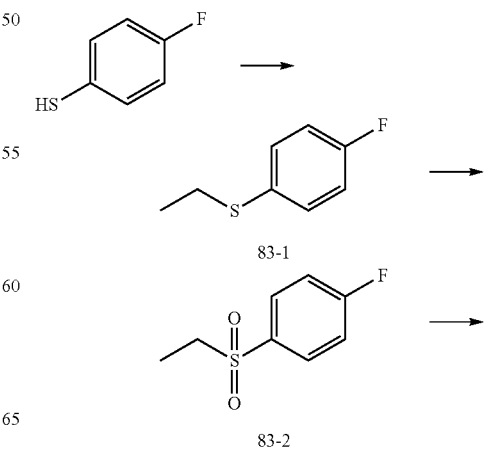

phase was washed with saturated saline, dried over anhydrous sodium sulfate, concentrated under reduced pressure and purified by column chromatography to give 85-2 (5.8 g) as an oil.

Step 3

85-2 (5.8 g, 18.9 mmol) was dissolved in DCM (100 mL), added dropwisely with phosphorus tribromide (2.6 mL, 27.5 mmol) at room temperature and stirred for 0.5 h. TLC showed the reaction was complete. The reaction mixture was quenched with water and extracted with EA. The organic phase was washed with saturated saline, dried over anhydrous sodium sulfate, and concentrated under reduced pressure to give 85-3 (6.5 g) as an oil.

Step 4

85-3 (6.5 g, 17.6 mmol) was dissolved in DMF (50 mL), added with sodium ethanethiolate (2.3 g, 27.5 mmol) and stirred at room temperature overnight. TLC showed the reaction was complete. The reaction mixture was diluted with water and extracted with EA. The organic phase was washed with saturated saline, dried over anhydrous sodium sulfate, and concentrated under reduced pressure to give 85-4 (5.8 g) as an oil.

Step 5

85-4 (5.8 g, 16.5 mmol) was dissolved in a mixed solvent (50 mL) of methanol:water=1:1, added with potassium hydrogenperoxymonosulfate (Oxone, 20.3 g, 33.02 mmol) at room temperature and stirred at room temperature for 2 h. LCMS detection showed the reaction was complete. The reaction mixture was added with water (100 mL), stirred for 0.5 h and then filtered. The filtered cake was washed 3 times with water, and then dried with ethanol to give 85-5 (7.0 g) as a white solid.

Step 6

85-5 (6.0 g, 15.7 mmol), bis(pinacolato)diboron (8.0 g, 31.3 mmol), Pd (dppf)Cl$_2$ (0.57 g, 0.78 mmol) and potassium acetate (3.0 g, 31.3 mmol) were added to 1,4-dioxane (60 mL) and stirred at 100° C. overnight under argon. LCMS detection showed that there existed the product. The reaction mixture was rotary evaporated to dryness, purified by column chromatography and slurried with petroleum ether to give M-85 (1.0 g) as a white solid.

Example 189: Synthesis of Borate M-83

Step 1

3-Bromo-4-fluorobenzaldehyde (5.0 g, 24.6 mmol) was dissolved in DMSO (50 mL), added with 2,6-dimethylphenol (3.6 g, 29.5 mmol) and cesium carbonate (12.02 g, 36.9 mmol) and stirred overnight at 90° C. under argon. TLC showed the reaction was complete. The reaction mixture was added with water and extracted with EA. The organic phase was washed with saturated saline, dried over anhydrous sodium sulfate, and concentrated under reduced pressure to give 85-1 (7.0 g) as an oil.

Step 2

85-1 (7.0 g, 22.9 mmol) was dissolved in methanol (100 mL), added in batches with sodium borohydride (1.3 g, 34.4 mmol) at room temperature and stirred for 30 min. TLC showed the reaction was complete. The reaction mixture was quenched with water and extracted with EA. The organic

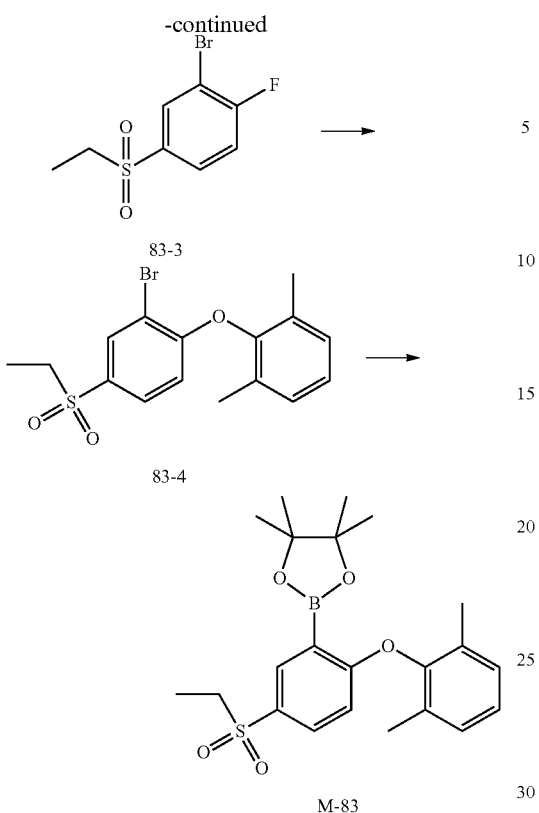

M-83

Step 1 p-fluorothiophenol (d=1.203 g/mL, 40.0 mL, 0.38 mol) and ethyl iodide (d=1.95 g/mL, 36.0 mL, 0.45 mol) were dissolved in THF (150 mL), added dropwisely with TEA (52.2 mL, 0.38 mol) at room temperature and stirred at room temperature for 2 h. EA (200 mL) was added, the organic phase was washed with water, dried over anhydrous sodium sulfate, and concentrated under reduced pressure to give 83-1 (51.0 g).

Step 2

83-1 (25.1 g, 0.16 mol) was dissolved in methanol (300 mL) and water (100 mL), added with potassium hydrogenperoxymonosulfate (Oxone, 56.7 g, 0.34 mol) under ice bath, stirred at room temperature for 1 h, diluted with 200 mL of water and extracted with EA. The organic phase was dried over anhydrous sodium sulfate, and concentrated under reduced pressure to give 83-2 (29.0 g) as a colorless oil.

Step 3

Under an ice bath, 83-2 (29.0 g, 154 mmol) was dissolved in concentrated sulfuric acid (50 mL), added with NBS (30.2 g, 170 mmol) in batches, stirred overnight at room temperature, and then heated at 50° C. for 6 h. The reaction mixture was poured into ice water and extracted with EA. The organic phase was washed with saturated saline, dried over anhydrous sodium sulfate and purified by column chromatography to give 83-3 (14.0 g).

Step 4

83-3 (5.0 g, 18.8 mmol), 2,6-dimethylphenol (2.5 g, 20.5 mmol) and cesium carbonate (9.2 g, 28.2 mmol) were added to DMSO (50 mL) and stirred at 80° C. for 2 h. TLC detection showed that the raw material reacted completely. The reaction solution was poured into water (50 mL) and extracted with EA (50 mL). The aqueous phase was extracted with EA (10 mL). The combined organic phase was washed with saline (20 mL) and water (20 mL) respectively, dried over anhydrous sodium sulfate, concentrated and passed through column chromatography to give 83-4 (6.0 g) as a yellowish oil.

Step 2

83-4 (6.0 g, 16.3 mmol), potassium acetate (4.8 g, 49.0 mmol), and bis(pinacolato)diboron (8.3 g, 32.7 mmol) were dissolved in 50 mL of dioxane, added with [1,1'-bis(diphenylphosphino)ferrocene]palladium dichloride (0.66 g, 0.81 mmol) under argon and heated to 100° C. to react for 3 h. The reaction mixture was cooled to room temperature and filtered through celite. The filtrate was added with water and ethyl acetate for layering. The organic layer was washed with saturated saline, dried over anhydrous sodium sulfate, rotary evaporated under vacuum to remove the solvent, and passed through silica gel chromatography and slurried in PE/EA=5:1 to give M-83 (2.1 g) as a white solid. $^1$H NMR (400 MHz, CDCl$_3$) δ 8.27 (d, J=2.4 Hz, 1H), 7.73 (dd, J=8.4, 2.4 Hz, 1H), 7.13-7.06 (m, 3H), 6.44 (d, J=8.8 Hz, 1H), 3.11 (q, J=7.6, 2H), 2.12 (s, 6H), 1.37 (s, 12H), 1.28 (t, J=7.6 Hz, 3H).

Example 190: Synthesis of Borate M-82

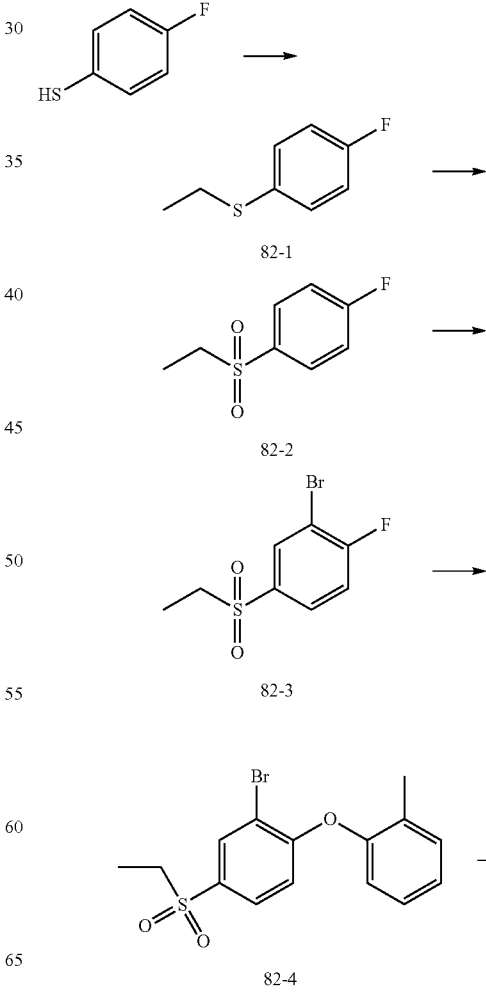

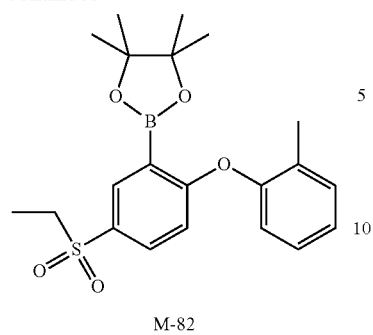

Borate M-82 was prepared in the same method as that in Example 189, except that o-methylphenol was used instead of 2,6-dimethylphenol in Step 4. $^1$H NMR (400 MHz, CDCl$_3$) δ 8.27 (d, J=2.4 Hz, 1H), 7.82 (dd, J=8.4, 2.4 Hz, 1H), 7.27 (d, J=5.6 Hz, 1H), 7.18 (t, J=7.0 Hz, 1H), 7.10 (t, J=6.8 Hz, 1H), 6.88 (d, J=7.2 Hz, 1H), 6.78 (d, J=8.8 Hz, 1H), 3.12 (q, J=7.2, 2H), 2.22 (s, 3H), 1.31-1.26 (m, 15H).

Example 191: Synthesis of Borate M-84

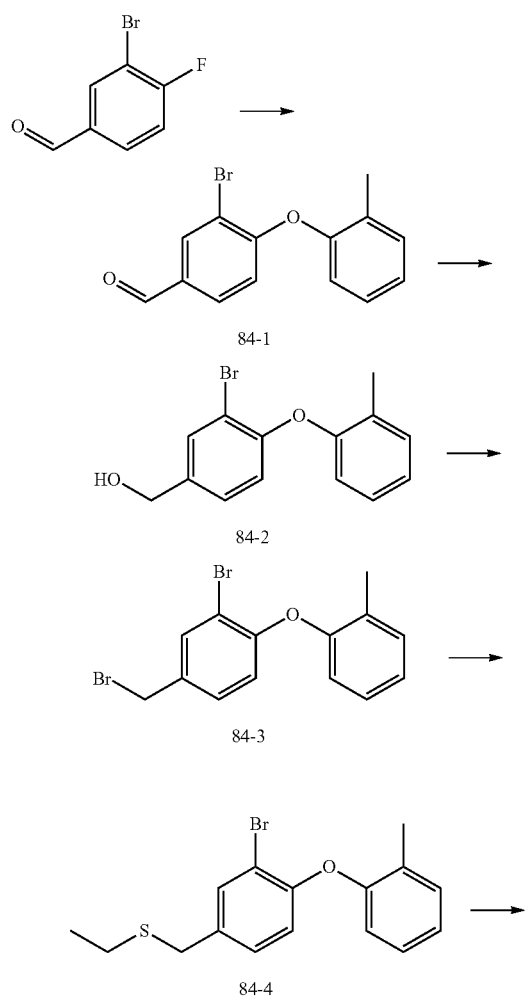

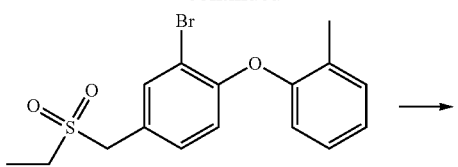

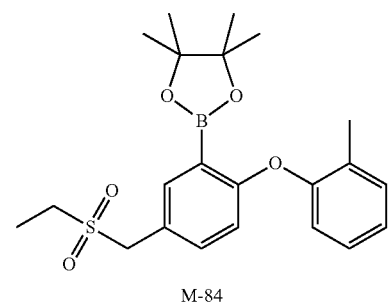

Borate M-84 was prepared in the same method as that in Example 188, except that o-methylphenol was used instead of 2,6-dimethylphenol in Step 1. $^1$H NMR (400 MHz, CDCl$_3$) δ 7.70 (d, J=2.4 Hz, 1H), 7.49 (dd, J=8.4 Hz, 2.0 Hz, 1H), 7.26 (d, J=6.4 Hz, 1H), 7.11 (t, J=6.4 Hz, 1H), 7.99 (t, J=6.4 Hz, 1H), 6.86 (d, J=8.4 Hz, 1H), 6.56 (d, J=7.6 Hz, 1H), 4.48 (s, 2H), 3.04 (q, J=7.6 Hz, 2H), 2.23 (s, 3H), 1.23 (t, J=7.6 Hz, 3H), 1.16 (s, 12H).

Example 192: Synthesis of Borate M-91

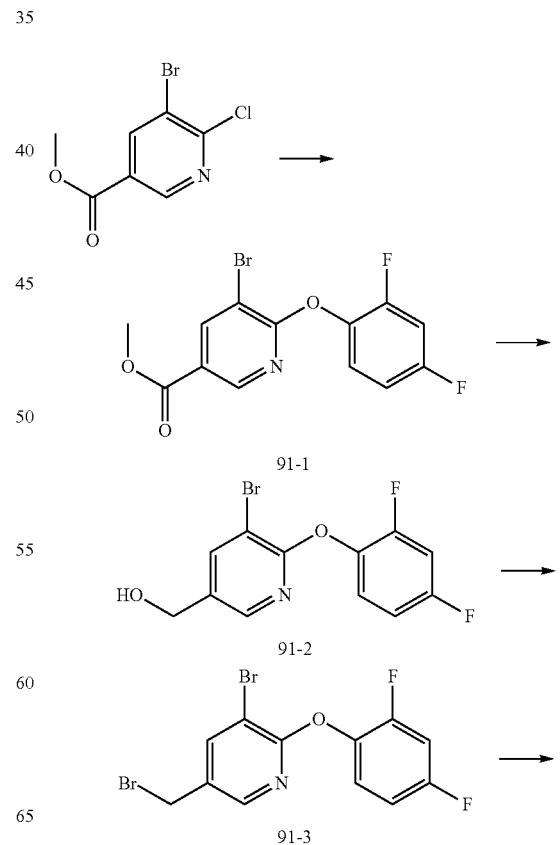

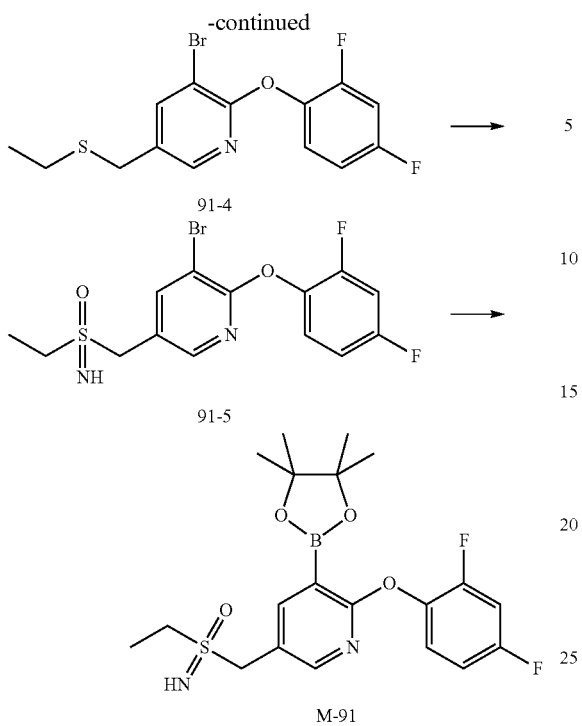

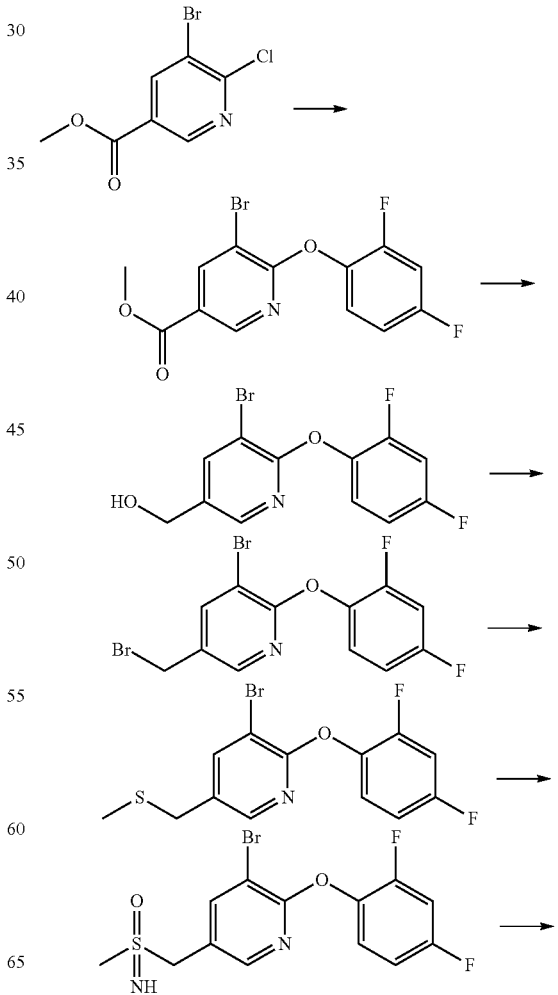

saturated saline, dried over anhydrous sodium sulfate, concentrated and purified by column chromatography to give 91-4 (2.75 g) as a yellowish-brown oil.

Step 5

91-4 (2.75 g, 7.7 mmol), iodobenzene diacetic acid (7.4 g, 23.0 mmol) and ammonium acetate (2.4 g, 31.1 mmol) were added to 40 mL of ethanol and stirred at room temperature for 1 h. TLC detection showed the raw material disappeared. The reaction solution was concentrated under reduced pressure and purified by column chromatography to give 91-5 (1.75 g) as a white solid.

Step 6

91-5 (1.72 g, 4.4 mmol), bis(pinacolato)diboron (3.35 g, 13.2 mmol), potassium acetate (1.29 g, 13.2 mmol) and $PdCl_2(dppf)$ (539 mg, 0.66 mmol) were added to 30 mL of dioxane and stirred at 100° C. for 2 h under nitrogen. LCMS detection showed that the raw material reacted completely. The reaction solution was cooled and filtered through celite. The filtrate was concentrated and purified by column chromatography to give M-91 (1.2 g) as a yellow foamy solid. $^1$H NMR (400 MHz, CDCl$_3$) δ 8.16 (d, J=2.4 Hz, 1H), 8.13 (d, J=2.8 Hz, 1H), 7.24-7.20 (m, 1H), 6.95-6.87 (m, 2H), 4.24 (d, J=13.6 Hz, 1H), 4.08 (d, J=13.2 Hz, 1H), 3.03 (q, J=7.6 Hz, 2H), 1.44 (t, J=7.2 Hz, 3H), 1.36 (s, 12H).

Example 193: Synthesis of Borate M-90

Step 1

Methyl 5-bromo-6-chloronicotinate (10.0 g, 40.0 mmol) and 2,4-difluorophenol (7.8 g, 60.0 mmol) were dissolved in 100 mL of dimethyl sulfoxide (DMSO), added with carbonic acid cesium (26.0 g, 80.0 mmol) and stirred at 95° C. for 3 h under nitrogen. TLC detection showed that the raw material reacted completely. After cooled, the mixture was poured into water and extracted with EA. The organic phase was washed with saturated saline, dried over anhydrous sodium sulfate, concentrated and purified by column chromatography to give 91-1 (4.9 g) as a white solid.

Step 2

91-1 (7.3 g, 21.3 mmol) was dissolved in 80 mL of ethanol, added with sodium borohydride (1.6 g, 42.6 mmol) and refluxed under stirring for 1 h. TLC detection showed that the raw material reacted completely. The reaction mixture was cooled, quenched with water, and extracted with EA. The organic phase was washed with saturated saline, dried over anhydrous sodium sulfate, concentrated and purified by column chromatography to give 91-2 (3.46 g) as a colorless oil.

Step 3

91-2 (3.46 g, 11.0 mmol) was dissolved in 30 mL of DMF, added with phosphorus tribromide (2.0 mL, 21.3 mmol) under ice bath and stirred for 0.5 h. TLC detection showed that the raw material reacted completely. The reaction solution was poured into water and extracted with EA. The organic phase was washed with saturated saline, dried over anhydrous sodium sulfate, and concentrated to give a crude 91-3 (5.32 g) as a yellow oil, which was directly used in the next step.

Step 4

91-3 (5.32 g, 14.1 mmol) was dissolved in 30 mL of DMF, added with sodium ethanethiolate (1.35 g, 21.2 mmol) under ice bath, returned to room temperature and stirred for 1 h. TLC detection showed that the raw material reacted completely. The reaction mixture was added with water and extracted with EA. The organic phase was washed with -continued

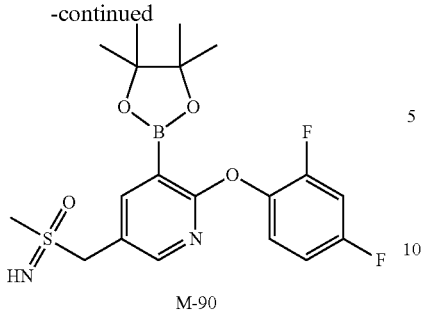

Borate M-90 was prepared in the same method as that in Example 192 except that sodium methylthiol was used instead of sodium ethylthiol in Step 4.

Example 194: Synthesis of Compound ZB-BD-230

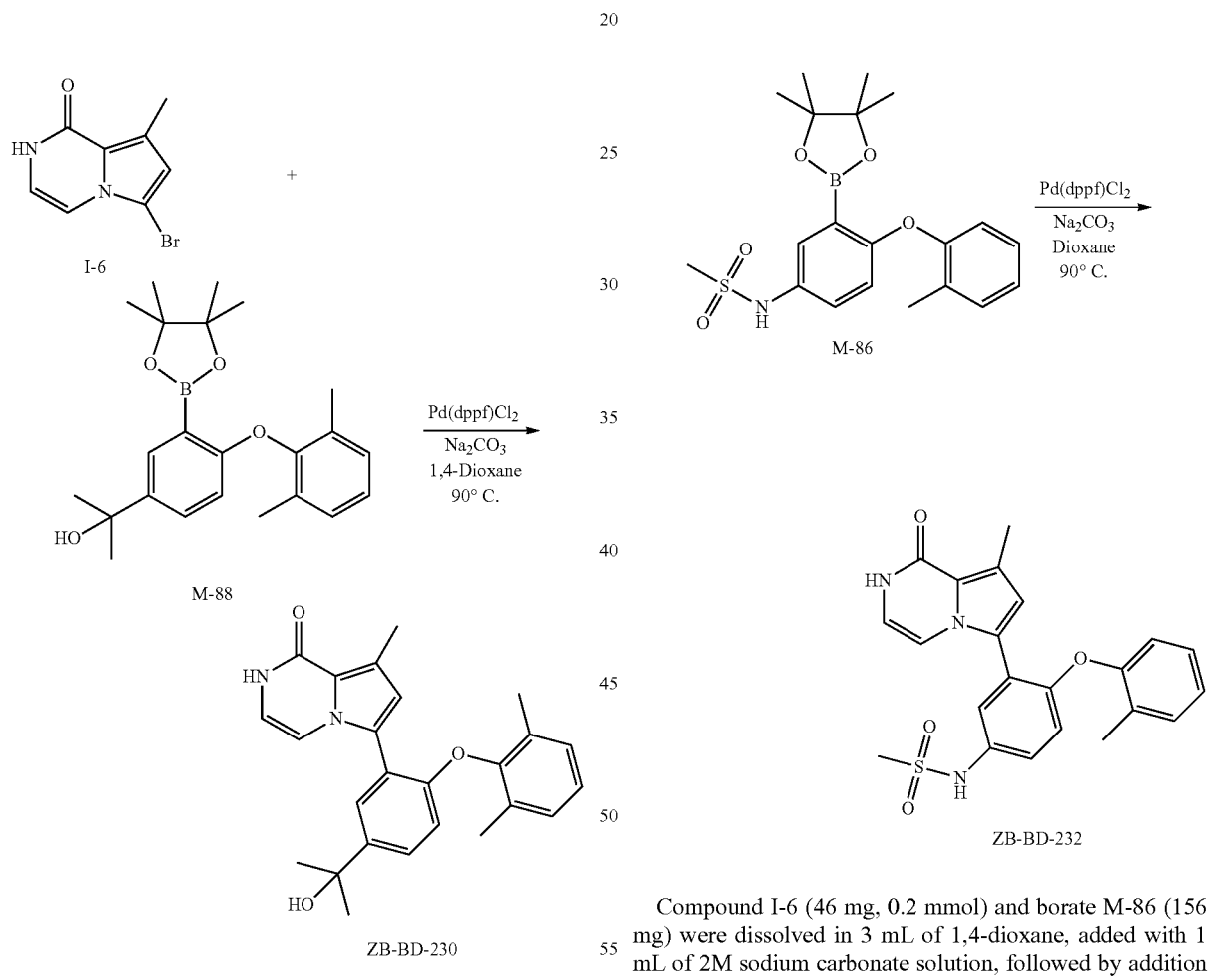

Compound I-6 (46 mg, 0.2 mmol) and borate M-88 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-230. $^1$H NMR (400 MHz, DMSO-d$_6$) δ 10.26 (d, J=5.5 Hz, 1H), 7.49 (d, J=2.3 Hz, 1H), 7.38 (dd, J=8.6, 2.3 Hz, 1H), 7.16-7.11 (m, 2H), 7.07 (dd, J=8.6, 6.2 Hz, 1H), 6.79 (d, J=5.8 Hz, 1H), 6.53-6.47 (m, 2H), 6.31 (d, J=8.6 Hz, 1H), 5.04 (s, 1H), 2.52 (s, 3H), 1.99 (s, 6H), 1.42 (s, 6H). HPLC-MS: [M+H]$^+$= 403.2

Example 195: Synthesis of Compound ZB-BD-232

Compound I-6 (46 mg, 0.2 mmol) and borate M-86 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-232. $^1$H NMR (400 MHz, DMSO-d$_6$) δ 10.26 (d, J=5.5 Hz, 1H), 9.77 (s, 1H), 7.30-7.25 (m, 2H), 7.23 (d, J=7.4 Hz, 1H), 7.12 (t, J=7.7 Hz, 1H), 7.01 (t, J=7.4 Hz, 1H), 6.89 (d, J=5.8 Hz, 1H), 6.86 (d, J=9.5 Hz, 1H), 6.75 (d, J=8.0 Hz, 1H), 6.47 (t, J=5.7 Hz, 1H), 6.44 (s, 1H), 3.03 (s, 3H), 2.45 (s, 3H), 2.10 (s, 3H). HPLC-MS: [M+H]$^+$=424.2

Example 196: Synthesis of Compound ZB-BD-236

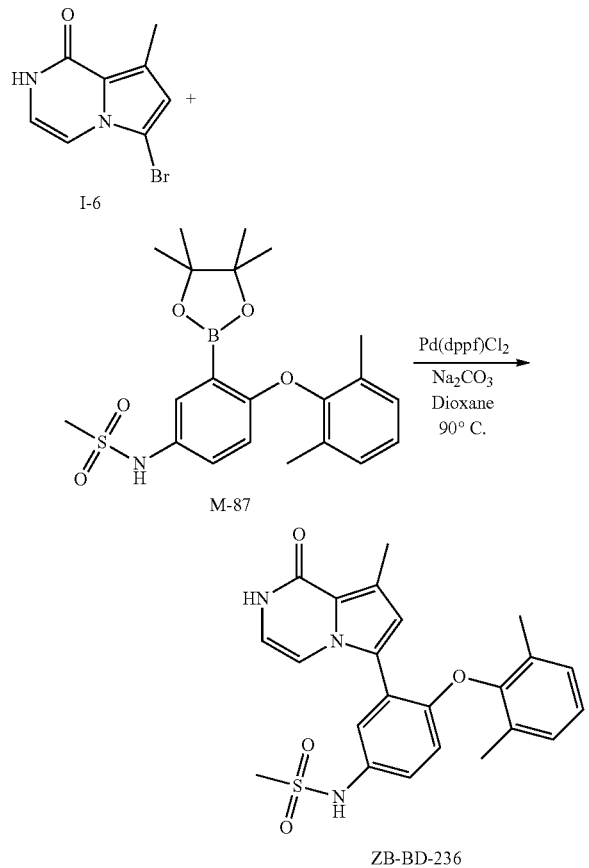

Compound I-6 (46 mg, 0.2 mmol) and borate M-87 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-236. $^1$H NMR (400 MHz, DMSO-d$_6$) δ 10.28 (d, J=5.4 Hz, 1H), 9.63 (s, 1H), 7.27 (d, J=2.7 Hz, 1H), 7.20-7.03 (m, 4H), 6.85 (d, J=5.8 Hz, 1H), 6.52 (d, J=2.9 Hz, 2H), 6.38 (d, J=8.9 Hz, 1H), 2.98 (s, 3H), 2.52 (s, 3H), 1.99 (s, 6H). HPLC-MS: [M+H]$^+$=438.3

Example 197: Synthesis of Compound ZB-BD-237

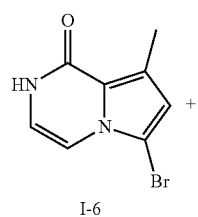

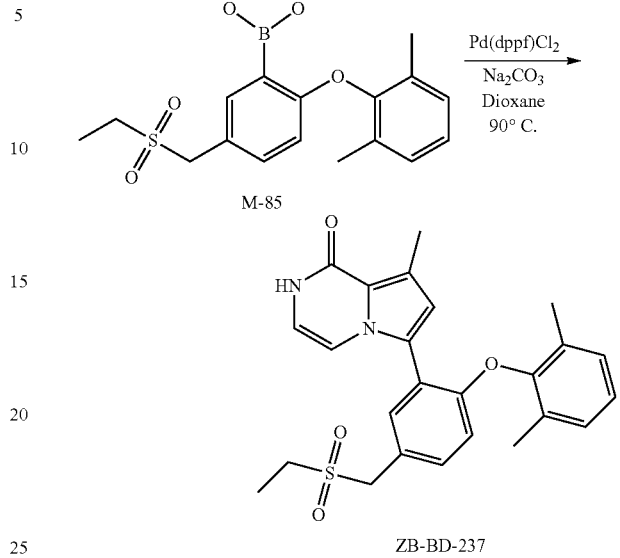

Compound I-6 (46 mg, 0.2 mmol) and borate M-85 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-237. $^1$H NMR (400 MHz, DMSO-d$_6$) δ 10.29 (d, J=5.4 Hz, 1H), 7.51 (d, J=2.2 Hz, 1H), 7.36 (dd, J=8.5, 2.2 Hz, 1H), 7.16-7.05 (m, 3H), 6.87 (d, J=5.8 Hz, 1H), 6.57-6.51 (m, 2H), 6.44 (d, J=8.5 Hz, 1H), 4.47 (s, 2H), 3.06 (q, J=7.4 Hz, 2H), 2.54 (s, 3H), 2.01 (s, 6H), 1.22 (t, J=7.4 Hz, 3H). HPLC-MS: [M+H]$^+$=451.2.

Example 198: Synthesis of Compound ZB-BD-239

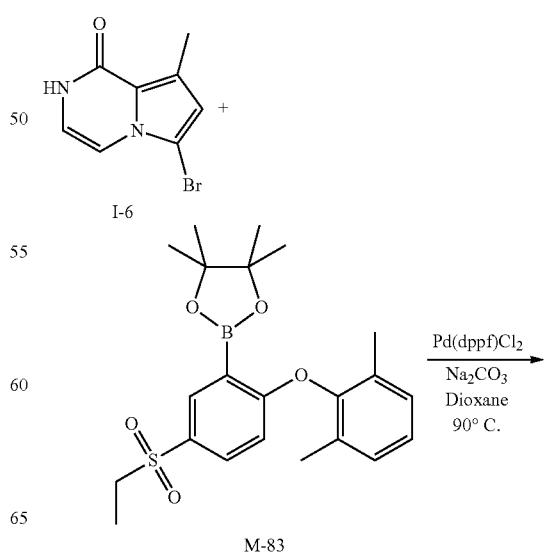

-continued

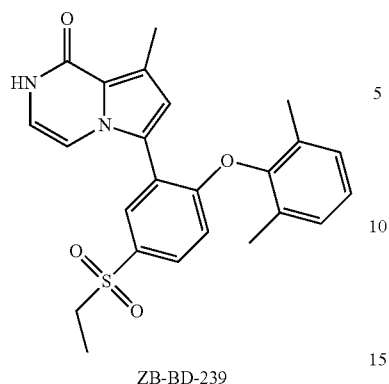

ZB-BD-239

-continued

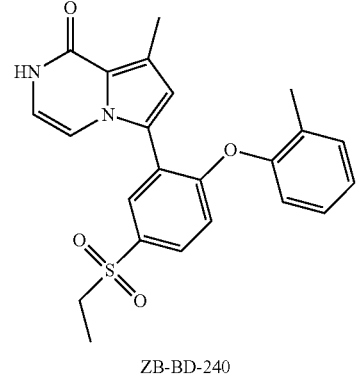

ZB-BD-240

Compound I-6 (46 mg, 0.2 mmol) and borate M-83 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-239. $^1$H NMR (400 MHz, DMSO-d$_6$) δ 10.33 (d, J=5.5 Hz, 1H), 7.89 (d, J=2.3 Hz, 1H), 7.85 (dd, J=8.7, 2.4 Hz, 1H), 7.20-7.12 (m, 3H), 6.85 (d, J=5.8 Hz, 1H), 6.66-6.59 (m, 2H), 6.54 (t, J=5.7 Hz, 1H), 3.32 (q, J=7.3 Hz, 2H), 2.52 (s, 3H), 2.01 (s, 6H), 1.13 (t, J=7.3 Hz, 3H). HPLC-MS: [M+H]$^+$=437.2

Example 199: Synthesis of Compound ZB-BD-240

Compound I-6 (46 mg, 0.2 mmol) and borate M-82 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-240. HPLC-MS: [M+H]$^+$=423.4

Example 200: Synthesis of Compound ZB-BD-249

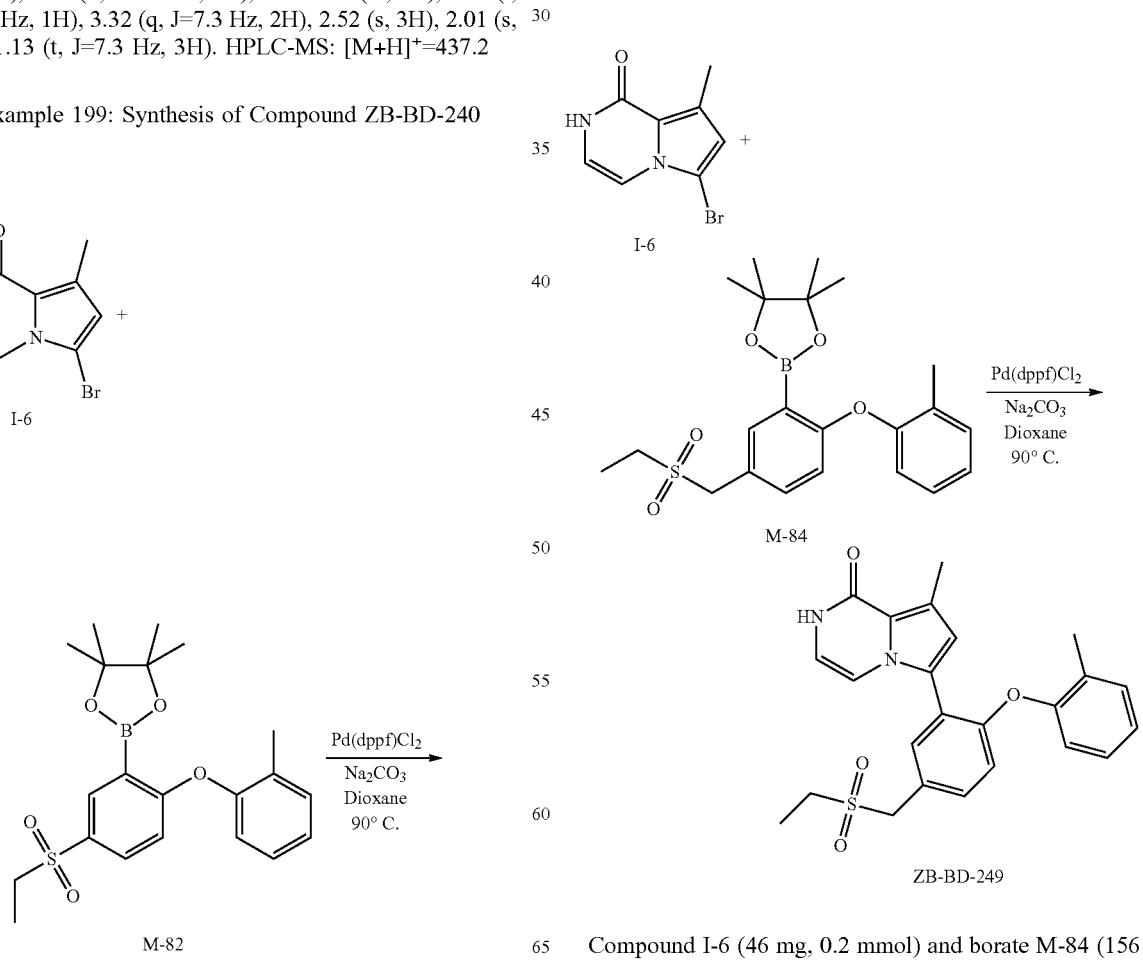

Compound I-6 (46 mg, 0.2 mmol) and borate M-84 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-249. $^1$H NMR (400 MHz, DMSO-d$_6$) δ 10.25 (d, J=5.4 Hz, 1H), 7.51 (d, J=2.2 Hz, 1H), 7.42 (dd, J=8.5, 2.2 Hz, 1H), 7.26 (d, J=7.4 Hz, 1H), 7.17 (t, J=7.4 Hz, 1H), 7.06 (t, J=7.4 Hz, 1H), 6.91 (d, J=5.8 Hz, 1H), 6.87 (d, J=7.9 Hz, 1H), 6.77 (d, J=8.5 Hz, 1H), 6.51-6.43 (m, 2H), 4.49 (s, 2H), 3.06 (q, J=7.4 Hz, 2H), 2.48 (s, 3H), 2.09 (s, 3H), 1.23 (t, J=7.4 Hz, 3H). HPLC-MS: [M+H]$^+$=437.2

Example 201: Synthesis of Compound ZB-BD-241

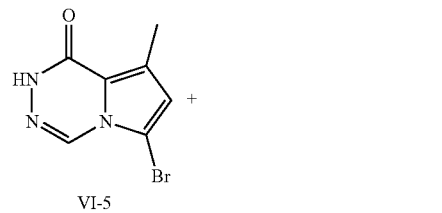

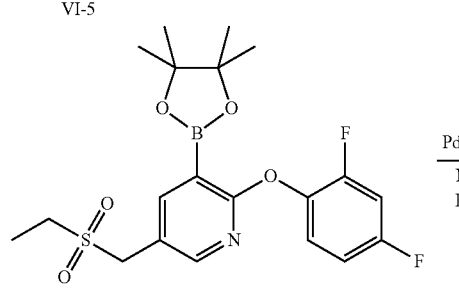

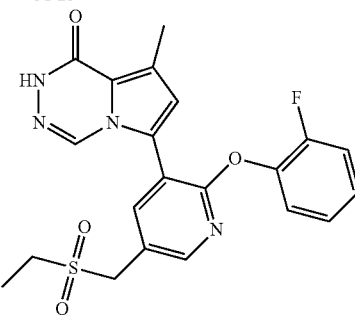

Compound VI-5 (46 mg, 0.2 mmol) and borate M-23 (156 mg) were dissolved in 3 mL of 1,4-dioxane, added with 1 mL of 2M sodium carbonate solution, followed by addition of [1,1'-bis(diphenylphosphino)ferrocene] palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-241. $^1$H NMR (400 MHz, DMSO-d$_6$) δ 11.68 (s, 1H), 8.29 (s, 1H), 8.18 (d, J=2.2 Hz, 1H), 8.05 (d, J=2.2 Hz, 1H), 7.55-7.42 (m, 2H), 7.17 (t, J=8.7 Hz, 1H), 6.82 (s, 1H), 4.56 (s, 2H), 3.12 (q, J=7.5 Hz, 2H), 2.51 (s, 3H), 1.24 (t, J=7.4 Hz, 3H). HPLC-MS: [M+H]$^+$=461.1

Example 202: Synthesis of Compound ZB-BD-242

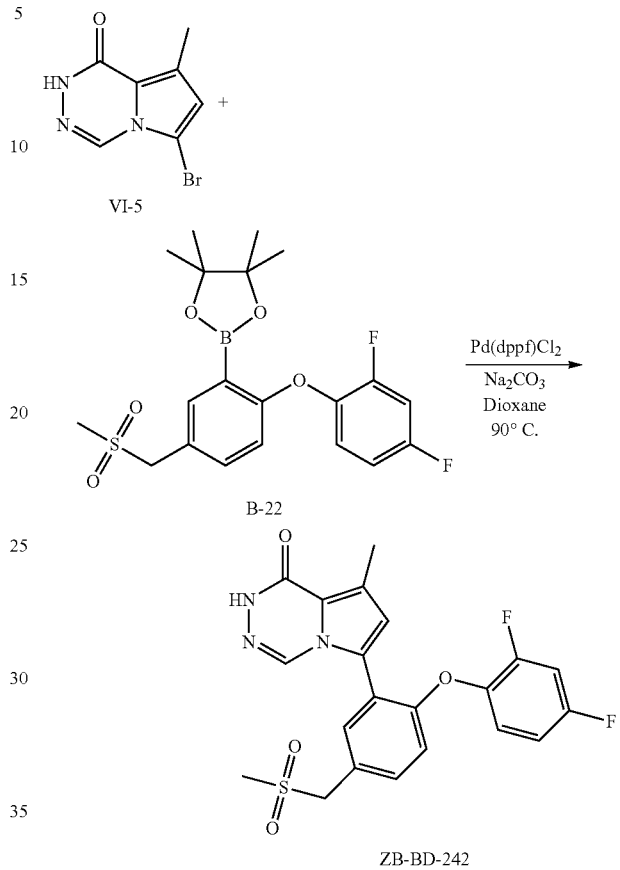

Compound VI-5 (46 mg, 0.2 mmol) and borate M-22 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-242. $^1$H NMR (400 MHz, DMSO-d$_6$) δ 11.62 (s, 1H), 8.13 (s, 1H), 7.59 (d, J=2.2 Hz, 1H), 7.53-7.45 (m, 2H), 7.40 (td, J=9.2, 5.6 Hz, 1H), 7.14 (t, J=8.5 Hz, 1H), 6.89 (d, J=8.5 Hz, 1H), 6.69 (s, 1H), 4.53 (s, 2H), 2.94 (s, 3H), 2.48 (s, 3H). HPLC-MS: [M+H]$^+$=446.3

Example 203: Synthesis of Compound ZB-BD-247

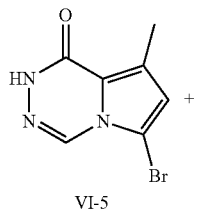

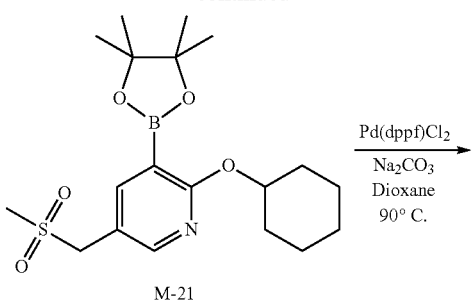

M-21

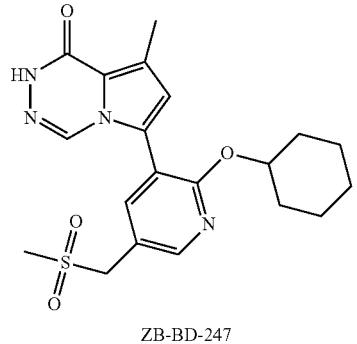

ZB-BD-247

Compound VI-5 (46 mg, 0.2 mmol) and borate M-21 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl₂) (29 mg, 0.04 mmol) under Ar. The mixture was stirred at 90° C. for 2 h, diluted with water, extracted with ethyl acetate, and purified by silica gel column chromatography to give compound ZB-BD-247. ¹H NMR (400 MHz, DMSO-d₆) δ 11.58 (s, 1H), 8.25 (d, J=2.3 Hz, 1H), 8.07 (s, 1H), 7.85 (d, J=2.3 Hz, 1H), 6.64 (s, 1H), 5.22-5.07 (m, 1H), 4.51 (s, 2H), 2.96 (s, 3H), 2.49 (s, 3H), 1.96-1.85 (m, 2H), 1.63-1.50 (m, 2H), 1.45-1.30 (m, 4H), 1.27-1.15 (m, 2H). HPLC-MS: [M+H]⁺=417.2

Example 204: Synthesis of Compound ZB-BD-248

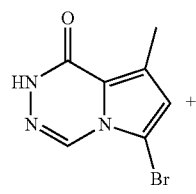

VI-5

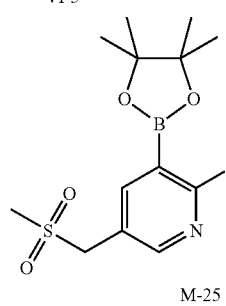

M-25

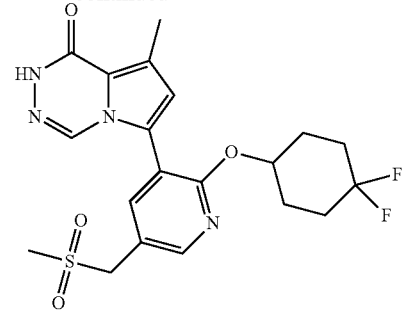

ZB-BD-248

Compound VI-5 (46 mg, 0.2 mmol) and borate M-25 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl₂) (29 mg, 0.04 mmol) under Ar. The mixture was stirred at 90° C. for 2 h, diluted with water, extracted with ethyl acetate, and purified by silica gel column chromatography to give compound ZB-BD-248. ¹H NMR (400 MHz, DMSO-d₆) δ 11.60 (s, 1H), 8.27 (d, J=2.3 Hz, 1H), 8.15 (s, 1H), 7.89 (d, J=2.3 Hz, 1H), 6.65 (s, 1H), 5.39-5.25 (m, 1H), 4.53 (s, 2H), 2.97 (s, 3H), 2.49 (s, 3H), 2.07-1.87 (m, 4H), 1.87-1.68 (m, 4H). HPLC-MS: [M+H]⁺=453.1

Example 205: Synthesis of Compound ZB-BD-252

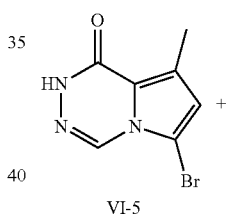

VI-5

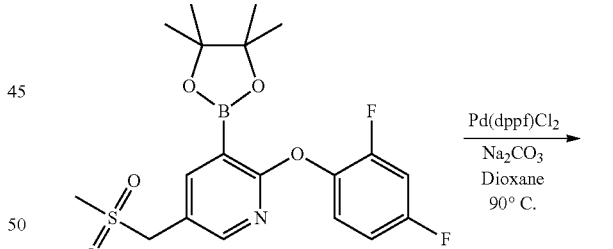

B-39

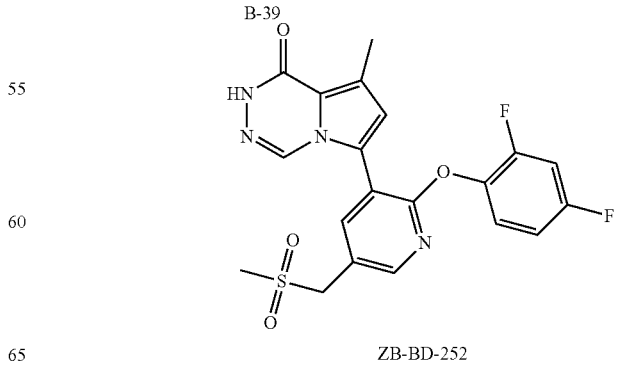

ZB-BD-252

Compound VI-5 (46 mg, 0.2 mmol) and borate M-39 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-252. $^1$H NMR (400 MHz, DMSO-d$_6$) δ 11.68 (s, 1H), 8.29 (s, 1H), 8.18 (d, J=2.2 Hz, 1H), 8.06 (d, J=2.2 Hz, 1H), 7.54-7.42 (m, 2H), 7.17 (t, J=8.2 Hz, 1H), 6.83 (s, 1H), 4.58 (s, 2H), 2.99 (s, 3H), 2.51 (s, 3H). HPLC-MS: [M+H]$^+$=447.1

Example 206: Synthesis of Compound ZB-BD-253

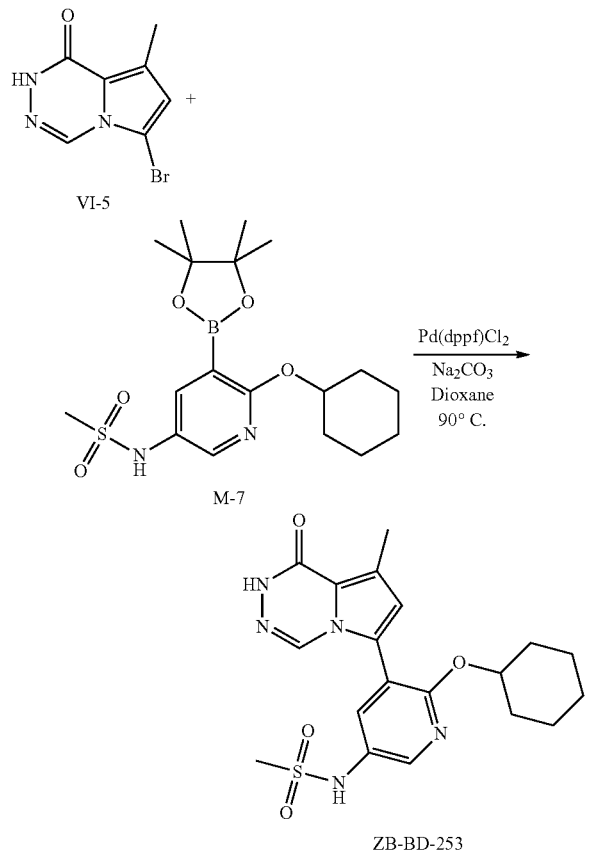

Compound VI-5 (46 mg, 0.2 mmol) and borate M-7 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-253. $^1$H NMR (400 MHz, DMSO-d$_6$) δ 11.58 (s, 1H), 9.68 (s, 1H), 8.11 (d, J=2.6 Hz, 1H), 8.03 (s, 1H), 7.64 (d, J=2.6 Hz, 1H), 6.66 (s, 1H), 5.14-5.02 (m, 1H), 3.02 (s, 3H), 2.49 (s, 3H), 1.94-1.85 (m, 2H), 1.59-1.50 (m, 2H), 1.40-1.15 (m, 6H). HPLC-MS: [M+H]$^+$=418.3

Example 207: Synthesis of Compound ZB-BD-254

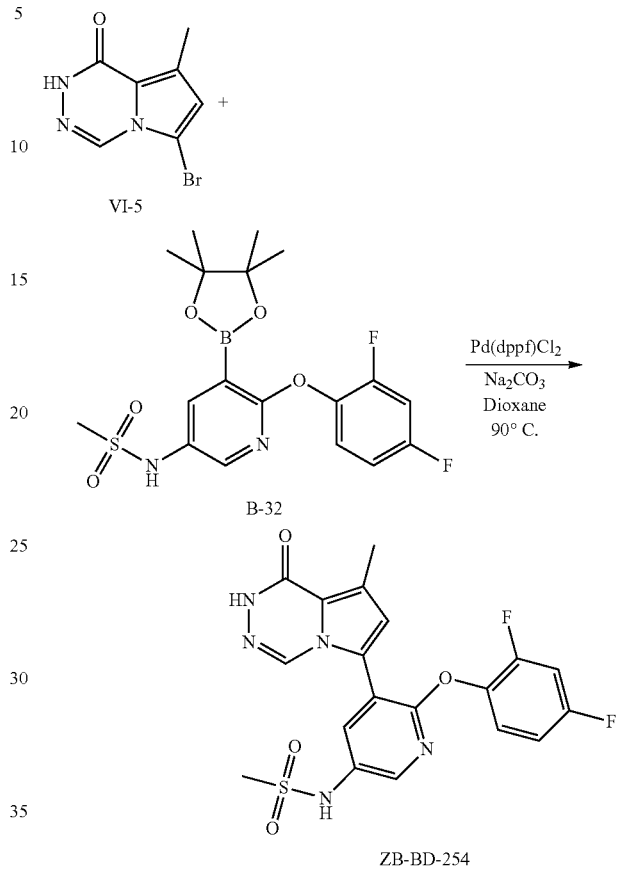

Compound VI-5 (46 mg, 0.2 mmol) and borate B-32 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-254. $^1$H NMR (400 MHz, DMSO-d$_6$) δ 11.67 (s, 1H), 9.85 (s, 1H), 8.26 (s, 1H), 8.02 (d, J=2.6 Hz, 1H), 7.81 (d, J=2.6 Hz, 1H), 7.50-7.41 (m, 2H), 7.15 (t, J=8.3 Hz, 1H), 6.83 (s, 1H), 3.08 (s, 3H), 2.50 (s, 3H). HPLC-MS: [M+H]$^+$=448.0

Example 208: Synthesis of Compound ZB-BD-255

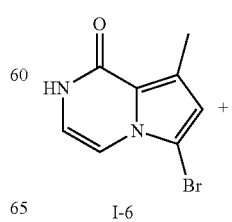

-continued

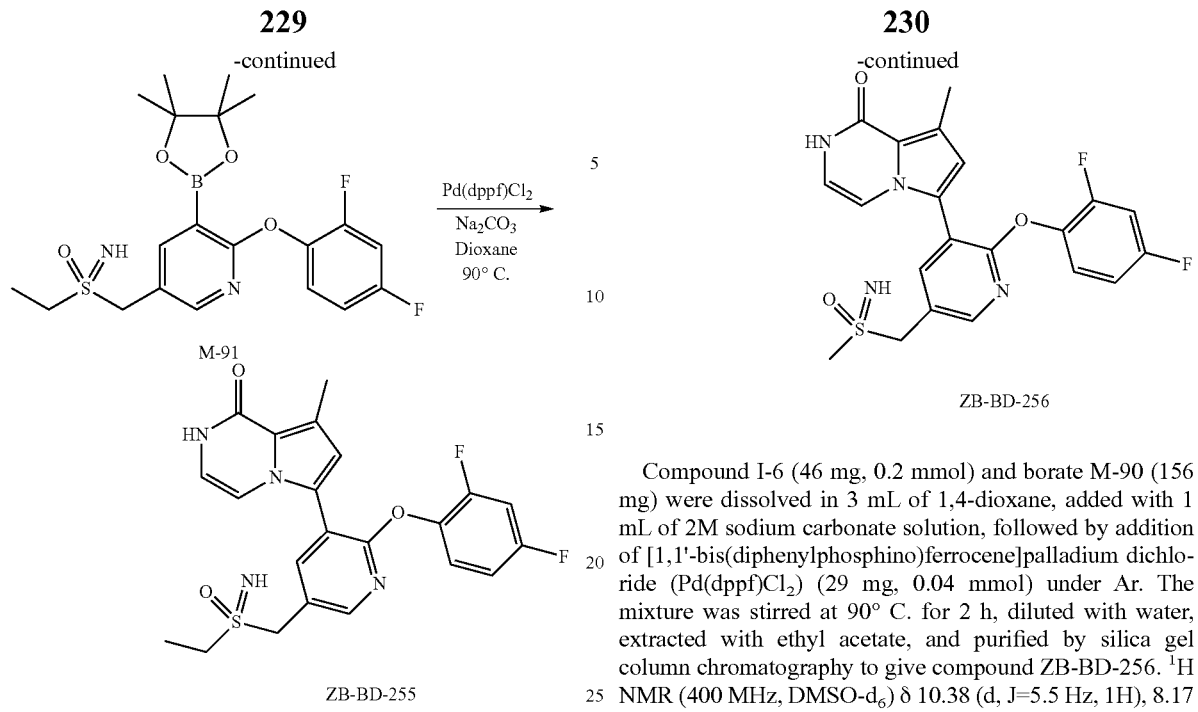

M-91

ZB-BD-255

Compound I-6 (46 mg, 0.2 mmol) and borate M-91 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-255. $^1$H NMR (400 MHz, DMSO-d$_6$) δ 10.39 (d, J=5.4 Hz, 1H), 8.15 (d, J=2.2 Hz, 1H), 8.01 (d, J=2.2 Hz, 1H), 7.50-7.39 (m, 2H), 7.15 (t, J=8.3 Hz, 1H), 7.03 (d, J=5.8 Hz, 1H), 6.63 (s, 1H), 6.53 (t, J=5.7 Hz, 1H), 4.48-4.34 (m, 2H), 3.18 (s, 1H), 2.96 (d, J=7.3 Hz, 2H), 2.52 (s, 3H), 1.24 (t, J=7.3 Hz, 3H). HPLC-MS: [M+H]$^+$=459.1

Example 209: Synthesis of Compound ZB-BD-256

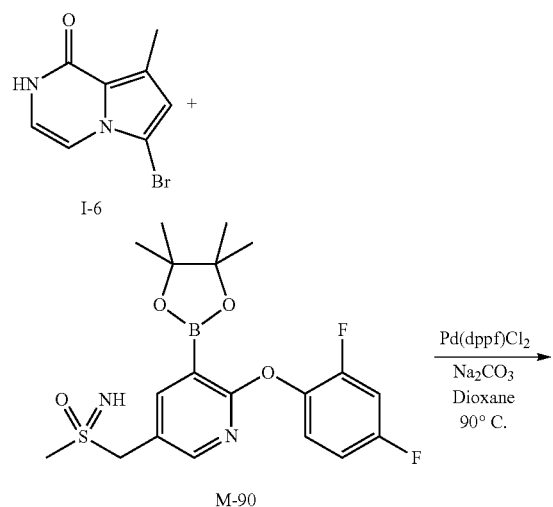

-continued

ZB-BD-256

Compound I-6 (46 mg, 0.2 mmol) and borate M-90 (156 mg) were dissolved in 3 mL of 1,4-dioxane, added with 1 mL of 2M sodium carbonate solution, followed by addition of [1,1'-bis(diphenylphosphino)ferrocene]palladium dichloride (Pd(dppf)Cl$_2$) (29 mg, 0.04 mmol) under Ar. The mixture was stirred at 90° C. for 2 h, diluted with water, extracted with ethyl acetate, and purified by silica gel column chromatography to give compound ZB-BD-256. $^1$H NMR (400 MHz, DMSO-d$_6$) δ 10.38 (d, J=5.5 Hz, 1H), 8.17 (s, 1H), 8.02 (s, 1H), 7.51-7.39 (m, 2H), 7.15 (t, J=8.3 Hz, 1H), 7.02 (d, J=5.9 Hz, 1H), 6.63 (s, 1H), 6.53 (t, J=5.7 Hz, 1H), 4.55-4.37 (m, 2H), 3.88 (s, 1H), 2.85 (s, 3H), 2.52 (s, 3H). HPLC-MS: [M+H]$^+$=445.1.

Example 210: Inhibitory Activity Assay of BRD4 Small Molecule Compounds

AlphaScreen kit (Perkin Elmer) was used to detect effect of the compounds on binding of BRD4 bromodomain to acetylated histone H4 polypeptide. The bromodomain BRD4_BD1 (49-170) protein constructed by recombination (Org. Biomol. Chem., 2017, 15, 9352-9361) has a purity greater than 95%, and contains hexahistine tag, namely (His)$_6$tag (hereinafter referred to as (His)$_6$tag), at the N-terminus of the amino acid sequence thereof. Each of fusion proteins containing (His)$_6$tag can be recognized and bound by Ni$^{2+}$. The acetylated histone H4 polypeptide was provided by Suzhou Qiangyao Biological Technology Co., Ltd, and the sequence was N-C: SGRG-K(Ac)-GG-K(Ac)-GLG-K(Ac)-GGA-K(Ac)—RHRKVGG-K (biotin), in which the lysine at positions 5, 8, 12 and 16 was acetylated, and the C-terminus of polypeptide was marked with biotin 5-(2-oxohexahydro-H-thieno[3,4-d]imidazole-4-yl)pentanoic acid, and the purity is greater than 95%. Donor microbeads and acceptor microbeads were purchased from Perkin Elmer (AlphaScreen Histidine Detection Kit (Nickle Chelate) 6760619M Lot: 2236078). The donor microbeads were coated with streptavidin and can bind to biotinylated acetylated H4 polypeptide. The acceptor microbeads were coated with Ni$^{2+}$ ions and can bind to the BD1 protein with (His)$_6$tag. When the BD1 protein recognized the acetylated H4 polypeptide, the donor microbeads and the acceptor microbeads can be brought closer to a certain distance. Within this range, the donor microbeads can produce singlet oxygen after being irradiated with a 680 nm excitation light, and transfer the singlet oxygen to the acceptor microbeads. After a series of cascade chemical reactions, the acceptor microbeads will generate an emission wave of 520-620 nm, which in turn can be detected a signal. In this experiment, the test system was 20 μL, and the compound needs to be diluted in buffer 1 (20 mM HEPES pH 7.4, 150 mM NaCl, 1 mM dithiothreitol). First, a solution of 20 mM compound was consecutively diluted twice, each in 10 times, totally in 100 times to a concentration of 200 µM. Then the solution of 200 µM compound was serially diluted in three times in the buffer 1 containing 1/100 DMSO to obtain a 8× working solution of a compound dilution series with a compound concentration of 200 µM to 10 nM (final concentrations: 25.0 µM, 8.33 µM, 2.77 µM, 0.926 µM, 0.309 µM, 0.103 µM, 0.0343 µM, 0.0114 µM, 0.00381 µM, 0.00127 µM). The positive compound used in the test was JQ (Nature 2010, 468, 1067-1073), which was purchased from Sigma. 2.5 µL of the compound solution was added to a white 384-well plate (OptiPlate-384, PerkinElmer 6007299). The recombinant BD1 protein solution and the acetylated histone H4 polypeptide were diluted in the buffer 2 (20 mM HEPES pH 7.4, 150 mM NaCl, 0.01% Triton X-100, 0.1% bovine serum protein (w/v, Sigma), 1 mM dithiothreitol) to 100 nM and 100 nM respectively, to obtain a 8×BD1 protein working solution and a 4× acetylated histone H4 polypeptide working solution. The donor microbeads and the acceptor microbeads are diluted together in the buffer 2, both in the ratio of 1:100, to obtain a 2× microbead mixed working solution. The plate was added with 2.5 µL of BD1 protein working solution and incubated with the compound for 20 min at room temperature, and then added with 5 µL of acetylated histone H4 polypeptide working solution and incubated at room temperature for 5 min, and finally added with 10 µL of microbead mixed working solution and incubated at room temperature for 60 min. Then the signals were read on an EnVision microplate reader (Perkin Elmer) (excitation wavelength was 680 nM, and detection wavelength was 520-620 nM). $IC_{50}$ values of the compounds at different concentrations for inhibiting the binding of BD1 protein to acetylated H4 polypeptide were calculated by fitting using GraphPad Prism 5.0 software.

| compound | ALPHA $IC_{50}$ (nM) | compound | ALPHA $IC_{50}$ (nM) |
|---|---|---|---|
| ZB-BD-68 | 910.2 | ZB-BD-69 | 434.4 |
| ZB-BD-70 | 42.9 | ZB-BD-73 | 905.3 |
| ZB-BD-74 | 76.9 | ZB-BD-77 | <200 |
| ZB-BD-78 | 228 | ZB-BD-80 | 180 |
| ZB-BD-83 | 78.6 | ZB-BD-87 | 137.9 |
| ZB-BD-90 | 83.6 | ZB-BD-94 | 14 |
| ZB-BD-96 | 15.5 | ZB-BD-99 | 134.3 |
| ZB-BD-100 | 132.4 | ZB-BD-102 | 113.8 |
| ZB-BD-103 | 92.6 | ZB-BD-117 | 21.4 |
| ZB-BD-110 | 161.3 | ZB-BD-120 | 36.6 |
| ZB-BD-119 | 124 | ZB-BD-130 | 326 |
| ZB-BD-121 | 471 | ZB-BD-92 | 36 |
| ZB-BD-82 | 128 | ZB-BD-97 | 68 |
| ZB-BD-95 | 780 | ZB-BD-105 | 110 |
| ZB-BD-98 | 15 | ZB-BD-131 | 58 |
| ZB-BD-118 | 48 | ZB-BD-148 | <200 |
| ZB-BD-141 | 52 | ZB-BD-140 | <200 |
| ZB-BD-112 | 15.9 | ZB-BD-113 | 14.4 |
| ZB-BD-116 | 8.8 | ZB-BD-128 | 51.7 |
| ZB-BD-129 | 78.7 | ZB-BD-142 | 48.4 |
| ZB-BD-143 | 76.7 | ZB-BD-147 | 7.4 |
| ZB-BD-151 | 288 | ZB-BD-153 | 239 |
| ZB-BD-218 | 50.3 | ZB-BD-163 | 106 |
| ZB-BD-164 | 219 | ZB-BD-166 | 82.5 |
| ZB-BD-167 | 198 | ZB-BD-172 | 34.6 |
| ZB-BD-174 | 247 | ZB-BD-179 | 6.1 |
| ZB-BD-183 | 41.9 | ZB-BD-214 | 49.2 |
| ZB-BD-185 | 71.3 | ZB-BD-187 | 85.2 |
| ZB-BD-188 | 26.9 | ZB-BD-189 | 11.6 |
| ZB-BD-196 | 189 | ZB-BD-197 | 117 |
| ZB-BD-198 | 41.3 | ZB-BD-202 | 2.2 |
| ZB-BD-216 | 14.1 | ZB-BD-217 | 20.9 |
| ZB-BD-220 | 25.8 | JQ1 (CAS number 1268524-70-4) | 102.8 |
| ZB-BD-232 | 118.6 | ZB-BD-240 | 130.6 |
| ZB-BD-241 | 14.3 | ZB-BD-242 | 4.5 |

Example 211: Cell Growth Inhibition Assay

Acute mononuclear leukemia cell MV4-11 cells (ATCC, CRL-9591) was cultured with the 1640 medium (Gibco, Life Technologies, 22400-089) containing 10% fetal bovine serum (Gibco, Life Technologies, 10099-141) and 1% antibiotics (penicillin and streptomycin, Life Technologies, 10378016) in a $CO_2$ incubator (37° C., 5% $CO_2$). In the proliferation inhibition assay of the compound, MV4-11 cells were seeded in a 96-well transparent plate (Corning, 3599) at a density of 10,000 cells/well with a seeded volume of 100 µL (fresh medium was seeded in rows A, H, and columns 1, 12, and MV4-11 cells were seeded in the remaining 60 wells). After seeding the cells in the plate, the cells were placed in a $CO_2$ incubator (37° C., 5% $CO_2$) and incubated for 1 h. In a 96-well plate (Corning, 3357), a dilution series of compound from 50 µM to 7.62 nM was prepared by serially diluting a solution of 20 mM compound in three times (in the first well, it was diluted with culture medium, and in the latter well, it was diluted with a medium containing 1/400 DMSO to make the DMSO concentration in each well uniform). 25 µL of the diluted compound solution was added to the appropriate wells of the cell plate, so that the final concentration of compound is 10.0 µM, 3.33 µM, 1.11 µM, 0.370 µM, 0.123 µM, 0.0412 µM, 0.0137 µM, 0.00457 µM and 0.00152 µM. After adding the compound, the cells were placed in a $CO_2$ incubator (37° C., 5% $CO_2$) for 72 h. CellTiter-Glo reagent (Promega, G7572) was used to determine cell survival. CellTiter-Glo reagent (Promega, G7572) was first added in 20 µL/well to appropriate wells of a white opaque 384-well plate (OptiPlate-384, PerkinElmer 6007299), and then the cells treated with compound in the 96-well plate (Corning, 3599) were well mixed separately and 40 µL was pipetted into the corresponding wells of the 384-well plate (PerkinElmer, 6007299), incubated at room temperature for 10 minutes, and then detect on a multi-label reader (EnVision, PerkinElmer) at 400-700 nm. The detection result was analyzed and fitted by GraphPad Prism 5.0 software to give $IC_{50}$ values.

| compound | cells MV4-11 $IC_{50}$ (nM) |
|---|---|
| ZB-BD-70 | 33.1 |
| ZB-BD-74 | 31.2 |
| ZB-BD-77 | 13.4 |
| ZB-BD-78 | 20.4 |
| ZB-BD-80 | 29.2 |
| ZB-BD-83 | 131.3 |
| ZB-BD-87 | 78.7 |
| ZB-BD-90 | 76.6 |
| ZB-BD-94 | 91 |
| ZB-BD-96 | <100 |
| ZB-BD-102 | <100 |
| ZB-BD-103 | <100 |
| ZB-BD-117 | <200 |
| ZB-BD-120 | 113 |
| ZB-BD-232 | 25.4 |
| ZB-BD-236 | 48.5 |

| compound | cells MV4-11 IC$_{50}$ (nM) |
|---|---|
| ZB-BD-237 | 21.6 |
| ZB-BD-239 | 90.6 |
| ZB-BD-240 | 5.3 |
| ZB-BD-241 | 7.9 |
| JQ1 | 116.2 |

Example 212: MM.1S Cell Growth Inhibition Assay

Multiple myeloma cells MM.1S was cultured with RPMI1640 medium (Invitrogen, Cat. No. 11875-093, Lot. No. 1960297) containing 10% fetal bovine serum (Gibco, Life Technologies, 10099-141) and 1% penicillin-streptomycin solution (Hyclone, Cat. No. SV30010, Lot. No. J180005) in a CO$_2$ incubator (37° C., 5% CO$_2$). The cell suspension was pipetted into a 15 mL centrifuge tube, and centrifuged at 800 rpm for 3 minutes. The supernatant was discarded. 2 mL of culture medium was added to the centrifuge tube, and the cells were resuspended evenly by gentle pipetting. The cell density was measure by a hemacytometer. Then the cell suspension was diluted to 50,000 cells/mL. The diluted cell suspension was added to a 96-well cell culture plate (Corning, 3599) in 100 μl/well (in column 1, there was 0.5% DMSO-containing medium in each well, and MM.1S cells were seeded in the remaining 88 wells). The plate was placed in a CO$_2$ incubator overnight.

The compound to be tested was prepared into 10 mM solution in DMSO, and then the compound was prepared into a 2 mM solution in DMSO, which was added to the compound plate, and then it was diluted with DMSO in a 4-fold gradient dilution to be 7 points. 0.5 μL of the compound in the plate of the compound to be tested was pipetted into the cell culture plate (the compound was added to rows A to G, and 0.5 μL of DMSO was added to row H as a control). The final concentrations of the compound were 10000 nM, 2500 nM, 625 nM, 156.25 nM, 39.06 nM, 9.77 nM, 2.44 nM. The plate was returned to the CO$_2$ incubator and incubated for 96 h. Then cell survival was detected by using CellTiter Glo reagent (Promega, Cat. No. G7573, Lot. No. 0000310975). The cell culture plate was taken out and equilibrated to room temperature. 100 μL of CellTiter Glo reagent was added to each well. The plate was shaken for 10 min in the dark, and incubated for 10 min. Then the culture plate was put into a multi-functional microplate reader EnSpire (PerkinElmer) for reading, and detected at 400-700 nm. The reading data were recorded. The inhibition rate was calculated according to the following equation: inhibition rate (%)=(1−(RLU compound−RLU blank)/(RLU DMSO−RLU blank))×100%. XLFit was used to plot the dose-response inhibition curve (four-parameter model [fit=(A+((B−A)/(1+((C/x)^D))))] and calculate the IC$_{50}$ values.

| compound | cells MM.1S IC$_{50}$ (nM) |
|---|---|
| ZB-BD-78 | 52.1 |
| ZB-BD-92 | 39.2 |
| ZB-BD-179 | 53.2 |
| ZB-BD-112 | 64.3 |
| ZB-BD-116 | 70.3 |
| ZB-BD-187 | 22.8 |
| ZB-BD-147 | 73.5 |
| ZB-BD-202 | 25.7 |
| ZB-BD-216 | 14.2 |
| JQ1 | 181 |

The invention claimed is:
1. A compound of formula I, or a pharmaceutically acceptable salt, enantiomer, diastereomer, atropisomer, racemate, polymorph, solvate, or isotopically labeled compound thereof,

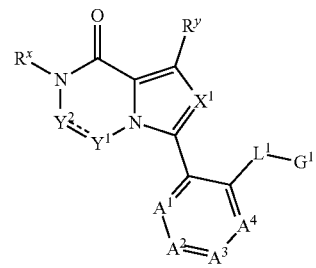

I wherein
⁓⁓⁓⁓⁓ is a single bond or a double bond;
R$^x$ is hydrogen, C$_1$-C$_3$ alkyl, or C$_1$-C$_3$ haloalkyl;
X$^1$ is N or CR$^{x1}$, wherein R$^{x1}$ is hydrogen, C$_1$-C$_6$ alkyl, C$_1$-C$_6$ haloalkyl, halogen or CN;
Y$^1$ is N, CR$^{y1}$ or CR$^{y1}$R$^{y2}$, wherein R$^{y1}$ and R$^{y2}$ are each independently hydrogen, C$_1$-C$_6$ alkyl, C$_1$-C$_6$ haloalkyl, halogen, CN;
Y$^2$ is N, CR$^{y3}$ or CR$^{y3}$R$^{y4}$, wherein R$^{y3}$ and R$^{y4}$ are each independently hydrogen, CN, C$_1$-C$_6$ alkyl, C$_1$-C$_6$ haloalkyl, —(C$_1$-C$_6$ alkylene)—OR$^{2a}$, —C(O)—R$^{ax1}$, —(C$_1$-C$_6$ alkylene)—C(O)—R$^{aX1}$, —C(O)OR$^{ax1}$, —(C$_1$-C$_6$ alkylene)—C(O)NHR$^{ax1}$, —(C$_1$-C$_6$ alkylene)—N(R$^{ax1}$)R$^{ax2}$, —C(O)N(R$^{ax1}$)$^{Rax2}$, G$^a$, or —(C$_1$-C$_6$ alkylene)-G$^a$;
R$^{ax1}$ and R$^{ax2}$ at each occurrence are each independently hydrogen, C$_1$-C$_6$ alkyl, C$_1$-C$_6$ haloalkyl, G$^a$, or —(C$_1$-C$_6$ alkylene)-G$^a$;
particularly, Y$^1$ and Y$^2$ are not N simultaneously; and when Y$^1$ or Y$^2$ is N, is a double bond;
A$^1$ is N or CR$^1$, A$^2$ is N or CR$^2$, A$^3$ is N or CR$^3$, A$^4$ is N or CR$^4$, with the proviso that none, one, two or three of A$^1$, A$^2$, A$^3$ and A$^4$ is/are N;
R$^1$ is hydrogen, C$_1$-C$_6$ alkyl, C$_2$-C$_6$ alkenyl, C$_2$-C$_6$ alkynyl, halogen, C$_1$-C$_6$ haloalkyl, CN, or NO$_2$;
R$^2$, R$^3$ and R$^4$ are each independently hydrogen, C$_1$-C$_6$ alkyl, C$_2$-C$_6$ alkenyl, C$_2$-C$_6$ alkynyl,

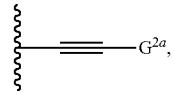

halogen, C$_1$-C$_6$ haloalkyl, CN, NO$_2$, G$^{2a}$, —OR$^{2a}$, —OC(O)R$^{2d}$, —OC(O)NR$^{2b}$R$^{2c}$, —SR$^{2a}$, —S(O)$_2$R$^{2d}$, —S(O)$_2$NR$^{2b}$R$^{2c}$, —C(O)R$^{2d}$, —C(O)OR$^{2a}$, —C(O)NR$^{2b}$R$^{2c}$, —NR$^{2b}$R$^{2c}$, —N(R$^{2e}$)C(O)R$^{2d}$, —N(R$^{2e}$)S(O)$_2$R$^{2d}$, —N(R$^{2e}$)C(O)OR$^{2d}$, —N(R$^{2e}$)C(O)NR$^{2b}$R$^{2c}$, —N(R$^{2e}$)S(O)$_2$NR$^{2b}$R$^{2c}$, —(C$_1$-C$_6$ alkylene)-G$^{2a}$, —(C$_1$-C$_6$ alkylene)—OR$^{2a}$, —(C$_1$-C$_6$ alkylene)—OC(O)R$^{2d}$, —(C$_1$-C$_6$ alkylene)—OC(O)NR$^{2b}$R$^{2c}$, —(C$_1$-C$_6$ alkylene)—S(O)$_2$R$^{2d}$, —(C$_1$-C$_6$ alkylene)—S(O)$_2$ NR$^{2b}$R$^{2c}$, —(C$_1$-C$_6$ alkylene)—C(O)R$^{2d}$, —(C$_1$-C$_6$ alkylene)—C(O)OR$^{2a}$, —(C$_1$-C$_6$ alkylene)—C(O)NR$^{2b}$R$^{2c}$, —(C$_1$-C$_6$ alkylene)—NR$^{2b}$R$^{2c}$, —(C$_1$-C$_6$ alkylene)—N(R$^{2e}$)C(O)R$^{2d}$, —(C$_1$-C$_6$ alkylene)—N(R$^{2e}$)S(O)$_2$R$^{2d}$, —(C$_1$-C$_6$ alkylene)—N(R$^{2e}$)C(O)OR$^{2a}$, —(C$_1$-C$_6$ alkylene)—N(R$^{2e}$)C(O)NR$^{2b}$R$^{2c}$, —(C$_1$-C$_6$ alkylene)—N(R$^{2e}$)S(O)$_2$NR$^{2b}$R$^{2c}$, —(C$_1$-C$_6$ alkylene)—CN, —S(=O)(=NH)R$^{2d}$, —(C$_1$-C$_6$ alkylene)—S(=O)(=NH)R$^{2d}$; wherein C$_1$-C$_6$ alkylene is unsubstituted or substituted with 1 to 6 substituents selected from CN, OH and C$_1$-C$_3$ alkyl;

R$^{2a}$, R$^{2b}$, R$^{2c}$ and R$^{2e}$ at each occurrence are each independently hydrogen, C$_2$-C$_6$ alkenyl, C$_2$-C$_6$ alkynyl, C$_1$-C$_6$ haloalkyl, G$^{2b}$, C$_1$-C$_6$ alkyl, or C$_1$-C$_6$ alkyl substituted by one selected from —OR$^{z1}$, —NR$^{z1}$R$^{z2}$, —C(O)OR$^{z1}$, —C(O)NR$^{z1}$R$^{z2}$, —S(O)$_2$R$^{z1}$, —S(O)$_2$ NR$^{z1}$R$^{z2}$ and G$^{2b}$;

R$^{2d}$ at each occurrence is independently C$_2$-C$_6$ alkenyl, C$_2$-C$_6$ alkynyl, C$_1$-C$_6$ haloalkyl, G$^{2b}$, C$_1$-C$_6$ alkyl, or C$_1$-C$_6$ alkyl substituted by one selected from —OR$^z$, —NR$^{z1}$R$^{z2}$, —C(O)OR$^{z1}$, —C(O)NR$^{z1}$R$^{z2}$, —S(O)$_2$ R$^{z1}$, —S(O)$_2$ NR$^{z1}$R$^{z2}$ and G$^{2b}$;

R$^{z1}$ and R$^{z2}$ at each occurrence are each independently hydrogen, C$_1$-C$_6$ alkyl, or C$_1$-C$_6$ haloalkyl G$^a$, G$^{2a}$ and G$^{2b}$ at each occurrence are each independently aryl, heteroaryl, heterocyclyl, cycloalkyl, or cycloalkenyl, which are each independently unsubstituted or substituted by 1, 2, 3, 4, or 5 R$^v$ s;

L$^1$ is absent, or is —CH$_2$—, —C(O)—, —C(H)(OH)—, —(CH$_2$)mO—, —(CH$_2$)mS(O)$_n$—, —NHC(O)—, —C(O)NH—, —NHC(O)NH—, —NHS(O)$_2$—, —S(O)$_2$ NH— or —(CH$_2$)mN(R$^z$)—, wherein n is 0, 1, or 2; m is 0 or 1; R$^z$ is hydrogen, C$_1$-C$_3$ alkyl, C$_1$-C$_3$ haloalkyl; (C$_2$-C$_3$ alkylene)—OH, or unsubstituted cyclopropyl;

G$^1$ is C$_1$-C$_6$ alkyl, alkoxyalkyl, G$^{1a}$ or —(C$_1$-C$_6$ alkylene)-G$^{1a}$; wherein each G$^{1a}$ is independently aryl, heteroaryl, heterocyclyl, cycloalkyl, or cycloalkenyl, and each G$^{1a}$ is independently unsubstituted or substituted with 1, 2, 3, 4, or 5 R$^w$ s;

R$^v$ and R$^w$ at each occurrence are each independently C$_1$-C$_6$ alkyl, C$_2$-C$_6$ alkenyl, C$_2$-C$_6$ alkynyl, halogen, C$_1$-C$_6$ haloalkyl, —CN, oxo, —OR$^h$, —OC(O)R$^i$, —OC(O)NR$^j$R$^k$, —SR$^h$, —S(O)$_2$R$^h$, —S(O)$_2$ NR$^j$R$^k$, —C(O)R$^h$, —C(O)-monocyclic heterocyclyl, —C(O)-monocyclic heteroaryl, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)OR$^i$, —N(R$^h$)C(O)NR$^j$R$^k$, —(C$_i$-C$_6$ alkylene)—OR$^h$, —(C$_1$-C$_6$ alkylene)—OC(O)R$^i$, —(C$_1$-C$_6$ alkylene)—OC(O)NR$^j$R$^k$, —(C$_1$-C$_6$ alkylene)—S(O)$_2$R$^h$, —(C$_1$-C$_6$ alkylene)—S(O)$_2$ NR$^j$R$^k$, —(C$_1$-C$_6$ alkylene)—C(O)R$^h$, (C$_1$-C$_6$ alkylene)—C(O)OR$^h$, —(C$_1$-C$_6$ alkylene)—C(O)NR$^j$R$^k$, —(C$_1$-C$_6$ alkylene)—NR$^j$R$^k$, —(C$_1$-C$_6$ alkylene)—N(R$^h$)C(O)R$^i$, —(C$_1$-C$_6$ alkylene)—N(R$^h$)S(O)$_2$R$^i$—(C$_1$-C$_6$ alkylene)—N(R$^h$)C(O)OR$^i$, —(C$_1$-C$_6$ alkylene)—N(R$^h$)C(O)NR$^j$R$^k$, or —(C$_1$-C$_6$ alkylene)—CN;

R$^h$, R$^j$, R$^k$ at each occurrence are each independently hydrogen, C$_1$-C$_6$ alkyl, or C$_1$-C$_6$ haloalkyl; and Ri at each occurrence is independently C$_1$-C$_6$ alkyl, or C$_1$-C$_6$ haloalkyl and with the proviso that the compound does not include together Y$^1$ is N, Y$^2$ is C, and X$^1$ is N.

2. The compound, or a pharmaceutically acceptable salt, enantiomer, diastereomer, atropisomer, racemate, polymorph, solvate, or isotopically labeled compound thereof according to the claim 1, wherein the compound of formula I is a compound represented by formula Ia, Ib, Ic, or Ie:

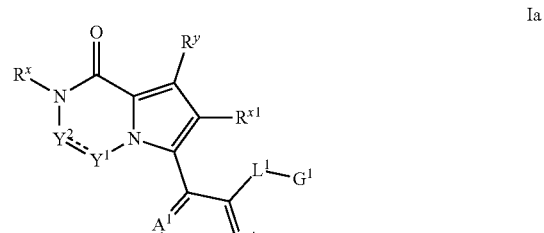

Ia

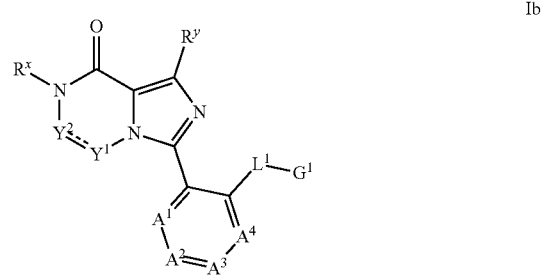

Ib

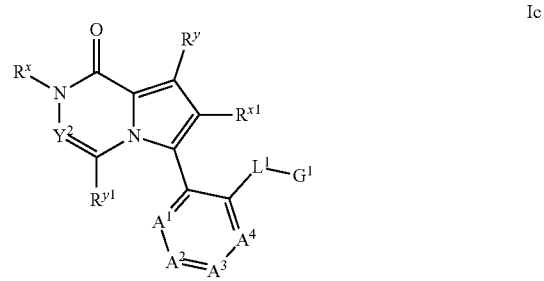

Ic

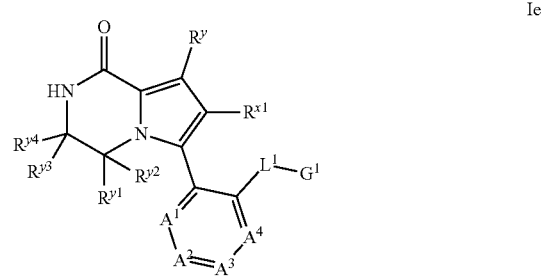

Ie wherein is a single bond or a double bond;

R$^x$, R$^y$, R$^{x1}$, R$^{yi}$, R$^{y2}$, R$^{y3}$, R$^{y4}$, y$^1$, Y$^2$, A$^1$, A$^2$, A$^3$, A$^4$, L$^1$ and G$^1$ have the same definition as those in the formula I of claim 1.

3. The compound, or a pharmaceutically acceptable salt, enantiomer, diastereomer, atropisomer, racemate, polymorph, solvate, or isotopically labeled compound thereof according to the claim 1, wherein the compound of formula I is a compound represented by formula Id or If:

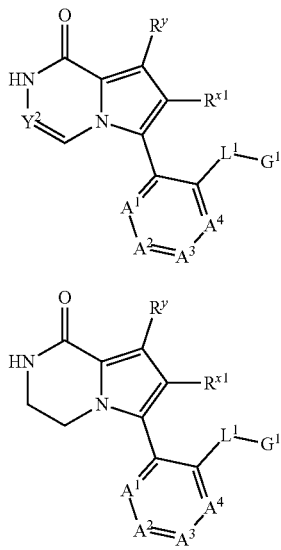

wherein $A^1$, $A^2$, $A^3$, $A^4$, $L^1$ and $G^1$ have the same definition as those in the formula I of claim 1; $Y^2$ is N or CH; $R^y$ is $C_1$-$C_3$ alkyl; $R^{x1}$ is H, $CH_3$ or halogen.

4. The compound, or a pharmaceutically acceptable salt, enantiomer, diastereomer, atropisomer, racemate, polymorph, solvate, or isotopically labeled compound thereof according to the claim 1, wherein the compound of formula I is a compound represented by formula Ig and Ih:

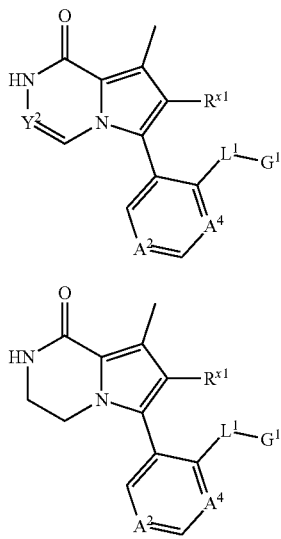

wherein $A^2$ has the same definition as that in the formula I of claim 1; $L^1$ is O or NH; $Y^2$ is CH or N; $R^{x1}$ is H, $CH_3$ or halogen; $A^4$ is CH or N; $G^1$ is $G^{1a}$ or —($CH_2$)-$G^{1a}$; wherein each $G^{1a}$ is independently aryl, heteroaryl, heterocycle, cycloalkyl, or cycloalkenyl, and each $G^{1a}$ is independently unsubstituted or substituted with 1 or 2 of $R^w$; $R^w$ is the same as defined in the formula I described above.

5. The compound, or a pharmaceutically acceptable salt, enantiomer, diastereomer, atropisomer, racemate, polymorph, solvate, or isotopically labeled compound thereof according to the claim 1, wherein the compound of formula I is a compound represented by formula Ii and Ij:

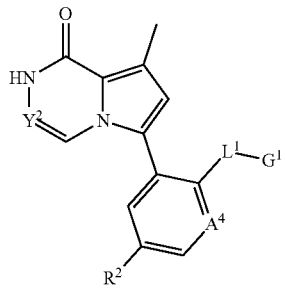

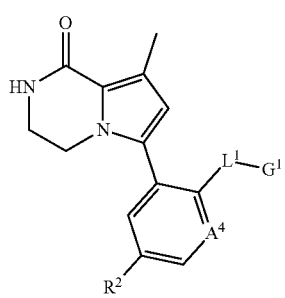

wherein, $Y^2$ is N or CH; L is O or NH; $A^4$ is CH or N;

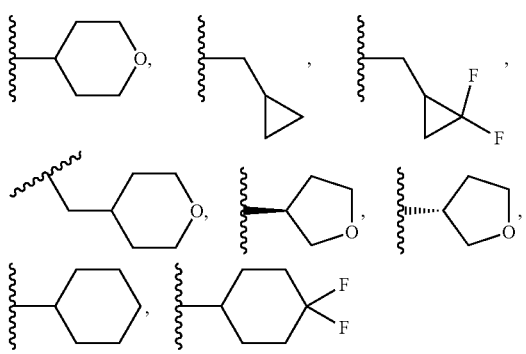

$G$-$^1$ is pyridyl, or phenyl substituted with 1 or 2 halogens; $R^2$ is —$S(O)_2R^{2d}$, —$NHS(O)_2R^{2d}$, —$S(O)_2$ $NR^{2b}R^{2c}$ or —($CH_2$)—$S(O)_2R^{2d}$; wherein $R^{2d}$ is an unsubstituted $C_1$-$C_3$ alkyl, and $R^{2b}$ and $R^{2c}$ are each independently hydrogen or an unsubstituted $C_1$-$C_3$ alkyl.

6. The compound, or a pharmaceutically acceptable salt, enantiomer, diastereomer, atropisomer, racemate, polymorph, solvate, or isotopically labeled compound thereof according to the claim 1, wherein the compound of formula I is selected from the group consisting of the following compounds:

ZB-BD-68
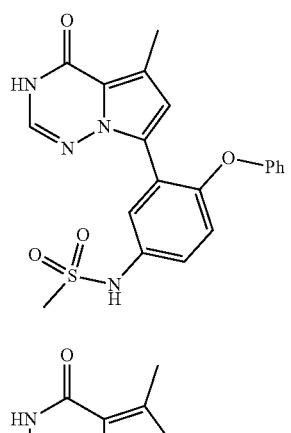
ZB-BD-69
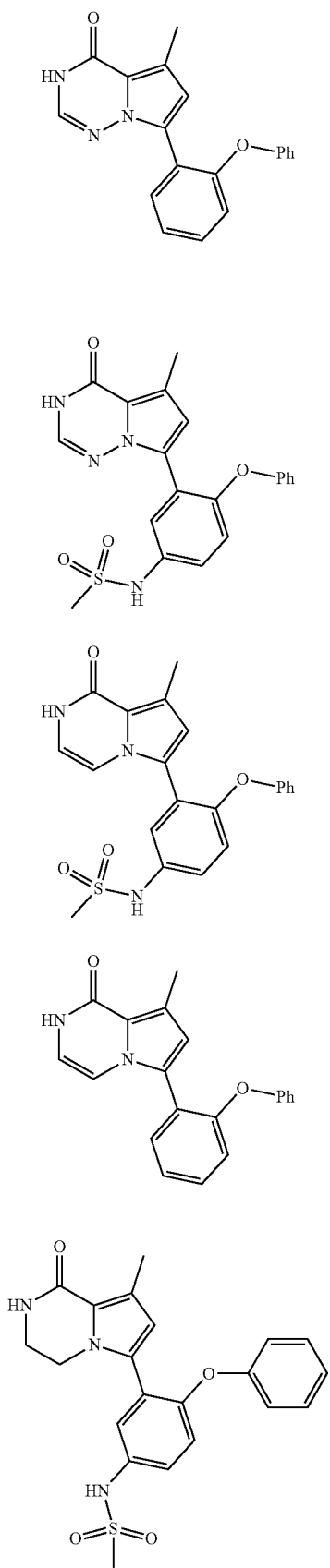
ZB-BD-70
ZB-BD-73
ZB-BD-74
ZB-BD-76
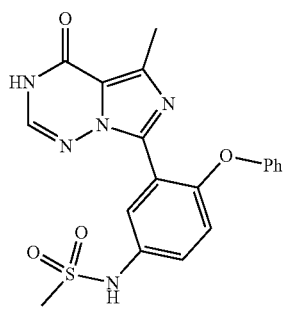
ZB-BD-77
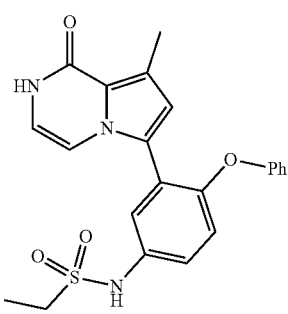
ZB-BD-78
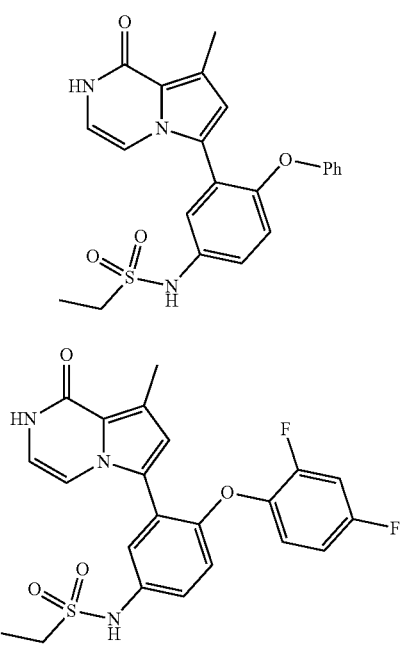
ZB-BD-79
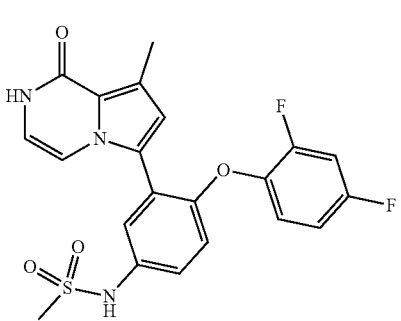
ZB-BD-80

-continued
ZB-BD-81
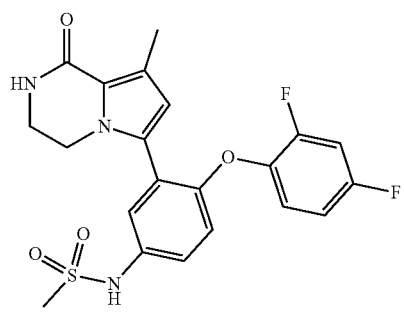
ZB-BD-90
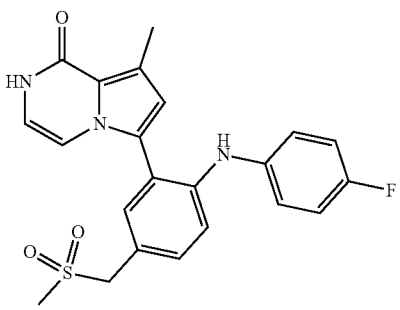
ZB-BD-82
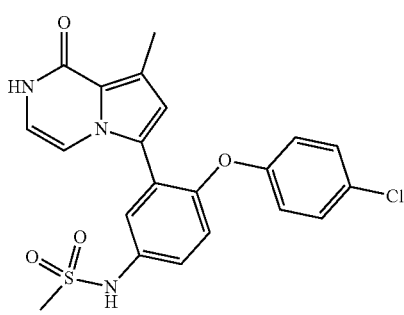
ZB-BD-91
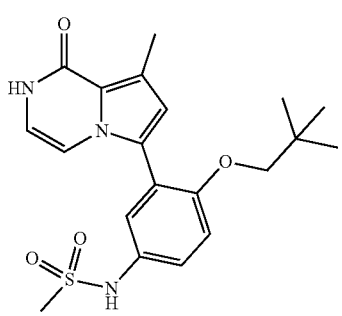
ZB-BD-83
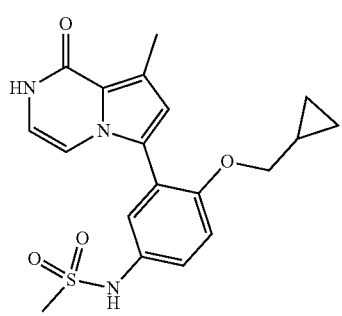
ZB-BD-92
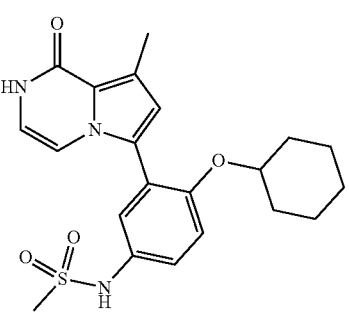
ZB-BD-86
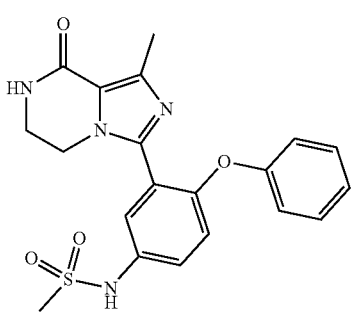
ZB-BD-93
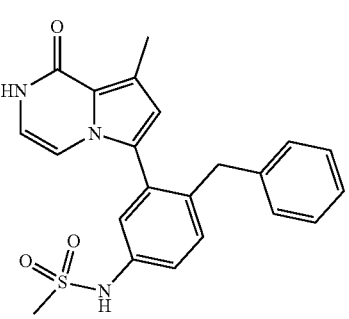
ZB-BD-87
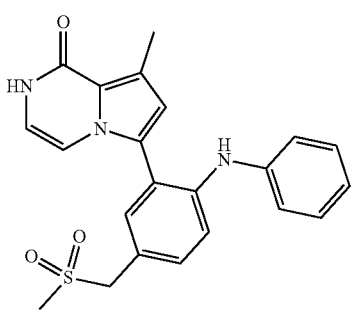
ZB-BD-94
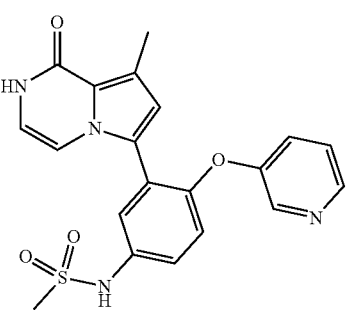

ZB-BD-95
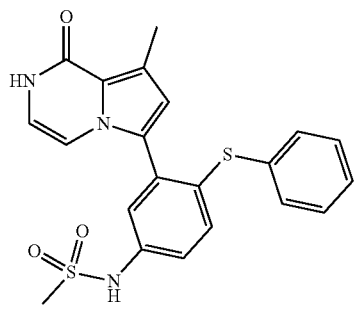
ZB-BD-96
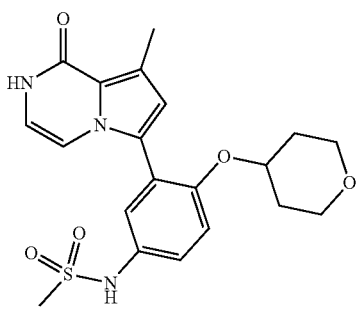
ZB-BD-97
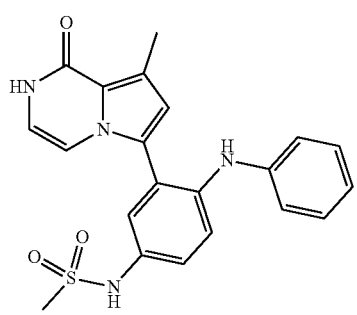
ZB-BD-98
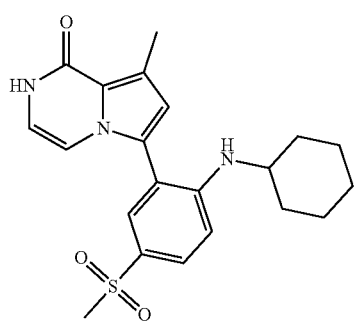
ZB-BD-99
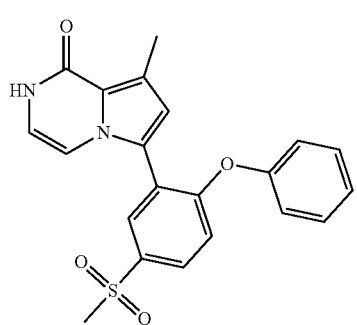
ZB-BD-100
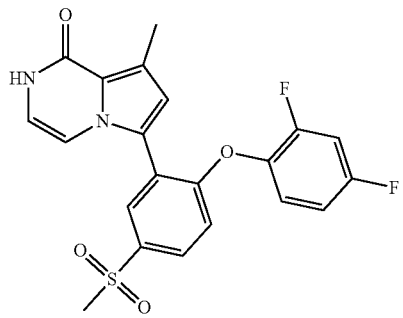
ZB-BD-102
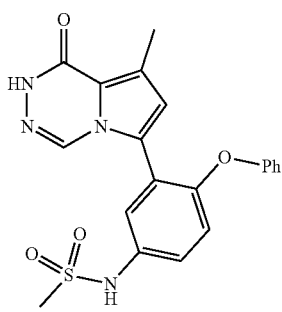
ZB-BD-103
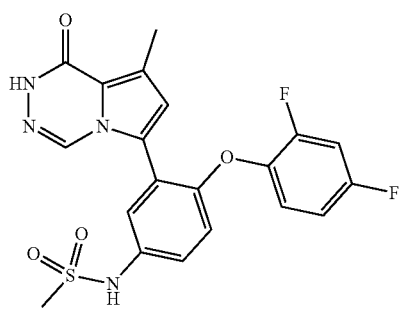
ZB-BD-105
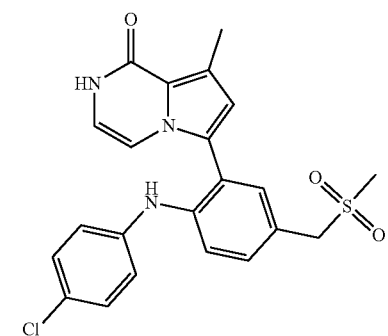

ZB-BD-110
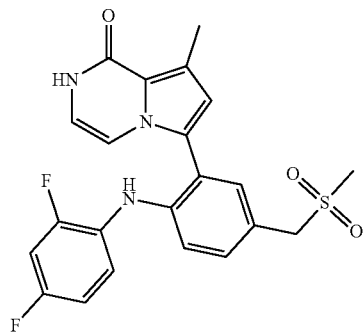
ZB-BD-112
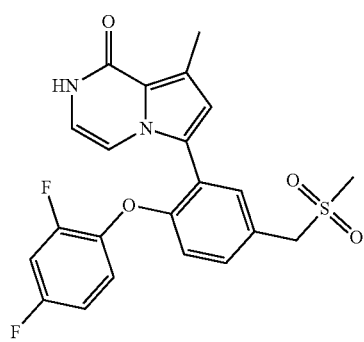
ZB-BD-113
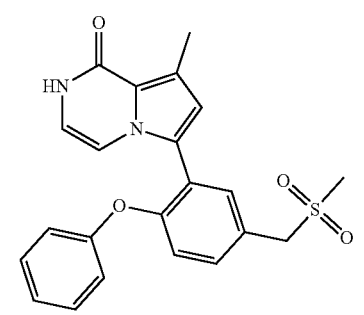
ZB-BD-114
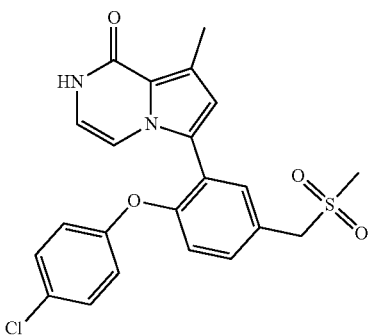
ZB-BD-115
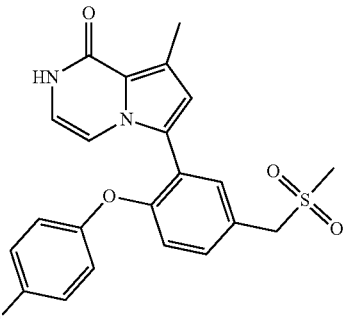
ZB-BD-116
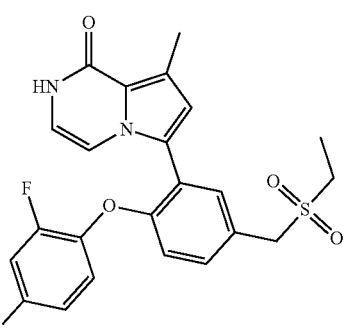
ZB-BD-117
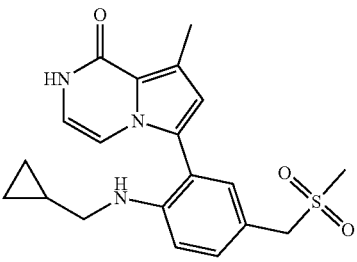
ZB-BD-118
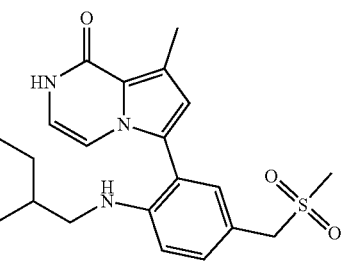
ZB-BD-119
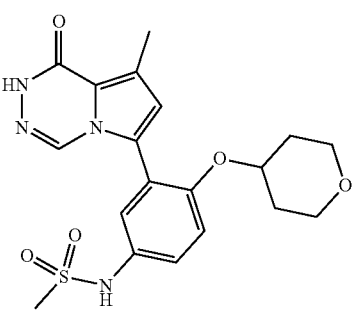

ZB-BD-120
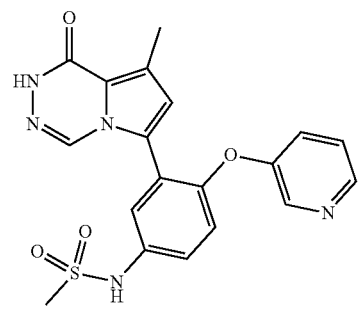
ZB-BD-121
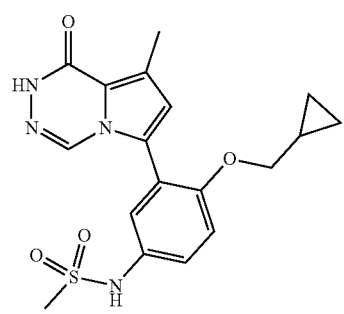
ZB-BD-122
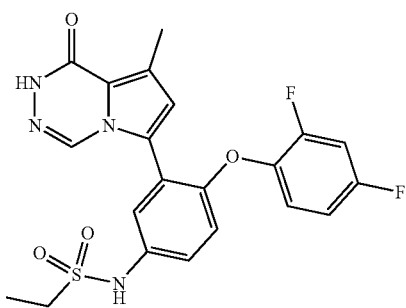
ZB-BD-123
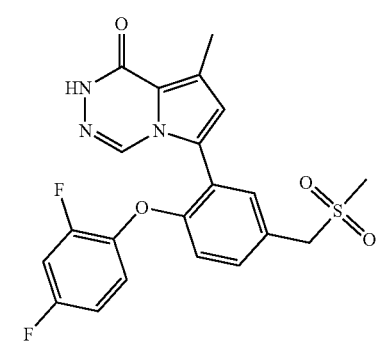
ZB-BD-124
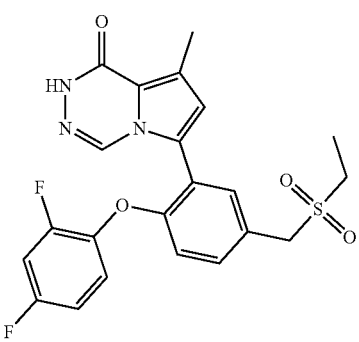
ZB-BD-125
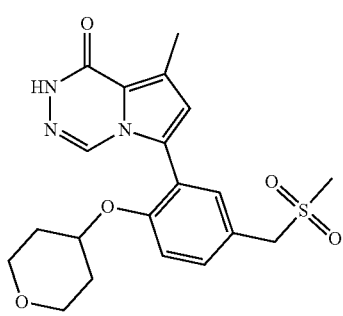
ZB-BD-126
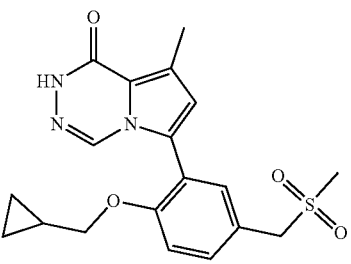
ZB-BD-127
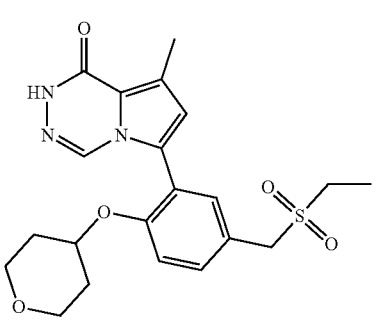
ZB-BD-128
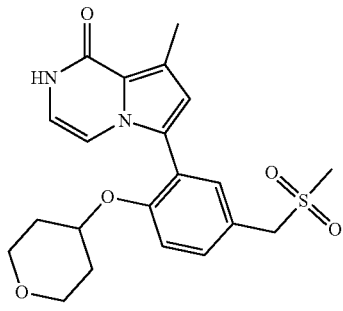

ZB-BD-129
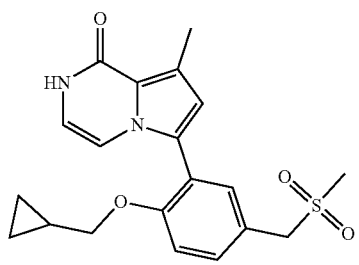
ZB-BD-130
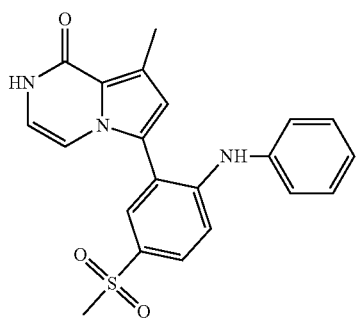
ZB-BD-131
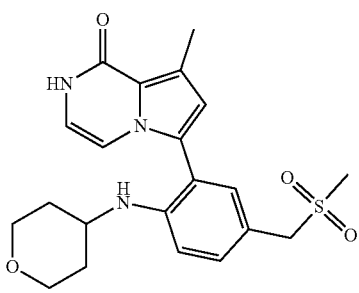
ZB-BD-132
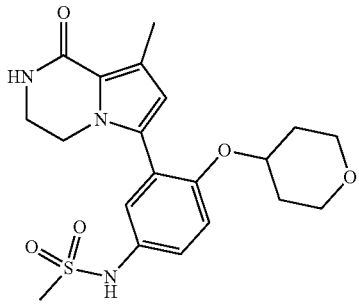
ZB-BD-133
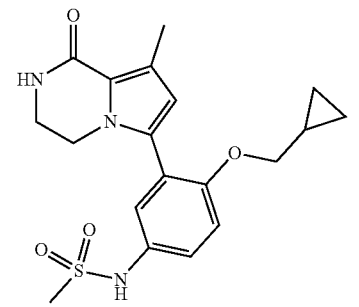
ZB-BD-134
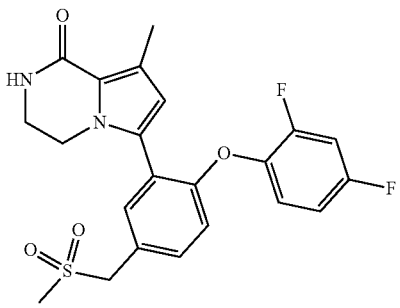
ZB-BD-135
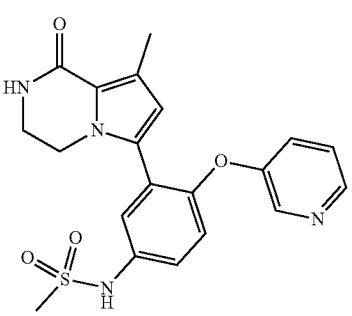
ZB-BD-136
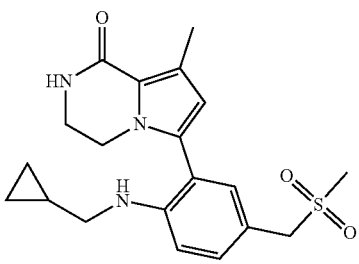
ZB-BD-137
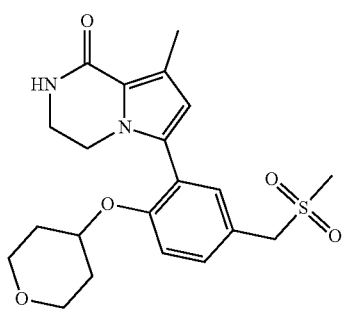
ZB-BD-140
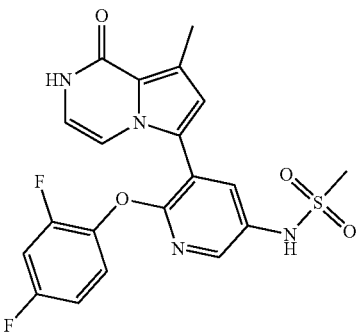

ZB-BD-141
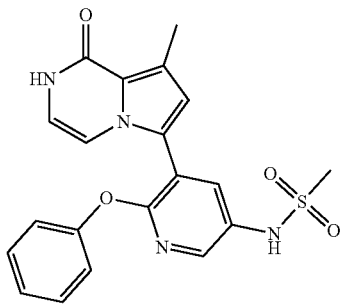
ZB-BD-142
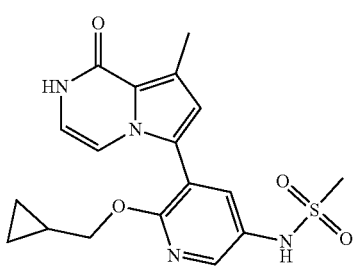
ZB-BD-143
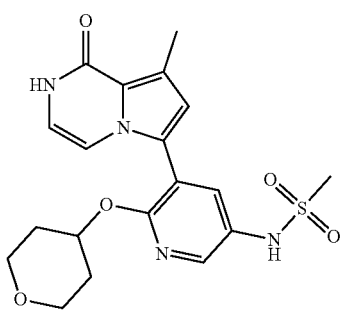
ZB-BD-144
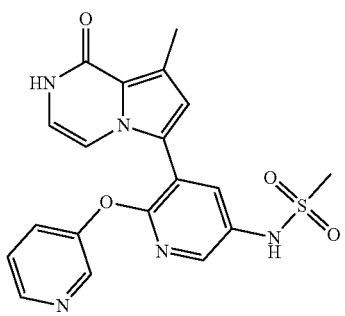
ZB-BD-145
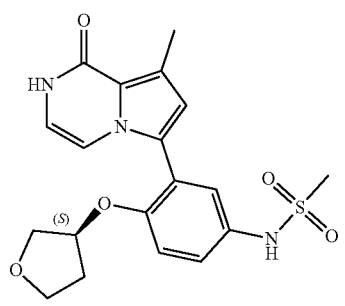
ZB-BD-146
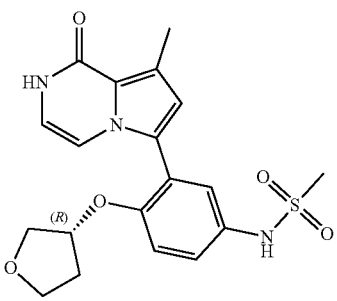
ZB-BD-147
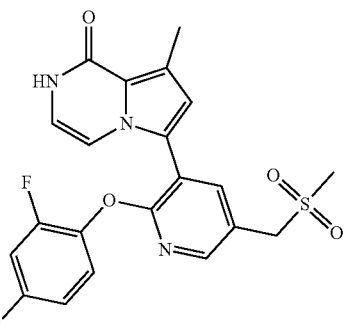
ZB-BD-148
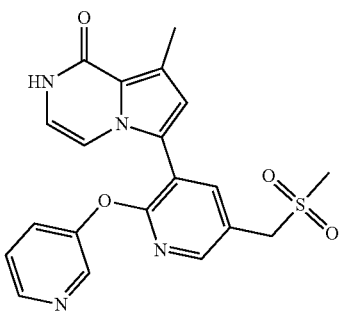
ZB-BD-149
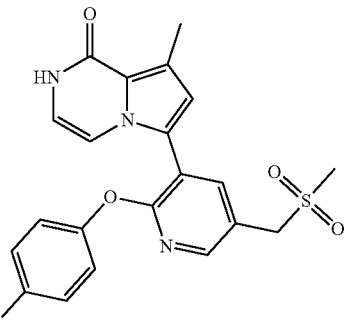

ZB-BD-150
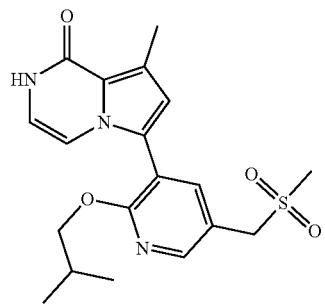
ZB-BD-151
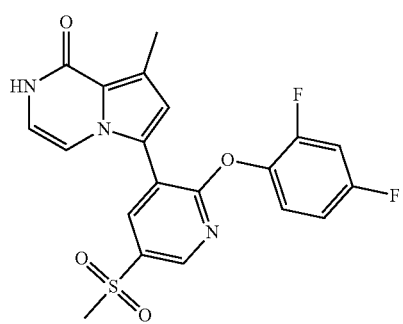
ZB-BD-152
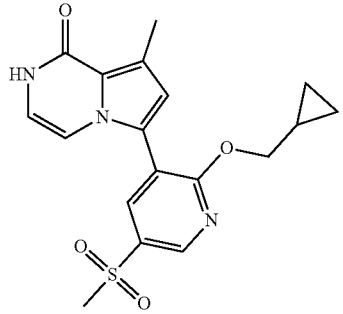
ZB-BD-153
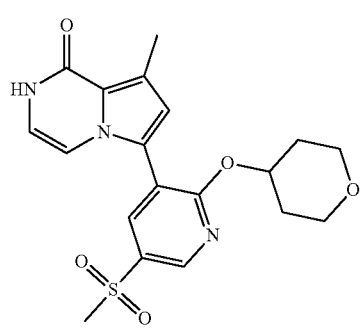
ZB-BD-154
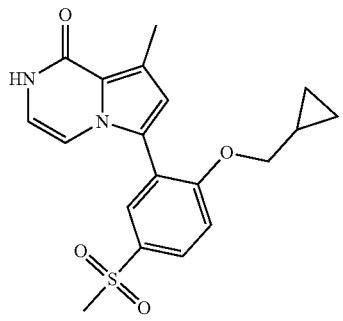
ZB-BD-155
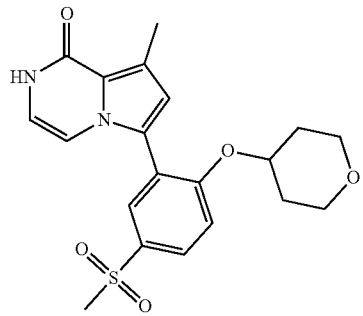
ZB-BD-156
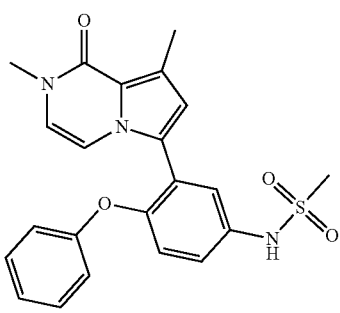
ZB-BD-162
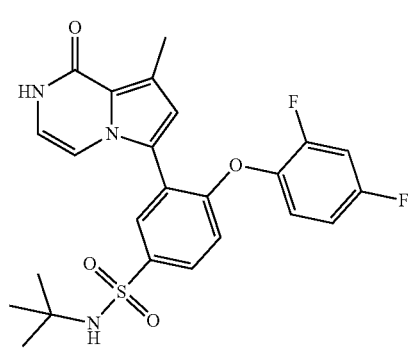
ZB-BD-163
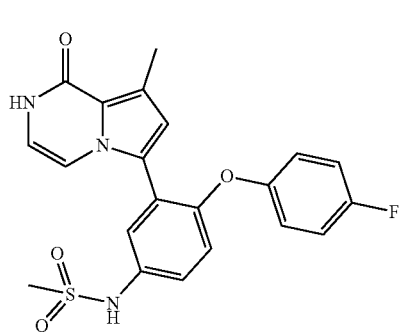

ZB-BD-164
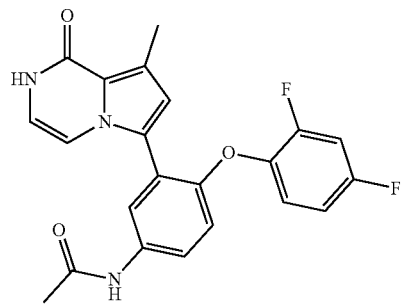
ZB-BD-166
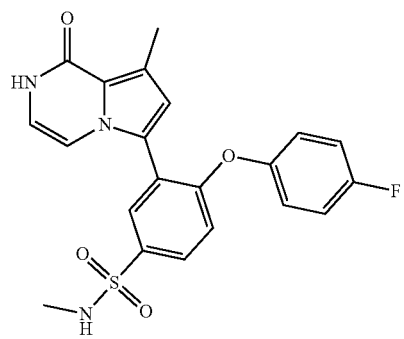
ZB-BD-167
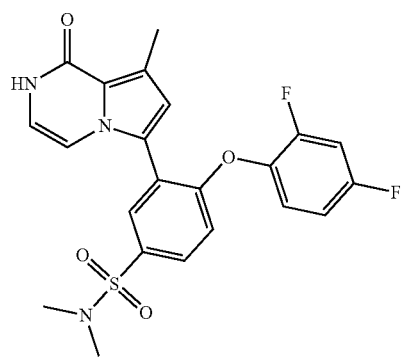
ZB-BD-172
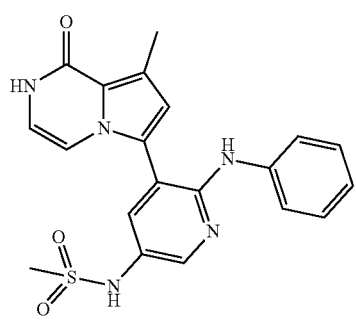
ZB-BD-173
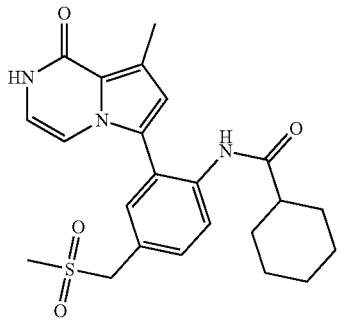
ZB-BD-174
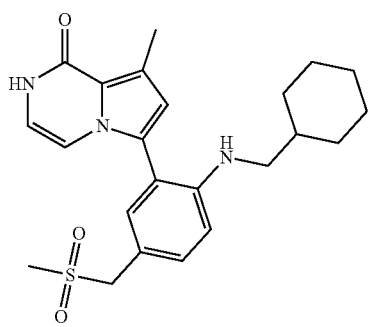
ZB-BD-175
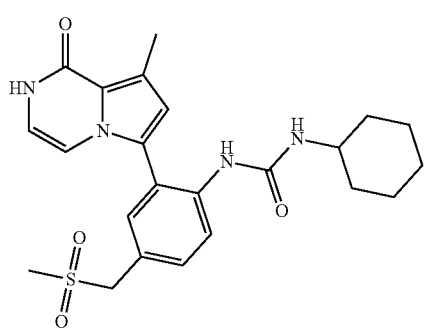
ZB-BD-179
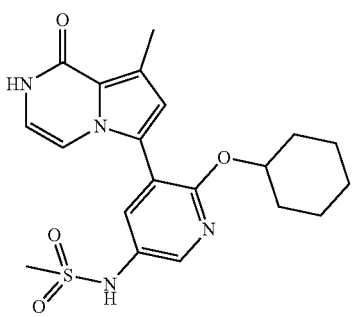

ZB-BD-183
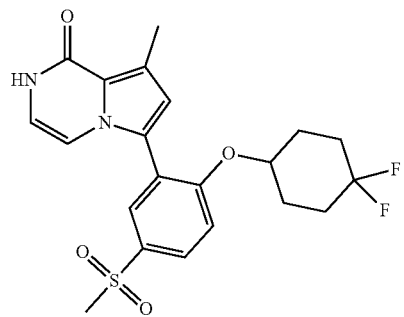
ZB-BD-188
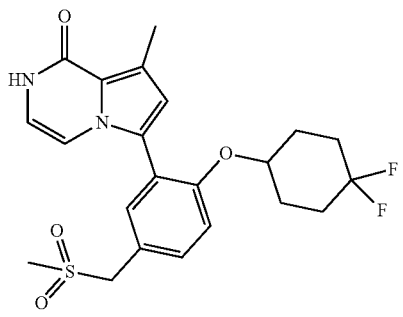
ZB-BD-184
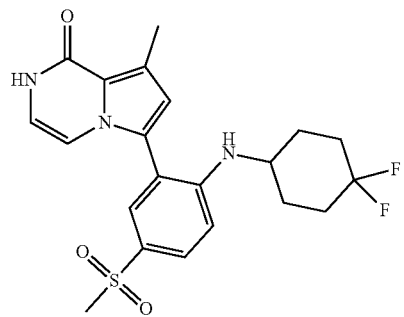
ZB-BD-189
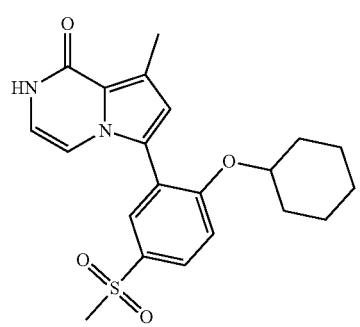
ZB-BD-185
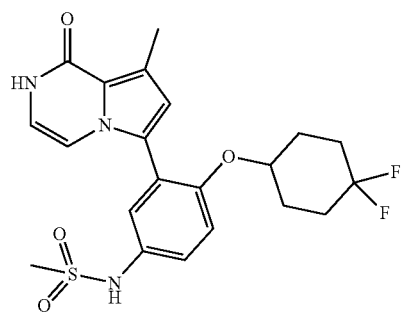
ZB-BD-190
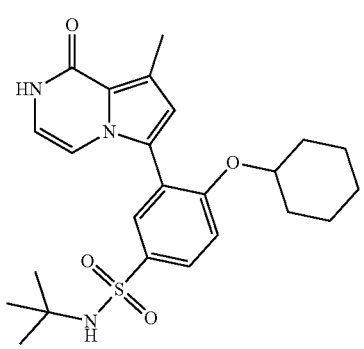
ZB-BD-187
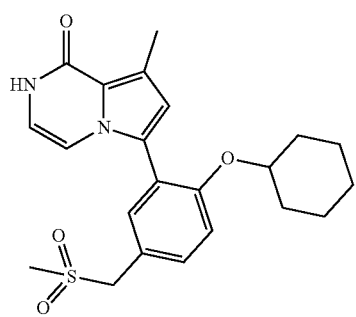
ZB-BD-191
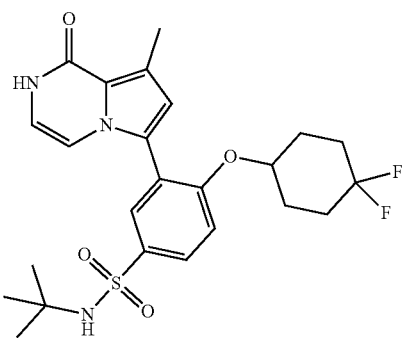

ZB-BD-194
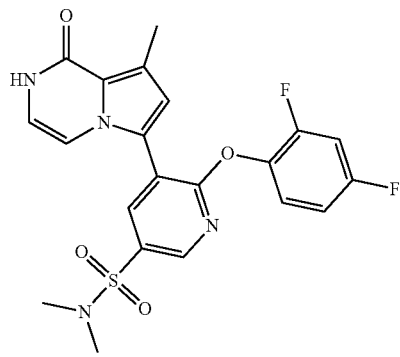
ZB-BD-195
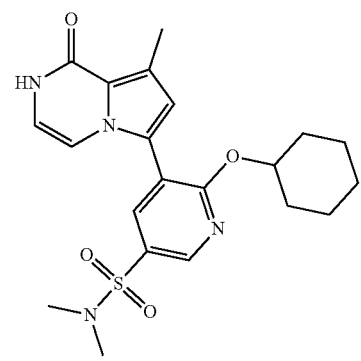
ZB-BD-196
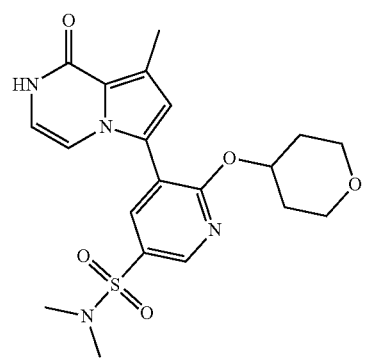
ZB-BD-197
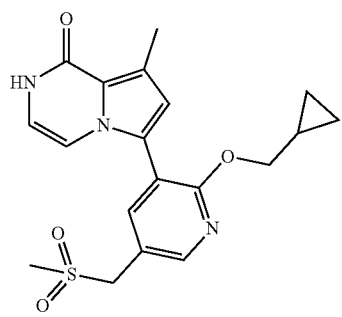
ZB-BD-198
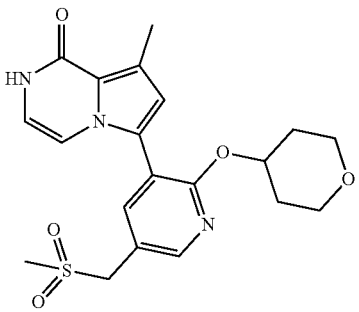
ZB-BD-202
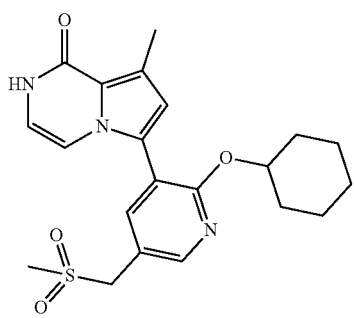
ZB-BD-216
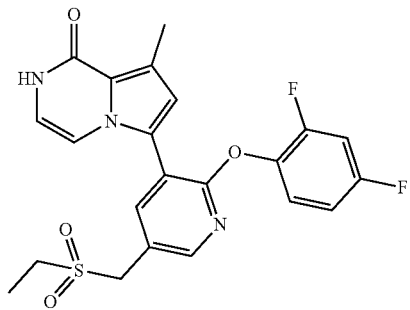
ZB-BD-217
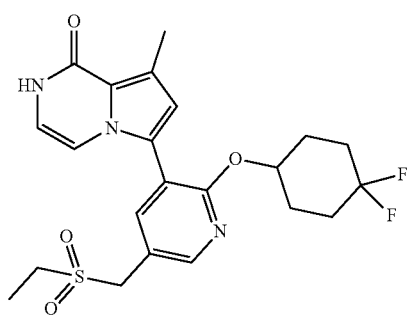
ZB-BD-220
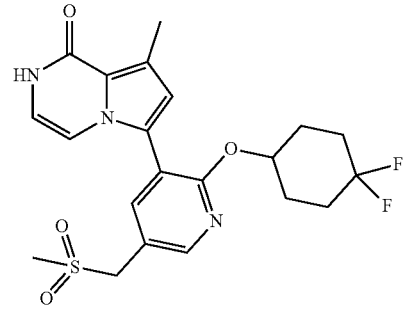

ZB-BD-199
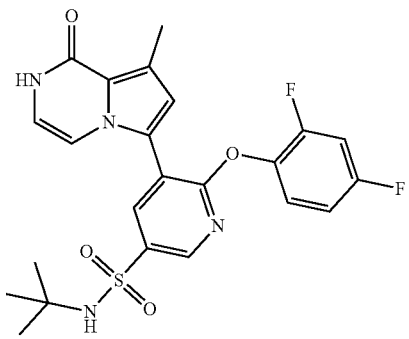
ZB-BD-203
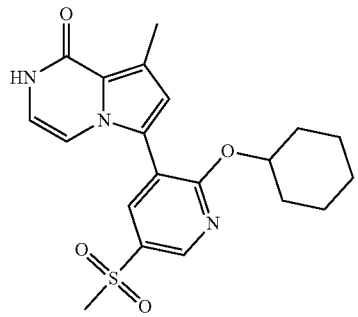
ZB-BD-218
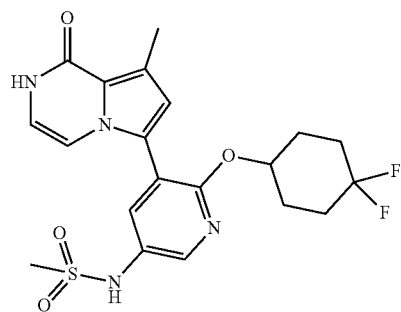
ZB-BD-214
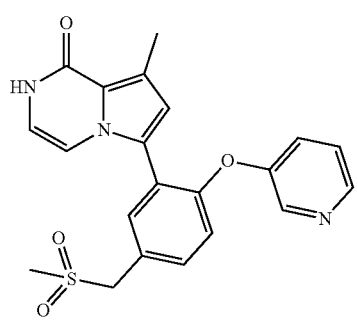
ZB-BD-230
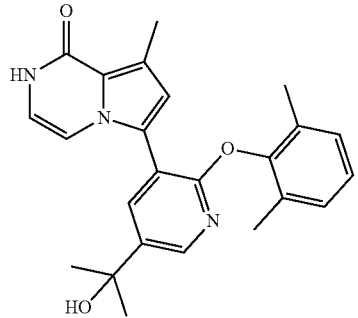
ZB-BD-232
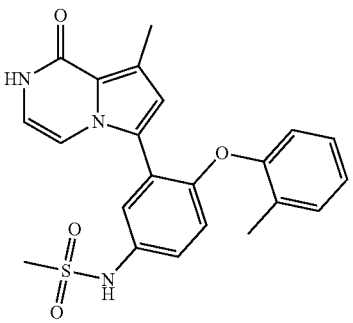
ZB-BD-236
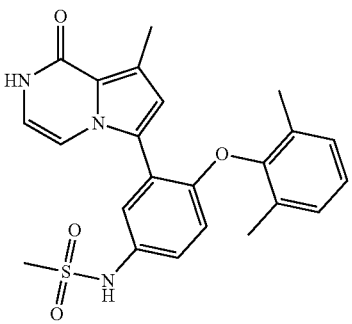
ZB-BD-237
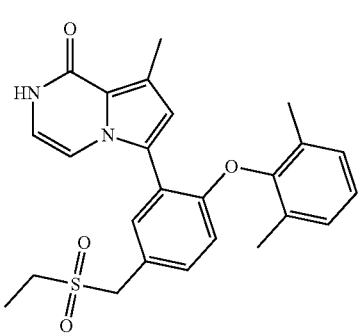
ZB-BD-239
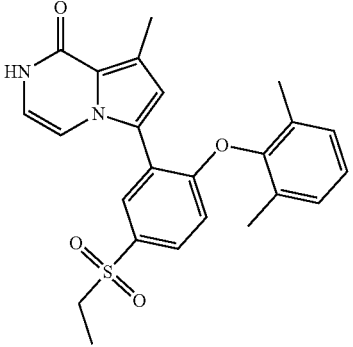

ZB-BD-240
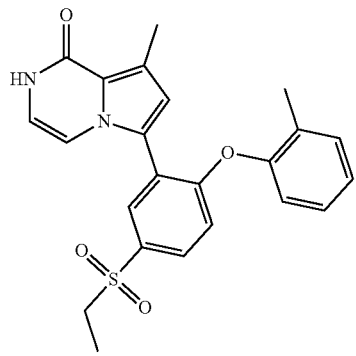
ZB-BD-249
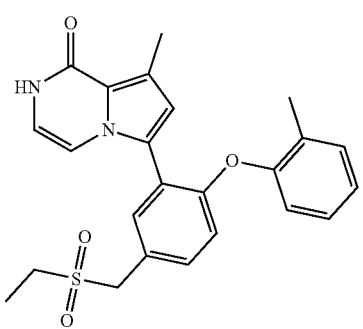
ZB-BD-241
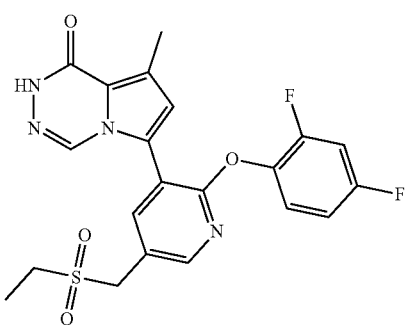
ZB-BD-242
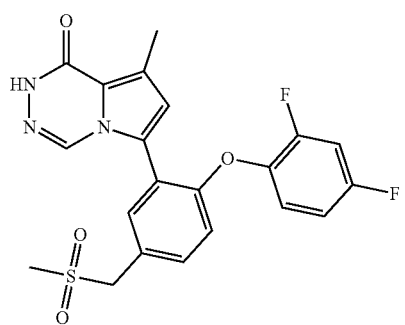
ZB-BD-247
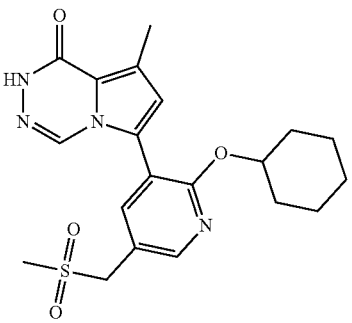
ZB-BD-248
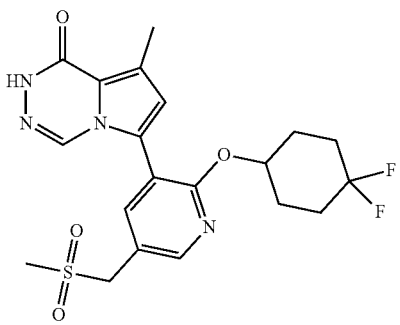
ZB-BD-252
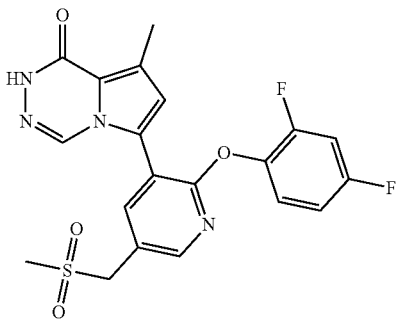
ZB-BD-253
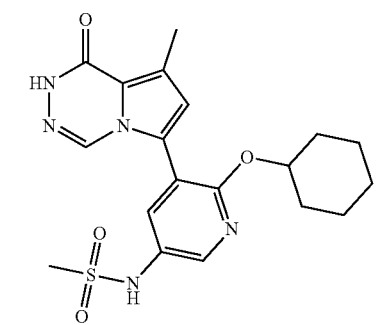

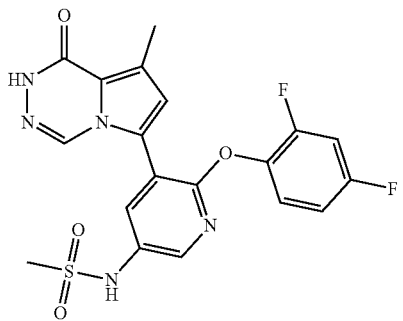
ZB-BD-254

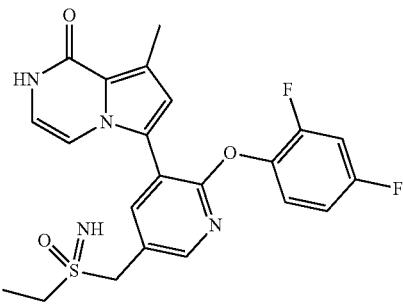
ZB-BD-255

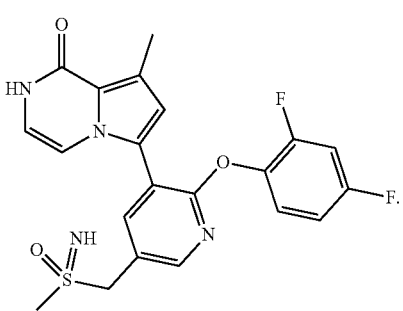
ZB-BD-256

7. A pharmaceutical composition comprising a therapeutically effective amount of the compound, or a pharmaceutically acceptable salt, enantiomer, diastereomer, atropisomer, racemate, polymorph, solvate, or isotopically labeled compound thereof according to claim 1, and a pharmaceutically acceptable carrier.

8. A method for treating a disease or disorder or condition in a subject, comprising:
administering to a subject in need of such treatment, an effective amount of the compound, or a pharmaceutically acceptable salt, enantiomer diastereomer, atropisomer, racemate, polymorph, solvate, or isotopically labeled compound thereof according to claim 1.

9. The method according to claim 8, wherein the disease or disorder or condition is selected from the group consisting of acoustic neuroma, acute leukemia, acute lymphocytic leukemia, acute myeloid leukemia (monocytic, myeloblastic, adenocarcinoma, angiosarcoma, astrocytoma, myelomonocytic and promyelocytic), acute t-cell leukemia, basal cell carcinoma, cholangiocarcinoma, bladder cancer, brain cancer, breast cancer, bronchial cancer, cervical cancer, chondrosarcoma, chordoma, choriocarcinoma, chronic leukemia, chronic lymphocytic leukemia, chronic myeloid (granulocytic) leukemia, chronic myelogenous leukemia, colon cancer, colorectal cancer, craniopharyngioma, cystadenocarcinoma, diffuse large B-cell lymphoma, adverse proliferative changes (dysplasia and metaplasia), embryonic cancer, endometrial cancer, endothelial sarcoma, ependymoma, epithelial cancer, erythroleukemia, esophageal cancer, estrogen receptor positive breast cancer, primary thrombocythemia, Ewing's sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, leukemia, liposarcoma, lung cancer, lymphatic endothelial sarcoma, lymphangiosarcoma, lymphoblastic leukemia, (Hodgkin's and non-Hodgkin's) lymphoma, malignant tumors and hyperproliferative disorders of bladder, breast, colon, lung, ovary, pancreas, prostate, skin and uterus, T-cell or B-cell derived lymphom, leukemia, lymphoma, medullary carcinoma, medulloblastoma, melanoma, meningioma, mesothelioma, multiple myeloma, myeloid leukemia, myeloma, myxosarcoma, neuroblastoma, NUT midline carcinoma (NMC), non-small cell lung cancer, oligodendroglioma, oral cancer, osteogenicsarcoma, ovarian cancer, pancreatic cancer, papillary adenocarcinoma, papillary carcinoma, pinealoma, polycythemia vera, prostate cancer, rectal cancer, renal cell carcinoma, retinoblastoma, rhabdomyosarcoma, sarcoma, sebaceous carcinoma, seminoma, skin cancer, small cell lung cancer, solid tumors (carcinoma and sarcoma), small cell lung cancer, gastric cancer, squamous cell carcinoma, synovial tumor, sweat adenoma, thyroid cancer, primary macroglobulinemia, testicular tumor, uterine cancer, and nephroblastoma, or
wherein the disease or disorder or condition is selected from the group consisting of Addison's disease, acute gout, ankylosing spondylitis, asthma, atherosclerosis, Behcet's disease, bullous skin disease, chronic obstructive pulmonary disease, Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, organs transplant rejection, osteoarthritis, pancreatitis, pericarditis, polyarteritis nodosa, localized pneumonia, primary biliary cirrhosis, psoriasis, psoriatic arthritis, rheumatoid arthritis, scleritis, sclerosing cholangitis, sepsis, systemic lupus erythematosus, Gauer's arteritis, toxic shock, thyroiditis, type I diabetes, ulcerative colitis, uveitis, vitiligo, vasculitis, and Wegener's Granuloma, or
wherein the disease or disorder or condition is selected from the group consisting of diabetic nephropathy, hypertensive nephropathy, HIV-related nephropathy, glomerulonephritis, lupus nephritis, IgA nephropathy, focal stage glomerulosclerosis, membranous glomerulonephritis, minimal change disease, polycystic kidney disease, and tubulointerstitial nephritis, or
wherein the disease or disorder or condition is selected from the group consisting of acute kidney injuries or diseases induced by ischemia-reperfusion, cardiotonics and major surgical procedures, percutaneous coronary intervention, radiocontrast agents, sepsis, pneumonia, or drug poisoning, or
wherein the disease or disorder or condition is acquired immunodeficiency syndrome (AIDS), or
wherein the disease or disorder or condition is obesity, dyslipidemia, hypercholesterolemia, Alzheimer's disease, metabolic syndrome, fatty liver, type II diabetes, insulin resistance, diabetic retinopathy or diabetic neuropathy.

10. A method for preventing pregnancy in a subject, comprising:

administering to a subject in need of such treatment an effective amount of the compound, or a pharmaceutically acceptable salt, enantiomer, diastereomer, atropisomer, racemate, polymorph, solvate, or isotopically labeled compound thereof according to claim 1.

11. A method for treating a disease or disorder or condition in a subject, comprising:
administering to a subject in need of such treatment, an effective amount of the pharmaceutical composition according to claim 7.

12. The method according to claim 11, wherein the disease or disorder or condition is selected from the group consisting of acoustic neuroma, acute leukemia, acute lymphocytic leukemia, acute myeloid leukemia (monocytic, myeloblastic, adenocarcinoma, angiosarcoma, astrocytoma, myelomonocytic and promyelocytic), acute t-cell leukemia, basal cell carcinoma, cholangiocarcinoma, bladder cancer, brain cancer, breast cancer, bronchial cancer, cervical cancer, chondrosarcoma, chordoma, choriocarcinoma, chronic leukemia, chronic lymphocytic leukemia, chronic myeloid (granulocytic) leukemia, chronic myelogenous leukemia, colon cancer, colorectal cancer, craniopharyngioma, cystadenocarcinoma, diffuse large B-cell lymphoma, adverse proliferative changes (dysplasia and metaplasia), embryonic cancer, endometrial cancer, endothelial sarcoma, ependymoma, epithelial cancer, erythroleukemia, esophageal cancer, estrogen receptor positive breast cancer, primary thrombocythemia, Ewing's sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, leukemia, liposarcoma, lung cancer, lymphatic endothelial sarcoma, lymphangiosarcoma, lymphoblastic leukemia, (Hodgkin's and non-Hodgkin's) lymphoma, malignant tumors and hyperproliferative disorders of bladder, breast, colon, lung, ovary, pancreas, prostate, skin and uterus, T-cell or B-cell derived lymphom, leukemia, lymphoma, medullary carcinoma, medulloblastoma, melanoma, meningioma, mesothelioma, multiple myeloma, myeloid leukemia, myeloma, myxosarcoma, neuroblastoma, NUT midline carcinoma (NMC), non-small cell lung cancer, oligodendroglioma, oral cancer, osteogenicsarcoma, ovarian cancer, pancreatic cancer, papillary adenocarcinoma, papillary carcinoma, pinealoma, polycythemia vera, prostate cancer, rectal cancer, renal cell carcinoma, retinoblastoma, rhabdomyosarcoma, sarcoma, sebaceous carcinoma, seminoma, skin cancer, small cell lung cancer, solid tumors (carcinoma and sarcoma), small cell lung cancer, gastric cancer, squamous cell carcinoma, synovial tumor, sweat adenoma, thyroid cancer, primary macroglobulinemia, testicular tumor, uterine cancer, and nephroblastoma, or wherein the disease or disorder or condition is selected from the group consisting of Addison's disease, acute gout, ankylosing spondylitis, asthma, atherosclerosis, Behcet's disease, bullous skin disease, chronic obstructive pulmonary disease, Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, organs transplant rejection, osteoarthritis, pancreatitis, pericarditis, polyarteritis nodosa, localized pneumonia, primary biliary cirrhosis, psoriasis, psoriatic arthritis, rheumatoid arthritis, scleritis, sclerosing cholangitis, sepsis, systemic lupus erythematosus, Gauer's arteritis, toxic shock, thyroiditis, type I diabetes, ulcerative colitis, uveitis, vitiligo, vasculitis, and Wegener's Granuloma, or wherein the disease or disorder or condition is selected from the group consisting of diabetic nephropathy, hypertensive nephropathy, HIV-related nephropathy, glomerulonephritis, lupus nephritis, IgA nephropathy, focal stage glomerulosclerosis, membranous glomerulonephritis, minimal change disease, polycystic kidney disease, and tubulointerstitial nephritis, or wherein the disease or disorder or condition is selected from the group consisting of acute kidney injuries or diseases induced by ischemia-reperfusion, cardiotonics and major surgical procedures, percutaneous coronary intervention, radiocontrast agents, sepsis, pneumonia, or drug poisoning, or wherein the disease or disorder or condition is acquired immunodeficiency syndrome (AIDS), or wherein the disease or disorder or condition is obesity, dyslipidemia, hypercholesterolemia, Alzheimer's disease, metabolic syndrome, fatty liver, type II diabetes, insulin resistance, diabetic retinopathy or diabetic neuropathy.

13. A method for preventing pregnancy in a subject, comprising:
administering to a subject in need of such treatment an effective amount of the pharmaceutical composition according to claim 7.

\* \* \* \* \*